United States Patent
Ishida et al.

(10) Patent No.: US 9,975,904 B2
(45) Date of Patent: May 22, 2018

(54) COMPOUND HAVING AGONISTIC ACTIVITY ON SOMATOSTATIN RECEPTOR, AND USE THEREOF FOR MEDICAL PURPOSES

(71) Applicant: ONO PHARMACEUTICAL CO., LTD., Osaka (JP)

(72) Inventors: Akiharu Ishida, Osaka (JP); Takeshi Matsushita, Osaka (JP); Tetsuya Sekiguchi, Osaka (JP); Tatsuya Komagata, Osaka (JP); Takuya Nishio, Osaka (JP)

(73) Assignee: ONO PHARMACEUTICAL CO., LTD., Osaka (JP)

( * ) Notice: Subject to any disclaimer, the term of this patent is extended or adjusted under 35 U.S.C. 154(b) by 0 days. days.

(21) Appl. No.: 15/460,466

(22) Filed: Mar. 16, 2017

(65) Prior Publication Data
US 2017/0183359 A1 Jun. 29, 2017

Related U.S. Application Data

(62) Division of application No. 14/412,564, filed as application No. PCT/JP2013/068084 on Jul. 2, 2013, now Pat. No. 9,630,976.

(30) Foreign Application Priority Data

Jul. 3, 2012 (JP) .................. 2012-149010

(51) Int. Cl.
| | |
|---|---|
| *C07D 498/04* | (2006.01) |
| *C07D 471/04* | (2006.01) |
| *A61K 31/4418* | (2006.01) |
| *A61K 31/454* | (2006.01) |
| *A61K 31/4545* | (2006.01) |
| *A61K 31/517* | (2006.01) |
| *C07D 213/82* | (2006.01) |
| *C07D 235/18* | (2006.01) |
| *C07D 401/04* | (2006.01) |
| *C07D 401/10* | (2006.01) |
| *C07D 401/12* | (2006.01) |
| *C07D 401/14* | (2006.01) |
| *C07D 405/14* | (2006.01) |
| *C07D 413/14* | (2006.01) |
| *C07D 417/14* | (2006.01) |
| *A61K 31/4184* | (2006.01) |

(52) U.S. Cl.
CPC ........ *C07D 498/04* (2013.01); *A61K 31/4184* (2013.01); *A61K 31/4418* (2013.01); *A61K 31/454* (2013.01); *A61K 31/4545* (2013.01); *A61K 31/517* (2013.01); *C07D 213/82* (2013.01); *C07D 235/18* (2013.01); *C07D 401/04* (2013.01); *C07D 401/10* (2013.01); *C07D 401/12* (2013.01); *C07D 401/14* (2013.01); *C07D 405/14* (2013.01); *C07D 413/14* (2013.01); *C07D 417/14* (2013.01); *C07D 471/04* (2013.01)

(58) Field of Classification Search
None
See application file for complete search history.

(56) References Cited

U.S. PATENT DOCUMENTS

| | | | |
|---|---|---|---|
| 4,140,696 | A | 2/1979 | Tarzia et al. |
| 4,472,192 | A | 9/1984 | Eicken et al. |
| 5,405,829 | A | 4/1995 | Hartfiel et al. |
| 2004/0006089 | A1 | 1/2004 | Thurieau et al. |
| 2004/0054173 | A1 | 3/2004 | Kimura et al. |
| 2004/0110808 | A1 | 6/2004 | Strobel et al. |
| 2004/0157904 | A1 | 8/2004 | Rudolph et al. |

(Continued)

FOREIGN PATENT DOCUMENTS

| | | |
|---|---|---|
| EP | 0586686 A1 | 9/1993 |
| EP | 0 776 894 A1 | 6/1997 |

(Continued)

OTHER PUBLICATIONS

Crider, Am. Somatostatin receptor agonists and antagonists. Expert Opinion. 2003, p. 1428.*

(Continued)

*Primary Examiner* — Taofiq A Solola
(74) *Attorney, Agent, or Firm* — Sughrue Mion, PLLC

(57) ABSTRACT

Provision of orally-available and low-toxic somatostatin receptor subtype 2 agonist. Since the compound represented by the general formula (I):

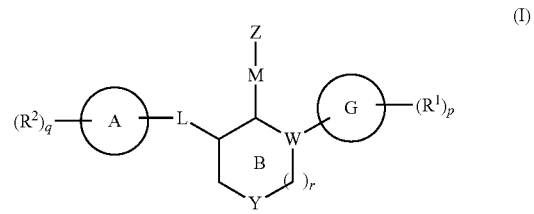

wherein all symbols represent the same meanings as those described in the description, a salt thereof, an N-oxide thereof, a solvate thereof, or a prodrug thereof is non-peptidic low-molecular compound which has strong somatostatin receptor subtype 2 agonist activity, the compound is orally-available. Additionally, since the compound is low-toxic, the compound is useful for the prevention and/or treatment of the somatostatin related diseases such as acromegaly or gastrointestinal obstruction.

2 Claims, No Drawings

(56) References Cited

U.S. PATENT DOCUMENTS

| | | | |
|---|---|---|---|
| 2008/0064734 | A1 | 3/2008 | Rudolph et al. |
| 2009/0258853 | A1 | 10/2009 | Eastman et al. |
| 2010/0099681 | A1 | 4/2010 | Barfacker et al. |
| 2011/0105543 | A1 | 5/2011 | Nardi et al. |
| 2011/0190297 | A1 | 8/2011 | McDonald et al. |
| 2011/0224204 | A1 | 9/2011 | Chesworth et al. |
| 2011/0230521 | A1 | 9/2011 | Cook et al. |

FOREIGN PATENT DOCUMENTS

| | | |
|---|---|---|
| EP | 1 070 711 A2 | 1/2001 |
| EP | 1 188 745 A1 | 3/2002 |
| EP | 1 193 254 A1 | 4/2002 |
| FR | 2802206 A1 | 6/2001 |
| JP | 58-24566 A | 2/1983 |
| JP | 61-286379 A | 12/1986 |
| JP | 5-43574 A | 2/1993 |
| JP | 7-505125 A | 6/1995 |
| JP | 11-130753 A | 5/1999 |
| JP | 2001-64258 A | 3/2001 |
| JP | 2001-247564 A | 9/2001 |
| JP | 2001-335563 A | 12/2001 |
| JP | 2002-284783 A | 10/2002 |
| JP | 2003-509495 A | 3/2003 |
| JP | 2004-67645 A | 3/2004 |
| JP | 2005-538123 A | 12/2005 |
| JP | 2006-525359 A | 11/2006 |
| JP | 2009-534386 A | 9/2009 |
| JP | 2011-20949 A | 2/2011 |
| JP | 2011-63565 A | 3/2011 |
| JP | 2011-513460 A | 4/2011 |
| JP | 2011-520806 A | 7/2011 |
| JP | 2013-060370 A | 4/2013 |
| WO | 92/13451 A1 | 8/1992 |
| WO | 93/019054 A1 | 9/1993 |
| WO | 96/04278 A1 | 2/1996 |
| WO | 01/21591 A1 | 3/2001 |
| WO | 2004/050650 A1 | 6/2004 |
| WO | 2004/099156 A1 | 11/2004 |
| WO | 2007/123936 A1 | 11/2007 |
| WO | 2008/051272 A2 | 5/2008 |
| WO | 2009/112461 | 9/2009 |
| WO | 2009/158467 A2 | 12/2009 |
| WO | 2010001169 A2 | 1/2010 |
| WO | 2010/020363 A1 | 2/2010 |
| WO | 2010/041054 A1 | 4/2010 |
| WO | 2012/080187 A1 | 6/2012 |
| WO | 2012/080729 A2 | 6/2012 |

OTHER PUBLICATIONS

Kimmey, Mb. Systematic review: acute colonic pseudo-obstruction (ACPO). Aliment. Pharmacol. Ther. 2005, p. 917.*
Griebenow, et al.; "Identification and Optimization of Substituted 5-Aminopyrazoles as Potent and Selective Adenosine A1 Receptor Antagonists", Bioorganic & Medicinal Chemistry Letters, Aug. 2010, vol. 20, pp. 5891-5894.
Wolkenberg, et al.; "Design, Synthesis, and Evaluation of Novel 3,6-Diaryl-4-aminoalkoxyquinolines as Selective Agonists of Somatostatin Receptor Subtype 2", Journal of Medicinal Chemistry, Mar. 2011, vol. 54, pp. 2351-2358.
Contour-Galcera, et al.; "3-Thio-1,2,4-triazoles, Novel Somatostatin $sst_2/sst_5$ Agonists", Bioorganic & Medicinal Chemistry Letters, May 2005, vol. 15, pp. 3555-3559.
Search Report dated Oct. 15, 2013, issued by the International Searching Authority in counterpart International Application No. PCT/JP2013/068084 [PCT/ISA/210].
European Patent Office, Extended European Search Report dated Feb. 11, 2016 in counterpart European Application No. 13813151.1.
Camps P. et al.:, "A One Step Synthesis of 2,6-Disubstituted Anilines From Aliphatic Compounds", Tetrahedron Letters, vol. 22, No. 26, 1981, pp. 2487-2490, XP0055246455, Pergamon Press Ltd.,Departmento de Quinica Organica, Facultad de Ciencias. Universidad Autonoma de Barcelona. Bellaterra, Barcelona, Spain.
Doherty, S. et al.:, "Ruthenium Complexes of K(P)- and K(P)-n6-Coordinated KITPHOS Monophosphines: Efficient Catalysts for the Direct Ortho Arylation of 2-Phenylpyridine and N-Phenylpyrazole with Aryl Chlorides" Organometallics, vol. 30, No. 21, 2011, pp. 6010-6016, XP0055246462, School of Chemistry, Bedson Building, Newcastle University, Newcastle upon Tyne NE1 7RU, U.K.
Ackerman, L. et al.: "[RuCl3(H2O),,]-catalyzed direct arylations" Tetrahedron, vol. 64, 2008, Jan. 16, 2008, pp. 6115-6124, XP0055246468, Institut fuer Organische und Biomolekulare Chemie, Georg-August Universitat Goettingen Tammannstrafle 2, D-37077, Goettingen, Germany.
Ackermann, L. et al: , "Catalytic Arylation Reactions by C-H Bond Activation with Aryl Tosylates", vol. 45, 2006, pp. 2619-2622, XP0055246486, Angewandte Chemie.
Ackerman, L. et al.:"[RuCl3(H2O)n]-Catalyzed Direct Arylations with Bromides as Electrophiles" Synlett, No. 18, Aug. 12, 2007, pp. 2833-2836, XP55244441, Institut fur Organische und Biomolekulare Chemie, Georg-August-Universitat Gottingen, Tammannstr. 2, 37077 Gottingen, Germany.
Azzena, U. et al.:, "Single electron transfer reductive cleavage of the aryl-nitrogen bond in phenyl-substituted dimethylanilines" Tetrahedron Letters, vol. 40, 1999, pp. 8291-8293, XP005024973, Dipartimento di Chimica, Universita di Sassari, Via Vienna 2, 1-07100 Sassari, Italy.
Ajith Dain, T. et al.: "Vilsmeier-Haack reactions of carbonyl compounds: synthesis of substituted pyrones and pyridines" Tetrahedron, vol. 60, 2004, pp. 5069-5076, XP0055246483, School of Chemical Sciences, Mahatma Gandhi University. Priyadarshini Hills, Kottayam 686560, India.
European Patent Office, Communication dated Feb. 10, 2017 in corresponding European Application No. 13 813 151.1.
Takagi et al., "Synthesis of pyrimidino[4,5-b][1,5]benzodiazepin-2-ones and pyrimidino[1,6-a]benzimidazol-1-ones from 4-[(ethoxycarbonyl)amino]-1H-1,5- benzodiazpine-3-carbonitrile via 4-(2-aminoanilino)pyrimidin-2(1H)-one- 5-carbonitriles", J. Heterocyclic Chem., vol. 23, No. 5, 1986, pp. 1443-1449.
Meinhard et al., "New Nickel(II) Diimine Complexes and the Control of Polyethylene Microstructure by Catalyst Design", J. Am. Chem. Soc., vol. 129, 2007, pp. 9182-9191.
Khlebnikov et al., "A Novel Strategy for the Synthesis of 3-(N-Heteryl)pyrrole Derivatives", Organic Letters, vol. 14, No. 14, 2012, pp. 3768-3771.
Sakakura et al., "Bulky diarylammonium arenesulfonated as mild and extremely active dehydrative ester condensation catalysts", Tetrahedron, vol. 62, 2006, pp. 422-433.
Carey, FA. Organic Chemistry 6th Ed. McGraw Hill. 2006, chapter 1, p. 9.
Greenwald, RB. et al. Drug Delivery Systems: Water Soluble Taxol 2'-Poly(ethylene glycol) Ester Prodrugs-Design and in Vivo Effectiveness. J. Med. Chem. 1996, vol. 39, p. 425.
Testa, B. et al. Lessons Learned from Marketed and Investigational Prodrugs. J. Med. Chem. 2004, vol. 47(10), p. 2393.
Cornelison, TL. Human papillomavirus genotype 16 vaccines for cervical cancer prophylaxis and treatment. Curr. Opin. Oncol. 2000, vol. 12(5), p. 466.
Communication issued by the Japanese Patent Office on Aug. 15, 2017 in counterpart Japanese Patent Application No. 2014-523742.
Masayuki Wasa et al., "$Pd^0/PR_3$-Catalyzed Arylation of Nicotinic and Isonicotinic Acid Derivatives", Angew. Chem. Int. Ed., 2010, pp. 1275-1277, vol. 49, DOI: 10.1002/anie.200906104.
Ranjana Aggarwal et al., "Synthesis and antibacterial activity of some new 1-heteroaryl-5-amino-3H/methyl-4-phenylpyrazoles", Bioorganic & Medicinal Chemistry, Nov. 21, 2005, pp. 1785-1791, vol. 14, doi:10.1016/j.bmc.2005.10.026
Communication dated Nov. 24, 2017, from the European Patent Office in counterpart European Application No. 13813151.1.
Communication dated Nov. 27, 2017, issued by the Japanese Patent Office in counterpart Japanese application No. 2014-523742.
Casado, et al., "Electrostatic and Electrophilic Catalysis in the Reductive Cleavage of Alkyl Aryl Ethers. The Influence of Ion

(56) References Cited

OTHER PUBLICATIONS

Pairing on the Regioselectivity" 2000, Journal of Organic Chemistry, vol. 65, No. 2, pp. 322-331.
European Patent Office, Communication dated Mar. 19, 2018 in copending European Application No. 13 813 151.1.
Kalinin et al., "The Directed Ortho Metalation-Ullmann Connection, A New Cu(l)-Catalyzed Variant for the Synthesis of Subsituted Diaryl Ethers", J. Org. Chem. 64, 1999, 2986-2987.
MacNeil et al., "Anionic N-Fries Rearrangement of N-Carbamoyl Diarylamines to Anthranilamides, Methodology and Application to acridone and Pyranoacridone Alkaloids", Organic Letters, vol. 8, No. 6, 2006, 1133-1136.

* cited by examiner

COMPOUND HAVING AGONISTIC ACTIVITY ON SOMATOSTATIN RECEPTOR, AND USE THEREOF FOR MEDICAL PURPOSES

CROSS-REFERENCE TO RELATED PATENT APPLICATION

This application is a Divisional Application of U.S. application Ser. No. 14/412,564 (allowed) filed Jan. 2, 2015, which is a National Stage application under 35 U.S.C. § 371 of International Application No. PCT/JP2013/068084, filed on Jul. 2, 2013, and claims the benefit of Japanese Application No. 2012-149010, filed on Jul. 3, 2012 in the Japanese Patent Office, the disclosures of which are incorporated herein by reference in their entireties.

TECHNICAL FIELD

The present invention is related to the compounds, which have somatostatin receptor agonist activity, especially somatostatin receptor subtype 2 agonist activity, represented by the general formula (I) described below, a salt thereof, a N-oxide thereof, a solvate thereof, or a prodrug thereof and medical use thereof.

BACKGROUND ART

Acromegaly is hormone disorder resulted from excess growth hormone secreted by pituitary gland caused by hypophysial adenoma, etc., and bones and soft tissues of head and limbs of patients with acromegaly are swell. Although acromegaly is not always a disease with high prevalence, which is approximately 60 per 1 million people, but it's a serious disease which increases the risk of death because the patients are interfered with their daily life by abnormality of parts of their body, and also one thirds of them have heart disease.

As treatment for the patients with acromegaly, along with an operation to remove adenoma which secrete growth hormone surgically or radiotherapy, there are medical therapies, etc., wherein somatostatin analogs, which are hormones to suppress the secretion of growth hormone, are administered extrinsically. As these somatostatin analogs like this, there are Novartis Pharmaceuticals's Octreotide acetate (Sandostatin$^B$) and Ipsen Pharma's Lanreotide acetate (Somatuline$^B$ LA), and effectiveness of them are confirmed. However, these medicines need to be taken by injection because they are peptidic medicines, and the patients reportedly suffer a lot of pain when its prolonged release preparation is administered by intramuscular injection to them once a several weeks. To solve the problem, it would appear that non-peptidic, low-molecular compound which can be administered orally is the best choice rather than the peptidic medicines which need to be administered by injection.

On the other hand, there are 5 subtypes, SSTR1 to SSTR5, identified so far as somatostatin receptors, said Octreotide acetate and Lanreotide acetate are reported to bind to somatostatin receptor subtype 2 (SSTR2) with high affinity. Moreover, they are reported to bind to somatostatin receptor subtype 3 (SSTR3) and somatostatin receptor r subtype 5 (SSTR5) with moderate affinity and not to bind somatostatin receptor subtype 1 (SSTR1) and somatostatin receptor subtype 4 (SSTR4).

As the difference of affinity of Octreotide acetate and Lanreotide acetate against these receptor subtypes become clearer scientifically, some non-peptidic, low-molecular weight compounds are synthesized as somatostatin receptor agonists.

For example, it is mentioned that the compounds represented by the general formula(A):

[1]

(A)

[wherein
$B_A$ and $D_A$ represent independently carbon or nitrogen, $A_A$ and $F_A$ represent independently CH or nitrogen, but only one or two among $A_A$, $B_A$, $D_A$ and $F_A$ are nitrogen simultaneously;
$R_{1A}$ and $R_{1aA}$ represent independently hydrogen or C1-12 alkyl, etc.;
$R_{2A}$ represents hydrogen or C1-12 alkyl, etc.;
$R_{3A}$ and $R_{4A}$ represent independently hydrogen, halogen or C1-12 alkyl, etc.;
$R_{5A}$ represents $(CH_2)_{mA}$C6-10 aryl or $(CH_2)_{mA}$C5-10 heterocyclyl;
$R_{6A}$ represents hydrogen, halogen or CN, etc.;
$R_{7A}$ represents hydrogen, halogen or C1-6 alkyl, etc.;
mA is an integer of 0 to 6;
xA is an integer of 1 to 3.]
and a pharmaceutically acceptable salt thereof, an ester thereof, an enantiomer thereof and a mixture thereof (definitions of each groups are excerpted) are SSTR2 selective agonists and they are useful for medical treatment of diabetic or related lesions (retinopathy, neurological disorder and nephropathy, etc.) in Patent Literature 1.

Alternatively, it is mentioned that the compounds represented by the formula (B):

[2]

(B)

have SSTR agonist activity, depresses growth hormone secretion by systemic administration and inhibits angiogenesis of eyes by local administration in Non-Patent Literature 1.

Additionally, it is mentioned that the compounds represents by the general formula (C):

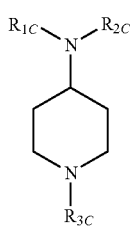

[3]

(C)

[wherein
$R_{1C}$ represents straight or branched (C1-C16) alkyl group, alkenyl group or alkynyl group etc;
$R_{2C}$ represents a group described by —C($Y_C$)NHX$_{1C}$, —C(O)X$_{2C}$, or —SO$_2$X$_{3C}$;
$Y_C$ represents oxygen or sulfur;
$R_{3C}$ represents hydrogen, alkyl group which may be substituted, alkenyl group, alkynyl group, aralkyl group which may be substituted, or heteroaryl alkyl group which may be substituted, etc.;
$X_{1C}$ represents straight or branched (C1-C15) alkyl group, alkenyl group or alkynyl group;
$X_{2C}$ represents alkenyl group, etc. which may be substituted with straight or branched (C1-C10) alkyl group or phenyl;
$X_{3C}$ represents alkenyl group, etc. which may be substituted with straight or branched (C1-C10) alkyl group or phenyl]
and a pharmaceutically acceptable inorganic or organic acid salt thereof (the definition of each groups are excerpted) show good affinity with somatostatin receptor and especially useful for medical treatment for the pathological state and diseases related with somatostatin receptor in Patent Literature 2.

And it is mentioned that the 3-thio-1,2,4-triazole compound represented by the formula (D) below:

[4]

(D)

is SSTR2 and SSTR5 agonist in Non-Patent Literature 2.

However, the present invention compounds represented by the general formula (I) described below, a salt thereof, an N-oxide thereof, a solvate thereof, or a prodrug thereof for medical use thereof are not shown in any prior art, and are not followed from any combination of them.

PRIOR ART DOCUMENTS

Patent Literature

[Patent Literature 1] A brochure of WO2008/051272
[Patent Literature 2] A specification of FR2802206

Non-Patent Literature

[Non-Patent Literature1] *Journal of Medicinal Chemistry*, 2011, vol.54, p2351-2358
[Non-Patent Literature 2] *Bioorganic & Medicinal Chemistry Letters*, 2005, vol.15, p3555-3559

SUMMARY OF THE INVENTION

Problems to be Solved by the Invention

The problem to be solved by the present invention is to provide orally administrable, low-toxic ant non-peptidic low-molecular weight compounds with somatostatin receptor agonist activity, especially SSTR2 agonist activity, not to provide peptidic medicine like existing somatostatin receptor agonists which need to be administered by injection.

Methods to Solve the Problem

The inventors intensively studied to solve the problem described above and found out that the compounds represented by the general formula (I) described below, a salt thereof, an N-oxide thereof, a solvate thereof or a prodrug thereof were able to solve the problem, and then carried farther study and completed the present invention.

That is, the present invention relates to:
[1] the compound represented by the general formula (I):

[5]

(I)

[wherein
$R^1$ represents (1) halogen, (2) hydroxyl, (3) C1-4 alkyl which may be substituted with the substituents selected from the group consisting of (a) —OR$^7$ and (b) halogen, (4) C1-4 alkoxy, or (5) C3-8 cycloalkyl;
p represents an integer of 0 to 3;
When p is 2 or more, more than one $R^1$ may be same or different;
$R^2$ represents (1) halogen, (2) oxo, (3) —OR$^3$, (4) —COR$^4$, (5) —COOR$^5$, (6) —SO$_2$R$^6$, (7) C1-4 alkyl which may be substituted with the substituents selected from the group consisting of (a) —OR$^7$, (b) —COR$^8$, (c) —COOR$^9$, (d) —SO$_2$R$^{10}$, (e) halogen and (f) cyano, (8) C3-6 monocyclic carbon ring which may be substituted with the substituents selected from the group consisting of (a) C1-4 alkyl, (b) phenyl and (c) hydroxymethyl, (9) 5 to 6 membered monocyclic hetero ring which may be substituted with the substituents selected from the group consisting of (a)

C1-4 alkyl, (b) phenyl, and (c) hydroxymethyl, (10) —NR$^{76}$R$^{77}$, (11) —CONR$^{78}$R$^{79}$, (12) —NR$^{80}$COR$^{81}$ or (13) cyano;

R$^3$ and R$^7$ represent independently (1) hydrogen, (2) C1-4 alkyl, (3) C1-4 haloalkyl, or (4) —COR$^4$;

R$^4$ and R$^8$ represent independently C1-4 alkyl or amino;

R$^5$, R$^6$, R$^9$ and R$^{10}$ represent independently hydrogen or C1-4 alkyl;

R$^{76}$ to R$^{81}$ represent independently hydrogen or C1-4 alkyl;

q represents an integer of 0 to 3;

When q is 2 or more, more than one R$^2$ may be same or different;

Ring A represents C5-10 monocyclic or bicyclic carbon ring or 5 to 10 membered monocyclic or bicyclic hetero ring;

Ring G represents cyclopropane, benzene, pyridine, pyrimidine, pyrazole, thiazole, quinolone or furan ring;

W and Y represent independently nitrogen or carbon;

r represents 0 or 1;

Ring B represents benzene when W and Y represent carbon and r represents 1, and pyrrole, pyrazole or pyridine when at least one or both of W and Y represent nitrogen and r represents 0 or 1;

L represents (1) bond, (2) —CR$^{21}$=CR$^{22}$→, (3) —X→, (4) —X—CR$^{23}$R$^{24}$→, (5) —CR$^{25}$R$^{26}$—X→, (6) —X—CR$^{27}$R$^{28}$—O→, (7) —X—O—CR$^{29}$R$^{30}$→, (8) —O—CR$^{31}$R$^{32}$—X→ or (9) —CR$^{33}$R$^{34}$—O—X→ (wherein the arrows represent binding position with Ring B.);

R$^{21}$ to R$^{34}$ represent independently hydrogen or C1-4 alkyl;

X represents (1) —O—, (2) —C(=O)—, (3) —NR$^{41}$—, (4) —C(=O)—NR$^{42}$— or (5) —NR$^{43}$—C(=O)—;

R$^{41}$ to R$^{43}$ represent independently hydrogen or C1-4 alkyl;

M represents (1) bond, (2) —C(=O)—, (3) —(C1-4 alkylene)-, (4) —O—(C1-3 alkylene)-, (5) —(C1-3 alkylene)-O— or (6) —(C1-2 alkylene)-O—(C1-2 alkylene)-;

Z represents —NR$^{51}$R$^{52}$, or 5 to 10 membered monocyclic or bicyclic nitrogen-containing hetero ring which may be substituted with the substituents selected from the group consisting of (a) halogen, (b) —NR$^{53}$R$^{54}$, (c) —OR$^{55}$, (d) C1-4 alkyl which may be substituted with —NR$^{56}$R$^{57}$ and/or —OR$^{58}$ and (e) oxo;

R$^{51}$ and R$^{52}$ represent independently (1) hydrogen, (2) C1-8 alkyl which may be substituted with the substituents selected from the group consisting of (a) —NR$^{61}$R$^{62}$, (b) —OR$^{63}$, and (c) Ring D1, (3) C5-6 monocyclic carbon ring which may be substituted with the substituents selected from the group consisting of (a) —NR$^{64}$R$^{65}$ and (b) C1-4 alkyl which may be substituted with —NR$^{66}$R$^{67}$, or (4) Ring D2;

Ring D1 and Ring D2 represent independently 5 to 6 membered nitrogen-containing saturated monocyclic hetero ring which may be substituted with the substituents selected from the group consisting of (a) halogen, (b) —NR$^{71}$R$^{72}$, (c) —OR$^{73}$, and (d) C1-4 alkyl which may be substituted with —NR$^{74}$R$^{75}$;

R$^{53}$ to R$^{58}$ represent independently hydrogen, C1-4 alkyl, C1-4 haloalkyl, C1-4 acyl, —C(=O)—O—(C1-4 alkyl), —C(=O)—OCH$_2$R$^{68}$, oxetanyl or oxolanyl;

R$^{61}$ to R$^{67}$ represent independently hydrogen, C1-4 alkyl, C1-4 haloalkyl, C5-6 monocyclic carbon ring or (C5-6 monocyclic carbon ring)-(C1-4 alkylene)-;

R$^{68}$ represents (1) C5-6 monocyclic carbon ring which may be substituted with the substituents selected from the group consisting of (a) C1-4 alkyl and (b) oxo, or (2) 5 to 6 membered monocyclic hetero ring which may be substituted with the substituents selected from the group consisting of (a) C1-4 alkyl and (b) oxo;

R$^{71}$ to R$^{75}$ represent independently hydrogen or C1-4 alkyl]

a salt thereof, an N-oxide thereof, a solvate thereof or a prodrug thereof;

[2] the compound described in [1] above wherein L is (1) —CR$^{21}$=CR$^{22}$→, (2) —O→, (3) —C(=O)→, (4) —NR$^{41}$→, (5) —C(=O)—NR$^{42}$→, (6) —NR$^{43}$—C(=O)→, (7) —CR$^{25}$R$^{26}$—C(=O)→, (8) —CR$^{25}$R$^{26}$—NR$^{41}$→, (9) —CR$^{25}$R$^{26}$—C(=O)—NR$^{42}$→, (10) —CR$^{25}$R$^{26}$—NR$^{43}$-C(=O)→, (11) —NR$^{41}$—O—CR$^{29}$R$^{30}$→, (12) —C(=O)—NR$^{42}$—O—CR$^{29}$R$^{30}$→, (13) —NR$^{43}$—C(=O)—O—CR$^{29}$R$^{30}$→, (14) —O—CR$^{31}$R$^{32}$—C(=O)→, (15) —O—CR$^{31}$R$^{32}$—NR$^{41}$→, (16) —O—CR$^{31}$R$^{32}$—C(=O)—NR$^{42}$→, (17) —O—CR$^{31}$R$^{32}$—NR$^{43}$—C(=O)→, (18) —CR$^{33}$R$^{34}$—O—C(=O)→, (19) —CR$^{33}$R$^{34}$—O—NR$^{41}$→, (20) —CR$^{33}$R$^{34}$—O—C(=O)—NR$^{42}$→ or (21) —CR$^{33}$R$^{34}$—O—NR$^{43}$—C(=O)→ (wherein all symbols represent the same meanings as those described in [1] above);

[3] The compounds described in [1] or [2], wherein Ring G is benzene;

[4] The compounds described in any one of [1] to [3] above, wherein

[6]

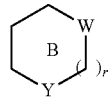

[wherein all symbols represent the same meanings as those described in [1] above] is

[7]

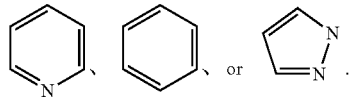

[5] The compound described in any one of [1] to [4], wherein when an atom which binds to Ring B is assigned as the first atom in the group represented by -M-Z, at least one atom of the forth to the seventh in the shortest path is nitrogen;

[6] The compound described in any one of [1] to [5]; wherein -M-Z is the group represented by the formula (MZ1):

[8]

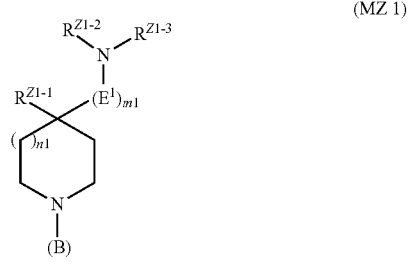

(MZ 1)

[wherein (B) represents binding position with Ring B;

$R^{Z1-1}$ represents hydrogen or the substituent selected from the group consisting of (a) halogen, (b) —$NR^{53}R^{54}$, (c) —$OR^{55}$, (d) C1-4 alkyl which may be substituted with —$NR^{56}R^{57}$ and/or —$OR^{58}$;

$E^1$ represents methylene;

m1 represents an integer of 0 to 3;

n1 represents an integer of 0 or 1;

m1+n1 represents an integer of 0 to 3;

$R^{Z1-2}$ and $R^{Z1-3}$ independently represent hydrogen, C1-4 alkyl, C1-4 haloalkyl, C1-4 acyl, —C(=O)—O—(C1-4 alkyl), oxolanyl, or oxetanyl;

the other symbols represent the same meanings as those described in [1] above.], the group represented by the formula (MZ2):

[9]

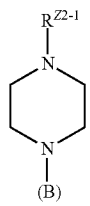

(MZ 2)

[wherein (B) represents the binding position with Ring B;

$R^{Z2-1}$ represents hydrogen or the substituent selected from the group consisting of (a) halogen, (b) —$NR^{53}R^{54}$, (c) —$OR^{55}$, (d) C1-4 alkyl which may be substituted with —$NR^{56}R^{57}$ and/or —$OR^{58}$;

the other symbols represent the same meanings as those described in [1] above.], the group represented by the formula (MZ3):

[10]

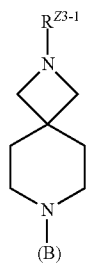

(MZ 3)

[wherein (B) represents the binding position with Ring B;

$R^{Z3-1}$ represents hydrogen or the substituent selected from the group consisting of (a) halogen, (b) —$NR^{53}R^{54}$, (c) —$OR^{55}$, (d) C1-4 alkyl which may be substituted with —$NR^{56}R^{57}$ and/or —$OR^{58}$;

the other symbols represent the same meanings as those described in [1] above.], the group represented by the formula (MZ4):

[11]

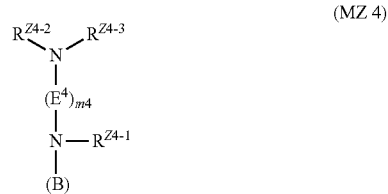

(MZ 4)

[wherein (B) represents the binding position with Ring B;

$R^{Z4-1}$ represents (1) hydrogen, (2) C1-8 alkyl which may be substituted with the substituents selected from the group consisting of (a) —$NR^{61}R^{62}$, (b) —$OR^{63}$, and (c) Ring D1, (3) C5-6 monocyclic carbon ring which may be substituted with the substituents selected from the group consisting of (a) —$NR^{64}R^{65}$, and (b) C1-4 alkyl which may be substituted with —$NR^{66}R^{67}$, or (4) Ring D2;

$E^4$ represents methylene;

m4 represents an integer of 2 to 5;

$R^{Z4-2}$ and $R^{Z4-3}$ independently represent hydrogen or the substituent selected from the group consisting of (a) —$NR^{61}R^{62}$, (b) —$OR^{63}$, or (c) Ring D1;

the other symbols represent the same meanings as those described in [1] above.], the group represented by the formula (MZ5):

[12]

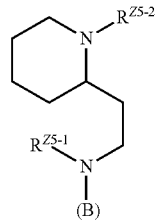

(MZ 5)

[wherein (B) represents the binding position with Ring B;

$R^{Z5-1}$ represents (1) hydrogen, (2) C1-8 alkyl which may be substituted with the substituents selected from the group consisting of (a) —$NR^{61}R^{62}$, (b) —$OR^{63}$, and (c) Ring D1, (3) C5-6 monocyclic carbon ring which may be substituted with the substituents selected from the group consisting of (a) —$NR^{64}R^{65}$, and (b) C1-4 alkyl which may be substituted with —$NR^{66}R^{67}$, or (4) Ring D2;

$R^{Z5-2}$ represents hydrogen, or the substituent which may be selected from the group consisting of (a) halogen, (b) —$NR^{71}R^{72}$, (c) —$OR^{73}$, or (d) C1-4 alkyl which may be substituted with —$NR^{74}R^{75}$;

the other symbols represent the same meanings as those described in [1] above.], the group represented by the formula (MZ6):

[13]

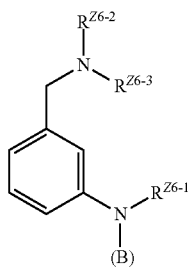

(MZ 6)

[wherein (B) represents the binding position with Ring B;

$R^{Z6-1}$ represents (1) hydrogen, (2) C1-8 alkyl which may be substituted with the substituents selected from the group consisting of (a) —$NR^{61}R^{62}$, (b) —$OR^{63}$, and (c) Ring D1, (3) C5-6 monocyclic carbon ring which may be substituted with the substituents selected from the group consisting of (a) —$NR^{64}R^{65}$, and (b) C1-4 alkyl which may be substituted with —$NR^{66}R^{67}$, or (4) Ring D2;

$R^{Z6-2}$ and $R^{Z6-3}$ represents independently hydrogen, C1-4 alkyl, C1-4 haloalkyl, C5-6 monocyclic carbon ring, or (C5-6 monocyclic carbon ring)-(C1-4 alkylene)-;

the other symbols represent the same meanings as those described in [1] above.], the group represented by the formula (MZ7):

[14]

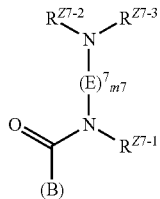

(MZ 7)

[wherein (B) represents the binding position with Ring B;

$R^{Z7-1}$ represents (1) hydrogen, (2) C1-8 alkyl which may be substituted with the substituents selected from the group consisting of (a) —$NR^{61}R^{62}$, (b) —$OR^{63}$, and (c) Ring D1, (3) C5-6 monocyclic carbon ring which may be substituted with the substituents selected from the group consisting of (a) —$NR^{64}R^{65}$, and (b) C1-4 alkyl which may be substituted with —$NR^{66}R^{67}$, or (4) Ring D2;

$E^7$ represents methylene;

M7 represents an integer of 1 to 4;

$R^{Z7-2}$ and $R^{Z7-3}$ independently represent hydrogen, C1-4 alkyl, C1-4 haloalkyl, C5-6 monocyclic carbon ring, or (C5-6 monocyclic carbon ring)-(C1-4 alkylene)-;

The other symbols represent the same meanings as those described in [1] above.]

the group represented by the formula (MZ8):

[15]

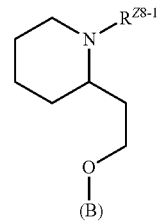

(MZ 8)

[wherein (B) represents the binding position with Ring B;

$R^{Z8-1}$ represents hydrogen or the substituent selected from the group consisting of (a) halogen, (b) —$NR^{53}R^{54}$, (c) —$OR^{55}$, (d) C1-4 alkyl which may be substituted with —$NR^{56}R^{57}$ and/or —$OR^{58}$;

the other symbols represent the same meanings as those described in [1] above.], or the group represented by the formula (MZ9):

[16]

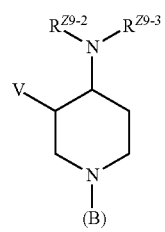

(MZ 9)

[wherein (B) represents the binding position with Ring B;

V represents hydrogen, halogen and —$OR^{Z9-1}$, $R^{Z9-1}$ represents hydrogen or C1-4 alkyl;

$R^{Z9-2}$ and $R^{Z9-3}$ represents independently hydrogen or C1-4 alkyl;

$R^{Z9-1}$ and $R^{Z9-2}$ may bind each other and form C1-4 alkylene when V is —$OR^{Z9-1}$;

the other symbols represent the same meanings as those described in [1] above.];

[7] The compound described in any one of [2] to [6]; wherein L is —C(=O)—$NR^{42}$→ or —$NR^{43}$—C(=O)→ [wherein all symbols represent the same meanings as those described in [1] above.];

[8] The compound represented by the general formula (I-1):

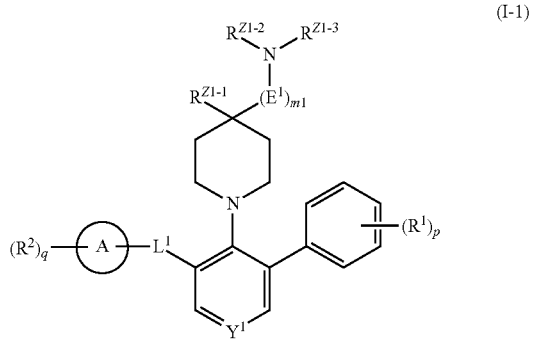

[wherein
Y$^1$ represents N or CH;
L$^1$ represents —C(=O)—NH— or —NH—C(=O)—;
the other symbols represent the same meanings as those described in [1] or [6] above.],
a salt thereof, an N-oxide thereof, a solvate thereof or a prodrug thereof;

[9] The compound described in any one of [1] to [8], wherein Ring A is benzene, benzimidazole, indazole, indole, imidazole, triazole, pyrazole, pyridine, pyrimidine, thiophene, oxazole, thiazole, or oxadiazole;

[10] A pharmaceutical composition which comprises the compound represented by the general formula (I) described in [1], a salt thereof, an N-oxide thereof, a solvate thereof, or a prodrug thereof and a pharmaceutically acceptable excipients;

[11] The pharmaceutical composition described in [10] above, which is a drug for the treatment and/or prevention of a somatostatin-related disease;

[12] The pharmaceutical composition described in [11] above, wherein a somatostatin-related disease is acromegaly, or digestive symptom with gastrointestinal obstruction;

[13] A medicine, which is made in combination of the compound represented by the general formula (I) described in [1] above, a salt thereof, an N-oxide thereof, a solvate thereof, or a prodrug thereof and at least one agent selected from the group consisting of pegvisomant, bromocriptine, and cabergoline.

[14] The medicine, which is made in combination of the compound represented by the general formula (I) described in [1] above, a salt thereof, an N-oxide thereof, a solvate thereof, or a prodrug thereof and at least one drug selected from the group consisting of prochlorperazine, levomepromazine, risperidone, metoclopramide, domperidone, diphenhydramine, chlorpheniramine, dimenhydrinate, promethazine, diprophylline, famotidine, cimetidine, scopolamine, tropisetron, granisetron, ondansetron, azasetron, ramosetron, indisetron, palonosetron, cisapride, mosapride, dexamethasone, betamethasone, prednisolone, aprepitant, olanzapine, quetiapine, perospirone, methylnaltrexone and morphine;

[15] A method for the prevention and/or treatment of the somatostatin-related disease, wherein the method is characterized by administration of therapeutically effective amount of the compound represented by the general formula (I) described in [1] above, a salt thereof, an N-oxide thereof, a solvate thereof, or a prodrug thereof;

[16] The compound represented by the general formula (I) described in [1] above, a salt thereof, an N-oxide thereof, a solvate thereof, or a prodrug thereof, for the prevention and/or treatment of the somatostatin-related disease;

[17] Use of the compound represented by the general formula (I) described in [1] above, a salt thereof, an N-oxide thereof, a solvate thereof, or a prodrug thereof, in the manufacture of a medicine for the prevention and/or treatment for a somatostatin-related disease;

[18] A medicine which comprising a compound represented by the general formula (I) described in [1], a salt thereof, an N-oxide thereof, a solvate thereof, or a prodrug thereof, for the prevention and/or treatment for the somatostatin-related disease;

[19] The medicine described in [13] above, which is for the prevention and/or treatment for acromegaly;

[20] The medicine described in [14] above, which is for the prevention and/or treatment for digestive symptom with gastrointestinal obstruction;

[21] The compound represented by the general formula (I-2):

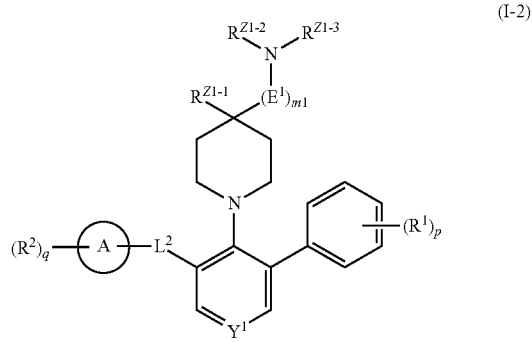

[wherein
L$^2$ represents bond;
the other symbols represent the same meanings as those described in [1], [6] or [8] above.],
a salt thereof, an N-oxide thereof, a solvate thereof or a prodrug thereof;

[22] The compound represented by the general formula (I-3):

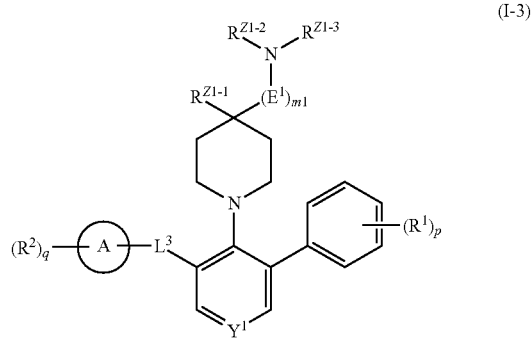

[wherein
L³ represents vinylene (—CH=CH—);
the other symbols represent the same meanings as those described in [1], [6] or [8] above.],
a salt thereof, an N-oxide thereof, a solvate thereof or a prodrug thereof;

[23] The compound described in [4] above, wherein the compound are (1) 1-{3-(3,5-dimethylphenyl)-5-[4-(trifluoromethyl)phenyl]-4-pyridinyl}-4-piperidinamine, (2) 1-{3-(3-fluoro-5-methylphenyl)-5-[4-(trifluoromethyl)phenyl]-4-pyridinyl}-4-piperidinamine, (3) 3-{(E)-2-[4-(4-amino-1-piperidinyl)-5-(3-fluoro-5-methylphenyl)-3-pyridinyl]vinyl}benzonitrile, (4) 4-(4-amino-1-piperidinyl)-N,5-bis(3,5-dimethyphenyl)pyridine-3-carboxamide, (5) 1-[3-(4,6-dimethyl-1H-benzimidazol-2-yl)-5-(3,5-dimethylphenyl)-4-pyridyl]piperidin-4-amine, (6) 1-[3-(4,6-dimethyl-1H-benzimidazol-2-yl)-5-(3,5-dimethyphenyl)-4-pyridinyl]-N-(3-oxetanyl)-4-piperidinamine, (7) 1-[3-(3,5-dimethoxyphenyl)-5-(5,7-dimethyl-1H-benzimidazol-2-yl)-4-pyridinyl]-N-(2-fluoroethyl)-4-piperidinamine, (8) 1-[3-(3-fluoro-5-methoxyphenyl)-5-(1H-indazol-6-yl)-4-pyridinyl]-4-piperidinamine, (9) 5-[4-(4-amino-1-piperidinyl)-5-(3-fluoro-5-methylphenyl)-3-pyridinyl]-2-methylphenol, (10) 1-[3-(5-chloro-1H-benzimidazol-2-yl)-5-(3-fluoro-5-methylphenyl)-4-pyridinyl]-N-(3-oxetanyl)-4-piperidinamine, (11) (3-{4-(4-amino-1-piperidinyl)-5-[4-(trifluoromethyl)phenyl]-3-pyridinyl}-5-fluorophenyl)methanol, or (12) {4-[4-(4-amino-1-piperidinyl)-5-(3-fluoro-5-methylphenyl)-3-pyridinyl]phenyl}acetonitrile;

[24] The compound described in [1] above, wherein the compounds are (1) 5-[(E)-2-{5-(3-fluoro-5-methylphenyl)-4-[rac-(4aR,8aR)-octahydro-6H-pyrido[3,4-b][1,4]oxazin-6-yl]-3-pyridinyl}vinyl]nicotinonitrile, (2) rac-(3R,4S)-4-amino-1-[3-(3,5-dimethoxyphenyl)-5-(4,6-dimethyl-1H-benzimidazol-2-yl)-4-pyridinyl]-3-piperidinol, (3) rac-(3R,4S)-4-amino-1-[3-(6-fluoro-1H-benzimidazol-2-yl)-5-(3-fluoro-5-methoxyphenyl)-4-pyridinyl]-3-piperidinol, or (4) rac-(4aR,8aR)-6-[3-(6-chloro-1H-benzimidazol-2-yl)-5-(3-fluoro-5-methylphenyl)-4-pyridinyl]octahydro-1H-pyrido[3,4-b][1,4]oxazine;

[25] A product comprising (1) the pharmaceutical composition which comprises the compound represented by the general formula (I) described in [1] above, a salt thereof, an N-oxide thereof, a solvate thereof, or a prodrug thereof and pharmaceutical acceptable excipients, (2) a container and (3) a direction, an operating manual, a package insert or a product label, which mentions that said pharmaceutical composition can be used for the prevention and/or treatment for a somatostatin-related disease;

[26] A product comprising (1) the pharmaceutical composition which comprises the compound represented by the general formula (I) described in [1] above, a salt thereof, an N-oxide thereof, a solvate thereof, or a prodrug thereof and pharmaceutical acceptable excipients, (2) a container, and (3) a direction, an operating manual, a package insert or a product label, which mentions that said pharmaceutical composition can be used for the prevention and/or treatment for an acromegaly;

[27] A product comprising (1) the pharmaceutical composition which comprises the compound represented by the general formula (I) described in [1] above, a salt thereof, an N-oxide thereof, a solvate thereof, or a prodrug thereof and pharmaceutical acceptable excipients, (2) a container and (3) a direction, an operating manual, a package insert or a product label, which mentions that said pharmaceutical composition can be used for the prevention and/or treatment for a digestive symptom with gastrointestinal obstruction;

[28] An advertising method of the pharmaceutical composition which comprises the compound represented by the general formula (I) described in [1] above, a salt thereof, an N-oxide thereof, a solvate thereof, or a prodrug thereof and pharmaceutical acceptable excipients, wherein the method includes encouraging intended audiences to use said composition for the prevention and/or treatment for the somatostatin-related disease;

[29] An advertising method of the pharmaceutical composition which comprises the compound represented by the general formula (I) described in [1] above, a salt thereof, an N-oxide thereof, a solvate thereof, or a prodrug thereof and pharmaceutical acceptable excipients, wherein the method includes encouraging intended audiences to use said composition for the prevention and/or treatment for an acromegaly; and

[30] An advertising method of the pharmaceutical composition which comprises the compound represented by the general formula (I) described in [1] above, a salt thereof, an N-oxide thereof, a solvate thereof, or a prodrug thereof and pharmaceutical acceptable excipients, wherein the method includes encouraging intended audiences to use said composition for the prevention and/or treatment for a digestive symptom with gastrointestinal obstruction;

The Effect of the Invention

The compounds represented by the general formula (I) in the invention, a salt thereof, an N-oxide thereof, a solvate thereof or a prodrug thereof (hereinafter, they are occasionally abbreviated to the present invention compounds) are non-peptidic, low-molecular weight compounds with high somatostatin receptor agonist activity, especially somatostatin receptor subtype 2 (SSTR2), need not to be administered by injection like existing peptidic medicines as represented by Octreotide acetate or Lanreotide acetate, which need to be administered by intramuscular injection, and are orally-available so that it can relieve pain with treatments of the patients. Since the present invention compounds have a feature of low-toxicity, the patients with somatostatin-related disease who need administration of it, especially the patients with acromegaly and gastrointestinal obstruction, can use the present invention compounds safely.

THE EMBODIMENTS OF THE PRESENT INVENTION

In the present invention, "halogen" includes, for example, fluorine, chlorine, bromine, and iodine, etc.

In the present invention, "C1-4 alkyl" includes methyl, ethyl, propyl, isopropyl, butyl, sec-butyl, tert-butyl and isobutyl.

In the present invention, "C1-8 alkyl" includes, for example, methyl, ethyl, propyl, isopropyl, butyl, sec-butyl, tert-butyl, isobutyl, pentyl, hexyl, heptyl, octyl and these isomer, etc.

In the present invention, "C1-4 haroalkyl" means "C1-4 alkyl" substituted with "halogen". "C1-4 haroalkyl" includes, for example, fluoromethyl, chloromethyl, bromomethyl, iodomethyl, difluoromethyl, trifluoromethyl, chlorodifluoromethyl, bromodifluoromethyl, dichlorofluoromethyl, 1-fluoroethyl, 2-fluoroethyl, 2-chloroethyl, 2-bromoethyl, 2-iodoethyl, 1,2-difluoroethyl, 2,2-difluoroethyl, 1,2-dichloroethyl, 2,2-dichloroethyl, 2,2,2-trifluoroethyl, 2,2,2-trichloroethyl, pentafluoroethyl, 1-fluoroisopropyl, 2-fluoropropyl, 3-fluoropropyl, 3-chloropropyl, 3-bromopropyl, heptafluoropropyl, 4-fluorobutyl, 4-chlorobutyl, nonafluorobutyl etc, preferably C1-4 alkyl substituted with 1 to 9 halogens and more preferably C1-4 alkyl substituted with 1 to 6 halogens, etc.

In the present invention, "C1-4 alkoxy" includes methoxy, ethoxy, propoxy, isopropoxy, butoxy, sec-butoxy, tert-butoxy and isobutoxy.

In the present invention, "C1-4 acyl" includes formyl, acetyl, propanoyl, N-butanoyl ($CH_3CH_2CH_2C(O)$—) and isobutyryl (($CH_3)_2CHC(O)$—) group.

In the present invention, "C1-2 alkylene" includes, for example, —$CH_2$—, —$(CH_2)_2$—, etc.

In the present invention, "C1-3 alkylene" includes, for example, —$CH_2$—, —$(CH_2)_2$—, —$(CH_2)_3$—, etc.

In the present invention, "C1-4 alkylene" includes, for example, —$CH_2$—, —$(CH_2)_2$—, —$(CH_2)_3$—, —$(CH_2)_4$—, etc.

In the present invention, "C3-8 cycloalkyl" includes cyclopropane, cyclobutane, cyclopentane, cyclohexane, cycloheptane and cyclooctane ring.

In the present invention, "C3-6 monocyclic carbon ring" includes, for example, cyclopropane, cyclobutane, cyclopentane, cyclohexane, cyclopentene, cyclohexene, cyclopentadiene, cyclohexadiene and benzene, etc.

In the present invention, "C5-6 monocyclic carbon ring" includes, for example, cyclopentane, cyclohexane, cyclopentene, cyclohexene, cyclopentadiene, cyclohexadiene and benzene, etc.

In the present invention, "5 to 6 membered monocyclic hetero ring" includes, for example,"5 to 6 membered monocyclic hetero ring including 1 to 4 nitrogens, 1 to 2 oxygens and/or a sulfer", etc. The "5 to 6 membered monocyclic hetero ring including 1 to 4 nitrogens, 1 to 2 oxygens and/or a sulfer" includes, for example, pyrrole, imidazole, triazole, tetrazole, pyrazole, pyridine, pyrazine, pyrimidine, pyridazine, furan, pyran, thiophene, thiopyran, oxazole, isooxazole, thiazole, isothiazole, furazan, oxadiazole, oxazine, oxadiazine, thiadiazole, thiazine, thiadiazine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydrofuran, tetrahydrofuran, dihydropyran, tetrahydropyran, dihydrothiophene, tetrahydrothiophene, dihydrothiopyran, tetrahydrothiopyran, dihydrooxazole, tetrahydrooxazole (oxazolidine), dihydroisooxazole, tetrahydroisooxazole (isooxazolidine), dihydrothiazole, tetrahydrothiazole (thiazolidine), dihydroisothiazole, tetrahydroisothiazole (isothiazolidine), dihydrofurazane, tetrahydrofurazane, dihydrooxadiazole, tetrahydrooxadiazole (oxadiazolidine), dihydrooxazine, tetrahydrooxazine, dihydrooxadiazine, tetrahydrothiazine, dihydrothiadiazine, tetrahydrothiadiazine, morphorine, thiomorphorine, oxathiane, dioxorane, dioxane and dioxol, etc.

In the present invention, "5 to 6 membered monocyclic nitrogen-containing saturated hetero ring" includes, saturated ring including at least one nitrogen and partially unsaturated ring including at least one nitrogen exemplified in said "5 to 6 membered monocyclic hetero ring". Specifically it includes saturated ring as exemplified by pyrrolidine, imidazolidine, triazolidine, tetrazolidine, pyrazolidine, piperidine, piperazine, perhydropyrimidine, perhydropyridazine, tetrahydrooxazole (oxazolidine), tetrahydroisoxazole (isoxazolidine), tetrahydrothiazole (thiazolidine), tetrahydroisothiazole (isothiazolidine), tetrahydrofurazan, tetrahydrooxadiazole (oxadiazolidine), tetrahydrooxazine, tetrahydrooxadiazine, tetrahydrothiadiazole (thiadiazolidine), tetrahydrothiazine, tetrahydrothiadiazine, morpholine, thiomorpholine, etc., and partially unsaturated ring as exemplified by oxazine, oxadiazine, thiazine, thiadiazine, pyrroline, imidazoline, triazoline , tetrazoline, pyrazoline, dihydropyridine, tetrahydropyridine, dihydropyrazine, tetrahydropyrazine, dihydropyrimidine, tetrahydropyrimidine, dihydropyridazine, tetrahydropyridazine, dihydrooxazole, dihydroisoxazole, dihydrothiazole, dihydroisothiazole, dihydrofurazan, dihydrooxadiazole, dihydrooxazine, dihydrooxadiazine, dihydrothiadiazole, dihydrothiazine, dihydrothiadiazine, etc.

In the present invention, "C5-10 monocyclic or bicyclic carbon ring" includes, for example, cyclopentane, cyclohexane, cycloheptane, cyclooctane, cyclononane, cyclodecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indane, naphthalene, dihydronaphthalene, tetrahydronaphthalene, perhydronaphthalene, etc. Said "C5-10 monocyclic or bicyclic carbon ring" also includes "C5-10 polycyclic spiro carbon ring" and "C5-10 cross-linked polycyclic carbon ring", specifically, it includes, for example, spiro[4.4]nonane, spiro[4.5]decane, bicyclo[2.2.1]heptane, bicyclo [2.2.1]hept-2-ene, bicyclo[3.1.1]heptane, bicyclo[3.1.1]hept-2-ene, bicyclo[2.2.2]octane, bicyclo[2.2.2]oct-2-ene, adamantane, noradamantane, etc.

In the present invention, "5 to 10 membered monocyclic or bicyclic hetero ring" includes, for example, "5 to 10 membered monocyclic or bicyclic hetero ring including 1 to 4 nitrogens, 1 to 2 oxygens and/or a sulfur", "5 to 10 membered polycyclic spiro hetero ring including 1 to 4 nitrogens, 1 to 2 oxygens and/or a sulfer" and "5 to 10 membered cross-linked polycyclic hetero ring including 1 to 4 nitrogens, 1 to 2 oxygens and/or a sulfer", etc. Wherein "5 to 10 membered monocyclic or bicyclic hetero ring including 1 to 4 nitrogens, 1 to 2 oxygens and/or a sulfur" includes, for example, pyrrole, imidazole, triazole, tetrazole, pyrazole, pyridine, pyrazine, pyrimidine, pyridazine, azepine, diazepine, furan, pyran, oxepin, thiophene, thiopyran, thiepin, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, pyrroline, pyrrolidine, imidazoline, imidazolidine, triazoline , triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrofuran, tetrahydrofuran, dihydropyran, tetrahydropyran, dihydrooxepin, tetrahydrooxepin, perhydrooxepin, dihydrothiophene, tetrahydrothiophene, dihydrothiopyran, tetrahydrothiopyran, dihydrothiepin, tetrahydrothiepin, perhydrothiepin, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, dioxolane, dioxane, dithiolane, dithiane, indole, isoindole, indolizine, benzofuran, isobenzofuran, benzothiophene, isobenzothiophene, dithianaphthalene, indazole, quinoline, isoquinoline, quinolizine, purine, phthalazine, pteridin, naphthyridine, quinoxaline, quinazoline, cinnoline, benzoxazole, benzothiazole, benzimidazole, chromene, benzofurazan, benzothiadiazole, benzotriazole, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzooxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dioxaindan, benzodioxane, chromane, benzodithiolane, benzodithiane, octahydropyridooxazine, tetrahydrobenzimidazole, benzisoxazole, etc. "5 to 10 membered polycyclic Spiro hetero ring including 1 to 4 nitrogens, 1 to 2 oxygens and/or a sulfer" includes, for example, azaspiro[4.4]nonane, oxazaspiro[4.4]nonane, dioxaspiro[4.4]nonane, azaspiro[4.5]decane, thiaspiro[4.5]decane, dioxaspiro[4.5]decane, oxazaspiro[4.5]decane, etc. "5 to 10 membered cross-linked polycyclic hetero ring including 1 to 4 nitrogens, 1 to 2 oxygens and/or a sulfer" includes, for example, azabicyclo[2.2.1]heptane, oxabicyclo[2.2.1]heptane, azabicyclo[3.1.1]heptane, azabicyclo[3.2.1]octane, oxabicyclo[3.2.1]octane, azabicyclo[2.2.2]octane, diazabicyclo[2.2.2]octane, etc.

In the present invention, "5 to 10 membered monocyclic or bicyclic nitrogen-containing hetero ring" includes the ring including at least one nitrogen exemplified in said "5 to 10 membered monocyclic or bicyclic hetero ring". Specifically, it includes, for example, pyrrole, imidazole, triazole, tetrazole, pyrazole, pyridine, pyrazine, pyrimidine, pyridazine, azepine, diazepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, indole, isoindole, indolizine, indazole, quinoline, isoquinoline, quinolizine, purine, phthalazine, pteridin, naphthyridine, quinoxaline, quinazoline, cinnoline, benzoxazole, benzothiazole, benzimidazole, benzofurazan, benzothiadiazole, benzotriazole, indoline, isoindoline, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, octahydropyridooxazine, tetrahydrobenzimidazole, benzisoxazole, azaspiro[4.4]nonane, oxazaspiro[4.4]nonane, azaspiro[4.5]decane, oxazaspiro[4.5]decane, azabicyclo[2.2.1]heptane, azabicyclo[3.1.1]heptane, azabicyclo[3.2.1]octane, azabicyclo[2.2.2]octane, diazabicyclo[2.2.2]octane, etc.

In the present invention, each ring, group or atom represented by Ring A, Ring B, Ring G, $R^1$, $R^2$, L, M, Z, W and Y are preferred, and the compounds represented by the general formula (I) including combinations thereof are more preferred, and the compounds described in Example are especially preferred. Preferred rings, preferred groups and preferred atoms are exemplified below, wherein all symbols represent the same meanings as those described above.

In the present invention, as $R^1$, for example, halogen, C1-4 alkyl, C1-4 alkyl substituted by halogens, C1-4 alkoxy, cyclopropyl, etc. are preferably exemplified, and fluorine, chlorine, methyl, trifluoromethyl, methoxy, etc. are more preferred. And hydroxy and hydroxymethyl are also preferred. Especially preferable $R_1$ is, for example, fluorine and methyl, etc.

In the present invention, as Ring G, for example, benzene, pyridine, pyrimidine, pyrazole, thiazole, cyclopropane, quinoline, furan, etc. are preferably exemplified. Benzene, pyrazole, cyclopropane, etc. are more preferred, and especially preferable Ring G is benzene, etc.

In the present invention, as $R^2$, for example, halogen, C1-4 alkyl, C1-4 alkyl substituted by halogen, C1-4 alkoxy, C1-4 alkoxy substituted by halogen, acetoxy, acetyl, oxo, hydroxyl, hydroxymethyl, dimethylamino, carbamoyl (—C(O)NH$_2$), methylamide (MeNHC(O)—), acetylamino (MeC(O)NH—), methoxycarbonyl (MeOC(O)—), cyanomethyl (—CH$_2$CN), cyano, pyrazolyl, oxadiazolyl, etc. are preferably exemplified. More preferred $R^2$ is, for example, fluorine, chlorine, methyl, difluoromethyl, trifluoromethyl, ethyl, methoxy, difluoromethoxy, ethoxy, acetoxy, acetyl, oxo, hydroxyl, dimethylamino, cyano, etc. Further preferable $R^2$ is fluorine, chlorine, methyl, trifluoromethyl, methoxy, hydroxyl, dimethylamino, cyano, etc. Especially preferable $R^2$ is, for example, methyl, trifluoromethyl, cyano, etc.

In the present invention, as Ring A, for example, benzene, cyclohexene, benzimidazole, benzoxazole, benzothiazole, indoline, isoindoline, tetrahydroquinazoline, quinazoline, indazole, indole, dihydrobenzoxazine, benzisoxazole and 5 to 6 membered monocyclic aromatic hetero ring including 1 to 3 nitrogens, an oxygen and/or a sulfur, etc., wherein "5 to 6 membered monocyclic aromatic heterocycle including 1 to 3 nitrogens, an oxygen and/or a sulfur" includes, for example, pyrrole, imidazole, triazole, pyrazole, pyridine, pyrazine, pyrimidine, pyridazine, furan, thiophene, oxazole, isoxazole, thiazole, isothiazole, furazan, oxadiazole, and thiadiazole, etc. More preferable Ring A is, for example, benzene, benzimidazole, indazole, indole, imidazole, triazole, pyrazole, pyridine, pyrimidine, thiophene, oxazole, thiazole, and oxadiazole, etc. and especially preferable Ring A is, for example, benzene, etc. Also, when L represents bond, benzene, pyridine, pyrimidine, benzimidazole, benzoxazole, benzothiazole, indazole, and indole, etc. are preferable as ring A, and benzene, pyridine, benzimidazole, and indazole, etc. are more preferable. Furthermore, when L represents vinylene (—CH=CH—), benzene and pyridine ring, etc. are preferable as Ring A.

In the present invention, Ring B preferably represents, for example, benzene when W and Y represent carbon and r represents 1, or pyrazole and pyridine, etc. when at least one of W and Y represents nitrogen and r represents 0 or 1. Specifically, preferable structure of general formula (I) includes Ring B represented by the general formula (a):

[20]

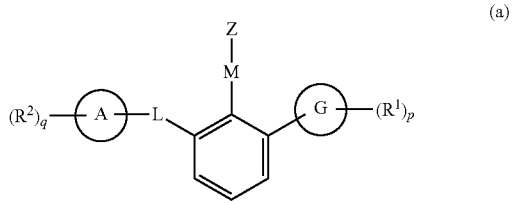

(a)

[wherein all symbols represent the same meanings as those described above], the general formula (b):

[21]

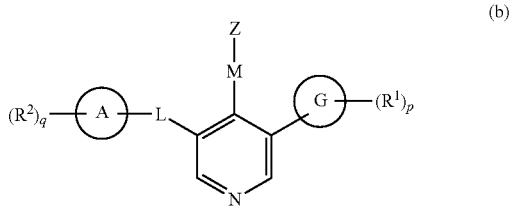

(b)

[wherein all symbols represent the same meanings as those described above], or the general formula (c):

[22]

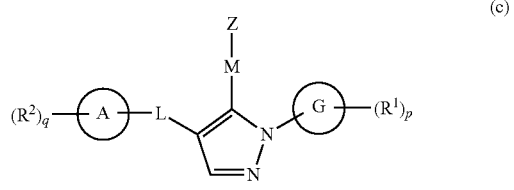

(c)

[wherein all symbols represent the same meanings as those described above].

In the present invention, as L, for example, (1) —CR$^{21}$=CR$^{22}$→, (2) —O—, (3) —C(=O)—, (4) —NR$^{41}$—, (5) —C(=O)—NR$^{42}$→, (6) —NR$^{43}$—C(=O)→, (7) —CR$^{25}$R$^{26}$—C(=O)→, (8) —CR$^{25}$R$^{26}$—NR$^{41}$→, (9) —CR$^{25}$R$^{26}$—C(=O)—NR$^{42}$→, (10) —CR$^{25}$R$^{26}$—NR$^{43}$—C(=O)→, (11) —NR$^{41}$—O—CR$^{29}$R$^{30}$→, (12) —C(=O)—NR$^{42}$—O—CR$^{29}$R$^{30}$→, (13) —NR$^{43}$—C(=O)—O—CR$^{29}$R$^{30}$→, (14) —O—CR$^{31}$R$^{32}$—C(=O)→, (15) —O—CR$^{31}$R$^{32}$—NR$^{41}$→, (16) —O—CR$^{31}$R$^{32}$—C(=O)—NR$^{42}$→, (17) —O—CR$^{31}$R$^{32}$—NR$^{43}$—C(=O)→, (18) —CR$^{33}$R$^{34}$—O—C(=O)→, (19) —CR$^{33}$R$^{34}$—O—NR$^{41}$→, (20) —CR$^{33}$R$^{34}$—O—C(=O)—NR$^{42}$→, or (21) —CR$^{33}$R$^{34}$—O—NR$^{43}$—C(=O)→, etc., are preferably exemplified. More preferable L is, for example, —C(=O)—NR$^{42}$→, —NR$^{43}$—C(=O)→, —CR$^{21}$=CR$^{22}$→, etc. Especially preferable L is, for example, —C(=O)—NH—, —NH—C(=O)—, etc. In addition, —CH=CH— is also especially preferable. Additionally, bond is also preferable. When L represents bond, -M-Z is preferably the structure represented by (MZ1). And as other preferable embodiments, -M-Z is preferably the structure represented by (MZ3), (MZ4), (MZ5), (MZ6), (MZ7), (MZ8), or (MZ9) when L represents bond. In addition, as other preferable embodiments, -M-Z is preferably the structure represented by (MZ1) when L represents —CH=CH—. Regarding L, when binding site of "—C(=O)—NH—" or "—NH—C(=O)—" with Ring B are not identified by allow, binding site with Ring B may be either site. That is, both represent the same meanings as "—C(=O)—NH→" and "—NH—C(=O)→".

In the present invention, as M, for example, bond, —C(=O)—, —O—(CH$_2$)$_3$—, —(CH$_2$)$_3$—O—, —(CH$_2$)$_2$—O—CH$_2$—, —CH$_2$—O—(CH$_2$)$_2$—, etc. are preferably exemplified. Especially preferable M is, for example, bond, etc.

In the present invention, as Z, for example, —NR$^{51}$R$^{52}$ and piperidine which may be substituted with the substituents selected from the group consisting of (a) halogen, (b) —NR$^{53}$R$^{54}$, (c) —OR$^{55}$, (d) C1-4 alkyl which may be substituted with —NR$^{56}$R$^{57}$ and/or —OR$^{58}$ and (e) oxo, etc. are preferably exemplified.

Especially when Z represents —NR$^{51}$R$^{52}$, either R$^{51}$ or R$^{52}$ is preferably C1-8 alkyl which may be substituted with (a) —NR$^{61}$R$^{62}$. Especially, C1-8 alkyl which may be substituted with —NH$_2$ is preferred.

In addition, when Z represents "a piperidine which may be substituted with the substituents selected from the group consisting of (a) halogen, (b) —NR$^{53}$R$^{54}$, (c) —OR$^{55}$, (d) C1-4 alkyl which may be substituted with —NR$^{56}$R$^{57}$ and/or —OR$^{58}$, and (e) oxo", the piperidine which substituted with C1-4 alkyl which may be substituted with (b) —NR$^{53}$R$^{54}$ or (d) —NR$^{56}$R$^{57}$ and/or —OR$^{58}$ is preferred. Among them, the piperidine wherein either R$^{53}$ or R$^{54}$, or either R$^{56}$ or R$^{57}$ is methyl, ethyl, 2-fluoroethyl, 2,2-difluoromethyl, oxolanyl, or oxetanyl is preferred. And the piperidine which substituted with —NH$_2$ or C1-4 alkyl which substituted with —NH$_2$ is preferred.

And also, as other preferable Z, for example, octahydropyridooxazine, etc. are exemplified.

Some of preferable Z can be represented by specific example below. For example,

[23]

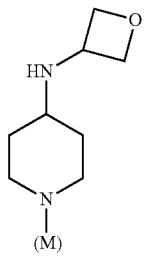

[wherein (M) represents binding position with M.],

[24]

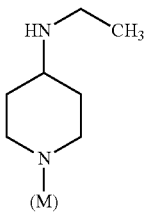

[wherein (M) represents binding position with M.],

[25]

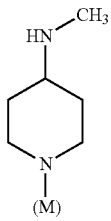

[wherein (M) represents binding position with M.],

[26]

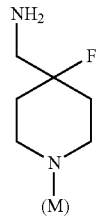

[wherein (M) represents binding position with M.],

[27]

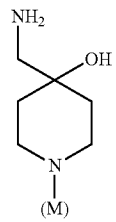

[wherein (M) represents binding position with M.],

[28]

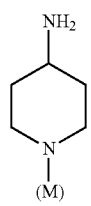

[wherein (M) represents binding position with M.],

[29]

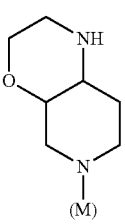

[wherein (M) represents binding position with M.], or

[30]

[wherein (M) represents binding position with M.], etc. are preferred.

In the present invention, the substituent represented by -M-Z is preferably the substituent wherein one of the $4^{th}$ to $7^{th}$ atoms through the shortest path from the $1^{st}$ atom, which bind to Ring B, is nitrogen. Kinds of the other atoms do not matter. An example of the way of counting is shown below, for example, when -M-Z is the formula described below:

[31]

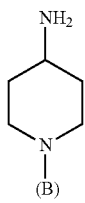

[wherein (B) represents binding position with Ring B], the nitrogen of the amino group which bind to the 4$^{th}$ carbon of piperidine is "the 5$^{th}$ atom through the shortest path from the 1$^{st}$ atom, which bind to Ring B". In addition, for example, when -M-Z is the formula described below:

[32]

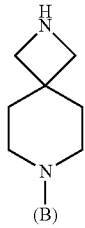

[wherein (B) represents binding position with Ring B] the nitrogen in the 4 membered ring, where the spiro atom is the 4$^{th}$ carbon of piperidine, is "the 6$^{th}$ atom through the shortest path from the 1$^{st}$ atom, which bind to Ring B".

Moreover, the preferable structure of the group represented by -M-Z may be represented by the formula of (MZ1), (MZ2), (MZ3), (MZ4), (MZ5), (MZ6), (MZ7), (MZ8),or (MZ9). Among them, the structure represented by formula (MZ1) is preferable, the compound represented by the general formula (I-1) including the formula (MZ1) in its structure:

[33]

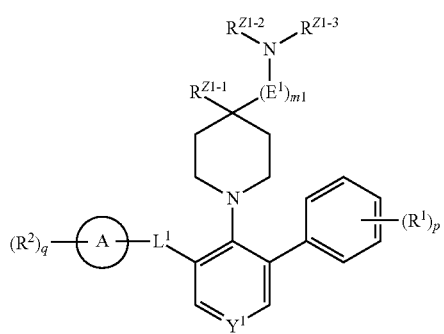

[wherein all symbols represent the same meanings as those described above.], the compounds represented by the general formula (I-2):

[34]

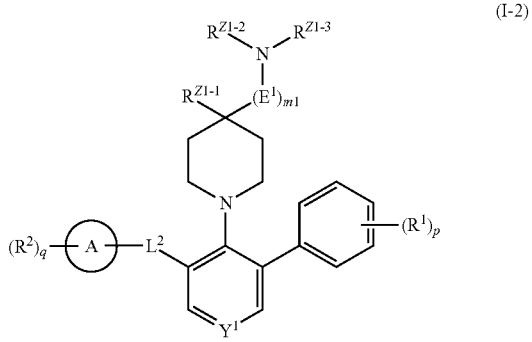

[wherein all symbols represent the same meanings as those described above.], or the compounds represented by the general formula (I-3):

[35]

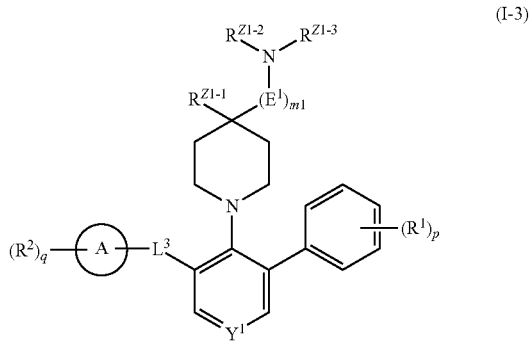

[wherein all symbols represent the same meanings as those described above.] may be exemplified as preferable embodiments in the present invention. The compounds represented by the general formula (I-2) and the general formula (I-3) described above are exemplified as more preferable embodiments, especially preferable embodiment is the compound represented by the general formula (I-2) above.

Especially, as the general formula (I-1), the general formula (I-2) or the general formula (I-3), the compounds wherein both R$^{Z1-2}$ and R$^{Z1-3}$ are hydrogen, or one of them is substituted by methyl, ethyl or oxetanyl, the compounds wherein R$^{Z1-1}$ represents hydrogen, fluorine or hydroxyl and the compounds wherein m1 represents 0 or 1, etc. are preferred.

In addition, in the present invention, unless it is declined in particular, as will be apparent to those skilled in the art,

[36]

the symbol ∕ represents binding to the reverse side (that is, α-configuration),

[37]

the symbol ∕ represents binding to the front side (that is, β-configuration), and

[38]

The symbol ╱ represents α-configuration, β-configuration or a mixture of them in any proportion. There is no particular limitation for the ratio of α-configuration and β-configuration in the mixture.

[Isomers]

Unless otherwise specifically mentioned, all isomers are included in the present invention. For example, alkyl, alkoxy and alkylene, etc. may include straight or branched chain. Moreover, all isomers due to double bond, ring and fused ring (E-, Z-, cis- and trans-forms), isomers due to the presence of asymmetric carbon(s), etc. (R-, S-, α- and β-configuration, enantiomer and diastereomer), optically active substances having optical rotation (D-, L-, d- and l-forms), polar compounds by chromatographic separation (more polar compounds and less polar compounds), equilibrium compounds, rotational isomers, a mixture thereof in any proportion and a racemic mixture are included in the present invention. Besides, all tautomers are included in the present invention.

Moreover, there are cases when compounds name include "rac" in the description. This is known method which means the compounds are rasemate. (For example, see Pure and Applied Chemistry,1996, vlo.68, 12, p.2193-2222 (especially, p.2216)).

[A Salt, an N-oxide, a Solvate]

A salt of the compound of formula (I) includes all pharmaceutically acceptable salts. With regard to the pharmaceutically acceptable salts, those which are low-toxicity and soluble in water are preferred. Examples of appropriate salts are salt with alkaline metal (such as potassium, sodium and lithium), salt with alkaline earth metal (such as calcium and magnesium), ammonium salt (such as tetramethylammonium salt and tetrabutylammonium salt), salt with organic amine (such as alkyl amine [e.g., methylamine, dimethylamine, trimethylamine, triethylamine, etc.], heterocyclic amine [e.g., pyridine, picoline, piperidine, etc.], alkanolamine [e.g., monoethanolamine, diethanolamine, triethanolamine, etc.], cyclopentylamine, cyclohexylamine, dicyclohexylamine, benzylamine, dibenzylamine, phenethylamine, N,N'-didibenzylethylenediamine, tris(hydroxymethyl)methylamine, N-methyl-D-glucamine, basic natural amino acid [e.g., arginine, lysine, ornithine, histidine, etc.]) and acid addition salt (such as inorganic acid salt (e.g., hydrochloride, hydrobromide, hydroiodide, sulfate, phosphate and nitrate) and organic acid salt (e.g., acetate, trifluoroacetate, lactate, tartrate, oxalate, fumarate, maleate, benzoate, citrate, methanesulfonate, ethanesulfonate, benzene sulfonate, toluene sulfonate, isethionate, glucuronic acid salt, gluconate), etc.), salt with acidic natural amino acid (e.g., aspartate, glutamate, etc.)).

The salt also includes a quaternary ammonium salt. The quaternary ammonium salt is the compound where the nitrogen of the compounds represented by formula (I) is quarternalized by $R^0$. Wherein $R^0$ is C1-8 alkyl which may be substituted with, for example, phenyl.).

The N-oxide of the compounds represented by the general formula (I) is the compound where nitrogen of the compound represented by formula (I) is oxidized. The N-oxide of the compounds represented by the general formula (I) may form a salt like as salt with alkali metals, salt with alkaline earth metals, ammonium salt, salt with organic amine, acid addition salt described above.

The compounds represented by the general formula (I), a salt thereof, or an N-oxide thereof may form a solvate with, for example, water or alcoholic solvent (such as ethanol, etc.) The solvate is preferably low-toxic and water-soluble.

The compounds represented by the general formula (I) can be converted into a salt thereof, an N-oxide thereof and a solvate thereof described above by known methods.

[Prodrug]

A prodrug of the compound represented by the formula (I) means a compound which is converted to the compound represented by the formula (I) by reaction with an enzyme, gastric acid or the like in the living body. Examples of prodrugs of the compounds represented by the formula (I) are, when the compound represented by the formula (I) has an amino group, compounds in which the amino group is, for example, acylated, alkylated or phosphorylated (e.g., compounds in which the amino group of the compound of formula (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, acetoxymethylated, tert-butylated, etc.); when the compound represented by the formula (I) has a hydroxyl group, compounds in which the hydroxyl group is, for example, acylated, alkylated, phosphorylated or borated (e.g., compounds in which the hydroxyl group of the compound represented by the formula (I) is acetylated, palmitoylated, propanoylated, pivaloylated, succinylated, fumarylated, alanylated or dimethylaminomethylcarbonylated); and when the compound represented by the formula (I) has a carboxyl group, compounds in which the carboxyl group is, for example, esterified or amidated (e.g., compounds in which the carboxyl group of the compound of formula (I) is made into ethyl ester, phenyl ester, carboxymethyl ester, dimethylaminomethyl ester, pivaloyloxymethyl ester, phthalidyl ester, 1-{(ethoxycarbonyl) oxy} ethyl ester, (5-methyl-2-oxo-1,3-dioxolen -4-yl)methyl ester, 1-{[(cyclohexyl oxy)carbonyl] oxy} ethyl ester or methyl amide).

A prodrug represented by the the compound represented by the general formula (I) may also be a compound which is converted to the compound represented by the general formula (I) under physiological conditions as described in "Iyakuhin no kaihatsu, Vol.7 (Bunshi-sekkei), pp. 163-198 (Hirokawa-Shoten), 1990", and may also be labeled by isotopes (such as $^2H$, $^3H$, $^{13}C$, $^{14}C$, $^{15}N$, $^{16}N$, $^{17}O$, $^{18}O$, $^{35}S$, $^{36}Cl$, $^{77}Br$, $^{125}I$, etc.). Those compounds represented by the general formula (I) may be produced by a known method per se. Furthermore, the prodrug of the compound represented by the general formula (I) may form, as with the compounds represented by the general formula (I), for example, a salt of alkaline metal, a salt of alkaline-earth metal, a ammonium salt, a salt of organic amine and a acid addition salt set forth above, and a solvate with water or alcoholic solvents, etc. (e.g., ethanol, etc.).

And, the each atom composing the compounds represented by the general formula (I) are not limited as above, but may be substituted by isotopes (e.g., $^2H$, $^3H$, $^{13}C$, $^{14}C$, $^{15}N$, $^{16}N$, $^{17}O$, $^{18}O$, $^{35}S$, $^{36}Cl$, $^{77}Br$, $^{125}I$, etc.)

[Method for Preparation]

The compound represented by the formula (I), a salt thereof, an N-oxide thereof, a solvate thereof or a prodrug thereof may be prepared by known methods, for example, a method described in following [A1] to [A6] or [B1], the method according to these methods, the methods described in the examples, the method according to these examples, or methods described in Comprehensive Organic Transformations: A Guide to Functional Group Preparations, 2nd Edition (Richard C. Larock, John Wiley & Sons Inc, 1999), etc., which are appropriately modified and combined, but the methods are not limited thereof. Salts of the starting materials may be used in following each method for preparation. Such salt includes the salt of the compounds represented by the general formula (I) set forth above.

[A1]

Among the present invention compounds represented by the general formula (I), the compounds wherein L includes amide bond, that is, the compounds represented by the general formula (IA1a):

[39]

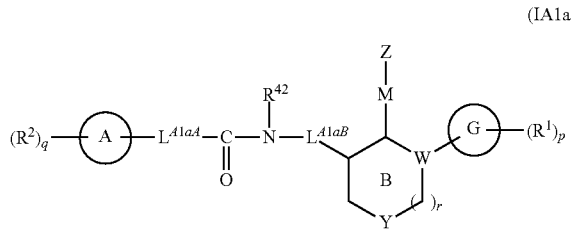
(IA1a)

(wherein $L^{A1aA}$ represents bond, $-CR^{25}R^{26}-$, $-O-CR^{31}R^{32}-$, or $-CR^{33}R^{34}-O-$, $L^{A1aB}$ represents bond, $-CR^{23}R^{24}-$, $-CR^{27}R^{28}-O-$, or $-O-CR^{29}R^{30}-$, all other symbols represent the same meanings as those above.), or the compounds represented by the general formula (IA1b):

[40]

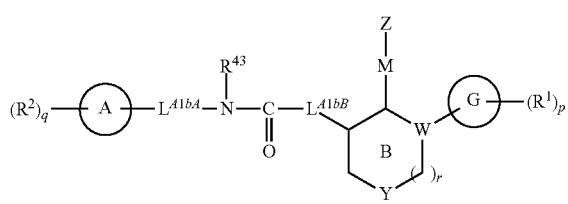
(IA1b)

(wherein $L^{A1bA}$ represents bond, $-CR^{25}R^{26}-$, $-O-CR^{31}R^{32}-$, or $-CR^{33}R^{34}-O-$, $L^{A1bB}$ represents bond, $-CR^{23}R^{24}-$, $-CR^{27}R^{28}-O-$, or $-O-CR^{29}R^{30}-$, all other symbols represent the same meanings as those above.) can be prepared by the amidation reaction of the compounds represented by the general formula (IA1a-1):

[41]

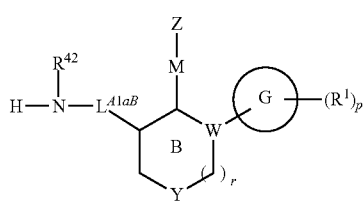
(IA1a-1)

(wherein all symbols represent the same meanings as those above.) with the compounds represented by the general formula (IA1a-2):

[42]

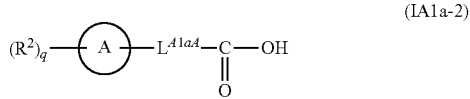
(IA1a-2)

(wherein all symbols represent the same meanings as those above.) or the compounds represented by the general formula (IA1b-1):

[43]

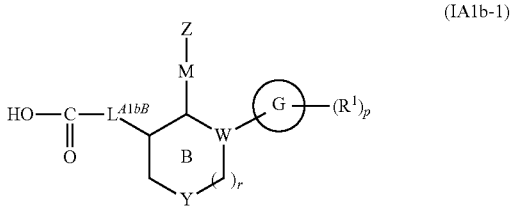
(IA1b-1)

(wherein all symbols represent the same meanings as those above.) with the compounds represented by the general formula (IA1b-2):

[44]

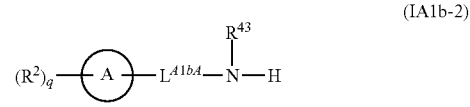
(IA1b-2)

(wherein all symbols represent the same meanings as those above.). Bisides, protection and/or deprotection reaction of the functional groups may be carried out, if needed.

The amidation reaction is well known, for example,
(1) A reaction procedure with use of an acid halide,
(2) A reaction procedure with use of a mixed acid anhydride, and
(3) A reaction procedure with use of a condensing agent. etc. are known.

To explain these methods in detail,
(1) The reaction procedure employing an acid halide is conducted in practice, for example, by reacting a carboxylic acid with an acid halogenating agent (e.g., oxalyl chloride, thionyl chloride, etc.) in an organic solvent (e.g., chloroform, dichloromethane, diethyl ether, tetrahydrofuran, or a solvent mixture thereof, etc.) at a temperature from −20° C. to the refluxing temperature, followed by the reaction of the resultant acid halide with an amine in an organic solvent (e.g., chloroform, dichloromethane, diethyl ether, tetrahydrofuran, or a solvent mixture thereof, etc.) in the presence of a base (e.g., pyridine, triethylamine, dimethylaniline, dimethylaminopyridine, diisopropylethylamine, etc.) at a temperature of 0 to 40° C. Alternatively, the procedure can be carried out by reacting the resultant acid halide with an amine in an organic solvent (e.g., dioxane, tetrahydrofuran, or a solvent mixture thereof, etc.) at a temperature of 0 to 40° C., using an aqueous alkali solution (e.g., an aqueous sodium bicarbonate or sodium hydroxide solution, etc.).

(2) The reaction procedure employing a mixed acid anhydride is conducted in practice, for example, by reacting a carboxylic acid with an acid halide (pivaloyl chloride, tosyl chloride, mesyl chloride, etc.) or an acid derivative (e.g., ethyl chloroformate, isobutyl chloroformate, etc.) in an organic solvent (e.g., chloroform, dichloromethane, diethyl ether, tetrahydrofuran, or a solvent mixture thereof, etc.) or solvent free in the presence of base (e.g., pyridine, triethylamine, dimethylaniline, dimethylaminopyridine, diisopropylethylamine, etc.) at a temperature of 0 to 40° C., followed by reaction of the resultant mixed acid anhydride with an amine in an organic solvent (e.g., chloroform, dichloroethane, diethyl ether, tetrahydrofuran, or a solvent mixture thereof, etc.) at a temperature of 0 to 40° C.

(3) The reaction procedure with use of a condensing agent is carried out, for example, by reacting a carboxylic acid with an amine in an organic solvent (e.g., chloroform, dichloromethane, dimethylformamide, diethyl ether, tetrahydrofuran, or a solvent mixture thereof, etc.) or solvent-free in the presence or absence of a base (e.g., pyridine, triethylamine, dimethylaniline, dimethylaminopyridine, etc.), with use of a condensing agent (e.g., 1,3-dicyclohexylcarbodiimide (DCC), 1-ethyl-3-[3-(dimethylamino)propyl]carbodiimide (EDC), 1,1'-carbonyldiimidazole (CDI), 2-chloro-1-methylpyridinium iodide, 1-propylphosphonic acid cyclic anhydride (1-propanephosphonic acid cyclic anhydride, PPA), (benzotriazol-1-yloxy) tris(dimethylamino)phosphonium hexafluorophosphate (BOP), (benzotriazol-1-yloxy) tripyrrolidinophosphonium hexafluorophosphate (pyBOP), etc.) and with or without use of 1-hydroxybenztriazole (HOBt), at a temperature of 0 to 40° C.

These reactions of (1), (2), and (3) are preferably carried out under inert gas (argon, nitrogen, etc.) and anhydrous condition.

As is easily understood by those skilled in the art, when the present invention compound represented by the general formula (IA1a) or (IA1b) and starting material represented by the general formula (IA1a-1), (IA1a-2) and (IA1b-2) have hydroxy, carboxy, amino or mercapto group, after these functional groups are protected adequately, the amidation reaction is carried out and followed by deprotection of the protective groups to obtain the target compound of the present invention.

A protective group for hydroxy includes, for example, methyl, trityl, methoxymethyl (MOM), 1-ethoxyethyl (EE), methoxyethoxymethyl (MEM), 2-tetrahydropyranyl (THP), trimethylsilyl (TMS), triethylsilyl (TES), tert-butyldimethylsilyl (TBDMS), tert-butyidiphenylsilyl (TBDPS), acetyl (Ac), pivaloyl, benzoyl, benzyl (Bn), p-methoxybenzyl, allyloxycarbonyl (Alloc) or 2,2,2-trichloroethoxycarbonyl (Troc), etc.

A protective group for carboxy includes, for example, methyl, ethyl, tert-butyl, allyl, phenacyl, benzyl, etc.

A protective group for amino includes, for example, benzyloxycarbonyl, tert-butoxycarbonyl, allyloxycarbonyl (Alloc), 1-methyl-1-(4-biphenyl)ethoxycarbonyl (Bpoc), trifluoroacetyl, 9-fluorenylmethoxycarbonyl, benzyl (Bn), p-methoxybenzyl, benzyloxymethyl (BOM), 2-(trimethylsilyl)ethoxymethyl (SEM), 2-nitrobenzenesulfonyl, etc.

A protective group for mercapto includes, for example, benzyl, methoxybenzyl, methoxymethyl (MOM), 2-tetrahydropyranyl (THP), diphenylmethyl, acetyl (Ac), etc.

Protective groups for hydroxy, carboxy, amino or mercapto group are not limited to those described above, but include groups which are easily and selectively deprotected. For example, those groups described in [Protective Groups in Organic Synthesis, (T. W. Greene, John Wiley & Sons Inc, 1999)] can be used.

The deprotection reacion of the protective groups of hydroxy, carboxy, amino or mercapto group is well-known and includes, for example,
(1) a deprotection reaction by alkali hydrolysis,
(2) a deprotection under acidic conditions,
(3) a deprotection reaction by hydrogenolysis,
(4) a deprotection reaction using a metal complex,
(5) a deprotection reaction using a metal,
(6) a deprotection reaction of silyl group,etc.

To explain these methods in detail:

(1) The deprotection reaction by alkali hydrolysis (e.g., deprotection reaction of trifluoroacetyl group etc.) is carried out, for example, in an organic solvent (methanol, tetrahydrofuran, 1,4-dioxane or a solvent mixture thereof, etc.) using a hydroxide of alkali metals (sodium hydroxide, potassium hydroxide, lithium hydroxide, etc.), hydroxide of alkaline earth metals (barium hydroxide, calcium hydroxide, etc.), carbonate (sodium carbonate, potassium carbonate, etc.), a solution thereof or a mixture thereof at a temperature of 0 to 40° C.

(2) The deprotection reaction under acidic conditions (e.g., deprotection reaction of t-butoxycarbonyl, trityl group, etc.) is carried out, for example, in water or an organic solvent (dichloromethane, chloroform, 1,4-dioxane, ethyl acetate, anisole, or a solvent mixture thereof, etc.), in an organic acid (acetic acid, trifluoroacetic acid, methanesulfonic acid, etc.) or an inorganic acid (hydrochloric acid, sulfuric acid, etc.) or a mixture thereof (hydrobromic acid/acetic acid, etc.) at a temperature of 0 to 100° C.

(3) The deprotection reaction by hydrogenolysis (e.g., deprotection reaction of benzyl, benzhydryl, benzyloxycarbonyl, allyloxycarbonyl group, etc.) is, for example, carried out in a solvent (e.g. ethers (such as tetrahydrofuran, 1,4-dioxane, dimethoxyethane, diethyl ether, etc.), alcohols (such as methanol, ethanol, etc.), benzenes (such as benzene, toluene, etc.), ketones (such as acetone, methylethylketone, etc.), nitriles (such as acetonitrile, etc.), amides (such as N,N-dimethylformamide, etc.), water, ethyl acetate, acetic acid or a solvent mixture thereof, etc.) in the presence of a catalyst (palladium-carbon, palladium black, palladium hydroxide, platinum oxide, Raney nickel, etc.) under an atmosphere of hydrogen at normal or increased pressure, or in the presence of ammonium formate at a temperature of 0 to 200° C.

(4) The deprotection reaction using a metal complex (e.g., deprotection reaction of allyloxycarbonyl group, etc.) is carried out, for example, in an organic solvent (dichloromethane, N,N-dimethylformamide, tetrahydrofuran, ethyl acetate, acetonitrile, 1,4-dioxane, ethanol, etc.), water or a mixture thereof, in the presence of a trapping reagent (tributyltin hydride, triethylsilane, dimedone, morpholine, diethylamine, pyrrolidine, etc.), an organic acid (acetic acid, formic acid, 2-ethylhexanecarboxylic acid, etc.) and/or a salt of an organic acid (sodium 2-ethylhexanoate, potassium 2-ethylhexanoate, etc.) in the presence or absence of a phosphine reagent (triphenylphosphine, etc.) using a metal complex (tetrakis(triphenylphosphine)palladium (0), bis(triphenylphosphine) palladium(II) dichloride, palladium(II) acetate, rhodium(I) tris(triphenylphosphine) chloride, etc.) at a temperature of 0 to 40° C.

(5) The deprotection reaction using a metal is carried out, for example, in an acidic solvent (acetic acid, a buffer of pH 4.2 to 7.2 or a mixture of the solution thereof and an organic solvent such as tetrahydrofuran, etc.) in the presence of zinc powder at a temperature of 0 to 40° C. optionally under sonication.

(6) The deprotection reaction of a silyl group is, for example, carried out in a water-miscible organic solvent (tetrahydrofuran, acetonitrile, a solvent mixture thereof, etc.) using tetrabutylammonium fluoride at a temperature of 0 to 40° C.

As is easily understood by those skilled in the art, the target compound of the present invention may be prepared easily by selecting these deprotection reactions.

Furthermore, secondary to this reaction, a operation to convert into objective salt may be carried out by known methods.

[A2]

Among the present invention compounds represented by the general formula (I), the compounds where L includes oxygen which abuts on carbon, that is, the compounds represented by the general formula (IA2a):

[45]

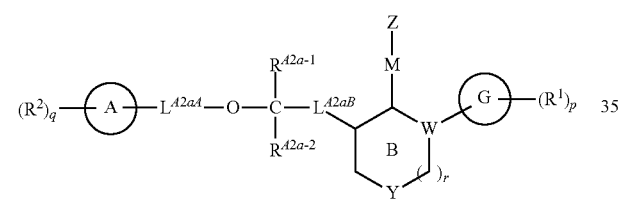

(IA2a)

(wherein $L^{A2aA}$ and $L^{A2aB}$ represent independently bond, —O—, —C(=O)—, —C(=O)—NR$^{42}$—, —NR$^{41}$—, or —NR$^{43}$—C(=O)—, $R^{A2a-1}$ and $R^{A2a-2}$ represent independently hydrogen or C1-4 alkyl, all other symbols represent the same meanings as those above.) or the compounds represented by the general formula (IA2b):

[46]

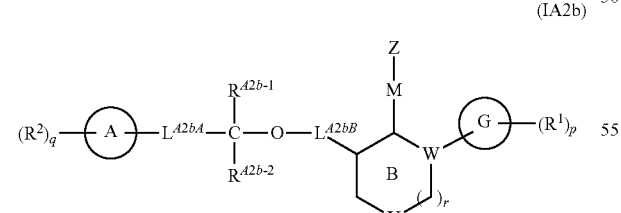

(IA2b)

(wherein $L^{A2bA}$ and $L^{A2bB}$ represent independently bond, —O—, —C(=O)—, —C(=O)—NR$^{42}$—, —NR$^{41}$—, or —NR$^{43}$—C(=O)—, $R^{A2b-1}$ and $R^{A2b-2}$ represent independently hydrogen or C1-4 alkyl, all other symbols represent the same meanings as those above.) are prepared by Mitsunobu reaction of the compounds represented by the general formula (IA2a-1):

[47]

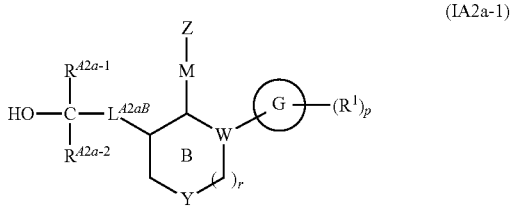

(IA2a-1)

(wherein all symbols represent the same meanings as those above.) with the compounds represented by the general formula (IA2a-2):

[48]

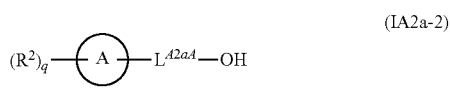

(IA2a-2)

(wherein all symbols represent the same meanings as those above.) or the compounds represented by the general formula (IA2b-1):

[49]

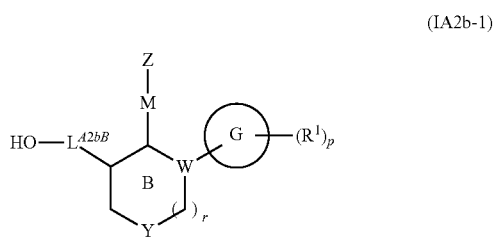

(IA2b-1)

(wherein all symbols represent the same meanings as those above.) with the compounds represented by the general formula (IA2b-2):

[50]

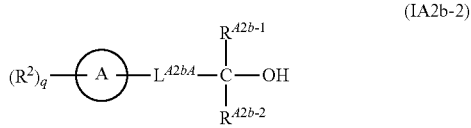

(IA2b-2)

(wherein all symbols represent the same meanings as those above.). At which time, protection and/or deprotection reaction of the functional groups described above may be carried out if needed.

Additionally, the compounds represented by the general formula (IA2a) described above are prepared by the substitution reaction of the compounds represented by the general formula (IA2a-3):

[51]

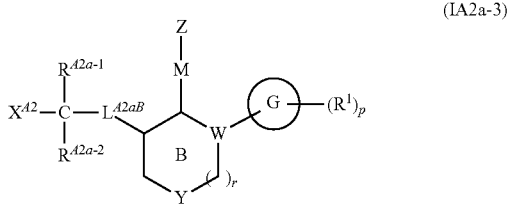
(IA2a-3)

(wherein $X^{A2}$ represents halogen, tosyl, mesyl, all the other symbols represent the same meanings as those described above.) with the compounds represented by the general formula (IA2a-2) described above, or the compounds represented by the general formula (IA2a-1) described above with the compounds represented by the general formula (IA2a-4):

[52]

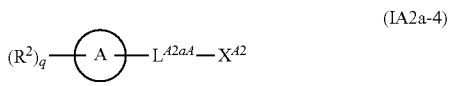
(IA2a-4)

(wherein all symbols represent the same meanings as those described above.).

And also the compounds represented by the general formula (IA2b) described above can be prepared by the substitution reaction of the compounds represented by the general formula (IA2b-3):

[53]

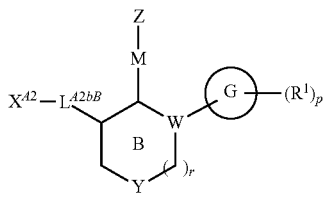
(IA2b-3)

(wherein all symbols represent the same meanings as those described above.) with the compounds represented by the general formula (IA2b-2) described above, or the compounds represented by the general formula (IA2b-1) with the compounds represented by the general formula (IA2b-4):

[54]

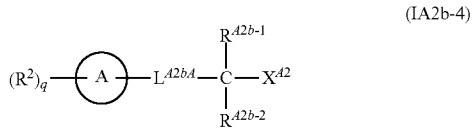
(IA2b-4)

(wherein all symbols represent the same meanings as those described above.). At which time, protection and/or deprotection reaction of the functional groups described above may be carried out if needed.

Mitsunobu reaction is well known, for example, the reaction can be carried out, for example, in an organic solvent (dichloromethane, diethyl ether, tetrahydrofuran, acetonitrile, benzene, toluene or a solvent mixture thereof, etc.), in presence of an azo compound (e.g., azodicarboxylic acid diethyl ester (DEAD), azodicarboxylic acid diisopropyl ester, 1,1'-(azodicarbonyl)dipiperidine, 1,1'-azobis(N,N-dimethyformamide), etc.) and phosphine compound (e.g., triphenylphosphine, tributylphosphine, trimethylphosphine, polymer supported triphenylphosphine, etc.), using a corresponding alcohol compound at a temperature of 0 to 60° C.

An etherification reaction by substitution is well known, for example, the reaction can be carried out in an organic solvent (e.g., dimethylformamide, dimethylsulfoxide, chloroform, dichloromethane, diethyl ether, tetrahydrofuran, methyl t-butyl ether or a solvent mixture thereof, etc.), in the presence of a hydroxide of alkali metals (sodium hydroxide, potassium hydroxide, lithium hydroxide, etc.), hydroxide of alkaline earth metals (barium hydroxide, calcium hydroxide, etc.), carbonate (sodium carbonate, potassium carbonate, etc.) or a solution thereof or a mixture thereof at a temperature of 0 to 100° C.

Furthermore, protection and/or deprotection reaction of the functional groups can be carried out by the same methods described above.

[A3]

Among the present invention compounds represented by the general formula (I), the compounds where L includes carbonyl group which abuts on carbon, that is, the compounds represented by the general formula (IA3a):

[55]

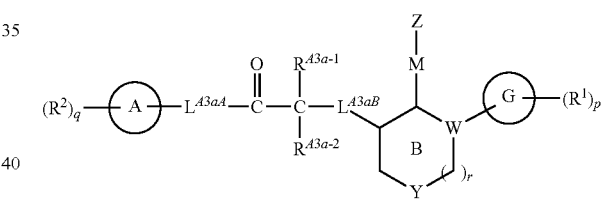
(IA3a)

(wherein $L^{A3aA}$ represents bond or —NR$^{43}$—, $L^{A3aB}$ represents bond or —O—, $R^{A3a-1}$ and $R^{A3a-2}$ represent independently hydrogen or C1-4 alkyl, all the other symbols represent the same meanings as those above.), or the compounds represented by the general formula (IA3b):

[56]

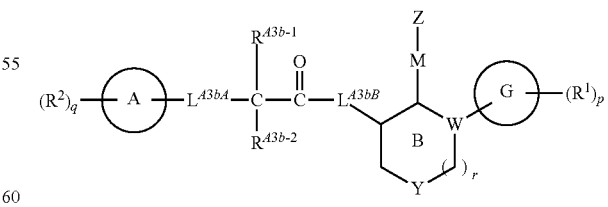
(IA3b)

(wherein $L^{A3bA}$ represents bond or —O—, $L^{A3bB}$ represents bond or —NR$^{42}$—, $R^{A3b-1}$ and $R^{A3b-2}$ represent independently hydrogen or C1-4 alkyl, all the other symbols represent the same meanings as those above.), can be prepared by the reaction of the compounds represented by the general formula (IA3a-1):

[57]

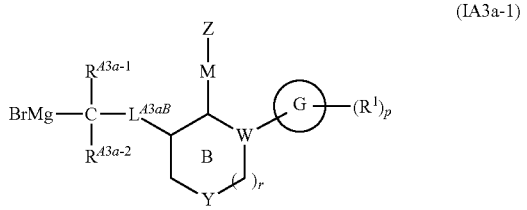
(IA3a-1)

(wherein all symbols represent the same meanings as those above.) with the compounds represented by the general formula (IA3a-2):

[58]

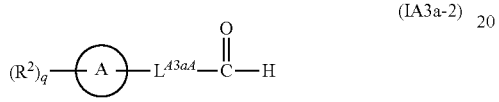
(IA3a-2)

(wherein all symbols represent the same meanings as those above.), or the compounds represented by the general formula (IA3b-1):

[59]

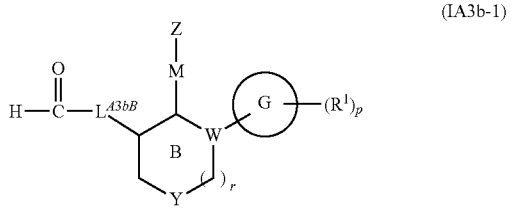
(IA3b-1)

(wherein all symbols represent the same meanings as those above.) with the compounds represented by the general formula (IA3b-2):

[60]

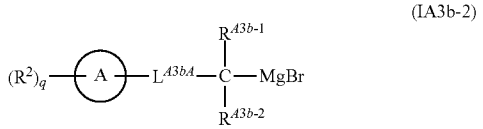
(IA3b-2)

(wherein all symbols represent the same meanings as those above.) to obtain alcohol compounds and followed by the oxidation reaction.

At which time, protection and/or deprotection reaction of the functional groups described above may be carried out if needed.

A reaction to prepare alcohol is well known and can be carried out, for example, in an organic solvent (e.g., tetrahydrofuran, diethyl ether, dichloromethane, toluene, benzene or a solvent mixture thereof, etc.) at a temperature of −100° C. to refluxing temperature. Also, the compounds represented by the general formula (IA3a-1) or the compounds represented by the general formula (IA3b-2) are well known or can be easily prepared by the reaction of a corresponding starting material with Grignard reagent (methylmagnesium bromide, isopropylmagnesium bromide, phenylmagnesium bromide, butyllithium, phenyllithium, etc.) or alkyllithium reagent (butyllithium, sec-butyllithium, tert-butyllithium, etc.).

Furthermore, oxidation reaction is well known and includes, for example, (1) A reaction procedure with use of Swern oxidation, (2) A reaction procedure with use of Dess-Martin reagent, (3) A reaction procedure with use of TEMPO reagent, etc.

To explain these methods in detail:

(1) The reaction procedure employing Swern oxidation can be conducted in practice, for example, in an organic solvent (e.g., chloroform, dichloromethane or a solvent mixture thereof, etc.), oxalyl chloride is reacted with dimethyl sulfoxide at −78° C. followed by resultant solution is reacted subsequently with alcohol compound and tertiary amine (e.g., triethylamine, N,N-diisopropylethylamine, N-methylmorpholine, N-ethylpiperidine, diazabicyclo[5.4.0]undec-7-ene, etc.) at −78 to 20° C.

(2) The reaction procedure employing Dess-Martin reagent can be conducted in practice, for example, in an organic solvent (e.g., chloroform, dichloromethane, 1,2-dichloroethane, tetrahydrofuran, acetonitrile, t-butylalcohol or a solvent mixture thereof, etc.), in the presence of Dess-Martin reagent (1,1,1-Triacetoxy-1,1-dihydro-1,2-benziodoxol-3(1H)-one), in the presence or absence of a base (e.g., pyridine, etc.) at 0 to 40° C.

(3) The reaction procedure employing TEMPO reagent can be conducted in practice, for example, in an organic solvent (e.g., chloroform, dichloromethane, tetrahydrofuran, toluene, acetonitrile, ethyl acetate, etc.), water or a solvent mixture thereof, using TEMPO reagent (2,2,6,6-tetramethylpiperidine 1-oxyl) and reoxidants (e.g., hydrogen peroxide solution, sodium hypochlorite, 3-chloroperoxybenzoic acid, iodobenzene diacetate, potassium peroxymonosulfate (Oxone®), etc.) in the presence or absence of quarternary ammonium salt (e.g., tetrabutyl ammonium chloride, tetrabutyl ammonium bromide, etc.), in the presence or absence of a mineral salt (e.g., sodium bromide, potassium bromide, etc.), in the presence or absence of inorganic base (e.g., sodium bicarbonate, sodium acetate, etc.), at 20 to 60° C.

Oxidation reaction is not limited to those described above, but includes reactions where alcohol is easily and selectively oxidized to ketone. For example, Jones oxidation, the oxidation by PCC, the oxidation by sulfur trioxide pyridine complex and those reaction described in Comprehensive Organic Transformations (Richard C. Larock, VCH Publishers Inc., 1989, p.604-614).

Furthermore, protection and/or deprotection reaction of the functional groups can be carried out by the same methods described above.

[A4]

Among the present invention compounds represented by the general formula (I), the compounds where L includes nitrogen which abuts on a carbon (the carbon have at least one hydrogen), that is, the compounds represented by the general formula (IA4a):

[61]

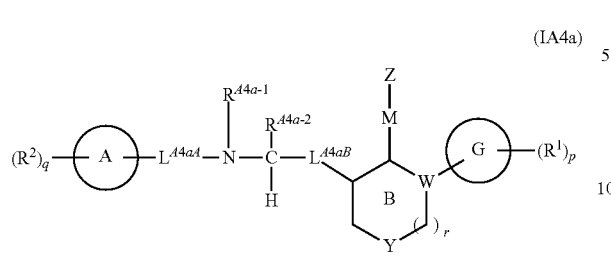

(IA4a)

(wherein $L^{A4aA}$ represents bond or —C(=O)—, $L^{A4aB}$ represents bond or —O—, $R^{A4a-1}$ and $R^{A4a-2}$ represent independently hydrogen or C1-4 alkyl, all the other symbols represent the same meanings as those described above.), or the compounds represented by the general formula (IA4b):

[62]

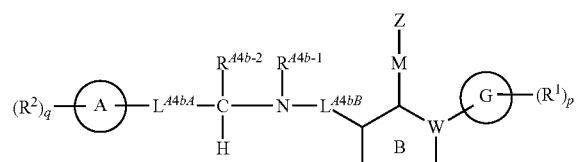

(IA4b)

(wherein $L^{A4bA}$ represents bond or —O—, $L^{A4bB}$ represents bond or —C(=O)—, $R^{A4b1}$ and $R^{A4b-2}$ represent independently hydrogen or C1-4 alkyl, all the other symbols represent the same meanings as those described above.) are prepared by reductive amination of the compounds represented by the general formula (IA4a-1):

[63]

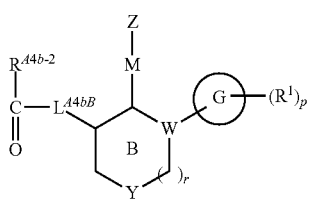

(IA4a-1)

(wherein all symbols represent the same meanings as those described above.) with the compounds represented by the general formula (IA4a-2):

[64]

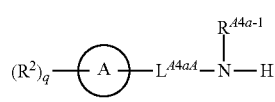

(IA4a-2)

(wherein all symbols represent the same meanings as those described above.) or the general formula (IA4b-1):

[65]

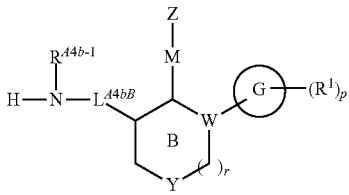

(IA4b-1)

(wherein all symbols represent the same meanings as those described above.) with the compounds represented by the general formula (IA4b-2):

[66]

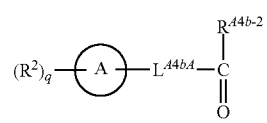

(IA4b-2)

(wherein all symbols represent the same meanings as those described above.). At which time, protection and/or deprotection reaction of the functional groups can be carried out by the same methods described above if needed.

Specifically, the compounds where $R^{A4a-2}$ represents hydrogen among the compounds represented by the general formula (IA4a) and the compounds where $R^{A4b-2}$ represents hydrogen among the compounds represented by the general formula (IA4b) are prepared by the reductive amination of the corresponding starting material using the following method (1), and the compounds where $R^{A4a-2}$ represents C1-4 alkyl among the compounds represented by the general formula (IA4a), and the compounds where $R^{A4b-2}$ represents C1-4 alkyl among the compounds represented by the general formula (IA4b) are prepared by the reductive amination of the corresponding starting material using the following method (2).

(1) The reductive amination is well known, resultant imine may be reduced after separation, or the imine may be reduced without separation (one-pot reaction). The production reaction of imine is well known and can be carried out, for example, in organic solvent (e.g., methanol, ethanol, dichloromethane, chloroform, dichloroethane, benzene, toluene or a solvent mixture thereof etc.), in the presence or non-presence of a dehydrating agent (e.g., anhydrous magnesium sulfate and molecular sieve (a trade name), etc.), in the presence or non-presence of a acid (e.g., hydrochloric acid, acetic acid, etc.), at a temperature of 20 to refluxing temperature. The reductive reaction of imine is also well known and can be carried out, for example, in an organic solvent (e.g., tetrahydrofuran, diethyl ether, dichloroethane, dichloromethane, dimethylformamide, acetic acid, methanol, ethanol or a solvent mixture thereof, etc.), in the presence of a reductant (e.g., sodium triacetoxyborohydride, sodium cyanoborohydride, sodium borohydride, zinc borohydride, diisobutylaluminiumhydride, etc.) at 0 to 40° C., or in a solvent (e.g., ethers (e.g., tetrahydrofuran, dioxane, dimethoxyethane, diethyl ether, etc.), alcohols (e.g., methanol, ethanol, etc.), benzenes (e.g., benzene, toluene, etc.), ketones (e.g., acetone, methylethylketone, etc.), nitriles (e.g., acetonitrile, etc.), amides (e.g., dimethylformamide, etc.), water, ethyl acetate, acetic acid, or a solvent mixture thereof.), in the presence of a catalyst (e.g., palladium carbon, palladium black, palladium hydroxide, platinum oxide, Raney nickel, etc.) under an atmosphere of hydrogen at normal or increased pressure, at 0 to 200° C. Moreover, the reductive amination of a imine without separation is well known and can be carried out, for example, in an organic solvent (dichloroethane, dichloromethane, dimethylformamide, acetic acid or a solvent mixture thereof, etc.), in the presence of a reductant (sodium triacetoxyborohydride, sodium cyanoborohydride, sodium borohydride, etc.) at 0 to 40° C.

(2) This reductive amination is well known and can be carried out, for example, in an organic solvent (e.g., dichloroethane, dichloromethane or a solvent mixture thereof, etc.) in the presence of a tertiary amine (e.g., triethylamine, diisopropylethylamine, etc.), using Lewis acid (e.t., titanium tetrachloride, etc.) at 0 to 40° C., after that, in the presence of a reductant (e.g., triacetoxyborohydride, sodium cyanoborohydride, etc.) at 0 to 40° C.

Furthermore, protection and/or deprotection reaction of the functional groups can be carried out by the same methods described above.

[A5]

Among the present invention compounds represented by the general formula (I), the compounds where L represents bond, that is, the compounds represented by the general formula (IA5):

[67]

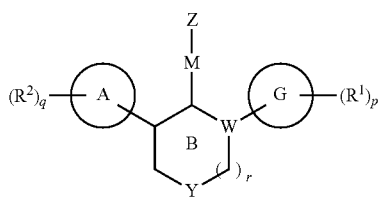
(IA5)

(wherein all symbols represents the same meanings as those described above.) are prepared by the reaction of the compounds represented by the general formula (IA5-1)

[68]

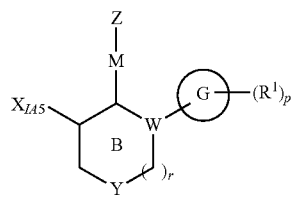
(IA5-1)

(wherein $X_{IA5}$ represents bromine or iodine, the other symbols represent the same meanings as those described above.) with the compounds represented by the general formula (IA5-2):

[69]

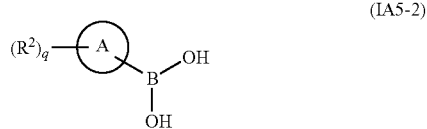
(IA5-2)

(wherein all symbols represents the same meanings as those described above.), or the compounds represented by the general formula (IA5-3):

[70]

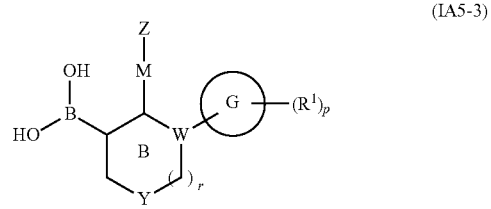
(IA5-3)

(wherein all symbols represents the same meanings as those described above.) with the compounds represented by the general formula (IA5-4):

[71]

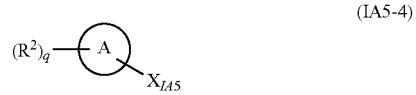
(IA5-4)

(wherein $X_{IA5}$ represents bromine or iodine, the other symbols represent the same meanings as those described above.).

At which time, protection and/or deprotection reaction of the functional groups can be carried out by the same methods described above.

This reaction is well known and can be carried out, for example, in an organic solvent (e.g., benzene, toluene, dimethylformamide, dioxane, tetrahydrofuran, methanol, acetonitrile, dimethoxyethane, acetone or a solvent mixture thereof, etc.), in the presence of a base (e.g., sodium ethylate, sodium hydroxide, potassium hydroxide, triethylamine, sodium carbonate, sodium hydrogen carbonate, potassium carbonate, cesium carbonate, thallium carbonate, tripotassium phosphate, cesium fluoride, barium hydroxide, tetrabutylammonium fluoride, etc.), a solution thereof, or a mixture thereof and a catalyst (e.g., bis(di-tert-butyl(4-dimethyaminophenyl)phosphine)dichloropalladium(II) ((A-ta-Phos)$_2$PdCl$_2$), tetrakis(triphenylphosphine)palladium (Pd (PPh$_3$)$_4$), bis(triphenylphosphne)palladium dichloride (PdCl$_2$(PPh$_3$)$_2$), palladium acetate (Pd(OAc)$_2$), palladium black, 1,1'-bis(diphenylphosphino)ferrocene)dichloropalladium (PdCl$_2$(dppf)$_2$), allylpalladium chloride dimer (PdCl$_2$(allyl)$_2$), iodo(phenyl)bis(triphenylphosphine)palladium(II) (PhPdI(PPh$_3$)$_2$), etc.), at room temperature to 120° C.

Furthermore, protection and/or deprotection reaction of the functional groups can be carried out by the same methods described above.

[A6]

Among the present invention compounds represented by the general formula (I), the compounds where L represents vinylene (—CH=CH—), that is, the compounds represented by the general formula (IA6):

[72]

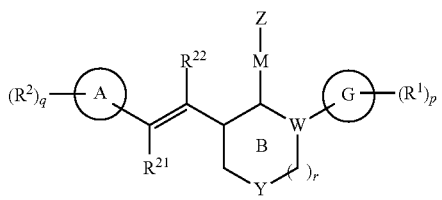
(IA6)

(wherein all symbols represents the same meanings as those described above.) can be prepared by the reaction of the compounds represented by the general formula (IA6-1):

[73]

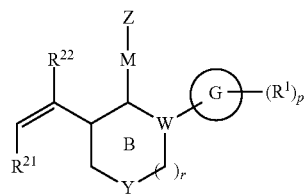
(IA6-1)

(wherein all symbols represents the same meanings as those described above.) with the compounds represented by the general formula (IA6-2)

[74]

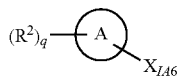
(IA6-2)

(wherein $X_{IA6}$ represents bromine or iodine, the other symbols represent the same meanings as those described above.), or the compounds represented by the general formula (IA6-3)

[75]

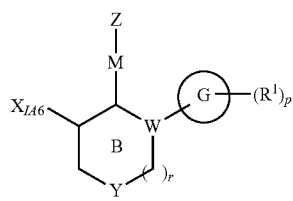
(IA6-3)

(wherein $X_{IA6}$ represents bromine or iodine, the other symbols represent the same meanings as those described above.) with the compounds represented by the general formula (IA6-4)

[76]

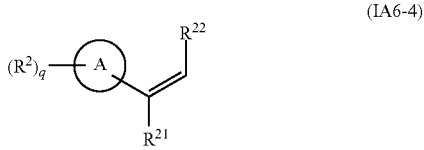
(IA6-4)

(wherein all symbols represents the same meanings as those described above.). At which time, protection and/or deprotection reaction of the functional groups can be carried out by the same methods described above, if needed.

This reaction is well known and can be carried out, for example, in an organic solvent (e.g., dioxane, toluene, dimethylacetamide, dimethylformamide, dimethyl sulfoxide, nitromethane, methanol, ethanol, acetonitrile or a solvent mixture thereof, etc.) or a mixture of an organic solvent and water, in the presence of base (e.g., dicyclohexyl(methyl)amine, tripotassium phosphate, potassium carbonate, sodium carbonate, silver carbonate, calcium carbonate, sodium hydrogen carbonate, potassium hydrogen carbonate, triethylamine, tributylamine, sodium acetate, cesium carbonate, potassium tert-butoxide, sodium tert-butoxide, lithium hydroxide, etc.), a aqueous solution thereof or a mixture thereof, in the presence of a catalyst (e.g., tetrakis (triphenylphosphine)palladium (Pd(PPh$_3$)$_4$), bis(tri-tert-butylphosphine)palladium(0) (Pd(tBu$_3$P)$_2$), palladium, palladium acetate (Pd(OAc)$_2$), tris(dibenzylidineacetone) dipalladium(0) (Pd(dba)$_2$), dichloro(1,2-bis (diphenylphosphino)ethane)palladium(II) (PdCl$_2$(dppe)), palladium dichloride (PdCl$_2$), allylpalladium chloride dimer (PdCl$_2$(allyl)$_2$), copper acetate (Cu(OAc)$_2$), tributylphosphine (PBu$_3$), triphenylphosphine (PPh$_3$), tri-o-tolyl phosphine (P(o-tolyl)$_3$) or mixture thereof, at room temperature to 160° C.

Furthermore, protection and/or deprotection reaction of the functional groups can be carried out by the same methods described above.

[B1]

The compounds represented by the general formula (I) can be prepared by the reaction of the compounds represented by the general formula (IB1-1):

[77]

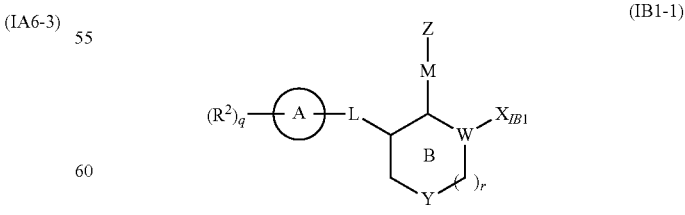
(IB1-1)

(wherein $X_{IB1}$ represents bromine or iodine, the other symbols represent the same meanings as those described above.) and the compounds represented by the general formula (IB1-2):

[78]

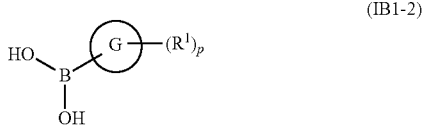

(IB1-2)

(wherein all symbols represents the same meanings as those described above.), or the compounds represented by the general formula (IB1-3):

[79]

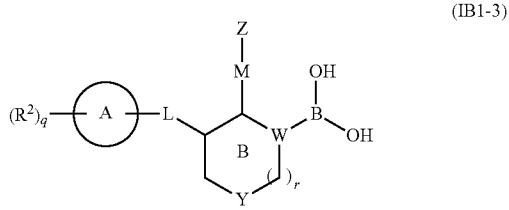

(IB1-3)

(wherein all symbols represents the same meanings as those described above.) and the compounds represented by the general formula (IB1-4):

[80]

(IB1-4)

(wherein $X_{IB1}$ represents bromine or iodine, the other symbols represent the same meanings as those described above.).

Furthermore, protection and/or deprotection reaction of the functional groups can be carried out by the same methods described above, if needed.

The reaction can be carried out by the same methods described in [A5] above.

Furthermore, protection and/or deprotection reaction of the functional groups can be carried out by the same methods described above.

The reaction products described in [A1] to [A6] and [B1], or the products, where protective groups are deprotected, have hydroxyl group, the hydroxyl group is converted to amino group by reductive reaction after azidation or by conversion to nosylamino group followed by denosylation.

Azidation is well-known and can be carried out in a solvent which is inert for the reaction (e.g., halogenated hydrocarbons, non-proton type polar solvents, ethers, aromatic hydrocarbons or a solvent mixture thereof), in the presence of acid catalyst (e.g., trichloroacetic acid, trifluoroacetic acid, boron trifluoride diethyl ether complex, etc.), in some cases an acid is used as a solvent, at −45° C. to reflux temperature, preferably at 0° C. to room temperature, using azidation reagent (e.g., sodium azide, lithium azide, trimethylsilylazide, etc.), generally stirred for 0.1 to 5 hours.

Reductive reaction is well-known and can be carried out in a solvent which is inert for the reaction (e.g., alcohols, ethers, ethyl acetate or a mixture of these and water), at 0° C. to reflux temperature, preferably at room temperature, using phosphine compound (e.g., triphenylphosphine, tributylphosphine, etc.) generally stirred for 1 to 24 hours. And, the reductive reaction can be carried out in a solvent which is inert for the reaction, at 0° C. to reflux temperature, preferably at room temperature, in the presence of catalyst for catalytic reduction (e.g. Palladium on carbon, Raney nickel, Platinum oxide, etc.) and a hydrogen source (e.g., hydrogen under normal or increased pressure, ammonium formate, etc.), generally stirred for 1 to 24 hours. In addition, the reductive reaction can be carried out using ethers or aromatic hydrocarbons as solvent, at 0° C. to reflux temperature, preferably at room temperature, using a reductant like lithium aluminium hydride.

Conversion of a hydroxyl group to a nosylamino group is well-known and can be carried out by the same methods as Mitsunobu reaction described in [A2] above.

Denosylation can be carried out by the same methods as deprotection of said functional group.

When the reaction products described in [A1] to [A6] and [B1], or the products where protective groups have been deprotected as necessary have hydroxy group, the hydroxyl group is converted to oxo group by oxidation. And the oxo group can be converted to non-substituted or any substituted amino group by reductive amination.

Oxidation can be carried out by the same methods as the reaction described in [A3] above.

Reductive amination can be carried out by the same methods as the reaction described in [A4] above.

When the reaction products described in [A1] to [A6] and [B1], or the products where protective groups is deprotected as necessary have amino or carboxy group, the amino or carboxy group are converted to non-substituted or any substituted amide group by amidation.

Amidation can be carried out by the same methods as the reaction described in [A1] above.

The optically active compounds among the present invention compounds can be prepared by using optically active starting material or reagent, optical resolution of racemic intermediate followed by leading to the present invention compounds, or by optical resolution of the racemic present invention compounds.

Optical resolution methods are well-known and include, for example, the methods to separate objective compounds after formation of salt or complex, etc. with other optical active compounds and recrystallization, or the methods to separate them directly by chiral column, etc.

The compounds represented by the general formula (IA1a-1), (IA1a-2), (IA1b-1), (IA1b-2), (IA2a-1), (IA2a-2), (IA2a-3), (IA2a-4), (IA2b-1), (IA2b-2), (IA2b-3), (IA2b-4), (IA3a-1), (IA3a-2), (IA3b-1), (IA3b-2), (IA4a-1), (IA4a-2), (IA4b-1), (IA4b-2), (IA5-1), (IA5-2), (IA5-3), (IA5-4), (IA6-1), (IA6-2), (IA6-3), (IA6-4), (IB1-1), (IB1-2), (IB1-3) or (IB1-4) using as starting material are well-known in itself, or can be prepared easily by the known methods, for example, the methods described in Comprehensive Organic Transformations: A Guide to Functional Group Preparations, 2nd Edition (Richard C. Larock, John Wiley & Sons Inc., 1999), which may be combined.

In each reaction exemplified in the specification, the reactions with heating may be carried out by any heating technique like a water bath, an oil bath, a sand bath, or microwave, etc.

In each reaction exemplified in the specification, a solid phase reagent may be used which is supported by a macromolecular polymer (for example, polystyrene, polyacrylamide, polypropylene or polyethyleneglycol, etc.).

The products of each reaction exemplified in the specification may be purified by conventional techniques, for example, by distillation at atmospheric or reduced pressure, by various chromatography (e.g., high performance liquid chromatography, thin layer chromatography or column chromatography) using silica gel, ion-exchange resin, scavenger resin or magnesium silicate, by washing, trituration or recrystallization. The purification may be carried out after each reaction stage or after several reaction stages.

[Toxicity]

The toxicity of the present invention compounds is low and therefore it may be considered safe for pharmaceutical use.

Test methods to evaluate the toxicity of the present invention compounds include, for example, assay of phospholipidosis inducibility using cultivated cell line. Drug-induced phospholipidosis (PLD) is a reaction which is characterized by accumulation of phospholipid in a cell and formation of layered and membranous inclusion in lysosome and a cause for concern at the regulatory authority (*Expert Opinion on Drug Safety*, 2006, vol.5, 4, p567-583). For example, the phospholipidosis inducibility of the present invention compounds can be evaluated by using the methods described below.

(Evaluation of the Phospholipidosis Inducibility Using Cultivated Cell Line)

A Chinese hamster CHL/IU cells isolated from the lung are suspended in MEM-E medium including non-essential amino acids, pyruvate sodium, and 10% fetal bovine serum, and are seeded on 96-well plates. The cells are incubated overnight in the incubator (5% carbon dioxide, 95% air, 37° C.) and its medium is replaced with a medium including test compounds (0, 6.25, 12.5, 25, 50, or 100×10$^{-6}$ mol/L) and NBD-PE (fluorescent labelled N-(7-nitrobenz-2-oxa-1,3-diazol-4-yl)-1,2-dihexadecanoyl-sn-glycero-3-phosphoethanolamine triethylammonium salt) purchased from Molecular Probes, and incubated for 24 hours. The phospholipidosis inducibility can be evaluated by measuring the concentration of NBD-PE taken in the cell. Specifically, after washing the cell by PBS twice, fluorescence of NBD-PE (exciting wavelength: 485 nm, fluorescence wavelength: 535 nm) taken in the cell is measured by Molecular device's SpectraMax plate reader. Furthermore, after measurement of fluorescence of NBD-PE, cell survival rate is evaluated by Premix WST-1 Cell Proliferation Assay System purchased from TAKARA BIO INC. As judgment of whether or not the compounds have the phospholipidosis inducibility, the compounds with more than 25% of maximal response of amiodarone, which is a positive control, are judged as positive.

[Application to Pharmaceutical Products]

The present invention compounds have somatostatin receptor agonist activity and can be used as a medicine to prevent and/or treat diseases of mammal, especially human related to somatostatin (diseases related to somatostatin itself or hormone regulated by somatostatin).

These diseases include, for example, hormonal disease (e.g. acromegaly, somatomegaly, pituitary gigantism, Cushing's disease, Graves' disease, hyperthyroidism, etc.), ateliosis (e.g. skeletal dysplasia, Noonan syndrome, adiposity, ateliosis with the obesity, uterine hypoplasia, renal failure with ateliosis, syndrome X, etc.), cancer or adenoma (e.g. leukemia, chondrosarcoma, melanoma, lipoma, meningioma, neuroblastoma, hypophyseal adenoma, headache with hypophyseal adenoma, growth hormone-producing adenoma, growth hormone releasing factor-producing adenoma, gonadotropin-producing adenoma, prolactin-producing adenoma, thyroid-stimulating hormone-producing adenoma, VIP-producing adenoma, ACTH-producing adenoma, thyroid cancer, thyroidal medulla cancer, lung cancer, breast cancer, liver cancer, nerve endocrine gland tumor of the stomach, intestines and pancreas, gastrin-producing tumor, carcinoid syndrome, colorectal cancer, pancreatic cancer, insuloma, insulin-producing tumor, glucagonoma, prostate cancer, cancerous cachexia, vessel tumor of colon, etc.), gastrointestinal disease (e.g. digestive symptom with gastrointestinal obstruction, gastroesophageal reflux, gastroduodenal reflux, excessive gastric acid secretion, peptic ulcer, Zollinger Ellison's syndrome, protein-losing gastroenteropathy, dumping syndrome, short small intestine syndrome, inflammatory bowel disease, crohn disease, irritable bowel syndrome, irritable colon syndrome, enterocutaneous fistula, functional dyspepsia, feeling like vomiting, vomiting, sense of abdomen distension, etc.), diarrhea (e.g. aqueous diarrhea syndrome, chronic secondary diarrhea, chemotherapy-induced diarrhea, intractable diarrhea with the acquired immunodeficiency syndrome, diarrhea with the irritable bowel syndrome, postoperative diarrhea, etc.), vascular disease (e.g. proliferative retinopathy, bleeding of the stomach and intestines, bleeding with the gastroduodenal ulcer, bleeding of the esophagus varix, varix bleeding of the cirrhosis patient, portal hypertension, bleeding of the transplant blood vessel, restenosis, scarring of the wound, psoriasis, systemic sclerosis (scleroderma), chronic rejection of the isograft, hypotension, atherosclerosis, restenosis after the PTCA, hypertrophic cardiomyopathy, arteriosclerosis, cardiac valvulopathy, myocardial infarction, etc.), fibrosis (e.g. skin fibrosis, central nervous system fibrosis, nose fibrosis, pulmonary fibrosis, liver fibrosis, kidney fibrosis, chemotherapy-induced fibrosis, etc.), diabetes and diabetic complication (e.g. diabetes, insulin-dependent diabetes, diabetic retinopathy, diabetic nephropathy, diabetic neuropathy, dawn phenomenon, insulin unresponsiveness, hyperinsulinemia, hyperlipidemia, etc.), inflammatory disease (e.g. arthritis, rheumatoid arthritis, psoriasis, local inflammation, sunburn, rash, etc.), central nervous system disease (e.g. dementia, alzheimer's disease, epilepsy, etc.), respiratory disease (e.g. sleep apnea syndrome, etc.), pancreatic disease (e.g. pancreatitis, acute pancreatitis, chronic pancreatitis, pancreas skin fistula, pancreas pseudocyst, ascite, pancreatic fistula, symptom with the pancreatic surgery, etc.), hepatic disease (e.g. cyst of the liver, etc.), renal disease (e.g. hepatorenal syndrome, cystic kidney, nephropathy, etc.), ovarian disease (e.g. polycystic ovary syndrome, etc.), bone and joint disease (e.g. osteoporosis, degenerative arthritis, etc.), pain, headache, etc. Moreover, the present invention compounds installed radioactive element (e.g. $^{123}$I, $^{125}$I, $^{111}$In, etc.) directly or through an appropriate spacer can be used as an imaging agent for tumors with somatostatin receptor. And also, the present invention compounds installed an anticancer drug directly or through an appropriate spacer can be used to target tumors with somatostatin receptor.

Of these, the present invention compounds are useful for the prevention and/or treatment for acromegaly, somatomegaly, pituitary gigantism, pituitary adenoma, headache with pituitary adenoma, growth hormone-producing adenoma, neurologic endocrinal tumor of the stomach, intestines and pancreas, gastrin-producing tumor, carcinoid syndrome, insulin-producing tumor, glucagonoma, digestive symptom with gastrointestinal obstruction, bleeding of the esophagus varix, portal hypertension, diabetic retinopathy, dementia, Alzheimer's disease, pain, headache, etc. In particular, the present invention compounds are favorable for the prevention and/or treatment for digestive symptom with gastrointestinal obstruction.

Digestive symptom with gastrointestinal obstruction includes, for example, digestive symptom with gastrointestinal obstruction in palliative treatment for the advanced or recurrence cancer patient, and the present invention compounds can remedy them.

Furthermore, the present invention compounds can be used for the prevention and/or treatment for some disease pathologically related with somatostatin, for example, the diseases described in *Life Sciences,* 1987, vol.40, p419-437 or *The European Journal of Medicine,* 1993, vol.2, p97-105.

When the present invention compounds apply to medicines, the present invention compounds are used not just alone but in combination with other active substances, for example, medicines described below or as concomitant drug for (1) the prevention, treatment and/or supplement and/or enhancement of improvement effect in symptoms, (2) the improvement of the pharmacokinetics/absorption and the reduction of dosage, and/or (3) the reduction of the adverse effect.

When the present invention compounds are used for the prevention and/or treatment for acromegaly, medicines used in combination with the present invention compounds include, for example, somatostatin analogs, growth hormone receptor antagonist, dopamine receptor agonist, etc.

Also, the patients with acromegaly are frequently associated with an adult disease such as diabetes, hypertension, hyperlipidemia, obesity, etc. or other various diseases, the present invention compound may be used in combination with, for example, diabetic medicine (e.g., insulin-sensitizing agent, insulin secretion promoting agent (e.g., sulfonyl urea agents, biguanide agents, insulin, α-glucosidase inhibitor, β3 adrenergic receptor agonist, dipeptidyl peptidase IV inhibitor, amylin agonist, phosphotyrosine phosphatase inhibitor, gluconeogenesis inhibitor, SGLT(sodium-glucose co-transporter) inhibitor, or other antidiabetic drug, etc.), therapeutic agents for diabetes complications (e.g. aldose reductase inhibitor, glycation inhibitor, protein kinase C inhibitor, neurotrophic factors, neurotrophic factor increasing medicine, nerve reproduction promotors, or other therapeutic agents for diabetes complications), antihypertensive drug (e.g., angiotensin-converting enzyme inhibitor, calcium antagonist, potassium channel opener, angiotensin II antagonist, etc.), hypolipidemic agent (e.g., HMG-CoA reductase inhibitor, fibrate-based medicine, squalene synthase inhibitor, antioxidant, etc.), anti-obesity drug (e.g., pancreatic lipase inhibitor, central antiobesity medicine, peptidic appetite depressant, cholecystokinin agonist, other anti-obesity drug, etc.), arthritis-treating agent, antianxiety agent, antidepressant drug, agent for treatment of osteoporosis, antiepileptic agent, chemotherapeutic agent, immunotherapeutic agent, antithrombotic drug, antidementia medicine, erectile dysfunction improvement medicine, drug for treatment of pollakisuria/incontinence, dysuria therapeutic drug, nonsteroidal anti-inflammatory drug, local anesthetic, vitamins, etc. In addition, it may be used in combination with other hormones which promote growth hormone secretion (e.g., GHRH), GH, IGF-1, cytokines, and cytokine action enhancer.

Furthermore, when the present invention compound are used for the prevention and/or treatment for digestive symptom with gastrointestinal obstruction, medicines which are combined with the present invention compounds include, for example, somatostatin analogs, dopamine D2 receptor antagonist, histamine H1 receptor antagonist, combination agent of histamine H1 receptor antagonist and the PDE inhibitor, histamine H2 receptor blocker, anticholinergic agent, serotonin 5HT3 receptor antagonist, serotonin 5HT4 receptor antagonist, corticosteroid, NK1 receptor antagonist, multi-acting receptor targeted antipsychotics (MARTA), opioid, opioid antagonist, etc. Alternatively, it may be used in combination with, for example, prochlorperazine, levomepromazine, etc.

Somatostatin analog includes, for example, octreotide, lanreotide, etc.

Growth hormone receptor antagonists include, for example, pegvisomant, etc.

Dopamine receptor agonists includes, for example, bromocriptine, cabergoline, etc.

Insulin-sensitizing agent includes, for example, balaglitazone, netoglitazone, pioglitazone, rivoglitazone, rosiglitazone, farglitazar, muraglitazar, naveglitazar, ragaglitazar, tesaglitazar, reglixane, BM-13.1258, FK-614, KRP-297, LM-4156, LY-510929, MBX-102, MX-6054, R-119702, T-131, THR-0921, the compounds described in WO2001/038325, the compounds described in WO1999/058510 (e.g., (E)-4-[4-(5-methyl-2-phenyl-4-oxazolylmethoxy)benzyloximino]-4-phenyl butyric acid), etc.

Sulfonyl urea agents include, for example, acetohexamide, chlorpropamide, glibenclamide, gliclazide, glimepiride, glipizide, glybuzole, glyclopyramide, mitiglinide, nateglinide, repaglinide, senaglinide, tolazamide, tolbutamide, JTT-608, etc.

Biguanide agents include, for example, buformin, fenformin, metformin, etc.

Insulins include, for example, animal insulin extracted from pancreas of bovine or pig, semisynthetic human insulin synthesized enzymatically from insulin extracted from pancreas of pig, synthetic human insulin by genetic engineering procedure using Escherichia coli and yeast, insulin zinc including 0.45 to 0.9 (w/w)% zinc, protamine zinc insulin manufactured from zinc chloride and protamine sulfate, etc. Insuline may include its fragments, derivatives (e.g., INS-1, etc.) and oral insulin preparations. Furthermore, insulins include many type such as rapid-acting type, short-acting type, two-phase type, intermediate-acting type, long-acting type, etc., and these are selected appropriately depend on the condition of the patients α-glucosidase inhibitors include, for example, acarbose, emiglitate, miglitol, voglibose, etc.

β3 adrenergic receptor agonists include, for example, AJ-9677, AZ40140, etc.

Dipeptidyl peptidase IV inhibitors include, for example, sitagliptin, alogliptin, vildagliptin, linagliptin, anagliptin, saxagliptin, teneligliptin, NVP-DPP-728, PT-100, P32/98, TS-021, TA-6666, KRP-104, DSP-7238, SYR-472 (trelagliptin), TAK-100, etc.

Amylin agonists include, for example, pramlintide, etc.

Phosphotyrosine phosphatase inhibitors include, for example, sodium vanadate, etc.

Gluconeogenesis inhibitors include, for example, glycogen phosphorylase inhibitor, glucose-6-phosphatase inhibitor, glucagon antagonist, etc.

SGLT (sodium-glucose co-transporter) inhibitors include, for example, T-1095, etc.

Antidiabetic drug other than those listed above include, for example, bromocriptine, leptin, BAY-27-9955, GLP-1 receptor agonist (e.g., GLP-1, GLP-1MR agent, liraglutide, AC-2993 (exendin-4), BIM-51077, Aib(8,35)hGLP-1(7,37)NH$_2$, CJC-1131, exenatide, etc.), GPR40 agonist, GPR119 agonist, 11β-hydroxy steroid dehydrogenase inhibitor (e.g., BVT-3498, etc.), adiponectin or its agonist, IKK inhibitor (e.g., AS-2686, etc.), leptin-resistant improvement medicine, somatostatin receptor agonist (e.g., the compounds described in WO2001/025228, WO2003/042204, WO1998/044921, WO1998/045285, and WO1999/022735, etc.), glucokinase activator (e.g., RO-28-1675, etc.).

Aldose reductase inhibitors include, for example, tolrestat, epalrestat, imirestat, zenarestat, fidarestat, zopolrestat, minalrestat, ranirestat, CT-112, etc.

Glycation inhibitors include, for example, pimagedine, ALT-946, ALT766, EXO-226, etc.

Protein kinase C inhibitors include, for example, ruboxistaurin mesylate, etc.

Neurotrophic factors include, for example, NGF, NT-3, BDNF, etc.

Neurotrophic factor-increasing medicines include, for example, neurotrophin production/secrete promotor described in WO2001/014372 (e.g., 4-(4-chlorophenyl)-2-(2-methyl-1-imidazoly)-5-[3-(2-methylphenoxy)propyl]oxazole, etc.) etc.

Nerve reproduction promotors include, for example, Y-128, VX-853, prosaptide, etc.

Therapeutic agents for diabetes complications other than those listed above include, for example, alprostadil, tiapride, cilostazol, mexiletine, ethyl icosapentate, memantine, pimagedline, AGE inhibitors (e.g., ALT-946, alagebrium, pyridorin, pyridoxamine, etc.), active oxygen scavengers (e.g., thioctic acid, etc.), somatostatin receptor agonists (e.g., BIM-23190), apoptotic signal regulating kinase-1 (ASK-1) inhibitors, etc.

Angiotensin converting enzyme inhibitors include, for example, captopril, enalapril, alacepril, delapril, lisinopril, imidapril, benazepril, cilazapril, temocapril, trandolapril, etc.

Calcium antagonists include, for example, manidipine, nifedipine, amlodipine, efonidipine, nicardipine, etc.

Potassium channel openers include, for example, levcromakalim, AL0671, NIP-121, etc.

Angiotensin II antagonists include, for example, losartan, candesartan cilexetil, eprosartan, valsartan, irbesartan, olmesartan medoxomi, E4177, 1-[[2'-(2,5-dihydro-5-oxo-4H-1,2,4-oxadiazol-3-yl)biphenyl-4-yl]methyl]-2-ethoxy-1H-benzimidazol-7-carboxylic acid, etc.

HMG-CoA reductase inhibitors include, for example, pravastatin, simvastatin, atorvastatin, fluvastatin, pitavastatin, rosuvastatin, etc.

Fibrate-based medicines include, for example, bezafibrate, clinofibrate, clofibrate, simfibrate, fenofibrate, etc.

Squalene synthase inhibitors include, for example, the compounds described in WO1997/010224 (e.g., N-[[(3R,5S)-1-(3-acetoxy-2,2-dimethypropyl)-7-chloro-5-(2,3-dimethoxyphenyl)-2-oxo-1,2,3,5-tetrahydro-4,1-benzooxazepin-3-yl]acetyl]piperidine-4-acetic acid, etc.), etc.

Antioxidants include, for example, lipoic acid, probucol, etc.

Pancreatic lipase inhibitors include, for example, orlistat, cetilistat, etc.

Central antiobesity medicines include, for example, mazindol, dexfenfluramine, fluoxetine, sibutramine, fenfluramine, phentermine, amfepramone, dexamfetamine, phenylpropanolamine, clobenzorex, etc.

Peptidic appetite depressants include, for example, leptin and CNTF (ciliary neurotrophic factor), etc.

Cholecystokinin agonists include, for example, lintitript and FPL-15849, etc.

Anti-obesity drugs other than those listed above include, for example, lipstatin, MCH receptor antagonists, (e.g., SB-568849, SNAP-7941, the compounds described in WO2001/082925 and the compounds described in WO2001/087834, etc.), neuropeptide Y antagonists (e.g., CP-422935, etc.), cannabinoid receptor antagonists (e.g., SR-141716, rimonabant, etc.), ghrelin antagonists, 11β-hydroxy steroid dehydrogenase inhibitors (e.g.,BVT-3498, etc.), β3 agonists (e.g., AJ-9677, AZ40140, etc.), appetite suppressing agents (e.g., P-57, etc.)

Arthritis-treating agents include, for example, ibuprofen, etc.

Antianxiety agents include, for example, chlordiazepoxide, diazepam, oxazolam, medazepam, cloxazolam, bromazepam, lorazepam, alprazolam, fludiazepam, etc.

Antidepressant drugs include, for example, fluoxetine, fluvoxamine, imipramine, paroxetine, sertraline, etc.

Agents for treatment of osteoporosis include, for example, alfacalcidol, calcitriol, elcatonin, calcitonin salmon, estriol, ipriflavone, risedronate disodium, pamidronate disodium, alendronate sodium hydrate, incadronate disodium, etc.

Antiepileptic agents include, for example, gabapentin, trileptal, keppra, zonegran, pregabalin, harkoseride, carbamazepine, etc.

Chemotherapeutic agents include, for example, alkylating agents (e.g., cyclophosphamide, ifosfamide, etc.), antimetabolites (e.g., methotrexate, 5-fluorouracil, 5-fluorouracil derivatives (e.g., doxifluridine, etc.), etc.), anticancer antibiotics (e.g., mitomycin, doxorubicin, etc.), anticancer agent derived from plants (e.g., vincristine, vindesine, paclitaxel, etc.), cisplatin, carboplatin, etoposide, etc.

Immunotherapeutic agents include, for example, microbial or bacterial ingredients (e.g., muramyl dipeptide derivatives, picibanil, etc.), polysaccharides with immunologic enhancement activity (e.g., lentinan, sizofiran, Krestin®, etc.), cytokine which is provided by genetic technique (e.g., interferon, interleukin: IL (e.g., IL-1, IL-2, IL-12, etc.), etc.), colony stimulating factors (e.g., granulocyte colony stimulating factor, erythropoietin: EPO, etc.), etc.

Antithrombotic drugs include, for example, heparin (e.g., dalteparin, heparin, etc.), warfarin (e.g., warfarin, etc.), antithrombin (e.g., argatroban, etc.), thrombolytic agents (e.g., urokinase, tisokinase, alteplase, nateplase, monteplase, pamiteplase, etc.), antiplatelet agent (e.g., ticlopidine, cilostazol, ethyl icosapentate, beraprost, sarpogrelate, etc.), etc.

Antidementia medicines include, for example, donepezil, galanthamine, rivastigmine, tacrine, etc.

Erectile dysfunction improvement medicines include, for example, apomorphine, sildenafil, etc.

Drugs for treatment of pollakisuria/incontinence include, for example, flavoxate, imidafenacin, oxybutynin, propiverine, etc.

Dysuria therapeutic drugs include, for example, acetyl choline esterase inhibitors (e.g., distigmine, etc.), etc.

Nonsteroidal anti-inflammatory drugs include, for example, acetaminophen, aspirin, indomethacin, etc.

Local anesthetics include, for example, capsaicin, lidocaine, etc.

Vitamins include, for example, vitamin B1, vitamin B12, etc.

Dopamine D2 receptor antagonists include, for example, prochlorperazine, levomepromazine, risperidone, metoclopramide, domperidone, etc.

Histamine H1 receptor antagonists include, for example, diphenhydramine, chlorpheniramine, dimenhydrinate, promethazine, etc.

Combination agents of histamine H1 receptor antagonists and the PDE inhibitors include, for example, combination agent of diphenhydramine/diprophylline, etc.

Histamine H2 receptor blockers include, for example, famotidine, cimetidine, etc.

Anticholinergic agents include, for example, scopolamine, etc.

Serotonin 5HT3 receptor antagonists include, for example, tropisetron, granisetron, ondansetron, azasetron, ramosetron, indisetron, palonosetron, etc.

Serotonin 5HT4 receptor antagonists include, for example, cisapride, mosapride, etc.

Corticosteroids include, for example, dexamethasone, betamethasone, prednisolone, etc.

NK1 receptor antagonists include, for example, aprepitant, fosaprepitant, etc.

Multi-acting receptor targeted antipsychotics (MARTA) include, for example, olanzapine, quetiapine, perospirone, etc.

Opioids include, for example, morphine, etc.

Opioid antagonists include, for example, methylnaltrexone, etc.

The companion drug comprising the present invention compounds and other drugs may be administered as combination drug where both substances are dispensed in one preparation, or separately formed preparations may be administered through same route or separate routes. When separately formed preparations are administered, coadministration of them is not always necessary, they may be administered at different intervals. When they are administered at different intervals, the order of them is not restricted, and may be adjusted appropriately to obtain expected efficacy.

The dosage of these other drugs which are combined with the present invention compounds may be increased and decreased appropriately based on the dosage of the drugs or similar drugs in clinical use. In addition, the ratio of the present invention compounds and other drugs is adjusted appropriately in view of age and weight of the patients, administration methods, administration time, target disease and symptoms, etc. Roughly, 1 pt.wt. of the present invention compounds may be combined with 0.01 to 100 pt.wt. of other drugs. As other drugs, some of them can be used together. Moreover, other drugs are not only the drugs listed above but also drugs which have same mechanism. These drugs include not only the existing drugs but also the drugs which are found from now.

The dosage of the present invention compounds depend on age, weight, symptoms, effect of treatment, administration methods, treating time, etc., as the usual adult dosage, from 1 mg to 300 mg is administered orally once or several times daily, or from 0.1 mg to 30 mg is administered parenterally once or several times daily, or by intravenous infusion for 1 to 24 hours Obviously, as previously indicated, the dosage depends on various conditions, there are times when less amount of said dosage is enough or when the dosage over the limit are need.

To use the present invention compounds as single drug or companion drug with other drugs for the prevention and/or treatment of said diseases, preparations are usually formed in active substances and various additives or pharmaceutically acceptable excipients, and are administered as oral or parenteral preparation systemically or locally. The pharmaceutically acceptable excipients mean materials except active substances which are generally used for preparations. The pharmaceutically acceptable excipients are preferably excipients which are harmlessness, and do not show any pharmacological effect and inhibit treatment effect of the active substances at the dosage of the drug products. In addition, the pharmaceutically acceptable excipients can be used to enhance effectiveness of the active substances, make production of the drugs easy, stabilize quality and improve usability. Specifically, the material described in "*Iyakuhin-tenkabutujiten*" (yakujinippousha, 2000), (edited by nihon-niyakuhinntennkazai kyokai)", etc. may be selected according to intentions.

Dosage forms for administration includes, for example, oral preparation (e.g. tablets, capsules, granules, powders, oral solutions, syrups, oral jelly agents, etc.), oro-mucosal preparation (e.g. tablets for oro-mucosal application, sprays for oro-mucosal application, semi-solid preparations for oro-mucosal application, gargles, etc.), preparations for injection (e.g. injections, etc.), preparations for dialysis (e.g. dialysis agents, etc.), preparation for inhalation (e.g. inhalations, etc.), preparation for ophthalmic application (e.g. ophthalmic liquids and solutions, ophthalmic ointments, etc.), preparation for otic application (e.g. ear preparation, etc.), preparations for nasal application (nasal preparations, etc.), preparation for recta (e.g. suppositories, semi-solid preparations for rectal application, enemas for rectal application, etc.), preparations for vaginal application (e.g. tablets for vaginal use, suppositories for vaginal use, etc.) and preparation for cutaneous application (e.g. solid preparations for cutaneous application, liquids and solutions for cutaneous application, sprays, ointment, creams, gels, patches, etc.).

[Oral Preparation]

Oral preparation include, for example, tablets, capsules, granules, powders, liquids and solution for oral administration, syrups, Jellies for oral administration, etc. As oral preparation, there are Immediate-release dosage forms showing a release pattern of active substances that is not intentionally modified and modified-release dosage forms are preparations showing modified pattern of active substances that is suitably modified for the desired purpose by means of a specific formulation design and/or manufacturing methods. Modified-release dosage forms include enteric-coated and extended-release preparations. Enteric-coated (delayed-release) preparations release the bulk of the active substances not in stomach but mainly in small intestine, in order to prevent degradation or decomposition of the active substances in stomach or to decrease the irritation of the active substances on stomach. Enteric-coated preparations are generally coated with an acid-insoluble enteric film. Extended-release preparations are designed to control the release rate and release period of active substances and to restrict the release to appropriate sites in the gastrointestinal tracts in order to decrease the dosing frequency and/or to reduce adverse or side effects. Extended-release preparations are generally prepared by using suitable agents that prolong the release of the active substances. Oral dosage forms such as capsules, granules and tablets can be coated with appropriate coating agents, such as sugars, sugar alcohols, or polymers, for the purpose of enabling the ingestion easy or of preventing degradation of the active substances.

(1) Tablets

Tablets are solid preparation having a desired shape and size, intended for oral administration, and include orally disintegrating tablets, chewable tablets, effervescent tablets, dispersible tablets, soluble tablets besides generally called tablets such as plain tablets, film-coated tablets, sugar-coated tablets, multi-layered tablets and pressure-coated tablets, etc. Plain tables are usually prepared according to the following methods (a), (b) and (c):

(a) Mix homogeneously active substances and excipients such as diluents, binders and disintegrators, granulate with water or a binder solution by suitable methods, mix with a lubricant, and then compress into a desired shape and size;
(b) Mix homogeneously active substances and excipients such as diluents, binders, and disintegrators, and then directly compress, or compress after adding active substances and lubricant to granules previously prepared from excipients and then mixing homogeneously;
(c) Mix homogeneously active substances and excipients such as diluents and binders, moisten with a solvent, form into a certain shape and size, and then dry by a suitable methods;

Film-coated tablets can be prepared, usually, by coating plain tablets using suitable coating agents such as polymers. Sugar-coated tablets can be prepared, usually, by coating plain tablets using suitable coating agents including sugars and sugar alcohols. Multiple-layer tablets can be prepared by compressing granules of different compositions to form layered tablets by a suitable method. Pressure-coated tablets can be prepared by compressing granules to cover inner core tablets with different compositions. In addition, tablets can be prepared as enteric coated tablets or timed-release tablet by suitable well-known methods. Orally disintegrating tablets, chewable tablets, effervescent tablets, dispersible tablets, soluble tablets are tablets which are added distinct role by selecting suitable excipients, and can be prepared according to said methods. Orally disintegrating tablets are tablets which are quickly dissolved or disintegrated in the oral cavity; Chewable tablets are tablets which are administered by chewing; Effervescent tablets are tablets which are quickly dissolved or dispersed with bubbles in water; Dispersible tablets are tablets which are administered after having been dispersed in water; Soluble tablets are tablets which are administered after having been dissolved in water. Effervescent tablets can be prepared using suitable acidic substances and carbonates or hydrogen carbonates as excipients.

(2) Capsules

Capsules are preparations enclosed in capsules or wrapped with capsule bases, intended for oral administration. Capsules are classified into hard capsules and soft capsules. Hard capsules can be prepared by a method where a homogeneous mixture of active substances with diluents and other suitable excipients, or granules or formed masses prepared by a suitable methods, are filled into capsule shells as they are or after slight compression. Soft capsules can be prepared by a method where active substances and suitable excipients are mixed, enclosed by a suitable capsule base such as gelation plasticized by addition of glycerin, D-sorbitol, etc. and molded in a suitable shape and size. Capsules can be prepared as enteric-coated or extended-release capsules by a suitable well-known method. Coloring agents and preservatives, etc. may be added to the capsule bases.

(3) Granules

Granules are preparations prepared by granulation, and include effervescent granules besides generally called granules. Granules can be prepared by the following methods (a), (b), and (c);
(a) To powdery active substances add diluents, binders, disintegrators, or other suitable excipients, mix to homogenize, and granulate by a suitable method;
(b) To previously granulated active substances add excipients such as diluents, and mix to homogenize;
(c) To previously granulated active substances add excipients such as diluents, and granulate by a suitable method;

Granules can be coated if necessary, and can be prepared as enteric-coated or extended-release granules. Effervescent granules can be prepared using suitable acidic substances and carbonates or hydrogen carbonates. Effervescent granules are granules which are quickly dissolved or dispersed with bubbles in water. Granules can be prepared as fine grain agents by adjusting particle size.

(4) Powders

Powders are preparations in powder form, and are usually prepared by homogeneously mixing active substances with diluents or other suitable excipients.

(5) Liquids and Solution for Oral Administration

Liquids and solution for oral administration are preparations in liquid form or flowable and viscous gelatinous state, and elixirs, suspensions, emulsions and lemonades are included in this category besides generally called Liquids and solution for oral administration. Liquids and solution for oral administration are usually prepared by dissolving, emulsifying or suspending active substances in purified water together with excipients, and by filtering if necessary. Elixirs are clear, sweetened and aromatic liquid preparations, containing ethanol, and are usually prepared by dissolving solid active substances or their extractives in ethanol and purified water, adding aromatic agents and sucrose, other sugars or sweetening agents, and clarifying by filtration or other procedure. Suspensions are liquid preparations of active substances suspended finely and homogeneously in a vehicle, and are usually prepared by adding suspending agent or other suitable excipients and purified water or oil to solid active substances, and suspending homogeneously as the whole by a suitable method. Emulsions are liquid preparations of active substances emulsified finely and homogeneously in a liquid vehicle, and are usually prepared by adding emulsifying agents and purified water to liquid active substances, and emulsifying finely and homogeneously by a suitable method. In addition, Lemonades are sweet and sour, clear liquid preparations, intended for oral administration.

(6) Syrups

Syrups are viscous liquid or solid preparations containing sugars or sweetening agents, and include preparation for syrups. Syrups are usually prepared by dissolving, mixing, suspending or emulsifying active substances in a solution of sucrose, other sugars or sweetening agents, or in simple syrup. Where necessary, the mixture is boiled, and filtered while hot. Preparations for syrups are preparations in form of granules or powders, which becomes syrups by adding water. They may be termed "dry syrups". Preparations for syrups are usually prepared with sugars or sweetening agents according to said preparation method of granules or powders.

(7) Jellies for Oral Administration

Jellies for oral administration are non-flowable gelatinous preparations having a certain shape and size, and usually prepared by mixing active substances with suitable excipients and polymer gel base, gelatinizing and forming into a certain shape and size by a suitable method.

[Preparation for Oro-mucosal Application]

(1) Tablets for Oro-mucosal Application

Tablets for oro-mucosal application are solid preparations having a certain form, and include troches/lozenges, sublingual tablets, buccal tablets, mucoadhesive tablets and medicated chewing gums. Preparations for oro-mucosal application are usually prepared according to said method of tablets. Troches/lozenges are tablets for oro-mucosal application, which are gradually dissolved or disintegrated in the mouth; Sublingual tablets are tablets for oro-mucosal application, from which active substances are quickly dissolved sublingually and absorbed via the oral mucosa; Buccal tablets are tablets for oro-mucosal applications, from which the active substances are dissolved gradually between the cheek and teeth, and absorbed via the oral mucosa; Mucoadhesive tablets are tablets for oro-mucosal application that are applied by adhesion to the oral mucosa; Medicated chewing gums are tablets for oro-mucosal application, releasing active substances by chewing.

(2) Spray for Oro-mucosal Application

Spray for oro-mucosal application are preparation that are applied active substances by spraying into the oral cavity in mist, powder, foam or paste forms, and are usually prepared by dissolving or suspending active substances and suitable excipients in a solvent, filter, where necessary, and fill into a container together with liquefied or compressed gas, or dissolving or suspending active substances and suitable excipients in a solvent, and fill into a container, and fit with a pump for spraying.

(3) Semi-solid Preparations for Oro-mucosal Application

Semi-solid preparations for oro-mucosal application are preparation in cream, gel or ointment forms, intended for application to the oral mucosa. Semi-solid preparations for oro-mucosal application are usually prepared by emulsifying active substances together with excipients using purified water and oil component such as petrolatum, or by homogenizing active substances together with suitable excipients using polymer gel or oil and fats as the base. Creams are semi-solid preparations, which are in the form of oil-in-water or water-in-oil emulsions. Hydrophobic preparations in the form of water-in-oil emulsions may be termed "Oily creams". Creams are usually prepared by mixing homogeneously and emulsifying an oil-phase component and a water-phase component, both warmed, of which either one contains the active substances. There components have the following constituents. Oil-phase component: Vaseline, fatty alcohols, etc., with or without emulsifying agents or other suitable excipients. Water-phase component: purified water with or without emulsifying agents or other suitable excipients. Gels are gelatinous preparations. There are aqueous gels and oily gels. Aqueous gels are usually prepared by adding polymers, other excipients and purified water to active substances, dissolving or suspending, and gelatinizing by warming and cooling or by adding gelatinizing agents. Oily gels are usually prepared by adding liquid oily bases such as glycols, fatty alcohols and other excipients to active substances and mixing. Ointments are semi-solid preparations, which dissolve or disperse active substances in a base. There are two types, hydrophobic ointments and hydrophilic ointments. Hydrophobic ointments are usually prepared by warming to melt hydrophobic bases such as fatty oils, waxes or paraffin, adding and mixing active substances in the base to be dissolved or dispersed, and kneading the whole to make homogeneous. Hydrophilic ointments are usually prepared by warming to melt hydrophilic bases such as macrogol, adding and mixing active substances in the bases, and kneading the whole to make homogenous.

(4) Preparations for Gargle

Preparations for gargle are liquid preparations intended to apply locally to the oral and throat cavities. Solid type preparations to be dissolved in water before use are also included in this category. Preparations for gargle are usually prepared by dissolving active substances in a solvent together with suitable excipients, and filtering where necessary. Solid preparations are prepared according to said method of tablets or granules.

[Preparation for Injection]

(1) Injections

Injections are sterile preparations to be administered directly into the body through skin, muscle or blood vessel, usually in form of a solution, a suspension or an emulsion of active substances, or of a solid that contains active substances to be dissolved or suspended before use, and include freeze-dried injections, powders, prefilled syringes, cartridges, parenteral infusions, implants/pellets and prolonged-release injections besides generally called injections. Injections are prepared by the following method (a) and (b):

(a) Dissolve, suspend or emulsify active substances with or without excipients in water for injection or an aqueous or non-aqueous vehicle homogeneously, fill into containers for injection, seal, and sterilize.

(b) Dissolve, suspend or emulsify active substances with or without excipients in water for injection or an aqueous or non-aqueous vehicle, and filtrate aseptically, or prepare aseptically a homogeneous liquid, fill into containers for injection, and seal;

Freeze-dried injections are usually prepared by dissolving active substances with or without excipients such as diluents in water for injection, sterilizing the solution by aseptic filtration, filling the filtrate directly into individual containers for injection and being freeze-dried, or dividing the filtrate in special containers, being freeze-dried and transferred into individual containers for injection. Powder for injections are usually prepared by filtrating aseptically a solution of active substances, obtaining powders by crystallization from the solution or mixing additionally the powders with sterilized excipients, and filling the powders into individual containers for injections. Prefilled syringes for injections are usually prepared by dissolving, suspending or emulsifying active substances with or without excipients in a vehicle, and filling into syringes. Cartridges are used by fixing in an injection device for exclusive use. Cartridges for injection are usually prepared by dissolving, suspending or emulsifying active substances with or without excipients in a vehicle, and filling into cartridges. Parenteral infusions are usually injections of not less than 100 mL, intended for intravenous administration. Implants/Pellets are solid or gel-like form injections, intended for subcutaneous or intramuscular administration by means of an implant device or operative treatment, for the purpose of releasing active substances for a long period of time. Implants/Pellets are usually prepared in a form of pellet, microsphere or gel using biodegradable polymers. Prolonged release injections are injections to be used for intramuscular administration, for the purpose of releasing active substances for a long period of time, and usually prepared by dissolving or suspending active substances in a non-aqueous vehicle such as vegetable oil, or by suspending microspheres prepared with biodegradable polymers.

[Preparations for Dialysis]

(1) Dialysis Agents

Dialysis agents are preparations in liquid, or in solid which are to be dissolved before use, intended for peritoneal dialysis or hemodialysis, and include peritoneal dialysis agents and hemodialysis agents. Peritoneal dialysis agents are sterile dialysis agents, intended to be used for peritoneal dialysis, and are usually prepared by dissolving active substances with suitable excipients in a vehicle to make a certain volume, or by filling active substances combined with suitable excipients in a container, and sealing it. Sterilize if necessary. In the case of solid preparations to be dissolved before use, it can be prepared according to said preparation method of tablets or granules. Hemodialysis agents are dialysis agents to be used for hemodialysis, and are usually prepared by dissolving active substances with excipients in a vehicle to make a certain volume, or by filling active substances with excipients in a container. In the case of the solid preparations to be dissolved before use, it can be prepared according to said preparation method of tablets or granules.

[Preparation for Inhalation]

Inhalations (1) Inhalations are preparations intended for administration as aerosols to the bronchial tubes or lung. Inhalations are classified to dry powder inhalers, inhalation liquid preparations and metered-dose inhalers. Dry powder inhalers are preparations which deliver a constant respiratory intake, intended for administration as solid particle aerosols, and are usually prepared by pulverizing active substances into fine particles. Where necessary, lactose or other suitable excipients are added to make homogeneous mixture. Inhalation liquid preparations are liquid inhalations which are administered by an inhalation device such as operating nebulizer. Inhalation liquid preparations are usually prepared by mixing active substances with a vehicle and suitable isotonic agents and/or pH adjusting agents to make a solution or suspension, and by filtering where necessary. Metered-dose inhalers are preparations which deliver a constant dose of active substances from the container together with propellant filled in. Metered-dose inhalers are usually prepared by dissolving active substances with a suitable dispersing agents and stabilizers in a vehicle to make a solution or suspension, and by filling in pressure-resistant containers together with liquid propellant, and setting metering valves.

[Preparation for Ophthalmic Application]

Ophthalmic Liquids and Solutions (1) Ophthalmic liquids and solutions are sterile preparations of liquid, or solid to be dissolved or suspended before use, intended for application to the conjunctival sac or other ocular tissues. Ophthalmic liquids and solutions are usually prepared by dissolving, suspending active substances in a vehicle after adding excipients to make a constant volume, or mixing active substances and excipients, and filling into containers.

(2) Ophthalmic Ointments

Ophthalmic ointments are sterile preparations of semi-solid, intended for application to the conjunstival sac and other ocular tissues. Ophthalmic ointments are usually prepared by mixing homogeneously solution of or finely powdered active substances with petrolatum or other bases, and filling into containers.

[Preparation for Otic Application]

(1) Ear Preparation

Ear preparations are liquid, semi-solid, or solid preparations which are to be dissolved or suspended before use, intended for application to the external or internal ear. Ear preparations are usually prepared by filling in containers with liquids in which active substances and excipients are dissolved or suspended in a vehicle to make a constant volume, or with powders in which active substances and excipients are mixed.

[Preparations for Nasal Application]

(1) Nasal Preparations

Nasal preparations are preparations intended for application to the nasal cavities or nasal mucous membrane. Nasal preparations are classified into Nasal dry powder inhalers and Nasal liquid preparations. Nasal dry powder inhalers are fine powdered preparations, intended for application to the nasal cavities. Nasal dry powder inhalers are usually prepared by pulverizing active substances into moderately fine particles, or by mixing homogeneously with excipients where necessary. Nasal liquids and solutions are liquid preparations, or solid preparations to be dissolved or suspended before use, intended for application to the nasal cavities. Nasal liquids and solutions are usually prepared by dissolving or suspending active substances in a vehicle together with excipients, and filtering where necessary. Isotonic agents and/or pH adjusting agents may be used.

[Preparations for Rectal Application]

(1) Suppositories for Rectal Application

Suppositories for rectal application are semi-solid preparations of a desired shape and size, intended for intrarectal application, which release active substances by melting at body temperature or dissolving or dispersing gradually in the secretions. Suppositories for rectal application are usually prepared by mixing homogeneously active substances and excipients such as dispersing agents and emulsifying agents, dissolving or suspending uniformly in a base which is liquefied by warming, filling a constant volume of the resultant material into containers, and molding it into a shape and size. Lipophilic bases or hydrophilic bases are usually used. l (2) Semi-solid Preparations for Rectal Application Semi-solid preparations for rectal application are preparations which are in a form of cream, gel or ointment intended for application to around or inside of the anus. Semi-solid preparations for rectal application are usually prepared by emulsifying active substances with excipients in purified water and oil component such as Vaseline, or by homogeneously mixing active substances and excipients in a base of polymer gel or grease. Creams for rectal application are usually prepared by mixing homogeneously and emulsifying an oil-phase component (such as vaseline, fatty alcohols, etc.) and a water phase component (such as purified water with or without emulsifying agents or other suitable excipients), both warmed, of which either one contains the active substances. Gels for rectal application are gelatinous preparation. There are aqueous gels and oily gels. Aqueous gels are prepared adding polymers, other excipients and purified water to active substances, and dissolving or suspending, and gelatinizing by warming and cooling or by adding gelatinizing agents. Oily gels are prepared by adding liquid oily bases such as glycols, fatty alcohols and other excipients to active substances and mixing. Ointments for rectal application are semi-solid preparations, which dissolve or disperse active substances in a base. There are two types, hydrophobic ointment and hydrophilic ointments. Hydrophobic ointments are usually prepared by warming to melt hydrophobic bases such as fatty oils, waxes or paraffin, adding and mixing active substances in the bases to be dissolved or dispersed, and kneading the whole to make homogeneous. Hydrophilic ointments are usually prepared by warming to melt hydrophilic bases such as macrogol, adding and mixing active substances in the bases, and kneading the whole to make homogeneous.

(3) Enemas for Rectal Application

Enemas for rectal application are preparations in liquid form or viscous and gelatinous state, intended for application via anus. Enemas for rectal application are preparations are usually prepared by dissolving or suspending active substances in purified water or suitable aqueous vehicle to make a given volume, and filling in containers. Dispersing agents, stabilizers and/or pH adjusting agents may be used.

[Preparations for Vaginal Application]

(1) Tablets for Vaginal Use

Tablets for vaginal use are solid applications of a desired shapes and size, intended for application to the vagina, which release active substances by dissolving or dispersing gradually in the secretions. Tablets for vaginal use are usually prepared according to said preparation method of tablets.

(2) Suppositories for Vaginal Use

Suppositories for vaginal use are semi-solid preparations of a desired shapes and size, intended for application to the vagina, which release active substances by melting at body temperature or by dissolving or dispersing gradually in the secretions. Suppositories for vaginal use are usually prepared according to said preparation method of suppositories for rectal applications.

[Preparation for Cutaneous Application]

(1) Solid Preparations for Cutaneous Application

Solid preparations for cutaneous application are solid preparations for cutaneous application skin (including scalp) or nails. Powders for cutaneous application are included in this category. Powders for cutaneous application are powdery solid preparations intended for external application. Powders for cutaneous application are usually prepared by mixing homogeneously active substances and excipients such as diluents and pulverizing the mixture.

(2) Liquids and Solutions for Cutaneous Application

Liquids and solutions for cutaneous application are liquid preparations intended for application to the skin (including scalp) or nails. Liniments and lotions are included in this category. Liquids and solutions for cutaneous application are usually prepared by mixing active substances and excipients in a vehicle, and filtering if necessary. Liniments are liquid or muddy preparations intended for external application to the skin by rubbing. Lotions are external liquids in which active substances are dissolved, emulsified or finely dispersed in an aqueous vehicle. Lotions are usually prepared by dissolving, suspending or emulsifying active substances in purified water with excipients and making homogeneous as a whole.

(3) Spray for Cutaneous Application

Spray for cutaneous application are preparations intended for spraying active substances onto the skin in mists, powders, forms or paste state. Spray for cutaneous application are classified into aerosols for cutaneous application and pump sprays for cutaneous application. Spray for cutaneous applications are usually prepared by dissolving or suspending active substances in a vehicle, filtering where necessary, and filling in containers. Aerosols for cutaneous application are sprays which atomize active substances together with liquefied or compressed gas filled in containers. Aerosols for cutaneous application are usually prepared by dissolving or suspending active substances in a vehicle, filling with liquefied propellants in pressure-resistant containers, and setting a continuous spray valve. If necessary, dispersing agents and stabilizer may be used. Pump sprays for cutaneous application are sprays which atomize active substances in containers by pumping. Pump sprays for cutaneous application are usually prepared by dissolving or suspending active substances with excipients in a vehicle, filling in containers and setting pumps to the containers.

(4) Ointments

Ointments are semi-solid preparations to be applied to the skin, which dissolve or disperse active substances in a base. There are two types, hydrophobic ointments and hydrophilic ointments. Hydrophobic ointments are usually prepared by warming to melt hydrophobic bases such as fatty oils, waxes or paraffin, adding and mixing active substances in the base to be dissolved or dispersed, and Kneading the whole to make homogeneous. Hydrophilic ointments are usually prepared by warming to melt hydrophilic bases such as macrogol, adding and mixing active substances in the bases, and kneading the whole to make homogenous.

(5) Creams

Creams are semi-solid preparations to be applied to the skin, which are in the form of oil-in-water or water-in-oil emulsions. Hydrophobic preparations in the form of water-in-oil emulsions may be termed "Oily creams". Creams are usually prepared by mixing homogeneously and emulsifying an oil-phase component and a water-phase component, both warmed, of which either one contains the active substances. There components have the following constituents. Oil-phase component: Vaseline, fatty alcohols, etc., with or without emulsifying agents or other suitable excipients. Water-phase component: purified water with or without emulsifying agents or other suitable excipients.

(6) Gels

Gels are gelatinous preparations intended for application to the skin. There are aqueous gels and oily gels. Aqueous gels are usually prepared by adding polymers, other excipients and purified water to active substances, dissolving or suspending, and gelatinizing by warming and cooling or by adding gelatinizing agents. Oily gels are usually prepared by adding liquid oily bases such as glycols, fatty alcohols and other excipients to active substances and mixing.

(7) Patches

Patches are preparations intended to be attached on the skin. Patched are classified into Tapes/Plasters and Cataplasms/Gel patches. Patches are usually prepared by mixing active substances homogeneously with a base such as a polymer or a mixture of polymers, spreading on a backing layer or liner, and cutting into a given size. Percutaneous absorption type preparations may be prepared by using a release rate-controlling membrane. Where necessary, adhesive agents or penetration enhancers may be used. Tapes/Plasters are patches which are prepared with bases of practically no water contain. Tapes/Plasters are usually prepared by mixing homogeneously active substances with or without excipients and a base of non water-soluble natural or synthetic polymers such as resins, plastics or rubber, and spreading on a cloth or spreading and sealing on a cloth or plastic film, cutting into a given size. The preparations may be also prepared by filling a mixture of active substances and a base with or without other excipients in releasers composed with a release-controlling film, supporter and liner. Cataplasms/Gels are patches using water containing bases. Cataplasms/Gels patches are usually prepared by mixing active substances, purified water, and glycerin or other liquid materials, or by mixing and kneading natural or synthetic polymers, which are soluble in water or absorbent of water, with purified water, adding active substances, mixing the whole homogeneously, spreading on a cloth or film, and cutting into a given size.

In the present invention, "Products" include at least one of (1) the pharmaceutical composition including the present invention compounds or the pharmaceutical composition which is compounding agents including other companion drugs and the present invention compounds. (2) containers including said pharmaceutical composition, and (3) a direction, a manual, a package insert or a product label (including the things equivalent to a label or labeling in the United States) which states that said compositions can be used for the prevention and/or treatment of acromegaly and/or digestive symptom with a gastrointestinal obstruction, where necessary, be combined with suitable companion drugs (preferably, somatostatin analogs, growth hormone receptor antagonists, dopamine receptor agonists, dopamine D2 receptor antagonists, histamine H1 receptor antagonists, combination drugs of histamine H1 receptor antagonists and PDE inhibitors, histamine H2 receptor antagonists, anticholinergic agents, serotonin 5HT3 receptor antagonists, serotonin 5HT4 receptor antagonists, corticosteroid, NK1 receptor antagonist, multi-acting receptor targeted antipsychotics (MARTA), opioid, and/or opioid antagonist, etc.).

The package insert is the official documents which states requirements for proper usage of drugs, such as "a package insert" in the Drugs, Cosmetics and Medical Instruments Act in Japan, Summary of Product Characteristics (SPC or SmPC) in the Directive in the European Union (EU), and US Package Insert (USPI) in the Code of Federal Regulations in US, or the documents equivalent to these in the other countries.

Matters described in these documents are usually information about adaptation disease, dose regimen, dosage, administration method, warning and/or contraindication, regulated in, for example, the Drugs, Cosmetics and Medical Instruments Act, Article 52, Article 54 and Article 68-4, regarding package inserts in Japan, (where necessary, refer to "yakuhatu No.606, 607 dated Apr. 25, 1997, and/or associated notice, Directive 2001/83/EC Article 11, etc., regarding summary of products information of EU (where necessary, refer to A guideline on SmPC, and/or associated guidelines), and 21 CFR 201.100, etc., regarding American package insert in US, (where necessary, refer to 21 CFR 201.57,and/or associated notice).

In addition, it is determined by 21 CFR 201 Subpart B that a part or all of matter stated in the American package inserts should be stated in Label or Labeling/Labelling besides said the American attached documents. Label means the things displayed on containers directly and labeling/labelling means concept including print in the packing and printed matter associated with the product, etc. besides label.

In the present invention, "Containers" means the things which include directly pharmaceutical composition including the present invention compounds or pharmaceutical composition which are compounding agents including other companion drugs and the present invention compounds, and are sometimes called "immediate container", "immediate wrapper" and "inner seals". "Containers" include cans, bottles, boxes, ampules, vials, tubes, unit dose containers for eye drops, paper, cloth, vinyl, plastic bags, SP sheets, PTP sheets, plastic containers, etc.

The containers including pharmaceutical composition are combined at least one of a direction, a manual, a package insert and a product label (including the thing equivalent to a label or a labeling in the United States), and are usually in outer container or wrapped in outer wrapper on the market.

Moreover, the present invention include advertising methods of pharmaceutical composition including the present invention compounds or pharmaceutical composition which is compounding agents including other companion drugs and the present invention compounds, and it discloses the method including encouraging target viewer to use said composition for the prevention and/or treatment acromegaly and/or digestive symptom with a gastrointestinal obstruction.

In said method, information of usefulness of using the pharmaceutical composition including the present invention compounds or the pharmaceutical composition which is compounding agents including other companion drug and the present invention compounds for the prevention and/or treatment of acromegary and/or digestive symptom with a gastrointestinal obstruction, especially benefit for health is publicly distributed. The information is distributed via suitable advertising medium besides verbal communication. As advertising medium, newspaper, magazine, TV, radio, video, brochure, leaflet, poster, social networking system, E-mail, electronic signboard, Digital Signage, Internet advertising (Homepage/website, banner ad, etc.), Outdoor advertising (poster board, neon sign, large-scale vision, etc.). Traffic advertisement (hanging posters, window advertisements, advertisements in frame in a train, a bus and a taxi, etc., and advertising posters in station, etc.), Movie, slide advertisement (screen advertisements of the movie theater), POP advertisement (store advertisement, advertisement in the shop), Direct advertising (direct mail, newspaper insert, handbill), Special advertisement (novelty advertisements such as a calendar or the ball-point pen), Other advertisements (skywriting, bench advertisement), etc. may be used. Those skilled in the art can produce these advertising media easily.

Unless it is defined elsewhere, all technical and scientific terms and abbreviations, which are used in the description, have same meanings which are usually understood by those skilled in the art.

The application claims the right of the priority based on JP2012-149010 applied for on Jul. 3, 2012, and the contents of the JP application are incorporated herein.

In the description, the contents of all Patent Literature, Non-Patent Literature and reference which are cited expressly may be cited as a part of the description.

EXAMPLE

The present invention is described in following Example and Biological example, but the present invention is not limited only to them. Name of the present invention compounds and compounds shown in Example are named by ACD/Name (Ver.6.00, Advanced Chemistry Development Inc.), or Chemdraw Ultra (Ver.12.0, Cambridge Soft).

The solvents in a parenthesis described at chromatography separation or TLC mean used eluting solvent or developing solvent, and the ratio means volume ratio. "NH silica" means that "CHROMATOREX NH TLC PLATE (catalog no. 3800003, (FUJI SILYSIA CHEMICAL LTD.))" are used.

"Hi-flash SI" or "Hi-flash NH" in a parenthesis at medium pressure liquid chromatography means used column type. (Hi-flash SI: silica gel (YAMAZEN CO.), Hi-flash NH: Aminopropyl-supported silica gel (YAMAZEN CO.))

LC-MS/ELSD Condition:

Condition (1) {Column: Waters Xterra MS $C_{18}$ (particle size: $5 \times 10^{-6}$ m; column length: 50×4.6 mm I.D.); flow rate: 1.5 mL/min; column temperature: 40° C.; mobile phase (A): aqueous solution of 0.1% trifluoroacetic acid; mobile phase (B):0.1% trifluoroacetic acid-methanol solution; gradient (rate of mobile phase (A): mobile phase (B)): [0 min] 95:5; [1 min] 95:5; [4 min] 0:100; [4.5 min] 0:100; [4.51 min] 95:5; [6 min] 95:5; detector: UV(PDA), ELSD, MS}

UPLC-MS/ELSD Condition:

Condition (2) {Column: Waters ACQUITY $C_{18}$ (particle size: $1.7 \times 10^{-6}$ m; column length: 30×2.1 mm I.D.); flow rate: 1.0 mL/min; column temperature: 40° C.; mobile phase (A): aqueous solution of 0.1% trifluoroacetic acid; mobile phase (B): 0.1% trifluoroacetic acid-acetonitrile solution; gradient (rate of mobile phase (A): mobile phase (B)): [0 min] 95:5; [0.1 min] 95:5; [1.2 min] 5:95; [1.4 min] 5:95; [1.41 min] 95:5; [1.5 min] 95:5; detector: UV(PDA), ELSD, MS}

The numerical value shown at the NMR data is measurements of the $^1$H NMR when the measurement solvent described there is used.

In addition, specific functional groups in the formula are shown by symbols and abbreviations. The symbols, the abbreviations and the meanings are described below.
Boc: tert-butoxycarbonyl group
Cbz: benzyloxicarbonyl group
Ns: 2-nitrobenzenesulfonyl group The following Biological Example 2 is exemplified as an example of test which shows usefulness of the present invention compounds against acromegary, and Biological Example 3 is exemplified as an example of test which shows usefulness of the present invention compounds against digestive symptom with a gastrointestinal obstruction. However, target diseases of the present invention compounds are not limited to them. According to the above, it is obvious that the present invention compounds are useful for the prevention and/or treatment for all of diseases which may be related with somatostatin itself or hormones regulated by somatostatin.

Reference Example 1 methyl 5-bromo-4-[4-(tert-butoxycarbonylamino)-1-piperidyl]pyridine-3-carboxylate To a dimethylformamide (20 mL) solution of methyl 5-bromo-4-iodopyridine-3-carboxylate (3.0 g), which was produced by the reaction of 5-bromo-4-iodopyridine-3-carboxylic acid (CAS #491588-98-8) and trimethylsilyldiazomethane, was added triethylamine (1.84 mL) and 4-tert-butoxycarbonylaminopiperidine (CAS #73874-95-0) (2.63 g), the mixture was stirred at 70 degrees C. for 5 hours. After cooling to room temperature, the reaction solution was diluted with ethyl acetare followed by washing with water and saturated brine sequentially. After drying, the organic layer was concentrated. The obtained residue was purified by preparative medium pressure liquid chromatography (Yamazen Corp. YFLC-Wprep-2XY) (Hi-flash SI) (n-hexane: ethyl acetate=1:1) to obtain the title compound (2.47 g) having the following physical property values.
Description: pale yellowish white powder;
TLC: Rf 0.26 (n-hexane:ethyl acetate=1:2);
NMR (300 MHz, CHLOROFORM-d): δ 8.65 (s, 1H), 8.57 (s, 1H), 4.54 (br.s, 1H), 3.95 (s, 3H), 3.76-3.63 (m, 1H), 3.36-3.25 (m, 2H), 3.16-3.03 (m, 2H), 2.09-1.98 (m, 2H), 1.71-1.59 (m, 2H), 1.47 (s, 9H).

Reference Example 2 methyl 4-[4-(tert-butoxycarbonylamino)-1-piperidyl]-5-phenylpyridine-3-carboxylate Tripotassium phosphate (425 mg), phenylboronic acid (CAS #98-80-6) (122 mg) and bis(di-tert-butyl(4-dimethylaminophenyl)phosphine)dichloropalladium(II) (7.1 mg) was added to a 1,4-dioxane solution (8 mL) of the compound (207 mg) produced in the Reference example 1, and the mixture was stirred at 90 degrees C. for 2 hours. After cooling to room temperature, the reaction solution was diluted with ethyl acetate and sequentially washed with water and saturated brine. After drying, the organic layer was concentrated. The obtained residue was purified by preparative medium pressure liquid chromatography (Yamazen Corp. YFLC-Wprep-2XY) (Hi-flash SI) (n-hexane:ethyl acetate=1:1) to obtain the title compound (206 mg) having the following physical property values.
Description: pale yellowish white oil;
TLC: Rf 0.31 (n-hexane:ethyl acetate=1:2);
MASS (APCI, Pos.): 412 (M+H)+.

Reference Example 3 tert-butyl N-[1-[3-[(3,5-dimethylphenyl)carbamoyl]-5-phenyl-4-pyridyl]-4-piperidyl]carbamate Under argon atmosphere, a solution of 3,5-dimethylaniline (CAS #108-69-0) (194 mg) in anhydrous tetrahydrofran (10 mL) was cooled to 0 degrees C. After N-butyllithium in hexane (1.6 mol, 2.0 mL) was added to it, and the mixture was stirred at room temperature for 10 min. The reaction solution was cooled to −78 degrees C., the solution of the compound (206 mg) produced in the reference example 2 in tetrahydrofuran (10 mL) was added to it. The reaction solution was warmed to room temperature over 3 hours or more, and quenched with aqueous solution of saturated ammonium chloride followed by extraction with ethyl acetate. The organic layer was washed with saturated brine and concentrated after drying. The obtained residue was purified by preparative medium pressure liquid chromatography (Yamazen Corp. YFLC-Wprep-2XY) (Hi-flash SI) (n-hexane:ethyl acetate=3:1) to obtain the title compound (52 mg) having the following physical property values.
Description: pale yellowish white powder;
TLC: Rf 0.33 (n-hexane:ethyl acetate=1:1);
MASS (APCI, Pos.): 501 (M+H)+.

Example 1

4-(4-amino-1-piperidyl)-N-(3,5-dimethylphenyl)-5-phenyl-pyridine-3-carboxamide

[81]

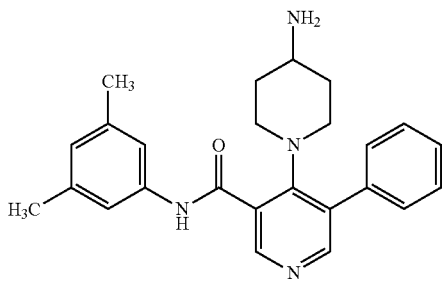

To a solution of the compound (52 mg) produced in the Reference example 3 in dichloromethane (2 mL) was added trifluoroacetic acid (2 mL) at room temperature, and the mixture was stirred for 30 min and concentrated. The obtained residue was purified by preparative medium pressure liquid chromatography (Yamazen Corp. YFLC-Wprep-2XY) (Hi-flash NH) (ethyl acetate:methanol=95:5) to obtain the present invention compound (26 mg) having the following physical property values.
Description: beige amorphous;
Purity (LC-MS/ELSD): 100% (retention time: 3.45 min);
TLC: Rf 0.24 (ethyl acetate:methanol=9:1, NH silica gel);

NMR (300 MHz, CHLOROFORM-d): δ 8.94 (br.s, 1H), 8.83 (s, 1H), 8.34 (s, 1H), 7.53-7.28 (m, 7H), 6.81 (s, 1H), 3.21-3.05 (m, 2H), 2.83-2.56 (m, 3H), 2.34 (s, 6H), 1.74-1.59 (m, 2H), 1.48 (br.s, 2H), 1.35-1.18 (m, 2H);
MASS (ESI, Pos.): 401 (M+H)+.

Example 2(1)-Example 2(30)

Using methyl 5-bromo-4-iodopyridine-3-carboxylate or a corresponding reagent in place of it, using 4-tert-butoxycarbonylaminopiperidine or a corresponding reagent in place of it, using 3,5-dimethylaniline or a corresponding reagent in place of it, using a corresponding reagent in place of phenylboronic acid, the present invention compounds having the following physical property values were obtained by following the same procedure as in Reference example 1→Reference example 3→Reference example 2→Example 1.

Example 2(1)

4-(4-amino-1-piperidinyl)-N-(3,5-dimethylphenyl)-6'-fluoro-3,3'-bipyridine-5-carboxamide

[82]

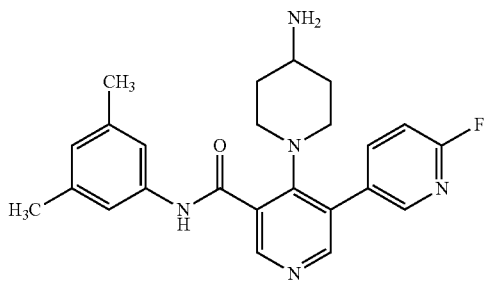

Description: colorless oil;
Purity (LC-MS/ELSD): 100% (retention time: 3.41 min);
MASS (ESI, Pos.): 420 (M+H)+.

Example 2(2)

4-(4-amino-1-piperidinyl)-N-(3,5-dimethylphenyl)-5-(1-methyl-1H-pyrazol-4-yl)pyridine-3-carboxamide Description: colorless oil;
Purity (LC-MS/ELSD): 95% (retention time: 3.41 min);
MASS (ESI, Pos.): 405 (M+H)+.

Example 2(3)

4-(4-amino-1-piperidinyl)-N-(3,5-dimethylphenyl)-5-(2-methylphenyl)pyridine-3-carboxamide Description: ivory powder;
Purity (LC-MS/ELSD): 100% (retention time: 3.53 min);
MASS (ESI, Pos.): 415 (M+H)+.

Example 2(4)

4-(4-amino-1-piperidinyl)-N-(3,5-dimethylphenyl)-5-(3-methylphenyl)pyridine-3-carboxamide Description: ivory powder;
Purity (LC-MS/ELSD): 100% (retention time: 3.56 min);
MASS (ESI, Pos.): 415 (M+H)+.

Example 2(5)

4-(4-amino-1-piperidinyl)-N-(3,5-dimethylphenyl)-5-(4-methylphenyl)pyridine-3-carboxamide Description: ivory powder;
Purity (LC-MS/ELSD): 100% (retention time: 3.56 min);
MASS (ESI, Pos.): 415 (M+H)+.

Example 2(6)

4-(4-amino-1-piperidinyl)-N-(3,5-dimethylphenyl)-5-(5-pyrimidinyl)pyridine-3-carboxamide Description: colorless oil;
Purity (LC-MS/ELSD): 99% (retention time: 3.39 min);
MASS (ESI, Pos.): 403 (M+H)+.

Example 2(7)

4-(4-amino-1-piperidinyl)-N-(3,5-dimethylphenyl)-5-(2,4-dimethyl-1,3-thiazol-5-yl)pyridine-3-carboxamide Description: colorless oil;
Purity (LC-MS/ELSD): 100% (retention time: 3.50 min);
MASS (ESI, Pos.): 436 (M+H)+.

Example 2(8)

4-(4-amino-1-piperidinyl)-5-(3,5-difluorophenyl)-N-(3,5-dimethylphenyl)pyridine-3-carboxamide Description: white powder;
Purity (LC-MS/ELSD): 100% (retention time: 3.42 min);
TLC: Rf 0.55 (ethyl acetate:methanol=9:1, NH silica gel);
NMR (300 MHz, CHLOROFORM-d): δ 8.75 (s, 1H), 8.39 (s, 1H), 8.31 (s, 1H), 7.29 (s, 2H), 6.96-6.81 (m, 4H), 3.24-3.09 (m, 2H), 2.92-2.62 (m, 3H), 2.35 (s, 6H), 1.77-1.61 (m, 2H), 1.52 (br.s, 2H), 1.35-1.19 (m, 2H);
MASS (ESI, Pos.): 437 (M+H)+.

Example 2(9)

4-(4-amino-1-piperidinyl)-5-(3,4-difluorophenyl)-N-(3,5-dimethylphenyl)pyridine-3-carboxamide Description: white powder;
Purity (LC-MS/ELSD): 100% (retention time: 3.44 min);
TLC: Rf 0.53 (ethyl acetate:methanol=9:1, NH silica gel);
MASS (ESI, Pos.): 437 (M+H)+.

Example 2(10)

4-(4-amino-1-piperidinyl)-5-(2,5-difluorophenyl)-N-(3,5-dimethylphenyl)pyridine-3-carboxamide Description: white powder;
Purity (LC-MS/ELSD): 100% (retention time: 3.49 min);
TLC: Rf 0.49 (ethyl acetate:methanol=9:1, NH silica gel);
MASS (ESI, Pos.): 437 (M+H)+.

Example 2(11)

4-(4-amino-1-piperidinyl)-5-(2,3-difluorophenyl)-N-(3,5-dimethylphenyl)pyridine-3-carboxamide Description: white powder;
Purity (LC-MS/ELSD): 100% (retention time: 3.52 min);
TLC: Rf 0.48 (ethyl acetate:methanol=9:1, NH silica gel);
MASS (ESI, Pos.): 437 (M+H)+.

Example 2(12)

4-(4-amino-1-piperidinyl)-5-(2,5-dimethylphenyl)-N-(3,5-dimethylphenyl)pyridine-3-carboxamide Description: white powder;
TLC: Rf 0.45 (ethyl acetate:methanol=9:1, NH silica gel);
NMR (300 MHz, CHLOROFORM-d): δ 9.09 (s, 1H), 8.85 (s, 1H), 8.24 (s, 1H), 7.32 (s, 2H), 7.21-7.10 (m, 2H), 6.94 (s, 1H), 6.81 (s, 1H), 3.24-3.14 (m, 1H), 3.10-3.00 (m, 1H), 2.89-2.78 (m, 1H), 2.66-2.52 (m, 2H), 2.35 (s, 3H), 2.34 (s, 6H), 2.14 (s, 3H), 1.72-1.55 (m, 2H), 1.51 (br.s, 2H), 1.31-1.05 (m, 2H);
Mass(APCI, Pos.): 429 (M+H)+.

Example 2(13)

4-(4-amino-1-piperidinyl)-5-(2-fluoro-5-methoxyphenyl)-N-(3,5-dimethylphenyl)pyridine-3-carboxamide Description: white powder;
Purity (UPLC-MS/ELSD): 100% (retention time: 0.6 min);
TLC: Rf 0.42 (ethyl acetate:methanol=9:1, NH silica gel);
MASS (ESI, Pos.): 449 (M+H)+.

Example 2(14)

4-(4-amino-1-piperidinyl)-5-(2-fluoro-5-methylphenyl)-N-(3,5-dimethylphenyl)pyridine-3-carboxamide Description: white powder;
Purity (UPLC-MS/ELSD): 100% (retention time: 0.6 min);
TLC: Rf 0.47 (ethyl acetate:methanol=9:1, NH silica gel);
MASS (ESI, Pos.): 433 (M+H)+.

Example 2(15)

4-(4-amino-1-piperidinyl)-5-(2-methoxy-5-methylphenyl)-N-(3,5-dimethylphenyl)pyridine-3-carboxamide Description: white powder;
Purity (UPLC-MS/ELSD): 100% (retention time: 0.6 min);
TLC: Rf 0.42 (ethyl acetate:methanol=9:1, NH silica gel);
MASS (ESI, Pos.): 445 (M+H)+.

Example 2(16)

4-(4-amino-1-piperidinyl)-5-(3,5-dimethoxyphenyl)-N-(3,5-dimethylphenyl)pyridine-3-carboxamide Description: white powder;
Purity (UPLC-MS/ELSD): 100% (retention time: 0.59 min);
TLC: Rf 0.39 (ethyl acetate:methanol=9:1, NH silica gel);
MASS (ESI, Pos.): 461 (M+H)+.

Example 2(17)

4-(4-amino-1-piperidinyl)-5-(2,5-difluorophenyl)-N-(3-chloro-4-fluorophenyl)pyridine-3-carboxamide Description: white powder;
Purity (UPLC-MS/ELSD): 100% (retention time: 0.57 min);
TLC: Rf 0.51 (ethyl acetate:methanol=9:1, NH silica gel);
NMR (300 MHz, CHLOROFORM-d): δ 9.11 (s, 1H), 8.85 (s, 1H), 8.32 (s, 1H), 7.96 (dd, J=6.50, 2.65 Hz, 1H), 7.48-7.38 (m, 1H), 7.21-7.09 (m, 3H), 7.05-6.97 (m, 1H), 3.20-3.10 (m, 2H), 2.87-2.64 (m, 3H), 1.80-1.64 (m, 2H), 1.54 (br.s, 2H), 1.30-1.12 (m, 2H);
MASS (ESI, Pos.): 461 (M+H)+.

Example 2(18)

4-(4-amino-1-piperidinyl)-5-(3,5-dimethoxyphenyl)-N-(3-chloro-4-fluorophenyl)pyridine-3-carboxamide Description: beige powder;
Purity (UPLC-MS/ELSD): 99.9% (retention time: 0.51 min);
TLC: Rf 0.56 (ethyl acetate:methanol=9:1, NH silica gel);
NMR (300 MHz, CHLOROFORM-d): δ 9.76 (s, 1H), 8.91 (s, 1H), 8.37 (s, 1H), 7.98 (dd, J=6.50, 2.65 Hz, 1H), 7.43 (ddd, J=9.00, 4.00, 2.70 Hz, 1H), 7.15 (dd, J=9.00, 8.50 Hz, 1H), 6.51 (t, J=2.40 Hz, 1H), 6.45 (d, J=2.38 Hz, 2H), 3.83 (s, 6H), 3.22-3.11 (m, 2H), 2.80 (s, 3H), 1.82-1.69 (m, 2H), 1.53 (br.s, 2H), 1.38-1.22 (m, 2H);
MASS (ESI, Pos.): 485 (M+H)+.

Example 2(19)

4-(4-amino-1-piperidinyl)-5-(4-hydroxy-3,5-dimethylphenyl)-N-(3,5-dimethylphenyl)pyridine-3-carboxamide Description: beige powder;
Purity (UPLC-MS/ELSD): 100% (retention time: 0.51 min);
TLC: Rf 0.54 (ethyl acetate:methanol=9:1, NH silica gel);
MASS (ESI, Pos.): 445 (M+H)+.

Example 2(20)

4-[4-(aminomethyl)-1-piperidinyl]-N,5-bis(3,5-dimethylphenyl)pyridine-3-carboxamide

[83]

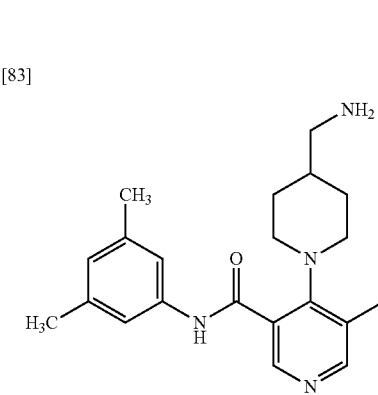

Description: white powder;
Purity (UPLC-MS/ELSD): 99.9% (retention time: 0.56 min);
TLC: Rf 0.40 (ethyl acetate:methanol=9:1, NH silica gel);
NMR (300 MHz, CHLOROFORM-d): δ 9.56 (br.s, 1H), 8.93 (s, 1H), 8.34 (s, 1H), 7.33 (s, 2H), 7.04 (s, 1H), 6.92 (s, 2H), 6.79 (s, 1H), 3.21-3.08 (m, 2H), 2.76-2.62 (m, 2H), 2.52 (d, J=5.49 Hz, 2H), 2.37 (s, 6H), 2.33 (s, 6H), 1.68-1.56 (m, 5H), 1.31-1.20 (m, 2H);
MASS (ESI, Pos.): 443 (M+H)+.

Example 2(21)

4-(4-amino-4-methyl-1-piperidinyl)-N,5-bis(3,5-dimethylphenyl)pyridine-3-carboxamide Description: white powder;
Purity (UPLC-MS/ELSD): 99.9% (retention time: 0.56 min);
TLC: Rf 0.62 (ethyl acetate:methanol=9:1, NH silica gel);
NMR (300 MHz, CHLOROFORM-d): δ 9.61 (s, 1H), 8.93 (s, 1H), 8.36 (s, 1H), 7.32 (s, 2H), 7.05 (s, 1H), 6.96 (s, 2H), 6.80 (s, 1H), 3.06-2.94 (m, 2H), 2.95-2.82 (m, 2H), 2.38 (s, 6H), 2.33 (s, 6H), 1.62-1.30 (m, 6H), 1.03 (s, 3H);
MASS (ESI, Pos.): 443 (M+H)+.

Example 2(22)

4-(4-amino-1-piperidinyl)-5-(3-hydroxy-5-methylphenyl)-N-(3,5-dimethylphenyl)pyridine-3-carboxamide Description: white powder;
Purity (UPLC-MS/ELSD): 99.9% (retention time: 0.50 min);
TLC: Rf 0.37 (ethyl acetate:methanol=9:1, NH silica gel);
MASS (ESI, Pos.): 431 (M+H)+.

Example 2(23)

4-[3-(aminomethyl)-1-pyrrolidinyl]-N,5-bis(3,5-dimethylphenyl)pyridine-3-carboxamide Description: beige powder;
Purity (UPLC-MS/ELSD): 99.5% (retention time: 0.58 min);
TLC: Rf 0.44 (ethyl acetate:methanol=9:1, NH silica gel);
NMR (300 MHz, CHLOROFORM-d): δ 8.48 (s, 1H), 8.15 (s, 1H), 8.13 (s, 1H), 7.27 (s, 2H), 6.99 (s, 1H), 6.92 (s, 2H), 6.82 (s, 1H), 3.27 (dd, J=10.1, 7.1 Hz, 1H), 3.20-3.08 (m, 2H), 2.89 (dd, J=10.1, 6.8 Hz, 1H), 2.55 (d, J=7.0 Hz, 2H), 2.35 (s, 6H), 2.34 (s, 6H), 2.16-2.03 (m, 1H), 1.93-1.81 (m, 1H), 1.57-1.40 (m, 3H);
MASS (ESI, Pos.): 429 (M+H)+.

Example 2(24)

N,5-bis(3,5-dimethylphenyl)-4-{[3-(2-piperidinyl)propyl]amino}pyridine-3-carboxamide Description: white powder;
Purity (UPLC-MS/ELSD): 99.5% (retention time: 0.62 min);
TLC: Rf 0.58 (ethyl acetate:methanol=9:1, NH silica gel);
NMR (300 MHz, CHLOROFORM-d): δ 8.55 (s, 1H), 8.19 (s, 1H), 8.08 (s, 1H), 7.25 (s, 2H), 7.01 (s, 1H), 6.96 (s, 2H), 6.89 (br.s, 1H), 6.82 (s, 1H), 3.05-2.935 (m, 1H), 2.81-2.69 (m, 2H), 2.59-2.46 (m, 1H), 2.35 (s, 6H), 2.34 (s, 6H), 2.32-2.22 (m, 1H), 1.84-0.86 (m, 11H);
MASS (ESI, Pos.): 471 (M+H)+.

Example 2(25)

4-(2,7-diazaspiro[3.5]non-7-yl)-N,5-bis(3,5-dimethylphenyl)pyridine-3-carboxamide Description: white powder;
Purity (UPLC-MS/ELSD): 93.3% (retention time: 0.58 min);
TLC: Rf 0.25 (ethyl acetate:methanol=9:1, NH silica gel);
NMR (300 MHz, CHLOROFORM-d): δ 8.76 (s, 1H), 8.67 (s, 1H), 8.35 (s, 1H), 7.25 (s, 2H), 7.04 (s, 1H), 6.92 (s, 2H), 6.83 (s, 1H), 3.55 (s, 4H), 2.89-2.82 (m, 4H), 2.36 (s, 6H), 2.33 (s, 6H), 2.07-1.47 (m, 5H);
MASS (ESI, Pos.): 455 (M+H)+.

Example 2(26)

4-[(4-aminobutyl)amino]-N,5-bis(3,5-dimethylphenyl)pyridine-3-carboxamide

Description: white powder;
Purity (UPLC-MS/ELSD): 99.6% (retention time: 0.60 min);
TLC: Rf 0.56 (ethyl acetate:methanol=9:1, NH silica gel);
NMR (300 MHz, CHLOROFORM-d): δ 8.55 (s, 1H), 8.11 (s, 1H), 7.97 (s, 1H), 7.22 (s, 2H), 7.02 (s, 1H), 6.98 (s, 2H), 6.94 (br.s, 1H), 6.83 (s, 1H), 2.81-2.72 (m, 2H), 2.53 (t, J=7.0 Hz, 2H), 2.36 (s, 6H), 2.34 (s, 6H), 1.44-1.18 (m, 6H);
MASS (ESI, Pos.): 417 (M+H)+.

Example 2(27)

2-(4-amino-1-piperidinyl)-N-(3,5-dimethylphenyl)-3',5'-dimethyl-3-biphenylcarboxamide Description: white powder;
TLC: Rf 0.36 (n-hexane:ethyl acetate=1:2, NH silica gel);
NMR (300 MHz, CHLOROFORM-d): δ 10.80 (br.s., 1H), 8.04 (t, J=4.8 Hz, 1H), 7.37 (s, 2H), 7.22 (d, J=4.8 Hz, 2H), 7.01 (s, 1H), 6.92 (s, 2H), 6.77 (s, 1H), 3.06 (d, J=12.6 Hz, 2H), 2.60-2.76 (m, 2H), 2.52 (m, 1H), 2.37 (s, 6H), 2.33 (s, 6H), 1.73 (d, J=9.3 Hz, 2H), 1.48-1.21 (m, 4H);
MASS (APCI, Pos.): 428 (M+H)+.

Example 2(28)

2-[4-(aminomethyl)-1-piperidinyl]-N-(3,5-dimethylphenyl)-3',5'-dimethyl-3-biphenylcarboxamide Description: white powder;
TLC: Rf 0.35 (n-hexane:ethyl acetate=1:4, NH silica gel);
NMR (300 MHz, CHLOROFORM-d): δ 11.35 (br.s., 1H), 8.12 (br.s., 1H), 7.39 (s, 2H), 7.25-7.19 (m, 2H), 7.01 (s, 1H), 6.91 (s, 2H), 6.76 (s, 1H), 3.10 (d, J=11.9 Hz, 2H), 2.64 (t, J=11.9 Hz, 2H), 2.53 (d, J=6.0 Hz, 2H), 2.36 (s, 6H), 2.32 (s, 6H), 1.64 (d, J=11.9 Hz, 2H), 1.50-1.12 (m, 5H);
MASS (APCI, Pos.): 442 (M+H)+.

Example 2(29)

4-[4-(2-aminoethyl)-1-piperidinyl]-N,5-bis(3,5-dimethylphenyl)pyridine-3-carboxamide Description: white powder;
Purity (UPLC-MS/ELSD): 100% (retention time: 0.60 min);
TLC: Rf 0.56 (ethyl acetate:methanol=9:1, NH silica gel);
NMR (300 MHz, CHLOROFORM-d): δ 9.56 (s, 1H), 8.92 (s, 1H), 8.33 (s, 1H), 7.34 (s, 2H), 7.05 (s, 1H), 6.93 (s, 2H), 6.80 (s, 1H), 3.19-3.07 (m, 2H), 2.75-2.61 (m, 4H), 2.38 (s, 6H), 2.34 (s, 6H), 1.63-1.12 (m, 9H);
MASS (ESI, Pos.): 457 (M+H)+.

Example 2(30)

4-[4-(aminoethyl)-4-hydroxy-1-piperidinyl]-N,5-bis(3,5-dimethylphenyl)pyridine-3-carboxamide Description: beige powder;
Purity (UPLC-MS/ELSD): 99.7% (retention time: 0.55 min);
TLC: Rf 0.47 (ethyl acetate:methanol=9:1, NH silica gel);
NMR (300 MHz, CHLOROFORM-d): δ 9.43 (s, 1H), 8.89 (s, 1H), 8.35 (s, 1H), 7.31 (s, 2H), 7.04 (s, 1H), 6.95 (s, 2H), 6.80 (s, 1H), 3.20-3.03 (m, 2H), 3.01-2.88 (m, 2H), 2.51 (s, 2H), 2.38 (s, 6H), 2.33 (s, 6H), 1.75-1.40 (m, 7H);
MASS (ESI, Pos.): 459 (M+H)+.

Example 3

4-(4-hydroxy-1-piperidinyl)-5-(3,5-dimethylphenyl)-N-(3,5-dimethylphenyl)pyridine-3-carboxamide

[84]

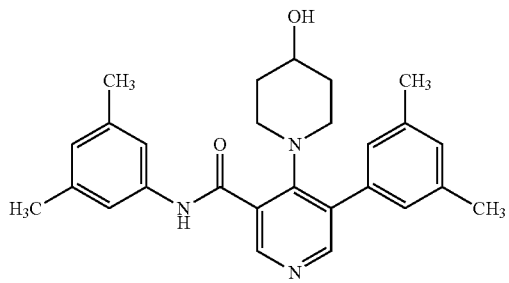

Using 4-hydroxypiperidine (CAS #5382-16-1) in place of 4-tert-butoxycarbonylaminopiperidine, using 3,5-dimethylphenylboronic acid (CAS #172975-69-8) in place of phenylboronic acid, the present invention compound having the following physical property values was obtained by following the same procedure as in Reference example 1→Reference example 3→Reference example 2.
Description: white powder;
Purity (UPLC-MS/ELSD): 99.4% (retention time: 0.73 min);
TLC: Rf 0.32 (n-hexane:ethyl acetate=1:1);
NMR (300 MHz, CHLOROFORM-d): δ 8.95 (s, 1H), 8.80 (s, 1H), 8.33 (s, 1H), 7.31 (s, 2H), 7.03 (s, 1H), 6.95 (s, 2H), 6.81 (s, 1H), 3.75-3.59 (m, 1H), 3.21-3.07 (m, 2H), 2.87-2.73 (m, 2H), 2.37 (s, 6H), 2.33 (s, 6H), 1.84-1.70 (m, 2H), 1.53-1.38 (m, 3H);
MASS (ESI, Pos.): 430 (M+H)+.

Reference Example 4 benzyl ((1-(3-(3,5-dimethylphenyl)-5-((3,5-dimethylphenyl)carbamoyl)pyridin-4-yl)-4-fluoropiperidin-4-yl)methyl)carbamate Using benzyl N-[(4-fluoro-4-piperidyl)methyl]carbamate (purchased from WUXIAPPTEC, catalog number: WXFS0319) in place of 4-tert-butoxycarbonylaminopiperidine, using 3,5-dimethylphenylboronic acid in place of phenylboronic acid, the present invention compound having the following physical property values was obtained by following the same procedure as in Reference example 1→Reference example 3→Reference example 2.
Description: white powder;
TLC: Rf 0.40 (n-hexane:ethyl acetate=1:1);
MASS (ESI, Pos.): 595 (M+H)+.

Example 4

4-[4-(aminomethyl)-4-fluoro-1-piperidinyl]-N,5-bis(3,5-dimethylphenyl)pyridine-3-carboxamide

[85]

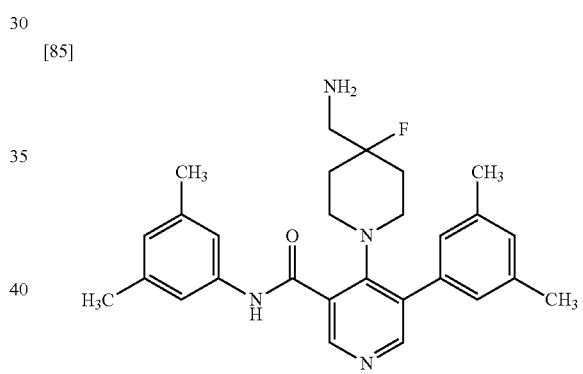

Under argon atmosphere, 10% palladium on carbon (ca.50% wet) (200 mg) was added to a ethanol (10 mL)/tetrahydrofuran (10 mL) solution of the compound puroduced in Reference example 4 at room temperature, the mixture was stirred for 3 hours under the hydrogen atmosphere. The reaction solution was filtered and the filtrate was concentrated. The obtained residue was purified by preparative medium pressure liquid chromatography (Yamazen Corp. YFLC-Wprep-2XY) (Hi-flash NH) (ethyl acetate:methanol=95:5) to obtain the present invention compound (290 mg) having the following physical property values.
Description: white powder;
Purity (UPLC-MS/ELSD): 100% (retention time: 0.56 min);
TLC: Rf 0.71 (ethyl acetate:methanol=9:1, NH silica gel);
NMR (300 MHz, CHLOROFORM-d) δ 9.08 (s, 1H), 8.83 (s, 1H), 8.36 (s, 1H), 7.28 (s, 2H), 7.04 (s, 1H), 6.94 (s, 2H), 6.81 (s, 1H), 3.12-2.96 (m, 4H), 2.69 (d, J=19.39 Hz, 2H), 2.37 (s, 6H), 2.33 (s, 6H), 1.83-1.43 (m, 6H);
MASS (ESI, Pos.): 461 (M+H)+.

Reference Example 5 methyl 4-[4-(tert-butoxycarbonylamino)-1-piperidyl]-5-(3,5-dimethylphenyl)pyridine-3-carboxylate Using 3,5-dimethylphenylboronic acid in place of phenylboronic acid, the title compound having the following physical property values was obtained by following the same procedure as in Reference example 2.

Description: pale yellow powder;
Purity (LC-MS/ELSD): 100% (retention time: 4.23 min);
TLC: Rf 0.14 (n-hexane:ethyl acetate=1:2);
MASS (ESI, Pos.): 440 (M+H)+.

Reference Example 6

4-[4-(tert-butoxycarbonylamino)-1-piperidyl]-5-(3,5-dimethylphenyl)pyridine-3-carboxylic acid To a methanol (10 mL) solution of the compound (220 mg) produced in Reference example 5 was added 2M aqueous solution of sodium hydroxide (2.00 mL), and the mixture was stirred at 45 degrees C. overnight. The reaction solution was neutralized by 2M hydrochloric acid (2.00 mL), and then the solvent was removed under reduced pressure. The obtained residue was diluted with saturated brine and extracted with ethyl acetate. The title compound obtained by concentrating the organic layer was used for next reaction without further purification.

Reference Example 7 tert-butyl N-[1-[3-(3,5-dimethylphenyl)-5-[(3,5-dimethylphenyl)carbamoyl]-4-pyridyl]-4-piperidyl] carbamate To a dichloromethane (5 mL) solution of the compound (<0.50 mmol) produced in Reference example 6 was added benzotriazol-1-yloxy-tri(pyrrolidino)phosphonium hexafluorophosphate (pyBOP) (390 mg), triethylamine (105 microL) and 3,5-dimethylaniline (91 mg) at room temperature, and the mixture was stirred for 15 hours. The reaction solution was purified by preparative medium pressure liquid chromatography (Yamazen Corp. YFLC-Wprep-2XY) (Hi-flash SI) (n-hexane:ethyl acetate=1:1) to obtain the title compound (239 mg) having the following charactaristics.
Description: pale yellowish white powder.

Example 5(1)-Example 5(14)

Using 4-tert-butoxycarbonylaminopiperidine, or a corresponding reagent in place of it, using 3,5-dimethylphenylboronic acid in place of phenylboronic acid, using 3,5-dimethylaniline, or a corresponding reagent in place of it, the present invention compounds having the following physical property values were obtained by following the same procedure as in Reference example 1→Reference example 2→Reference example 6→Reference example 7→Example 1.

Example 5(1)

4-(4-amino-1-piperidinyl)-N,5-bis(3,5-dimethylphenyl)pyridine-3-carboxamide

[86]

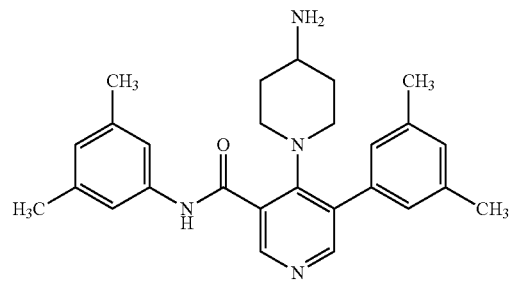

Description: pale yellow powder;
Purity (LC-MS/ELSD): 100% (retention time: 3.63 min);
TLC: Rf 0.42 (ethyl acetate:methanol=9:1, NH silica gel);
NMR (300 MHz, CHLOROFORM-d): δ 9.11 (s, 1H), 8.83 (s, 1H), 8.33 (s, 1H), 7.31 (s, 2H), 7.04 (s, 1H), 6.94 (s, 2H), 6.81 (s, 1H), 3.20-3.06 (m, 2H), 2.75 (s, 2H), 2.70-2.54 (m, 1H), 2.38 (s, 6H), 2.34 (s, 6H), 1.79-1.64 (m, 2H), 1.55 (br.s, 2H), 1.38-1.18 (m, 2H);
MASS (ESI, Pos.): 429 (M+H)+.

Example 5(2)

4-(4-amino-1-piperidinyl)-5-(3,5-dimethylphenyl)-N-(4,6-dimethyl-2-pyridyl)pyridine-3-carboxamide Description: white powder;
Purity (LC-MS/ELSD): 100% (retention time: 3.35 min);
TLC: Rf 0.65 (ethyl acetate:methanol=9:1, NH silica gel);
NMR (300 MHz, CHLOROFORM-d): δ 10.37 (br.s, 1H), 8.96 (s, 1H), 8.36 (s, 1H), 8.04 (s, 1H), 7.04 (s, 1H), 6.92 (s, 2H), 6.77 (s, 1H), 3.16-3.05 (m, 2H), 2.77-2.49 (m, 3H), 2.40 (s, 3H), 2.38 (s, 6H), 2.37 (s, 3H), 1.76-1.54 (m, 4H), 1.51 (br.s, 2H);
MASS (ESI, Pos.): 430 (M+H)+.

Example 5(3)

4-[(3-aminopropyl)amino]-N,5-bis(3,5-dimethylphenyl)pyridine-3-carboxamide

Description: white powder;
Purity (LC-MS/ELSD): 100% (retention time: 3.77 min);
TLC: Rf 0.47 (ethyl acetate:methanol=9:1, NH silica gel);
NMR (300 MHz, CHLOROFORM-d): δ 8.54 (s, 1H), 8.15 (s, 1H), 8.12-8.07 (m, 1H), 7.24-7.20 (m, 2H), 7.05-6.95 (m, 4H), 6.85-6.80 (m, 1H), 2.90-2.79 (m, 2H), 2.56 (t, J=6.80 Hz, 2H), 2.36 (s, 6H), 2.34 (s, 6H), 1.53-1.27 (m, 4H);
MASS (ESI, Pos.): 403 (M+H)+.

Example 5(4)

4-(4-amino-1-piperidinyl)-N-(3,4-difluorophenyl)-5-(3,5-dimethylphenyl)pyridine-3-carboxamide Description: white powder;
TLC: Rf 0.53 (ethyl acetate:methanol=9:1, NH silica gel);

NMR (300 MHz, CHLOROFORM-d): δ 9.84 (s, 1H), 8.94 (s, 1H), 8.36 (s, 1H), 7.94-7.84 (m, 1H), 7.24-7.10 (m, 2H), 7.05 (s, 1H), 6.91 (s, 2H), 3.16-3.05 (m, 2H), 2.79-2.59 (m, 3H), 2.38 (s, 6H), 1.80-1.68 (m, 2H), 1.54 (br.s, 2H), 1.36-1.20 (m, 2H);

MASS (APCI, Pos.): 437 (M+H)+.

Example 5(5)

4-(4-amino-1-piperidinyl)-N-(3-chloro-4-fluorophenyl)-5-(3,5-dimethylphenyl)pyridine-3-carboxamide Description: white powder;
TLC: Rf 0.55 (ethyl acetate:methanol=9:1, NH silica gel);
NMR (300 MHz, CHLOROFORM-d): δ 9.80 (br.s, 1H), 8.93 (s, 1H), 8.36 (s, 1H), 8.02-7.95 (m, 1H), 7.46-7.38 (m, 1H), 7.19-7.10 (m, 1H), 7.05 (s, 1H), 6.91 (s, 2H), 3.16-3.06 (m, 2H), 2.80-2.58 (m, 3H), 2.38 (s, 6H), 1.79-1.20 (m, 6H);
MASS (APCI, Pos.): 453 (M+H)+.

Example 5(6)

N,5-bis(3,5-dimethylphenyl)-4-(4-piperidinylamino)pyridine-3-carboxamide

Description: white powder;
Purity (UPLC-MS/ELSD): 99.6% (retention time: 0.67 min);
TLC: Rf 0.63 (ethyl acetate:methanol=9:1, NH silica gel);
NMR (300 MHz, CHLOROFORM-d): δ 8.61 (s, 1H), 8.14 (s, 1H), 8.07 (s, 1H), 7.24-7.21 (m, 2H), 7.05-7.02 (m, 1H), 6.99-6.95 (m, 2H), 6.83-6.81 (m, 1H), 6.53 (d, J=9.89 Hz, 1H), 3.01-2.82 (m, 3H), 2.36 (s, 6H), 2.34 (s, 6H), 2.24-2.13 (m, 2H), 1.70-1.61 (m, 2H), 1.54 (br.s, 1H), 1.19-1.05 (m, 2H);
MASS (ESI, Pos.): 429 (M+H)+.

Example 5(7)

N,5-bis(3,5-dimethylphenyl)-4-[4-(methylamino)-1-piperidyl]pyridine-3-carboxamide Description: white powder;
Purity (UPLC-MS/ELSD): 100% (retention time: 0.64 min);
TLC: Rf 0.63 (ethyl acetate:methanol=9:1, NH silica gel);
MASS (ESI, Pos.): 443 (M+H)+.

Example 5(8)

N,5-bis(3,5-dimethylphenyl)-4-(1-piperazinyl)pyridine-3-carboxamide

Description: pale yellow powder;
Purity (UPLC-MS/ELSD): 100% (retention time: 0.62 min);
TLC: Rf 0.72 (ethyl acetate:methanol=9:1, NH silica gel);
NMR (300 MHz, CHLOROFORM-d): δ 8.68 (s, 1H), 8.35 (s, 1H), 8.27 (br.s, 1H), 7.28 (s, 2H), 7.04 (s, 1H), 6.92 (s, 2H), 6.83 (s, 1H), 3.16-3.08 (m, 4H), 2.94-2.84 (m, 4H), 2.36 (s, 6H), 2.33 (s, 6H);
MASS (ESI, Pos.): 415 (M+H)+.

Example 5(9)

4-[3-(aminomethyl)-1-azetidinyl]-N,5-bis(3,5-dimethylphenyl)pyridine-3-carboxamide Description: ivory powder;
Purity (UPLC-MS/ELSD): 99.6% (retention time: 0.55 min);
TLC: Rf 0.40 (ethyl acetate:methanol=9:1, NH silica gel);
NMR (300 MHz, CHLOROFORM-d): δ 8.40 (s, 1H), 8.12 (s, 1H), 7.51 (br.s, 1H), 7.28 (br.s, 2H), 7.02-6.96 (m, 3H), 6.82 (br.s, 1H), 3.84-3.76 (m, 2H), 3.42-3.35 (m, 2H), 2.72 (d, J=7.0 Hz, 2H), 2.47-2.38 (m, 1H), 2.36 (s, 6H), 2.34 (s, 6H), 1.60-1.43 (m, 2H);
MASS (ESI, Pos.): 415 (M+H)+.

Example 5(10)

N,5-bis(3,5-dimethylphenyl)-4-[(3-piperidinylmethyl)amino]pyridine-3-carboxamide Description: white powder;
Purity (UPLC-MS/ELSD): 99.6% (retention time: 0.61 min);
TLC: Rf 0.60 (ethyl acetate:methanol=9:1, NH silica gel);
NMR (300 MHz, CHLOROFORM-d): δ 8.54 (s, 1H), 8.09 (s, 1H), 7.88 (br.s, 1H), 7.21 (s, 2H), 7.14-7.06 (m, 1H), 7.03-6.99 (m, 1H), 6.97 (s, 2H), 6.84-6.81 (m, 1H), 2.93-2.78 (m, 2H), 2.64-2.55 (m, 2H), 2.46-2.38 (m, 2H), 2.36 (s, 6H), 2.34 (s, 6H), 2.11-2.00 (m, 1H), 1.58 (br.s, 1H), 1.53-1.21 (m, 3H), 0.90-0.77 (m, 1H);
MASS (ESI, Pos.): 443 (M+H)+.

Example 5(11)

N,5-bis(3,5-dimethylphenyl)-4-{[2-(2-piperidinyl)ethyl]amino}pyridine-3-carboxamide Description: ivory powder;
Purity (UPLC-MS/ELSD): 99.9% (retention time: 0.61 min);
TLC: Rf 0.59 (ethyl acetate:methanol=9:1, NH silica gel);
NMR (300 MHz, CHLOROFORM-d): δ 8.55 (s, 1H), 8.11 (s, 1H), 7.99 (br.s, 1H), 7.23 (s, 2H), 7.02 (s, 1H), 6.98 (s, 2H), 6.82 (s, 1H), 6.78-6.71 (m, 1H), 2.97-2.88 (m, 2H), 2.86-2.77 (m, 1H), 2.36 (s, 6H), 2.34 (s, 6H), 2.45-2.23 (m, 2H), 1.75-1.17 (m, 8H), 0.97-0.81 (m, 1H);
MASS (ESI, Pos.): 457 (M+H)+.

Example 5(12)

4-(4-amino-1-piperidinyl)-5-(3,5-dimethylphenyl)-N-[3-(hydroxymethyl)-5-methylphenyl]pyridine-3-carboxamide Description: pale yellow powder;
Purity (UPLC-MS/ELSD): 99.1% (retention time: 0.49 min);
TLC: Rf 0.42 (ethyl acetate:methanol=9:1, NH silica gel);
NMR (300 MHz, CHLOROFORM-d): δ 9.81 (br.s, 1H), 8.96 (s, 1H), 8.37 (s, 1H), 7.83-7.79 (m, 1H), 7.30-7.28 (m, 1H), 7.06-7.04 (m, 1H), 6.91-6.89 (m, 3H), 4.67 (s, 2H), 3.19-3.00 (m, 2H), 2.81-2.58 (m, 3H), 2.39 (s, 3H), 2.37 (s, 6H), 1.73-1.39 (m, 7H);
MASS (ESI, Pos.): 445 (M+H)+.

Example 5(13)

4-(4-amino-1-piperidinyl)-5-(3,5-dimethylphenyl)-N-[3-(1-methyl-1H-pyrazol-3-yl)phenyl]pyridine-3-carboxamide Description: white powder;
Purity (UPLC-MS/ELSD): 97.5% (retention time: 0.56 min);
TLC: Rf 0.46 (ethyl acetate:methanol=9:1, NH silica gel);
NMR (300 MHz, CHLOROFORM-d): δ 9.92 (br.s, 1H), 8.99 (s, 1H), 8.36 (s, 1H), 8.00-7.89 (m, 2H), 7.56-7.51 (m, 1H), 7.46-7.39 (m, 1H), 7.37 (d, J=2.30 Hz, 1H), 7.06 (s, 1H), 6.93 (s, 2H), 6.59 (d, J=2.20 Hz, 1H), 3.93 (s, 3H), 3.08-3.21 (m, 2H), 2.65-2.82 (m, 2H), 2.52-2.67 (m, 1H), 2.39 (s, 6H), 1.82-1.33 (m, 6H);
MASS (ESI, Pos.): 481 (M+H)+.

Example 5(14)

4-(4-amino-1-piperidinyl)-5-(3,5-dimethylphenyl)-N-[3-(1,3,4-oxadiazol-2-yl)phenyl]pyridine-3-carboxamide Description: white powder;
Purity (UPLC-MS/ELSD): 99.6% (retention time: 0.50 min);
TLC: Rf 0.45 (ethyl acetate:methanol=9:1, NH silica gel);
NMR (300 MHz, CHLOROFORM-d): δ 10.21 (br.s, 1H), 9.01 (s, 1H), 8.48 (s, 1H), 8.40-8.36 (m, 2H), 8.09-8.02 (m, 1H), 7.90-7.84 (m, 1H), 7.60-7.53 (m, 1H), 7.06 (s, 1H), 6.93 (s, 2H), 3.19-3.10 (m, 2H), 2.81-2.69 (m, 2H), 2.69-2.58 (m, 1H), 2.39 (s, 6H), 1.83-1.25 (m, 6H);
MASS (ESI, Pos.): 469 (M+H)+.

Reference Example 8 tert-butyl N-[1-[3-(3,5-dimethylphenyl)-5-(hydroxymethyl)-4-pyridyl]-4-piperidyl]carbamate To a suspension of lithium aluminum hydride (326 mg) in tetrahydrofuran (6 mL) was added the tetrahydrofuran (15 mL) solution of the compound (945 mg) produced in Reference example 5 at 0 degrees C., and the mixture was stirred at room temperature for 2 hours. To the reaction solution was added saturated aqueous solution of sodium sulfate (5 mL) and tetrahydrofuran (30 mL), and stirred for 30 min. To the reaction solution was added sodium sulfate anhydrous, and filtered. After that the filtrate was concentrated. The obtained residue was purified by preparative medium pressure liquid chromatography (Yamazen Corp. YFLC-Wprep-2XY) (Hi-flash SI) (n-hexane:ethyl acetate=1:4) to obtain the title compound (460 mg) having the following physical property values.
Description: colorless oil;
TLC: Rf 0.30 (ethyl acetate);
MASS (ESI, Pos.): 412 (M+H)+.

Reference Example 9 tert-butyl N-[1-[3-[(3,5-dimethylphenoxy)methyl]-5-(3,5-dimethylphenyl)-4-pyridyl]-4-piperidyl]carbamate Under argon atmosphere, diisopropylazodicarboxylate (40 microL) was added to an anhydrous tetrahydrofuran (4 mL) solution of the compound (41 mg) produced in Reference example 8, 3,5-dimethylphenol (CAS #108-68-9) (24 mg) and triphenylphosphine (52 mg) at 0 degrees C., and the mixture was stirred at room temperature for 1 hour followed by concentration. The obtained residue was purified by preparative medium pressure liquid chromatography (Yamazen Corp. YFLC-Wprep-2XY) (Hi-flash SI) (n-hexane:ethyl acetate=1:1) to obtain the title compound (51 mg) having the following physical property values.
Description: colorless oil;
TLC: Rf 0.58 (n-hexane:ethyl acetate=1:1);
MASS (ESI, Pos.): 516 (M+H)+.

Example 6

1-[3-[(3,5-dimethylphenoxy)methyl]-5-(3,5-dimethylphenyl)-4-pyridyl]piperidin-4-amine

[87]

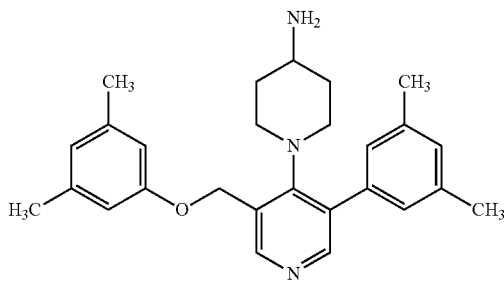

Using the compound produced in Reference example 9 in place of the compound produced in Reference example 3, the present invention compound (23 mg) having the following physical property values was obtained by following the same procedure as in Example 1.
Description: colorless oil;
Purity (LC-MS/ELSD): 100% (retention time: 3.81 min);
TLC: Rf 0.50 (ethyl acetate:methanol=9:1, NH silica gel);
NMR (300 MHz, CHLOROFORM-d): δ 8.55 (s, 1H), 8.29 (s, 1H), 6.99 (s, 1H), 6.91 (s, 2H), 6.63 (s, 1H), 6.61 (s, 2H), 5.06 (s, 2H), 3.09-3.01 (m, 2H), 2.66-2.55 (m, 3H), 2.37 (s, 6H), 2.30 (s, 6H), 1.69-1.60 (m, 2H), 1.51 (br.s, 2H), 1.33-1.23 (m, 2H);
MASS (ESI, Pos.): 416 (M+H)+.

Reference Example 10 tert-butyl N-[1-[3-(3,5-dimethylphenyl)-5-formyl-4-pyridyl]-4-piperidyl]carbamate To a dichloromethane (10 mL) solution of the compound (395 mg) produced in Reference example 8 was added Dess-Martin periodinate (814 mg) at room temperature, and the mixture was stirred for 2 hours. The reaction solution was purified by preparative medium pressure liquid chromatography (Yamazen Corp. YFLC-Wprep-2XY) (Hi-flash SI) (n-hexane:ethyl acetate=1:1) to obtain the title compound (400 mg) having the following physical property values.
Description: beige powder;
TLC: Rf 0.55 (n-hexane:ethyl acetate=1:1);
MASS (ESI, Pos.): 410 (M+H)+.

Reference Example 11 tert-butyl N-[1-[3-(3,5-dimethylphenyl)-5-[2-(3,5-dimethylphenyl)-1-hydroxyethyl]-4-pyridyl]-4-piperidyl]carbamate Under argon atmosphere, [(3,5-dimethylphenyl)methyl]magnesium bromide (CAS #111823-36-0) (10.6 mL, 0.25 mol/L in tetrahydrofuran) was added to an anhydrous tetrahydrofuran (10 mL) solution of the compound (360 mg) produced in Reference example 10 at 0 degrees C., and the mixture was stirred at room temperature for 1 hour. To the reaction solution was added saturated aqueous solution of ammonium chloride followed by extraction with ethyl acetate. The organic layer was washed, dried and concentrated. The obtained residue was purified by preparative medium pressure liquid chromatography (Yamazen Corp. YFLC-Wprep-2XY) (Hi-flash SI) (n-hexane:ethyl acetate=1:1) to obtain the title compound (466 mg) having the following physical property values.

Description: yellow oil;
TLC: Rf 0.31 (n-hexane:ethyl acetate=1:1).

Example 7

1-[4-(4-amino-1-piperidyl)-5-(3,5-dimethylphenyl)-3-pyridyl]-2-(3,5-dimethylphenyl)ethanone

[88]

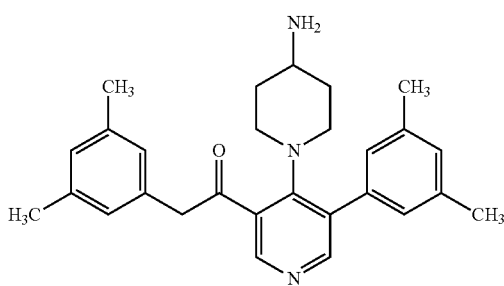

Using the compound produced in Reference example 11 in place of the compound produced in Reference example 8, the present invention compound (36 mg) having the following physical property values was obtained by following the same procedure as in Reference example 10→Example 1.

Description: pale yellow oil;
Purity (LC-MS/ELSD): 100% (retention time: 3.80 min);
TLC: Rf 0.65 (ethyl acetate:methanol=9:1, NH silica gel);
NMR (300 MHz, CHLOROFORM-d): δ 8.46 (s, 1H), 8.25 (s, 1H), 7.00 (s, 1H), 6.97 (s, 2H), 6.90 (s, 1H), 6.86 (s, 2H), 4.12 (s, 2H), 2.9-2.83 (m, 2H), 2.71-2.57 (m, 3H), 2.36 (s, 6H), 2.29 (s, 6H), 1.57-1.48 (m, 4H), 1.19-1.04 (m, 2H);
MASS (ESI, Pos.): 428 (M+H)+.

Reference Example 12 tert-butyl N-[1-[3-amino-5-(3,5-dimethylphenyl)-4-pyridyl]-4-piperidyl]carbamate Under argon atmosphere, diphenylphosphoryl azide (2.16 mL) was added to a 1,4-dioxane (30 mL) solution of the compound (2.20 g) produced in Reference example 6 and triethylamine (2.79 mL) at room temperature, and the mixture was stirred at 70 degrees C. for 1 hour. Water (3 mL) was added to the reaction solution and stirred at 70 degrees C. for 3 hours. After cooling to room temperature, the reaction solution was diluted with ethyl acetate and sequentially washed with water, saturated aqueous solution of sodium hydrogen carbonate and saturated brine. The organic layer was concentrated after drying. The obtained residue was purified by preparative medium pressure liquid chromatography (Yamazen Corp. YFLC-Wprep-2XY) (Hi-flash NH) (ethyl acetate:methanol=95:5) to obtain the title compound (1.12 g) having the following physical property values. Description; pale yellow amorphous;

TLC: Rf 0.41 (ethyl acetate, NH silica gel);
NMR (300 MHz, CHLOROFORM-d): δ 8.05 (s, 1H), 7.78 (s, 1H), 7.00 (s, 1H), 6.85 (s, 2H), 4.45-4.33 (m, 1H), 3.88 (s, 2H), 3.47-3.31 (m, 1H), 2.95-2.81 (m, 2H), 2.54-2.41 (m, 2H), 2.35 (s, 6H), 1.94-1.83 (m, 2H), 1.42 (s, 9H), 1.41-1.28 (m, 2H);
MASS (ESI, Pos.): 397 (M+H)+.

Reference Example 13 tert-butyl N-[1-[3-(3,5-dimethylphenyl)-5-[(3,5-dimethylphenyl)methylamino]-4-pyridyl]-4-piperidyl]carbamate To an anhydrous 1,2-dichloroethane (10 mL) solution of the compound (40 mg) produced in Reference example 12 and 3,5-dimethylbenzaldehyde (CAS #5779-95-3) (67 mg) was added sodium borohydride (76 mg) and methanol (10 mL) at room temperature, and the mixture was stirred at 80 degrees C. for 5 hours. The reaction solution was diluted with ethyl acetate and sequentially washed with water, saturated aqueous solution of sodium hydrogen carbonate and saturated brine. The organic layer was concentrated after drying. The obtained residue was purified by preparative medium pressure liquid chromatography (Yamazen Corp. YFLC-Wprep-2XY) (Hi-flash SI) (n-hexane:ethyl acetate=1:1) to obtain the title compound (22 mg) having the following physical property values.

Description: pale yellow oil;
TLC: Rf 0.62 (n-hexane:ethyl acetate=1:1).

Example 8(1)-Example 8(3)

Using a corresponding phenylboronic acid in place of phenylboronic acid, using 3,5-dimethylbenzaldehyde, or a corresponding reagent in place of it, the present invention compounds having the following physical property values were obtained by following the same procedure as in Reference example 1→Reference example 2→Reference example 6→Reference example 12→Reference example 13→Example 1.

Example 8(1)

4-(4-amino-1-piperidyl)-5-(3,5-dimethylphenyl)-N-[(3,5-dimethylphenyl)methyl]pyridin-3-amine

[89]

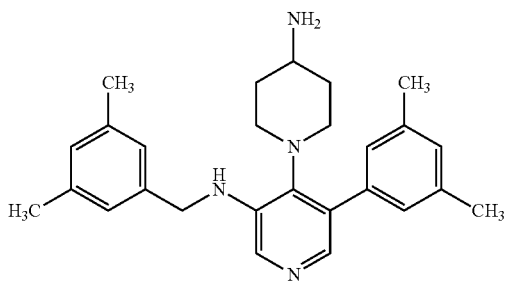

Description: pale yellow oil;
TLC: Rf 0.64 (ethyl acetate:methanol=9:1, NH silica gel);
NMR (300 MHz, CHLOROFORM-d): δ 7.93 (s, 1H), 7.76 (s, 1H), 7.03-6.97 (m, 3H), 6.92 (s, 1H), 6.90-6.84 (m, 2H), 4.79 (t, J=5.50 Hz, 1H), 4.33 (d, J=5.49 Hz, 2H), 2.97-2.84 (m, 2H), 2.65-2.39 (m, 3H), 2.36 (s, 6H), 2.32 (s, 6H), 1.80-1.65 (m, 2H), 1.54 (br.s, 2H), 1.33-1.16 (m, 2H)
MASS (ESI, Pos.): 415 (M+H)+.

Example 8(2)

4-(4-amino-1-piperidinyl)-5-(3,5-dimethylphenyl)-N-[(1-methyl-1H-pyrazol-4-yl)methyl]-3-pyridinamine Description: colorless oil;
Purity (UPLC-MS/ELSD): 100% (retention time: 0.57 min);
TLC: Rf 0.43 (ethyl acetate:methanol=9:1, NH silica gel);
NMR (300 MHz, CHLOROFORM-d): δ 7.98 (s, 1H), 7.78 (s, 1H), 7.50 (s, 1H), 7.36 (s, 1H), 7.00 (s, 1H), 6.86 (s, 2H), 4.58 (t, J=5.50 Hz, 1H), 4.26 (d, J=5.49 Hz, 2H), 3.90 (s, 3H), 2.91-2.80 (m, 2H), 2.65-2.51 (m, 1H), 2.46-2.38 (m, 2H), 2.35 (s, 6H), 1.72 (d, J=11.90 Hz, 2H), 1.57 (br.s, 2H), 1.31-1.15 (m, 2H);
MASS (ESI, Pos.): 391 (M+H)+.

Example 8(3)

4-(4-amino-1-piperidinyl)-N-(3-chlorobenzyl)-5-(3-fluoro-5-methylphenyl)-3-pyridinamine Description: yellow amorphous powder;
Purity (UPLC-MS/ELSD): 100% (retention time: 0.55 min);
TLC: Rf 0.64 (ethyl acetate:methanol=10:1, NH silica gel);
NMR (300 MHz, CHLOROFORM-d): δ 7.88 (s, 1H), 7.77 (s, 1H), 7.41-7.23 (m, 4H), 6.96-6.74 (m, 3H), 4.88 (t, J=5.7 Hz, 1H), 4.41 (d, J=5.7 Hz, 2H), 2.99-2.86 (m, 2H), 2.74-2.56 (m, 1H), 2.53-2.37 (m, 5H), 1.83-1.71 (m, 2H), 1.36-1.19 (m, 2H);
MASS (ESI, Pos.): 425 (M+H)+.

Example 9

N,5-bis(3,5-dimethylphenyl)-4-(4-oxo-1-piperidyl)pyridine-3-carboxamide

[90]

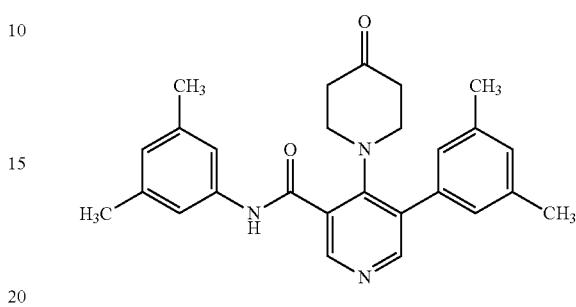

Using the compound produced in Example 3 in place of the compound produced in Reference example 8, the present invention compound (150 mg) having the following physical property values was obtained by following the same procedure as in Reference example 10.

Description: pale yellow powder;
Purity (UPLC-MS/ELSD): 99.4% (retention time: 0.80 min);
TLC: Rf 0.53 (n-hexane:ethyl acetate=1:1);
NMR (300 MHz, CHLOROFORM-d): δ 8.69 (s, 1H), 8.39 (s, 1H), 8.13 (s, 1H), 7.25 (s, 2H), 7.04 (s, 1H), 6.99 (s, 2H), 6.83 (s, 1H), 3.28 (t, J=6.04 Hz, 4H), 2.36 (s, 6H), 2.33 (s, 6H), 2.29 (t, J=6.00 Hz, 4H);
MASS (ESI, Pos.): 428 (M+H)+.

Example 10

4-[4-(dimethylamino)-1-piperidyl]-N,5-bis(3,5-dimethylphenyl)pyridine-3-carboxamide

[91]

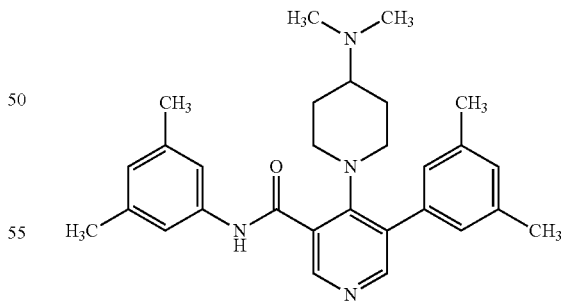

To an anhydrous 1,2-dichloroethane (10 mL) solution of the compound (115 mg) produced in Example 9 and dimethylamine (CAS #124-40-3) (1.35 mL, 2 mol/L in methanol) was added sodium triacetoxyborohydride (286 mg) at room temperature, and the mixture was stirred for 5 hours. The reaction solution was diluted with ethyl acetate and sequentially washed with water, saturated aqueous solution of sodium hydrogen carbonate and saturated brine. The organic layer was concentrated after drying. The obtained residue was purified by preparative medium pressure liquid chromatography (Yamazen Corp. YFLC-Wprep-2XY) (Hi-flash NH) (ethyl acetate:methanol=95:5) to obtain the present invention compound (111 mg) having the following physical property values.

Description: white powder;
Purity (UPLC-MS/ELSD): 98.9% (retention time: 0.59 min);
TLC: Rf 0.65 (ethyl acetate:methanol=9:1, NH silica gel);
NMR (300 MHz, CHLOROFORM-d): δ 9.19 (br.s, 1H), 8.86 (s, 1H), 8.32 (s, 1H), 7.33 (s, 2H), 7.05 (s, 1H), 6.93 (s, 2H), 6.79 (s, 1H), 3.25-3.15 (m, 3H), 2.77-2.65 (m, 2H), 2.38 (s, 6H), 2.32 (s, 6H), 2.19 (s, 6H), 1.69-1.42 (m, 4H);
MASS (ESI, Pos.): 457 (M+H)+.

Reference Example 14 tert-butyl N-[[1-(3-bromo-5-nitro-4-pyridyl)-4-piperidyl]methyl]carbamate

To a tetrahydrofuran (20 mL) solution of 3-bromo-4-chloro-5-nitropyridine (CAS #31872-63-6) (1.12 g) was added triethylamine (987 microL) and tert-butyl N-(4-piperidylmethyl)carbamate (CAS #135632-53-0) (2.63 g), and stirred at 70 degrees C. for 5 hours. After cooling to room temperature, the reaction solution was diluted with ethyl acetate, and sequentially washed with water and saturated brine. The organic layer was concentrated after drying. The obtained residue was purified by preparative medium pressure liquid chromatography (Yamazen Corp. YFLC-Wprep-2XY) (Hi-flash SI) (n-hexane:ethyl acetate=1:1) to obtain the title compound (1.80 g) having the following physical property values.
Description: pale yellow powder;
TLC: Rf 0.50 (n-hexane:ethyl acetate=1:1).

Reference Example 15 tert-butyl N-[[1-[3-(3,5-dimethylphenyl)-5-nitro-4-pyridyl]-4-piperidyl]methyl]carbamate Using the compound produced in Reference example 14 in place of the compound produced in Reference example 1, using 3,5-dimethylphenylboronic acid in place of phenylboronic acid, the title compound having the following physical property values was obtained by following the same procedure as in Reference example 2.
Description: orange powder;
TLC: Rf 0.50 (n-hexane:ethyl acetate=1:1);
MASS (ESI, Pos.): 441 (M+H)+.

Reference Example 16 tert-butyl N-[[1-[3-amino-5-(3,5-dimethylphenyl)-4-pyridyl]-4-piperidyl]methyl]carbamate Under argon atmosphere, 20 wt % palladium hydroxide on carbon (Pd(OH)$_2$—C) (500 mg, 50 wt % wet) was added to the ethanol (40 mL) solution of the compound (1.90 g) produced in Reference example 15, and the mixture was stirred for 8 hours under hydrogen atmosphere. The reaction solution was filtered and the filtrate was concentrated. The obtained residue was purified by preparative medium pressure liquid chromatography (Yamazen Corp. YFLC-Wprep-2XY) (Hi-flash NH) (ethyl acetate) to obtain the title compound (1.77 g) having the following physical property values.
Description: colorless oil;
TLC: Rf 0.50 (ethyl acetate, NH silica gel);
MASS (ESI, Pos.): 411 (M+H)+.

Reference Example 17 tert-butyl N-[[1-[3-[(3,5-dimethylbenzoyl)amino]-5-(3,5-dimethylphenyl)-4-pyridyl]-4-piperidyl]methyl]carbamate To an anhydrous pyridine (3 mL) solution of the compound produced in Reference example 16 was added 3,5-dimethylbenzoylchloride (CAS #6613-44-1) (222 microL) at room temperature, and stirred for 1 hour. After adding water, the mixture was extracted with ethyl acetate and washed with saturated brine. The organic layer was concentrated after drying. The obtained residue was purified by preparative medium pressure liquid chromatography (Yamazen Corp. YFLC-Wprep-2XY) (Hi-flash SI) (n-hexane:ethyl acetate=1:1) to obtain the title compound (128 mg) having the following physical property values.
Description: colorless amorphous powder;
TLC: Rf 0.41 (n-hexane:ethyl acetate=1:1);
MASS (ESI, Pos.): 543 (M+H)+.

Example 11(1)-Example 11(68)

Using 3-bromo-4-chloro-5-nitropyridine, or a corresponding reagent in place of it, using tert-butyl N-(4-piperidylmethyl)carbamate, or a corresponding reagent in place of it, using a corresponding reagent in place of phenylboronic acid, using 3,5-dimethylbenzoyl chloride, or a corresponding reagent in place of it, the present invention compounds having the following physical property values were obtained by following the same procedure as in Reference example 14→Reference example 2→Reference example 16→Reference example 17→Example 1.

Example 11(1)

N-[4-(4-amino-1-piperidinyl)-5-(3,5-dimethylphenyl)-3-pyridinyl]-3-fluorobenzamide

[92]

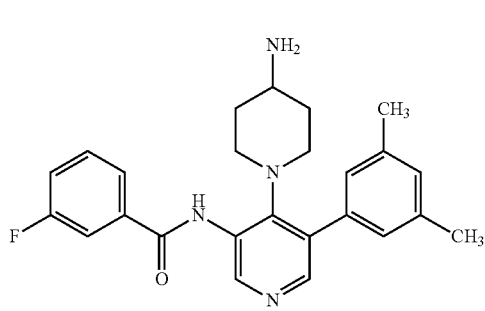

Purity (LC-MS/ELSD): 100% (retention time: 0.51 min);
MASS (ESI, Pos.): 419 (M+H)+.

Example 11(2)

N-[4-(4-amino-1-piperidinyl)-5-(3,5-dimethylphenyl)-3-pyridinyl]-3-chlorobenzamide Purity (LC-MS/ELSD): 100% (retention time: 0.54 min); MASS (ESI, Pos.): 435 (M+H)+.

Example 11(3)

N-[4-(4-amino-1-piperidinyl)-5-(3,5-dimethylphenyl)-3-pyridinyl]-3,5-difluorobenzamide Purity (LC-MS/ELSD): 100% (retention time: 0.52 min); MASS (ESI, Pos.): 437 (M+H)+.

Example 11(4)

N-[4-(4-amino-1-piperidinyl)-5-(3,5-dimethylphenyl)-3-pyridinyl]-3-chloro-4-fluorobenzamide Purity (LC-MS/ELSD): 100% (retention time: 0.55 min); MASS (ESI, Pos.): 453 (M+H)+.

Example 11(5)

N-[4-(4-amino-1-piperidinyl)-5-(3,5-dimethylphenyl)-3-pyridinyl]-4-(5-methyl-1,2,4-oxadiazol-3-yl)benzamide Purity (LC-MS/ELSD): 73% (retention time: 0.55 min); MASS (ESI, Pos.): 483 (M+H)+.

Example 11(6)

N-[4-(4-amino-1-piperidinyl)-5-(3,5-dimethylphenyl)-3-pyridinyl]-2-pyridinecarboxamide Purity (LC-MS/ELSD): 99% (retention time: 0.53 min); MASS (ESI, Pos.): 402 (M+H)+.

Example 11(7)

N-[4-(4-amino-1-piperidinyl)-5-(3,5-dimethylphenyl)-3-pyridinyl]pyridine-4-carboxamide Purity (LC-MS/ELSD): 100% (retention time: 0.46 min); MASS (ESI, Pos.): 402 (M+H)+.

Example 11(8)

N-[4-(4-amino-1-piperidinyl)-5-(3,5-dimethylphenyl)-3-pyridinyl]-1,3-thiazole-4-carboxamide Purity (LC-MS/ELSD): 100% (retention time: 0.50 min); MASS (ESI, Pos.): 408 (M+H)+.

Example 11(9)

N-[4-(4-amino-1-piperidinyl)-5-(3,5-dimethylphenyl)-3-pyridinyl]-4-methoxybenzamide Purity (LC-MS/ELSD): 100% (retention time: 0.51 min); MASS (ESI, Pos.): 431 (M+H)+.

Example 11(10)

N-[4-(4-amino-1-piperidinyl)-5-(3,5-dimethylphenyl)-3-pyridinyl]-3-methoxybenzamide Purity (LC-MS/ELSD): 100% (retention time: 0.52 min); MASS (ESI, Pos.): 431 (M+H)+.

Example 11(11)

N-[4-(4-amino-1-piperidinyl)-5-(3,5-dimethylphenyl)-3-pyridinyl]-2-fluorobenzamide Purity (LC-MS/ELSD): 100% (retention time: 0.52 min); MASS (ESI, Pos.): 419 (M+H)+.

Example 11(12)

N-[4-(4-amino-1-piperidinyl)-5-(3,5-dimethylphenyl)-3-pyridinyl]-3,5-dimethoxybenzamide Purity (LC-MS/ELSD): 100% (retention time: 0.55 min); MASS (ESI, Pos.): 461 (M+H)+.

Example 11(13)

N-[4-(4-amino-1-piperidinyl)-5-(3,5-dimethylphenyl)-3-pyridinyl]-1-methyl-1H-imidazole-5-carboxamide Purity (LC-MS/ELSD): 100% (retention time: 0.44 min); MASS (ESI, Pos.): 405 (M+H)+.

Example 11(14)

N-[4-(4-amino-1-piperidinyl)-5-(3,5-dimethylphenyl)-3-pyridinyl]-5-methyl-1,2-oxazole-3-carboxamide Purity (LC-MS/ELSD): 100% (retention time: 0.52 min); MASS (ESI, Pos.): 406 (M+H)+.

Example 11(15)

N-[4-(4-amino-1-piperidinyl)-5-(3,5-dimethylphenyl)-3-pyridinyl]-1,3-thiazole-2-carboxamide Purity (LC-MS/ELSD): 100% (retention time: 0.54 min); MASS (ESI, Pos.): 408 (M+H)+.

Example 11(16)

N-[4-(4-amino-1-piperidinyl)-5-(3,5-dimethylphenyl)-3-pyridinyl]pyridine-3-carboxamide Purity (LC-MS/ELSD): 100% (retention time: 0.47 min); MASS (ESI, Pos.): 402 (M+H)+.

Example 11(17)

N-[4-(4-amino-1-piperidinyl)-5-(3,5-dimethylphenyl)-3-pyridinyl]-1-methyl-1H-imidazole-4-carboxamide Purity (LC-MS/ELSD): 100% (retention time: 0.49 min); MASS (ESI, Pos.): 405 (M+H)+.

Example 11(18)

N-[4-(4-amino-1-piperidinyl)-5-(3,5-dimethylphenyl)-3-pyridinyl]-5-methyl-1,2-oxazole-4-carboxamide Purity (LC-MS/ELSD): 99% (retention time: 0.56 min); MASS (ESI, Pos.): 406 (M+H)+.

Example 11(19)

N-[4-(4-amino-1-piperidinyl)-5-(3,5-dimethylphenyl)-3-pyridinyl]-1,5-dimethyl-1H-pyrazole-3-carboxamide Purity (LC-MS/ELSD): 100% (retention time: 0.51 min); MASS (ESI, Pos.): 419 (M+H)+.

Example 11(20)

N-[4-(4-amino-1-piperidinyl)-5-(3,5-dimethylphenyl)-3-pyridinyl]-5-(methylsulfonyl)-2-thiophenecarboxamide Purity (LC-MS/ELSD): 95% (retention time: 0.53 min); MASS (ESI, Pos.): 485 (M+H)+.

Example 11(21)

N-[4-(4-amino-1-piperidinyl)-5-(3,5-dimethylphenyl)-3-pyridinyl]-1-methyl-1H-pyrazole-4-carboxamide Purity (LC-MS/ELSD): 100% (retention time: 0.46 min); MASS (ESI, Pos.): 405 (M+H)+.

Example 11(22)

N-[4-(4-amino-1-piperidinyl)-5-(3,5-dimethylphenyl)-3-pyridinyl]-1,3-dimethyl-1H-pyrazole-4-carboxamide Purity (LC-MS/ELSD): 100% (retention time: 0.48 min); MASS (ESI, Pos.): 419 (M+H)+.

Example 11(23)

N-[4-(4-amino-1-piperidinyl)-5-(3,5-dimethylphenyl)-3-pyridinyl]-1,3-thiazole-5-carboxamide Purity (LC-MS/ELSD): 100% (retention time: 0.48 min); MASS (ESI, Pos.): 408 (M+H)+.

Example 11(24)

5-acetyl-N-[4-(4-amino-1-piperidinyl)-5-(3,5-dimethylphenyl)-3-pyridinyl]-2-thiophenecarboxamide Purity (LC-MS/ELSD): 99% (retention time: 0.53 min); MASS (ESI, Pos.): 449 (M+H)+.

Example 11(25)

N-[4-(4-amino-1-piperidinyl)-5-(3,5-dimethylphenyl)-3-pyridinyl]-4,6-dimethoxy-2-pyrimidinecarboxamide Purity (LC-MS/ELSD): 100% (retention time: 0.52 min); MASS (ESI, Pos.): 463 (M+H)+.

Example 11(26)

N-[4-(4-amino-1-piperidinyl)-5-(3,5-dimethylphenyl)-3-pyridinyl]-1,3-oxazole-2-carboxamide Purity (LC-MS/ELSD): 100% (retention time: 0.50 min); MASS (ESI, Pos.): 392 (M+H)+.

Example 11(27)

N-[4-(4-amino-1-piperidinyl)-5-(3,5-dimethylphenyl)-3-pyridinyl]-5-methyl-1,3-thiazole-2-carboxamide Purity (LC-MS/ELSD): 100% (retention time: 0.56 min); MASS (ESI, Pos.): 422 (M+H)+.

Example 11(28)

N-[4-(4-amino-1-piperidinyl)-5-(3,5-dimethylphenyl)-3-pyridinyl]-1,3-oxazole-4-carboxamide Purity (LC-MS/ELSD): 100% (retention time: 0.49 min); MASS (ESI, Pos.): 392 (M+H)+.

Example 11(29)

N-[4-(4-amino-1-piperidinyl)-5-(3,5-dimethylphenyl)-3-pyridinyl]-4-methyl-1,3-oxazole-5-carboxamide Purity (LC-MS/ELSD): 100% (retention time: 0.50 min); MASS (ESI, Pos.): 406 (M+H)+.

Example 11(30)

N-[4-(4-amino-1-piperidinyl)-5-(3,5-dimethylphenyl)-3-pyridinyl]-1-methyl-1H-pyrazole-5-carboxamide Purity (LC-MS/ELSD): 97% (retention time: 0.49 min); MASS (ESI, Pos.): 405 (M+H)+.

Example 11(31)

N-[4-(4-amino-1-piperidinyl)-5-(3,5-dimethylphenyl)-3-pyridinyl]-1-methyl-1H-pyrazole-3-carboxamide Purity (LC-MS/ELSD): 100% (retention time: 0.50 min); MASS (ESI, Pos.): 405 (M+H)+.

Example 11(32)

N-[4-(4-amino-1-piperidinyl)-5-(3,5-dimethylphenyl)-3-pyridinyl]-1,5-dimethyl-1H-1,2,3-triazole-4-carboxamide Purity (LC-MS/ELSD): 100% (retention time: 0.53 min);
MASS (ESI, Pos.): 420 (M+H)+.

Example 11(33)

N-[4-(4-amino-1-piperidinyl)-5-(3,5-dimethylphenyl)-3-pyridinyl]-4-methyl-1,3-thiazole-2-carboxamide Purity (LC-MS/ELSD): 100% (retention time: 0.55 min);
MASS (ESI, Pos.): 422 (M+H)+.

Example 11(34)

N-[4-(4-amino-1-piperidinyl)-5-(3,5-dimethylphenyl)-3-pyridinyl]-2,5-dimethyl-1,3-thiazole-4-carboxamide Purity (LC-MS/ELSD): 100% (retention time: 0.57 min);
MASS (ESI, Pos.): 436 (M+H)+.

Example 11(35)

N-[4-(4-amino-1-piperidinyl)-5-(3,5-dimethylphenyl)-3-pyridinyl]-2-methyl-1,3-oxazole-4-carboxamide Purity (LC-MS/ELSD): 99% (retention time: 0.50 min);
MASS (ESI, Pos.): 406 (M+H)+.

Example 11(36)

N-[4-(4-amino-1-piperidinyl)-5-(3,5-dimethylphenyl)-3-pyridinyl][1,2,4]triazolo[1,5-a]pyrimidine-2-carboxamide Purity (LC-MS/ELSD): 99% (retention time: 0.51 min);
MASS (ESI, Pos.): 443 (M+H)+.

Example 11(37)

N-[4-(4-amino-1-piperidinyl)-5-(3,5-dimethylphenyl)-3-pyridinyl]-2-methyl-1,3-thiazole-4-carboxamide Purity (LC-MS/ELSD): 96% (retention time: 0.53 min);
MASS (ESI, Pos.): 422 (M+H)+.

Example 11(38)

N-[4-(4-amino-1-piperidinyl)-5-(3,5-dimethylphenyl)-3-pyridinyl]benzamide

Purity (LC-MS/ELSD): 100% (retention time: 0.50 min);
MASS (ESI, Pos.): 401 (M+H)+.

Example 11(39)

N-[4-(4-amino-1-piperidinyl)-5-(3,5-dimethylphenyl)-3-pyridinyl]-3,5-dimethylbenzamide Description: white powder;
Purity (UPLC-MS/ELSD): 99.9% (retention time: 0.50 min);
TLC: Rf 0.64 (ethyl acetate:methanol=9:1, NH silica gel);
NMR (300 MHz, CHLOROFORM-d): δ 9.70 (s, 1H), 9.04 (s, 1H), 8.13 (s, 1H), 7.56 (s, 2H), 7.21 (s, 1H), 7.05 (s, 1H), 6.89 (s, 2H), 2.94-2.83 (m, 2H), 2.67-2.49 (m, 3H), 2.41 (s, 6H), 2.38 (s, 6H), 1.81 (d, J=9.52 Hz, 2H), 1.70-1.23 (m, 4H);
MASS (ESI, Pos.): 429 (M+H)+.

Example 11(40)

benzyl [4-(4-amino-1-piperidinyl)-5-(3,5-dimethylphenyl)-3-pyridinyl]carbamate

Description: white powder;
Purity (UPLC-MS/ELSD): 100% (retention time: 0.56 min);
TLC: Rf 0.61 (ethyl acetate:methanol=9:1, NH silica gel);
NMR (300 MHz, CHLOROFORM-d): δ 9.21 (br.s, 1H), 8.06 (s, 1H), 7.48-7.30 (m, 6H), 7.02 (s, 1H), 6.85 (s, 2H), 5.26 (s, 2H), 2.86-2.75 (m, 2H), 2.66-2.40 (m, 3H), 2.36 (s, 6H), 1.82-1.24 (m, 6H);
MASS (ESI, Pos.): 431 (M+H)+.

Example 11(41)

N-[4-[4-(aminoethyl)-1-piperidyl]-5-(3,5-dimethylphenyl)-3-pyridyl]-3,5-dimethylbenzamide Description: white powder;
Purity (UPLC-MS/ELSD): 100% (retention time: 0.56 min);
TLC: Rf 0.52 (ethyl acetate:methanol=9:1, NH silica gel);
NMR (300 MHz, CHLOROFORM-d): δ 9.73 (s, 1H), 9.17 (s, 1H), 8.14 (s, 1H), 7.57 (s, 2H), 7.21 (s, 1H), 7.05 (s, 1H), 6.90 (s, 2H), 2.95-2.85 (m, 2H), 2.61-2.48 (m, 4H), 2.40 (s, 6H), 2.38 (s, 6H), 1.81-1.67 (m, 2H), 1.46 (br.s, 2H), 1.30-1.10 (m, 3H);
MASS (ESI, Pos.): 443 (M+H)+.

Example 11(42)

N-{4-[4-(2-aminoethyl)-1-piperidinyl]-5-(3,5-dimethylphenyl)-3-pyridinyl}-3,5-dimethylbenzamide Description: white powder;
Purity (UPLC-MS/ELSD): 100% (retention time: 0.59 min);
TLC: Rf 0.48 (ethyl acetate:methanol=9:1, NH silica gel);
NMR (300 MHz, CHLOROFORM-d): δ 9.73 (s, 1H), 9.16 (s, 1H), 8.12 (s, 1H), 7.58 (s, 2H), 7.21 (s, 1H), 7.05 (s, 1H), 6.89 (s, 2H), 2.93-2.83 (m, 2H), 2.74-2.65 (m, 2H), 2.58-2.46 (m, 2H), 2.41 (s, 6H), 2.38 (s, 6H), 1.74-1.15 (m, 9H);
MASS (ESI, Pos.): 457 (M+H)+.

Example 11(43)

N-[4-(4-amino-1-piperidinyl)-5-(3,5-dimethylphenyl)-3-pyridinyl]-3-hydroxybenzamide Description: white powder;
Purity (UPLC-MS/ELSD): 99.9% (retention time: 0.47 min);
TLC: Rf 0.42 (ethyl acetate:methanol=4:1, NH silica gel);
NMR (300 MHz, CHLOROFORM-d): δ 9.67 (s, 1H), 8.39 (s, 1H), 8.05 (s, 1H), 7.46-7.31 (m, 3H), 7.05-6.94 (m, 4H), 2.99-2.89 (m, 2H), 2.75-2.56 (m, 2H), 2.47-2.37 (m, 1H), 2.33 (s, 6H), 1.49-1.37 (m, 2H), 1.13-0.98 (m, 2H);
MASS (ESI, Pos.): 417 (M+H)+.

Example 11(44)

N-{4-[(3-amino-2,2-dimethylpropyl)amino]-5-(3,5-dimethylphenyl)-3-pyridinyl}-3,5-dimethylbenzamide Description: beige powder;
Purity (UPLC-MS/ELSD): 99.9% (retention time: 0.54 min);
TLC: Rf 0.60 (ethyl acetate:methanol=9:1, NH silica gel);
NMR (300 MHz, CHLOROFORM-d): δ 9.36 (s, 1H), 8.67 (s, 1H), 8.06 (s, 1H), 7.51 (s, 2H), 7.17 (s, 1H), 7.03 (s, 1H), 6.99 (s, 2H), 4.76 (br.s, 1H), 2.95 (s, 2H), 2.46 (s, 2H), 2.38 (s, 6H), 2.36 (s, 6H), 1.60 (br.s, 2H), 0.69 (s, 6H);
MASS (ESI, Pos.): 431 (M+H)+.

Example 11(45)

N-{4-[(3-aminopentyl)amino]-5-(3,5-dimethylphenyl)-3-pyridinyl}-3,5-dimethylbenzamide Description: brown viscous oil;
Purity (UPLC-MS/ELSD): 99.7% (retention time: 0.54 min);
TLC: Rf 0.63 (ethyl acetate:methanol=9:1, NH silica gel);
NMR (300 MHz, CHLOROFORM-d): δ 8.77 (br.s., 1H), 8.64 (s, 1H), 8.07 (s, 1H), 7.53 (s, 2H), 7.19 (s, 1H), 7.02 (s, 1H), 6.99 (s, 2H), 6.96 (s, 1H), 3.25-3.13 (m, 1H), 3.05-2.92 (m, 1H), 2.54-2.43 (m, 1H), 2.39 (s, 6H), 2.36 (s, 6H), 1.80-1.03 (m, 6H), 0.77 (t, J=7.40 Hz, 3H);
MASS (ESI, Pos.): 431 (M+H)+.

Example 11(46)

methyl 3-{[4-(4-amino-1-piperidinyl)-5-(3,5-dimethylphenyl)-3-pyridinyl]carbamoyl}benzoate Description: white powder;
Purity (UPLC-MS/ELSD): 100% (retention time: 0.51 min);
TLC: Rf 0.50 (ethyl acetate:methanol=9:1, NH silica gel);
NMR (300 MHz, CHLOROFORM-d): δ 9.76 (s, 1H), 9.49 (s, 1H), 8.65-8.60 (m, 1H), 8.35-8.31 (m, 1H), 8.26-8.22 (m, 1H), 8.16 (s, 1H), 7.69-7.63 (m, 1H), 7.07 (s, 1H), 6.90 (s, 2H), 3.97 (s, 3H), 2.96-2.84 (m, 2H), 2.65-2.52 (m, 3H), 2.38 (s, 6H), 1.92-1.78 (m, 2H), 1.70-1.39 (m, 4H);
MASS (ESI, Pos.): 459 (M+H)+.

Example 11(47)

3-{[4-(4-amino-1-piperidinyl)-5-(3,5-dimethylphenyl)-3-pyridinyl]carbamoyl}benzoic acid dihydrochloride Description: beige powder;
Purity: (UPLC-MS/ELSD): 100% (retention time: 0.51 min);
TLC: Rf 0.68 (methanol: 28% NH₃(aq)=19:1)
NMR (300 MHz, CHLOROFORM-d): δ 8.73 (d, J=1.46 Hz, 1H), 8.59 (d, J=1.28 Hz, 1H), 8.37-8.29 (m, 2H), 8.23 (d, J=1.28 Hz, 1H), 7.73 (t, J=7.78 Hz, 1H), 7.18 (s, 1H), 7.10 (s, 2H), 3.66-3.56 (m, 2H), 3.23-3.11 (m, 1H), 3.06-2.91 (m, 2H), 2.42 (s, 6H), 1.87-1.74 (m, 2H), 1.60-1.39 (m, 2H);
MASS (ESI, Pos.): 445 (M+H)+.

Example 11(48)

N-{4-[(3-aminopropyl)(methyl)amino]-5-(3,5-dimethylphenyl)-3-pyridinyl}-3,5-dimethylbenzamide Description: white powder;
Purity (UPLC-MS/ELSD): 99.9% (retention time: 0.56 min);
TLC: Rf 0.50 (ethyl acetate:methanol=9:1, NH silica gel);
NMR (300 MHz, CHLOROFORM-d): δ 9.63 (s, 1H), 9.30 (s, 1H), 8.14 (s, 1H), 7.52 (s, 2H), 7.20 (s, 1H), 7.05 (s, 1H), 6.90 (s, 2H), 2.71 (s, 3H), 2.62-2.55 (m, 4H), 2.40 (s, 6H), 2.37 (s, 6H), 1.55-1.40 (m, 2H), 1.19 (br.s., 2H);
MASS (ESI, Pos.): 417 (M+H)+.

Example 11(49)

N-{4-[4-(aminomethyl)-1-piperidinyl]-5-(3,5-dimethylphenyl)-3-pyridinyl}benzamide Description: white powder;
Purity (UPLC-MS/ELSD): 99.9% (retention time: 0.51 min);
TLC: Rf 0.55 (ethyl acetate:methanol=9:1, NH silica gel);
NMR (300 MHz, CHLOROFORM-d): δ 9.70 (s, 1H), 9.12 (s, 1H), 8.15 (s, 1H), 7.99-7.90 (m, 2H), 7.62-7.47 (m, 3H), 7.05 (s, 1H), 6.90 (s, 2H), 2.96-2.84 (m, 2H), 2.61-2.47 (m, 4H), 2.37 (s, 6H), 1.78-1.09 (m, 7H);
MASS (ESI, Pos.): 415 (M+H)+.

Example 11(50)

N-{4-[4-(aminomethyl)-4-hydroxy-1-piperidinyl]-5-(2,5-difluorophenyl)-3-pyridinyl}-3-chloro-4-fluorobenzamide Description: white powder;
Purity (UPLC-MS/ELSD): 99.9% (retention time: 0.48 min);
TLC: Rf 0.37 (ethyl acetate:methanol=9:1, NH silica gel);
NMR (300 MHz, CHLOROFORM-d): δ 9.65 (s, 1H), 8.96 (s, 1H), 8.15 (s, 1H), 7.98 (dd, J=6.77, 2.20 Hz, 1H), 7.86 (ddd, J=8.51, 4.39, 2.10 Hz, 1H), 7.37-7.25 (m, 1H), 7.23-7.10 (m, 2H), 7.07-6.91 (m, 1H), 3.08-2.91 (m, 2H), 2.85-2.68 (m, 2H), 2.58 (s, 2H), 1.95-1.35 (m, 7H);
MASS (ESI, Pos.): 491 (M+H)+.

Example 11(51)

N-{4-[4-(aminomethyl)-1-piperidinyl]-5-(3,5-dimethylphenyl)-3-pyridinyl}-3,5-dimethoxybenzamide Description: white powder;
Purity (UPLC-MS/ELSD): 99.9% (retention time: 0.54 min);
TLC: Rf 0.48 (ethyl acetate:methanol=9:1, NH silica gel);
NMR (300 MHz, CHLOROFORM-d): δ 9.70 (s, 1H), 9.15 (s, 1H), 8.14 (s, 1H), 7.08 (d, J=2.20 Hz, 2H), 7.05 (s, 1H), 6.89 (s, 2H), 6.65 (t, J=2.20 Hz, 1H), 3.85 (s, 6H), 2.95-2.84 (m, 2H), 2.61-2.47 (m, 4H), 2.37 (s, 6H), 1.77-1.14 (m, 7H);
MASS (ESI, Pos.): 475 (M+H)+.

Example 11(52)

N-[4-{[(3-aminopropyl)[2-(benzyloxy)ethyl]amino}-5-(3,5-dimethylphenyl)-3-pyridinyl]-3,5-dimethylbenzamide Description: yellow oil;
TLC: Rf 0.60 (ethyl acetate:methanol=9:1, NH silica gel);
NMR (300 MHz, CHLOROFORM-d): δ 9.79 (s, 1H), 9.69 (s, 1H), 8.12 (s, 1H), 7.51 (s, 2H), 7.24-7.17 (m, 3H), 7.09 (s, 2H), 7.06-6.98 (m, 3H), 6.88 (s, 2H), 4.09 (s, 2H), 3.32 (t, J=4.9 Hz, 2H), 2.98 (t, J=4.9 Hz, 2H), 2.68 (t, J=7.1 Hz, 2H), 2.56 (t, J=7.0 Hz, 2H), 2.34 (s, 6H), 2.31 (s, 6H), 1.56-1.19 (m, 4H);
MASS (APCI, Pos.): 537 (M+H)+.

Example 11(53)

N-{4-[(3-aminopropyl)(2-hydroxyethyl)amino]-5-(3,5-dimethylphenyl)-3-pyridinyl}-3,5-dimethylbenzamide Description: white powder;
TLC: Rf 0.12 (ethyl acetate:methanol: 28% ammonia water=9:1:0.1);
NMR (300 MHz, CHLOROFORM-d): δ 10.00 (br.s., 1H), 9.75 (d, J=0.7 Hz, 1H), 8.10 (d, J=0.7 Hz, 1H), 7.63 (s, 2H), 7.16 (s, 1H), 7.04 (s, 1H), 6.90 (s, 2H), 3.72 (br.s., 2H), 3.11 (br.s., 2H), 2.79-2.50 (m, 4H), 2.38 (s, 6H), 2.37 (s, 6H), 2.01-1.36 (m, 2H), 1.37-1.16 (m, 2H);
MASS (APCI, Pos.): 447 (M+H)+.

Example 11(54)

N-{4-[(4-amino-2-butanyl)amino]-5-(3,5-dimethylphenyl)-3-pyridinyl}-3,5-dimethylbenzamide Description: white powder;
TLC: Rf 0.43 (ethyl acetate:methanol=9:1, NH silica gel);
NMR (300 MHz, CHLOROFORM-d): δ 9.42 (br.s., 1H), 8.69 (s, 1H), 8.05 (s, 1H), 7.51 (s, 2H), 7.33-7.23 (m, 1H), 7.17 (s, 1H), 7.04 (s, 1H), 6.97 (s, 2H), 3.59-3.80 (m, 1H), 2.79-2.55 (m, 2H), 2.39 (s, 6H), 2.38-2.27 (m, 6H), 1.65-1.13 (m, 4H), 0.93 (d, J=6.2 Hz, 3H);
MASS (APCI, Pos.): 417 (M+H)+.

Example 11(55)

N-{4-[3-(aminomethyl)-1-pyrrolidinyl]-5-(3,5-dimethylphenyl)-3-pyridinyl}-3-chloro-4-fluorobenzamide Description: orange powder;
Purity (UPLC-MS/ELSD): 99.8% (retention time: 0.59 min);
TLC: Rf 0.47 (ethyl acetate:methanol=9:1, NH silica gel);
NMR (300 MHz, CHLOROFORM-d): δ 9.40 (s, 1H), 9.07 (br.s, 1H), 8.16 (s, 1H), 8.04-7.98 (m, 1H), 7.86-7.78 (m, 1H), 7.32-7.28 (m, 1H), 7.04 (s, 1H), 6.88 (s, 2H), 3.08-2.83 (m, 4H), 2.64 (d, J=6.04 Hz, 2H), 2.37 (s, 6H), 2.27-2.13 (m, 1H), 2.01-1.82 (m, 1H), 1.63-1.41 (m, 3H)
MASS (ESI, Pos.): 453 (M+H)+.

Example 11(56)

N-[4-(4-amino-1-piperidinyl)-5-(3,5-dimethylphenyl)-3-pyridinyl]-4,6-dimethyl-2-pyridinecarboxamide Description: white powder;
Purity (UPLC-MS/ELSD): 99.9% (retention time: 0.57 min);
TLC: Rf 0.48 (ethyl acetate:methanol=9:1, NH silica gel);
NMR (300 MHz, CHLOROFORM-d): δ 10.79 (s, 1H), 9.76 (s, 1H), 8.14 (s, 1H), 8.00 (s, 1H), 7.17 (s, 1H), 7.05 (s, 1H), 6.90 (s, 2H), 2.98-2.87 (m, 2H), 2.62 (s, 3H), 2.60-2.49 (m, 3H), 2.44 (s, 3H), 2.38 (s, 6H), 1.87-1.61 (m, 4H), 1.48 (br.s, 2H);
MASS (ESI, Pos.): 430 (M+H)+.

Example 11(57)

N-[4-(4-amino-1-piperazinyl)-5-(3,5-dimethylphenyl)-3-pyridinyl]-3,5-dimethylbenzamide Description: white powder;
Purity (UPLC-MS/ELSD): 99.7% (retention time: 0.61 min);
TLC: Rf 0.63 (ethyl acetate:methanol=9:1, NH silica gel);
NMR (300 MHz, CHLOROFORM-d): δ 9.70 (s, 1H), 9.03 (s, 1H), 8.13 (s, 1H), 7.58 (s, 2H), 7.23 (s, 1H), 7.05 (s, 1H), 6.89 (s, 2H), 2.85-2.79 (m, 4H), 2.73-2.53 (m, 4H), 2.43 (s, 6H), 2.38 (s, 6H), 1.58 (br.s, 2H);
MASS (ESI, Pos.): 430 (M+H)+.

Example 11(58)

2-{4-[4-(aminomethyl)-1-piperidinyl]-5-(3,5-dimethylphenyl)-3-pyridinyl}-1H-isoindole-1,3(2H)-dione Description: yellow viscous oil;
Purity (UPLC-MS/ELSD): 99.7% (retention time: 0.61 min);
TLC: Rf 0.26 (ethyl acetate:methanol=9:1, NH silica gel);
NMR (300 MHz, CHLOROFORM-d): δ 8.33 (s, 1H), 8.21 (s, 1H), 8.03-7.95 (m, 2H), 7.88-7.80 (m, 2H), 7.05 (s, 2H), 7.00 (s, 1H), 3.07-2.97 (m, 2H), 2.67-2.53 (m, 2H), 2.42-2.37 (m, 2H), 2.36 (s, 6H), 1.55-0.72 (m, 7H);
MASS (ESI, Pos.): 441 (M+H)+.

Example 11(59)

N-{4-[(3-aminophenyl)amino]-5-(3,5-dimethylphenyl)-3-pyridinyl}-3,5-dimethylbenzamide Description: beige powder;
Purity (UPLC-MS/ELSD): 100% (retention time: 0.75 min);
TLC: Rf 0.64 (ethyl acetate:methanol=9:1, NH silica gel);
NMR (300 MHz, CHLOROFORM-d): δ 9.53 (s, 1H), 8.33 (s, 1H), 7.73-7.68 (m, 1H), 7.13-7.04 (m, 3H), 7.00-6.96 (m, 2H), 6.93-6.89 (m, 2H), 6.39-6.35 (m, 1H), 6.31-6.26 (m, 1H), 6.19-6.15 (m, 1H), 5.65 (s, 1H), 3.68 (br.s, 2H), 2.33 (s, 6H), 2.25 (s, 6H);
MASS (ESI, Pos.): 437 (M+H)+.

Example 11(60)

N-[4-(4-amino-1-piperidinyl)-5-(3,5-dimethylphenyl)-3-pyridinyl]-3,5-dimethyl-1-piperidinecarboxamide Description: white powder;
Purity (UPLC-MS/ELSD): 99.9% (retention time: 0.54 min);
TLC: Rf 0.50 (ethyl acetate:methanol=9:1, NH silica gel);
NMR (300 MHz, CHLOROFORM-d): δ 9.35 (s, 1H), 7.98 (s, 1H), 7.77 (s, 1H), 7.03 (s, 1H), 6.87 (s, 2H), 4.15-4.02 (m, 2H), 3.65-3.55 (m, 1H), 3.20-3.09 (m, 1H), 2.88-2.77 (m, 4H), 2.64-2.40 (m, 5H), 2.36 (s, 6H), 2.04-1.20 (m, 6H), 1.04-0.91 (m, 6H);
MASS (ESI, Pos.): 436 (M+H)+.

Example 11(61)

N-[5-(3,5-dimethylphenyl)-4-(1-methyl-1,4,6,7-tetrahydro-5H-imidazo[4,5-c]pyridin-5-yl)-3-pyridinyl]-3,5-dimethylbenzamide Description: white powder;
Purity (UPLC-MS/ELSD): 99.9% (retention time: 0.59 min);
TLC: Rf 0.69 (ethyl acetate:methanol=9:1, NH silica gel);
NMR (300 MHz, METHANOL-d4): δ 8.78 (s, 1H), 8.14 (s, 1H), 7.42 (s, 1H), 7.38 (s, 2H), 7.22 (s, 1H), 7.06 (s, 1H), 7.03 (s, 2H), 4.00 (s, 2H), 3.51 (s, 3H), 3.08 (t, J=5.49 Hz, 2H), 2.45 (t, J=5.49 Hz, 2H), 2.31 (s, 6H), 2.31 (s, 6H);
MASS (ESI, Pos.): 466 (M+H)+.

Example 11(62)

N-[2-(4-amino-1-piperidinyl)-2',5'-difluoro-3-biphenylyl]-3-hydroxybenzamide

Description: amber powder;
TLC: Rf 0.48 (ethyl acetate:methanol=10:1, NH silica gel);
NMR (300 MHz, CHLOROFORM-d): δ 9.97 (s, 1H), 8.70-8.60 (m, 1H), 7.71-7.58 (m, 1H), 7.49 (t, J=2.0 Hz, 1H), 7.40 (t, J=7.9 Hz, 1H), 7.30-7.21 (m, 1H), 7.15-7.02 (m, 3H), 6.97 (ddd, J=8.1, 5.3, 2.7 Hz, 1H), 6.83 (dd, J=7.7, 1.5 Hz, 1H), 3.83-3.55 (m, 1H), 3.15-2.61 (m, 4H), 1.87-1.59 (m, 4H);
MASS (ESI, Pos.): 424 (M+H)+.

Example 11(63)

N-[2-(4-amino-1-piperidinyl)-3',5'-dimethyl-3-biphenylyl]-3-hydroxybenzamide

Description: white powder;
TLC: Rf 0.48 (ethyl acetate:methanol=10:1, NH silica gel);
NMR (300 MHz, CHLOROFORM-d): δ 10.06 (s, 1H), 8.59 (dd, J=8.1, 1.4 Hz, 1H), 7.69 (d, J=7.9 Hz, 1H), 7.53 (s, 1H), 7.40 (t, J=8.0 Hz, 1H), 7.22 (t, J=7.9 Hz, 1H), 7.09-6.98 (m, 2H), 6.90 (s, 2H), 6.86 (dd, J=7.6, 1.6 Hz, 1H), 2.96-2.77 (m, 3H), 2.62-2.44 (m, 2H), 2.37 (s, 6H), 1.84-1.68 (m, 4H);
MASS (ESI, Pos.): 416 (M+H)+.

Example 11(64)

N-[2-(4-amino-1-piperidinyl)-3',5'-dimethoxy-3-biphenylyl]-3-hydroxybenzamide

Description: white powder;
TLC: Rf 0.48 (ethyl acetate:methanol=10:1, NH silica gel);
NMR (300 MHz, CHLOROFORM-d): δ 9.99 (s, 1H), 8.60 (dd, J=8.2, 1.5 Hz, 1H), 7.65 (d, J=7.9 Hz, 1H), 7.51 (s, 1H), 7.39 (t, J=8.0 Hz, 1H), 7.22 (t, J=8.0 Hz, 1H), 7.05 (dd, J=8.1, 2.0 Hz, 1H), 6.91-6.84 (m, 1H), 6.51-6.47 (m, 1H), 6.44 (d, J=2.4 Hz, 2H), 3.82 (d, J=0.5 Hz, 6H), 2.96-2.82 (m, 3H), 2.63 (td, J=11.8, 2.8 Hz, 2H), 1.87-1.62 (m, 4H);
MASS (ESI, Pos.): 448 (M+H)+.

Example 11(65)

N-[4-(4-acetamide-1-piperidinyl)-5-(3,5-dimethylphenyl)-3-pyridinyl]-3,5-dimethylbenzamide Description: white powder;
Purity (UPLC-MS/ELSD): 100% (retention time: 0.70 min);
TLC: Rf 0.26 (ethyl acetate);
NMR (300 MHz, CHLOROFORM-d): δ 9.67 (s, 1H), 8.96 (s, 1H), 8.13 (s, 1H), 7.54 (s, 2H), 7.22 (s, 1H), 7.07 (s, 1H), 6.88 (s, 2H), 5.21-5.13 (m, 1H), 3.79-3.64 (m, 1H), 2.93-2.82 (m, 2H), 2.71-2.59 (m, 2H), 2.42 (s, 6H), 2.38 (s, 6H), 2.01-1.80 (m, 2H), 1.94 (s, 3H), 1.29-1.45 (m, 2H);
MASS (ESI, Pos.): 471 (M+H)+.

Example 11(66)

N-{5-(3,5-dimethylphenyl)-4-[4-(ethylamino)-1-piperidinyl]-3-pyridinyl}-3,5-dimethylbenzamide Description: white powder;
Purity (UPLC-MS/ELSD): 100% (retention time: 0.58 min);
TLC: Rf 0.59 (ethyl acetate:methanol=9:1, NH silica gel);
NMR (300 MHz, CHLOROFORM-d): δ 9.68 (s, 1H), 8.97 (s, 1H), 8.13 (s, 1H), 7.55 (s, 2H), 7.20 (s, 1H), 7.06 (s, 1H), 6.89 (s, 2H), 2.97-2.85 (m, 2H), 2.66-2.49 (m, 3H), 2.41 (s, 6H), 2.38 (s, 6H), 1.92-1.80 (m, 2H), 1.48 (br.s., 1H), 1.42-1.24 (m, 3H), 1.06 (t, J=7.14 Hz, 3H);
MASS (ESI, Pos.): 457 (M+H)+.

Example 11(67)

N-[4-(4-amino-1-piperidinyl)-5-(3,5-dimethylphenyl)-3-pyridinyl]-2,6-dimethylpyridine-4-carboxamide Description: yellow oil;
TLC: Rf 0.58 (ethyl acetate:methanol=9:1, NH silica gel);
NMR (300 MHz, METHANOL-d4): δ 8.47 (s, 1H), 8.06 (s, 1H), 7.61 (s, 2H), 7.07 (s, 1H), 6.98 (s, 2H), 3.08 (d, J=13.2 Hz, 2H), 2.61 (s, 9H), 2.37 (s, 6H), 1.69-1.50 (m, 2H), 1.33-1.03 (m, 2H);
MASS (APCI, Pos.): 430 (M+H)+.

Example 11(68)

N-[4-(4-amino-1-piperidinyl)-5-(3,5-dimethylphenyl)-3-pyridinyl]-2-phenoxyacetamide Purity (LC-MS/ELSD): 100% (retention time: 0.54 min);
MASS (ESI, Pos.): 431 (M+H)+.

Example 12

N-[5-(3,5-dimethylphenyl)-4-[3-hydroxypropyl(isobutyl)amino]-3-pyridyl]-3,5-dimethylbenzamide

[93]

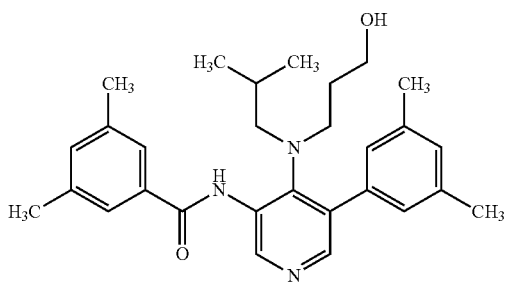

Using 3-(isobutylamino)propan-1-ol (CAS #285124-45-0) in place of tert-butyl N-(4-piperidylmethyl)carbamate, using 3,5-dimethylphenylboronic acid in place of phenylboronic acid, the present invention compound having the following physical property values was obtained by following the same procedure as in Reference example 14→Reference example 2→Reference example 16→Reference example 17.
Description: white powder;
TLC: Rf 0.32 (n-hexane:ethyl acetate=1:1);
MASS (ESI, Pos.): 460 (M+H)+.

Reference Example 18

N-[5-(3,5-dimethylphenyl)-4-[isobutyl-[3-[(2-nitrophenyl)sulfonylamino]propyl]amino]-3-pyridyl]-3,5-dimethylbenzamide Using the compound (188 mg) produced in Example 12 and 2-nitrobenzenesulfonamide (CAS #5455-59-4) (404 mg), the title compound having the following physical property values was obtained by following the same procedure as in Reference example 9, and used for next reaction without further purification.

Example 13

N-[4-[3-aminopropyl(isobutyl)amino]-5-(3,5-dimethylphenyl)-3-pyridyl]-3,5-dimethylbenzamide dihydrochloride

[94]

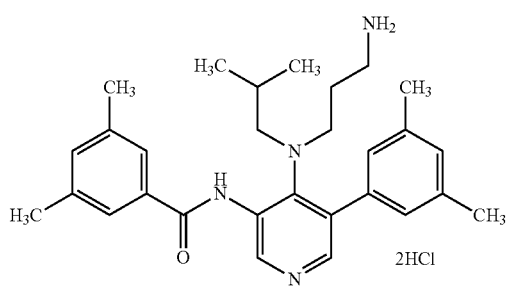

To a acetonitrile (15 mL) solution of the compound produced in Reference example 18 and 4-chlorothiophenol (730 mg) was added cesium carbonate (1.65 g), the mixture was stirred at room temperature for 15 hours. After adding water, the reaction solution was extracted with ethyl acetate and washed with saturated brine. The organic layer was concentrated after drying. The obtained residue was purified by preparative medium pressure liquid chromatography (Yamazen Corp. YFLC-Wprep-2XY) (Hi-flash NH) (ethyl acetate:methanol=95:5), and treated with hydrogen chloride in ethyl acetate to obtain the present invention compound (60 mg) having the following physical property values.
Description: white powder;
Purity (UPLC-MS/ELSD): 99.2% (retention time: 0.72 min);
TLC: Rf 0.61 (ethyl acetate:methanol=9:1, NH silica gel);
MASS (ESI, Pos.): 459 (M+H)+.

Example 14

N-(2-aminoethyl)-3-[(3-chloro-4-fluorobenzoyl)amino]-5-(3,5-dimethylphenyl)pyridine-4-carboxamide

[95]

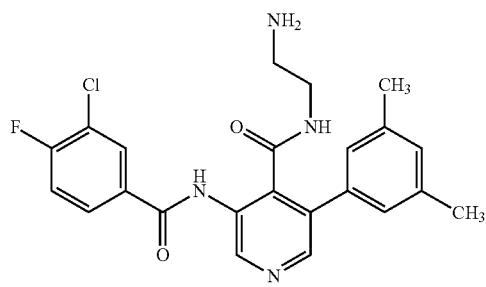

Using ethyl 3-amino-5-bromopyridine-4-carboxylate (purchased from ATLANTIC, catalog number: ES00288) in place of the compound produced in Reference example 16, using 3-chloro-4-fluorobenzoylchloride (CAS #157373-00-7) in place of 3,5-dimethylbenzoylchloride, using 3,5-dimethylphenylboronic acid in place of phenylboronic acid, using tert-butyl N-(2-aminoethyl)carbamate (CAS #57260-73-8) in place of 3,5-dimethylaniline, the present invention compound having the following physical property values was obtained by following the same procedure as in Reference example 17→Reference example 2→Reference example 6→Reference example 7→Example 1.

Description: beige powder;
Purity (UPLC-MS/ELSD): 94.8% (retention time: 0.81 min);
TLC: Rf 0.60 (ethyl acetate:methanol=9:1, NH silica gel);
NMR (300 MHz, METHANOL-d4): δ 9.65 (s, 1H), 8.13 (s, 1H), 8.08 (dd, J=7.04, 2.29 Hz, 1H), 7.90-7.97 (m, 1H), 7.62 (s, 2H), 7.41 (t, J=8.78 Hz, 1H), 7.07 (s, 1H), 3.54 (t, J=6.13 Hz, 2H), 2.91 (t, J=6.10 Hz, 2H), 2.38 (s, 6H);
MASS (ESI, Pos.): 441 (M+H)+.

Reference Example 19

[3-[[3-(3,5-dimethylphenyl)-5-nitro-4-pyridyl]amino]phenyl]methanol

Using (3-aminophenyl)methanol (CAS #1877-77-6) in place of tert-butyl N-(4-piperidylmethyl)carbamate, using 3,5-dimethylphenylboronic acid in place of phenylboronic acid, the title compound having the following physical property values was obtained by following the same procedure as in Reference example 14→Reference example 2.

Description: yellow powder;
TLC: Rf 0.28 (n-hexane:ethyl acetate=1:1);
MASS (APCI, Pos.): 350 (M+H)+.

Reference Example 20

(3-((3-amino-5-(3,5-dimethylphenyl)pyridin-4-yl)amino)phenyl)methanol

To a ethanol (30 mL) solution of the compound produced in Reference example 19 was added ammonium chloride (1.60 g) and water (3 mL), the mixture was heated to 50 degrees C. To the reaction solution was added zinc (784 mg), and stirred for 15 min. The reaction solution was diluted with tetrahydrofuran and cooled back to room temperature. The reaction solution was filtered and the filtrate was concentrated to obtain the title compound which was used for next reaction without further purification.

Example 15

N-(5-(3,5-dimethylphenyl)-4-((3-(hydroxymethyl)phenyl)amino)pyridin-3-yl)-3,5-dimethylbenzamide

[96]

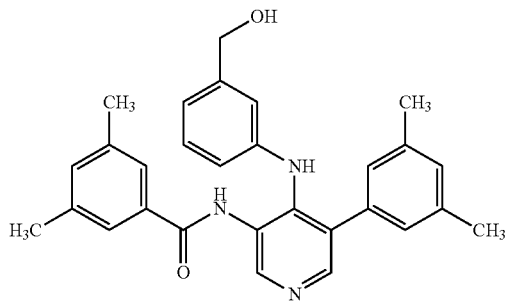

Using the compound produced in Reference example 20 in place of the compound produced in Reference example 16, the present invention compound having the following physical property values was obtained by following the same procedure as in Reference example 17:

Description: pale brown amorphous;
TLC: Rf 0.26 (ethyl acetate);
MASS (APCI, Pos.): 452 (M+H)+.

Reference Example 21

N-(4-((3-(azidemethyl)phenyl)amino)-5-(3,5-dimethylphenyl)pyridin-3-yl)-3,5-dimethylbenzamide To a tetrahydrofuran (6 mL) solution of the compound (187 mg) produced in Example 15 and bis(p-nitrophenyl) azidophosphonate (CAS #51250-91-0) (365 mg) was added 1,5-diazabicyclo[4.3.0]non-5-ene (124 microL) at room temperature, and the mixture was stirred for 7 hours. The reaction solution was concentrated and the obtained residue was purified by preparative medium pressure liquid chromatography (Yamazen Corp. YFLC-Wprep-2XY) (Hi-flash SI) (n-hexane:ethyl acetate=1:1) to obtain the title compound (156 mg) having the following physical property values.

Description: colorless oil;
TLC: Rf 0.44 (n-hexane:ethyl acetate=1:1);
MASS (APCI, Pos.): 477 (M+H)+.

Example 16

N-(4-((3-(aminomethyl)phenyl)amino)-5-(3,5-dimethylphenyl)pyridin-3-yl)-3,5-dimethylbenzamide

[97]

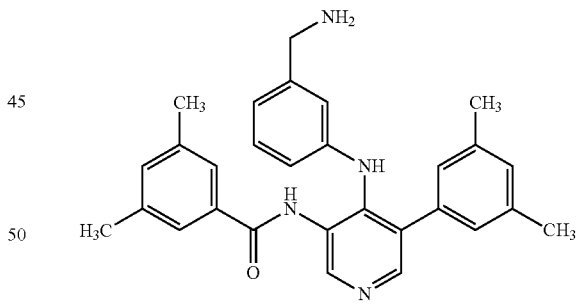

Using the compound produced in Reference example 21 in place of the compound produced in Reference example 15, the present invention compound having the following physical property values was obtained by following the same procedure as in Reference example 16.

Description: white powder;
Purity (UPLC-MS/ELSD): 99.8% (retention time: 0.59 min);
TLC: Rf 0.51 (ethyl acetate:methanol=9:1, NH silica gel).
NMR (300 MHz, CHLOROFORM-d): δ 9.43 (s, 1H), 8.34 (s, 1H), 7.56 (s, 1H), 7.30-7.21 (m, 1H), 7.05 (d, J=6.95 Hz, 2H), 6.98-6.91 (m, 3H), 6.83 (s, 2H), 6.80-6.71 (m, 2H), 5.85 (s, 1H), 3.75 (s, 2H), 2.32 (s, 6H), 2.22 (s, 6H), 1.49 (br.s, 2H);MASS (ESI, Pos.): 451 (M+H)+.

Reference Example 22 tert-butyl N-[1-[3-[(2-aminobenzoyl)amino]-5-(3,5-dimethylphenyl)-4-pyridyl]-4-piperidyl]carbamate Using the compound produced in Reference example 12 in place of the compound produced in Reference example 16, using 2-nitrobenzoyl chloride (CAS #610-14-0) in place of 3,5-dimethylbenzoylchloride, the title compound having the following physical property values was obtained by following the same procedure as in Reference example 17→Reference example 6→Reference example 16.
Description: colorless oil;
TLC: Rf 0.64 (ethyl acetate);
MASS (APCI, Pos.): 516 (M+H)+.

Reference Example 23 tert-butyl (1-(3-(3,5-dimethylphenyl)-5-(2,4-dioxo-1,2-dihydroquinazolin-3(4H)-yl)pyridin-4-yl)piperidin-4-yl)carbamate To a dichloroethane (8 mL) solution of the compound (233 mg) produced in Reference example 22 was added diisopropylethylamine (78 microL) and triphosgene (CAS #32315-10-9) (67 mg) at room temperature, and the mixture was stirred for 15 hours. After adding water, the mixture was extracted with ethyl acetate and washed with saturated brine. The organic layer was concentrated after drying to obtain the title compound which was used for next reaction without further purification.

Example 17

3-[4-(4-amino-1-piperidyl)-5-(3,5-dimethylphenyl)-3-pyridyl]-1H-quinazoline-2,4-dione

[98]

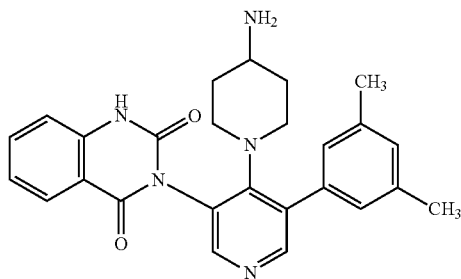

Using the compound produced in Reference example 23 in place of the compound produced in Reference example 3, the present invention compound having the following physical property values was obtained by following the same procedure as in Example 1.
Description: white powder;
Purity (UPLC-MS/ELSD): 99.8% (retention time: 0.54 min);
TLC: Rf 0.20 (ethyl acetate:methanol=9:1, NH silica gel);
NMR (300 MHz, CHLOROFORM-d): δ 8.35 (s, 1H), 8.23 (s, 1H), 8.22-8.17 (m, 1H), 7.71-7.64 (m, 1H), 7.33-7.27 (m, 2H), 7.11-7.04 (m, 3H), 7.01 (s, 1H), 3.08-2.97 (m, 2H), 2.65-2.53 (m, 2H), 2.53-2.41 (m, 1H), 2.37 (s, 6H), 2.20-1.20 (br, 2H), 1.51-1.40 (m, 2H), 1.02-0.83 (m, 2H); MASS (ESI, Pos.): 442 (M+H)+.

Example 18 ethyl (1-(3-(3,5-dimethylbenzamide)-5-(3,5-dimethylphenyl)pyridin-4-yl)piperidin-4-yl)carbamate

[99]

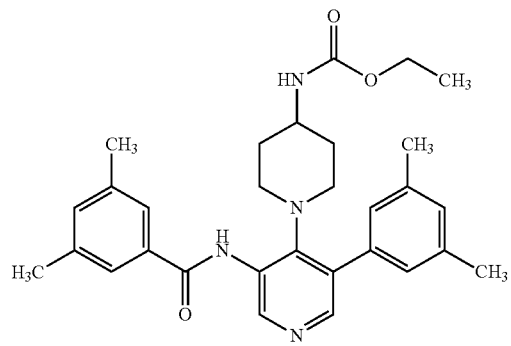

Using the compound produced in Reference example 11(39) in place of the compound produced in Reference example 16, using ethyl chloroformate (CAS #541-41-3) in place of 3,5-dimethylbenzoylchloride, the present invention compound having the following physical property values was obtained by following the same procedure as in Reference example 17.
Description: white powder;
Purity (UPLC-MS/ELSD): 100% (retention time: 0.83 min);
TLC: Rf 0.56 (ethyl acetate);
NMR (300 MHz, CHLOROFORM-d): δ 9.68 (s, 1H), 8.98 (br.s., 1H), 8.14 (s, 1H), 7.54 (s, 2H), 7.22 (s, 1H), 7.07 (s, 1H), 6.88 (s, 2H), 4.46-4.34 (m, 1H), 4.09 (q, J=7.26 Hz, 2H), 3.52-3.35 (m, 1H), 2.93-2.82 (m, 2H), 2.69-2.55 (m, 2H), 2.42 (s, 6H), 2.38 (s, 6H), 2.00-1.89 (m, 2H), 1.48-1.31 (m, 2H), 1.23 (t, J=7.30 Hz, 3H);
MASS (ESI, Pos.): 501 (M+H)+.

Reference Example 24

3-bromo-2-[3-(1,3-dioxoindolin-2-yl)propoxy]benzaldehyde

To a dimethylformamide (10 mL) solution of 3-bromo-2-hydroxybenzaldehyde (CAS #1829-34-1) (1.00 g) and 2-(3-bromopropyl)isoindoline-1,3-dione (CAS #5460-29-7) (2.00 g) was added cesium carbonate (2.40 g) at room temperature, and the mixture was stirred at 80 degrees C. for 15 hours. After cooling to room temperature, the reaction solution was diluted with ethyl acetate, and sequentially washed with water, saturated aqueous solution of sodium hydrogen carbonate and saturated brine. The organic layer was concentrated after drying. The obtained residue was purified by preparative medium pressure liquid chromatography (Yamazen Corp. YFLC-Wprep-2XY) (Hi-flash SI) (n-hexane:ethyl acetate=1:1) to obtain the title compound (1.84 g) having the following physical property values.
Description: white powder;
TLC: Rf 0.63 (n-hexane:ethyl acetate=1:1).

Reference Example 25

2-[3-[2-(1H-benzimidazol-2-yl)-6-bromophenoxy]propyl]isoindoline-1,3-dione

To a dimethylformamide (3 mL)/ethanol (10 mL) solution of the compound (397 mg) produced in Reference example 24 and 2-nitroaniline (CAS #88-74-4) (141 mg) was added sodium hydrosulfite (871 mg) and water (5 mL) at room temperature, and the mixture was stirred at 80 degrees C. for 5 hours. After cooling to room temperature, the reaction solution was diluted with ethyl acetate, and then sequentially washed with water, saturated aqueous solution of sodium hydrogen carbonate and saturated brine. The organic layer was concentrated after drying to obtained title compound which was used for next reaction without further purification.

Reference Example 26

2-[3-[2-(1H-benzimidazol-2-yl)-6-(3,5-dimethylphenyl)phenoxy]propyl]isoindoline-1,3-dione Using the compound produced in Reference example 25 in place of the compound produced in Reference example 1, using 3,5-dimethylphenylboronic acid in place of phenylboronic acid, the title compound having the following physical property values was obtained by following the same procedure as in Reference example 2.
Description: beige powder;
TLC: Rf 0.68 (ethyl acetate);
MASS (ESI, Pos.): 502 (M+H)+.

Example 19

3-[2-(1H-benzimidazol-2-yl)-6-(3,5-dimethylphenyl)phenoxy]propan-1-amine hydrochloride

[100]

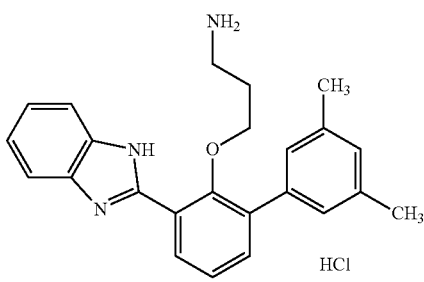

To a ethanol (10 mL) solution of the compound (220 mg) produced in Reference example 26 was added hydrazine monohydrate (0.5 mL) at room temperature, the mixture was stirred at 80 degrees C. for 3 hours, and then concentrated. The obtained residue was purified by preparative medium pressure liquid chromatography (Yamazen Corp. YFLC-Wprep-2XY) (Hi-flash NH) (ethyl acetate:methanol=95:5), and then treated with hydrogen chloride in 1,4-dioxane solution to obtain the present invention compound (110 mg) having the following physical property values.
Description: white powder;
Purity (UPLC-MS/ELSD): 100% (retention time: 0.66 min);
TLC: Rf 0.52 (ethyl acetate:methanol=9:1, NH silica gel);
NMR (300 MHz, METHANOL-d4): δ 7.98-7.88 (m, 3H), 7.76 (dd, J=7.70, 1.70 Hz, 1H), 7.72-7.64 (m, 2H), 7.61-7.54 (m, 1H), 7.28 (s, 2H), 7.15 (s, 1H), 3.57 (t, J=6.04 Hz, 2H), 2.73-2.63 (m, 2H), 2.42 (s, 6H), 1.85-1.68 (m, 2H);
MASS (ESI, Pos.): 372 (M+H)+.

Reference Example 27 tert-butyl (1-(3-amino-5-bromopyridin-4-yl)piperidin-4-yl)carbamate

Using the compound produced in Reference example 1 in place of the compound produced in Reference example 5, the title compound having the following physical property values was obtained by following the same procedure as in Reference example 6→Reference example 12.
Description: ivory amorphous powder;
TLC: Rf 0.33 (n-hexane:ethyl acetate=1:1).

Example 20

N-(4-(4-aminopiperidin-1-yl)-5-(3,5-dimethylphenyl)pyridin-3-yl)-N-ethyl-3,5-dimethylbenzamide

[101]

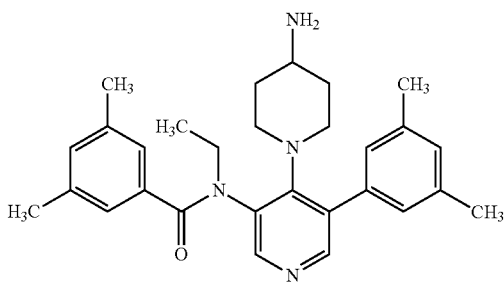

Using acetaldehyde (CAS #75-07-0) in place of the compound produced in Reference example 9, using the compound produced in Reference example 27 in place of dimethylamine, using 3,5-dimethylphenylboronic acid in place of phenylboronic acid, using tetrakis(triphenylphosphine)palladium (Pd(PPh$_3$)$_4$) in place of bis(di-tert-butyl(4-dimethylaminophenyl)phosphine)dichloropalladium(II), the present invention compound having the following physical property values was obtained by following the same procedure as in Example 10→Reference example 17→Reference example 2→Example 1.
Description: colorless oil;
Purity (UPLC-MS/ELSD): 99.9% (retention time: 0.67 min);
TLC: Rf 0.50 (ethyl acetate:methanol=9:1, NH silica gel);
MASS (ESI, Pos.): 457 (M+H)+.

Reference Example 28 tert-butyl N-[1-[3-[(2-amino-3,5-dimethylphenyl)carbamoyl]-5-(3,5-dimethylphenyl)-4-pyridyl]-4-piperidyl]carbamate Using 3,5-dimethylbenzene-1,2-diamine (CAS #3171-46-8) in place of 3,5-dimethylaniline, the title compound having the following physical property values was obtained by following the same procedure as in Reference example 7.
Description: pale brown powder;
TLC: Rf 0.41 (ethyl acetate, NH silica gel);

Reference Example 29 tert-butyl N-[1-[3-(4,6-dimethyl-1H-benzimidazol-2-yl)-5-(3,5-dimethylphenyl)-4-pyridyl]-4-piperidyl]carbamate To a toluene (7 mL) solution of the compound (750 mg) produced in Reference example 28 was added acetic acid (7 mL), and stirred at 90 degrees C. overnight. The reaction solution was sequentially washed with 1M aqueous solution of sodium hydroxide and saturated brine. The organic layer was concentrated after dring. The obtained residue was purified by preparative medium pressure liquid chromatography (Yamazen Corp. YFLC-Wprep-2XY) (Hi-flash NH) (ethyl acetate:methanol=95:5) to obtain the title compound having the following physical property values.

TLC: Rf 0.70 (ethyl acetate:methanol=9:1).

Example 21(1)-Example 21(39)

Using methyl 5-bromo-4-iodopyridine-3-carboxylate, or a corresponding reagent in place of it, using 4-tert-butoxycarbonylaminopiperidine, or a corresponding reagent in place of it, using a corresponding reagent in place of phenylboronic acid, using a corresponding benzene-1,2-diamine derivative, 2-aminothiophenol derivative or 2-aminophenol derivative in place of 3,5-dimethylaniline, the present invention compounds having the following physical property values were obtained by following the same procedure as in Reference example 1→Reference example 2→Reference example 6→Reference example 7→Reference example 29→Example 1.

Example 21(1)

1-[3-(4,6-dimethyl-1H-benzimidazol-2-yl)-5-(3,5-dimethylphenyl)-4-pyridyl]piperidin-4-amine

[102]

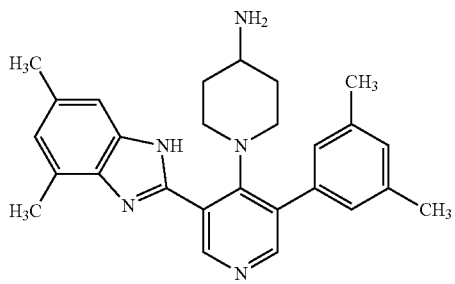

Description: pale yellow amorphous powder;
TLC: Rf 0.49 (ethyl acetate:methanol=9:1, NH silica gel);
NMR (300 MHz, METHANOL-d4): δ 8.43 (s, 1H), 8.23 (s, 1H), 7.26 (s, 1H), 7.09 (s, 1H), 7.05 (s, 2H), 6.96 (s, 1H), 3.15-3.04 (m, 2H), 2.78-2.62 (m, 1H), 2.56 (s, 3H), 2.56-2.48 (m, 2H), 2.45 (s, 3H), 2.40 (s, 6H), 1.56-1.43 (m, 2H), 1.31-1.09 (m, 2H);
MASS (ESI, Pos.): 426 (M+H)+.

Example 21(2)

1-[3-(3,5-dimethoxyphenyl)-5-(4,6-dimethyl-1H-benzimidazol-2-yl)-4-pyridinyl]-4-piperidinamine Description: white powder;
TLC: Rf 0.30 (ethyl acetate:methanol=19:1, NH silica gel);
NMR (300 MHz, CHLOROFORM-d): δ 11.25 and 10.64 (br.s, 1H), 9.37 and 9.19 (s, 1H), 8.33 (s, 1H), 7.50 and 7.15 (s, 1H), 6.95 (s, 1H), 6.52 (s, 1H), 6.46 (s, 2H), 3.84 (s, 6H), 3.18-2.94 (m, 2H), 2.80-2.51 (m, 6H), 2.48 (s, 3H), 1.88-1.64 (m, 2H), 1.61-1.19 (m, 4H);
MASS (ESI, Pos.): 458 (M+H)+.

Example 21(3)

1-{1-[3-(3,5-dimethoxyphenyl)-5-(4,6-dimethyl-1H-benzimidazol-2-yl)-4-pyridinyl]-4-piperidinyl}methanamine Description: white powder;
TLC: Rf 0.16 (ethyl acetate:methanol=19:1, NH silica gel);
NMR (300 MHz, CHLOROFORM-d): δ 11.35 and 10.78 (br.s., 1H), 9.41 and 9.21 (s, 1H), 8.33 (s, 1H), 7.50 and 7.08 (s, 1H), 6.94 (br.s., 1H), 6.52 (br.s., 1H), 6.47 (s, 2H), 3.84 (s, 6H), 3.08 (d, J=9.7 Hz, 2H), 2.80-2.50 (m, 6H), 2.48 (s, 3H), 1.82-1.58 (m, 2H), 1.58-0.98 (m, 4H);
MASS (ESI, Pos.): 472 (M+H)+.

Example 21(4)

1-[3-(2,5-difluorophenyl)-5-(4,6-dimethyl-1H-benzimidazol-2-yl)-4-pyridinyl]-4-piperidinamine Description: pale brown amorphous powder;
TLC: Rf 0.30 (ethyl acetate:methanol=19:1, NH silica gel);
NMR (300 MHz, CHLOROFORM-d): δ 10.93 and 10.37 (br.s., 1H), 9.27 and 9.07 (s, 1H), 8.27 (s, 1H), 7.55-6.93 (m, 5H), 3.02 (m, 2H), 2.78-2.52 (m, 6H), 2.48 (m, 3H), 1.83-1.09 (m, 6H)
MASS (ESI, Pos.): 434 (M+H)+.

Example 21(5)

1-{1-[3-(2,5-difluorophenyl)-5-(4,6-dimethyl-1H-benzimidazol-2-yl)-4-pyridinyl]-4-piperidinyl}methanamine Description: pale brown amorphous powder;
TLC: Rf 0.16 (ethyl acetate:methanol=19:1, NH silica gel);
NMR (300 MHz, CHLOROFORM-d): δ 11.07 and 10.42 (br.s., 1H), 9.37 and 9.13 (s, 1H), 8.29 (s, 1H), 7.57-6.98 (m, 4H), 6.95 (s, 1H), 3.07 (t, J=11.8 Hz, 2H), 2.77-2.38 (m, 9H), 1.81-0.97 (m, 6H);
MASS (ESI, Pos.): 448 (M+H)+.

Example 21(6)

1-[3-(4,6-dimethyl-1H-benzimidazol-2-yl)-3',5'-dimethoxy-2-biphenylyl]-4-piperidinamine Description: ivory powder;
TLC: Rf 0.48 (ethyl acetate:methanol=20:1, NH silica gel);
NMR (300 MHz, METHANOL-d4): δ 7.53 (dd, J=7.3, 1.8 Hz, 1H), 7.30 (d, J=1.8 Hz, 1H), 7.27 (d, J=2.0 Hz, 1H), 7.24-7.17 (m, 2H), 6.90 (s, 1H), 6.53-6.48 (m, 3H), 3.81 (s, 6H), 2.97 (d, J=12.4 Hz, 2H), 2.56 (s, 3H), 2.53-2.41 (m, 5H), 2.35-2.20 (m, 1H), 1.42 (d, J=11.7 Hz, 2H), 1.04-0.91 (m, 2H);
MASS (ESI, Pos.): 457 (M+H)+.

Example 21(7)

1-[3-(1H-benzimidazol-2-yl)-5-(3,5-dimethylphenyl)-4-pyridinyl]-4-piperidinamine Description: white powder;
TLC: Rf 0.50 (ethyl acetate:methanol=9:1, NH silica gel);
NMR (300 MHz, CHLOROFORM-d): δ 11.52 (br.s., 1H), 9.19-8.92 (m, 1H), 8.35-8.17 (m, 1H), 7.67 (br.s., 2H), 7.42-7.15 (m, 2H), 7.04 (s, 1H), 6.90 (s, 2H), 2.96 (d, J=12.4 Hz, 2H), 2.80-2.48 (m, 3H), 2.46-1.84 (m, 8H), 1.63 (d, J=11.9 Hz, 2H), 1.40-1.09 (m, 2H);
MASS (ESI, Pos.): 398 (M+H)+.

Example 21(8)

1-[3-(4,6-dimethyl-1H-benzimidazol-2-yl)-2',5'-difluoro-2-biphenylyl]-4-piperidinamine Description: amber powder;
TLC: Rf 0.42 (ethyl acetate:methanol=20:1, NH silica gel);
NMR (300 MHz, METHANOL-d4): δ 7.54 (dd, J=7.2, 1.9 Hz, 1H), 7.38-7.26 (m, 2H), 7.26-7.09 (m, 4H), 6.92 (s, 1H), 2.97 (d, J=12.4 Hz, 2H), 2.55 (s, 3H), 2.52-2.40 (m, 6H), 1.47 (d, J=11.3 Hz, 2H), 1.02-0.92 (m, 2H);
MASS (ESI, Pos.): 433 (M+H)+.

Example 21(9)

1-[3-(4,6-dimethyl-1H-benzimidazol-2-yl)-3',5'-dimethyl-2-biphenylyl]-4-piperidinamine Description: pale orange powder;
TLC: Rf 0.45 (ethyl acetate:methanol=20:1, NH silica gel);
NMR (300 MHz, METHANOL-d4): δ 7.49 (dd, J=7.2, 1.9 Hz, 1H), 7.33-7.15 (m, 3H), 7.01 (s, 1H), 6.99 (s, 2H), 6.91 (s, 1H), 2.99-2.91 (m, 2H), 2.55 (s, 3H), 2.49-2.40 (m, 5H), 2.39-2.33 (m, 7H), 1.45-1.36 (m, 2H), 1.11-0.82 (m, 2H);
MASS (ESI, Pos.): 425 (M+H)+.

Example 21(10)

1-[3-cyclopropyl-5-(4,6-dimethyl-1H-benzimidazol-2-yl)-4-pyridinyl]-4-piperidinamine bis(trifluoroacetate)

Description: white powder;
TLC: Rf 0.29 (ethyl acetate:methanol=9:1, NH silica gel);
NMR (300 MHz, METHANOL-d4): δ 8.68 (s, 1H), 8.41 (s, 1H), 7.47 (s, 1H), 7.25 (s, 1H), 3.82 (d, J=13.7 Hz, 2H), 3.42-3.25 (m, 1H), 3.12 (t, J=13.7 Hz, 2H), 2.64 (s, 3H), 2.51 (s, 3H), 2.16-1.94 (m, 3H), 1.75 (qd, J=12.2, 3.9 Hz, 2H), 1.32-1.20 (m, 2H), 1.08-0.97 (m, 2H);
MASS (ESI, Pos.): 362 (M+H)+.

Example 21(11)

1-[3-(4,6-dimethyl-1H-benzimidazol-2-yl)-5-(3,5-dimethylphenyl)-4-pyridinyl]-N-(3-oxetanyl)-4-piperidinamine Description: white amorphous powder;
TLC: Rf 0.48 (ethyl acetate:methanol=9:1, NH silica gel);
NMR (300 MHz, METHANOL-d4): δ 8.39 (s, 1H), 8.18 (s, 1H), 7.23 (br.s., 1H), 7.06 (s, 1H), 7.02 (s, 2H), 6.93 (s, 1H), 4.63 (t, J=6.9 Hz, 2H), 4.33 (t, J=6.5 Hz, 2H), 3.96-3.80 (m, 1H), 3.03 (d, J=12.8 Hz, 2H), 2.66-2.30 (m, 14H), 2.22 (s, 1H), 1.32 (d, J=10.1 Hz, 2H), 1.11-0.90 (m, 2H);
MASS (ESI, Pos.): 482 (M+H)+.

Example 21(12)

4-(aminomethyl)-1-[3-(5,7-dimethyl-1H-benzimidazol-2-yl)-5-(3,5-dimethylphenyl)-4-pyridinyl]-4-piperidinol Description: pale yellow powder;
TLC: Rf 0.14 (ethyl acetate:methanol: 28% ammonia water=90:10:1);
NMR (300 MHz, METHANOL-d4): δ 8.42 (s, 1H), 8.23 (s, 1H), 7.30-7.20 (m, 1H), 7.07 (s, 3H), 6.95 (s, 1H), 2.99-2.75 (m, 4H), 2.65 (s, 2H), 2.57 (s, 3H), 2.44 (s, 3H), 2.38 (s, 6H), 1.36-1.18 (m, 4H);
MASS (ESI, Pos.): 456 (M+H)+.

Example 21(13)

1-[3-(1H-benzimidazol-2-yl)-5-(3,5-dimethylphenyl)-4-pyridinyl]-N,N-dimethyl-4-piperidinamine Description: brown powder;
Purity (UPLC-MS/ELSD): unclear (retention time: 0.51 min);
TLC: Rf 0.50 (ethyl acetate:methanol=9:1, NH silica gel);
NMR (300 MHz, CHLOROFORM-d): δ 11.01 (br.s, 1H), 9.27 (s, 1H), 8.33 (s, 1H), 7.93-7.84 (m, 1H), 7.54-7.47 (m, 1H), 7.36-7.28 (m, 2H), 7.08 (s, 1H), 6.93 (s, 2H), 3.11-3.00 (m, 2H), 2.65-2.52 (m, 2H), 2.40 (s, 6H), 2.25 (s, 6H), 2.08-1.93 (m, 1H), 1.80-1.69 (m, 2H), 1.54-1.40 (m, 2H);
MASS (ESI, Pos.): 426 (M+H)+.

Example 21(14)

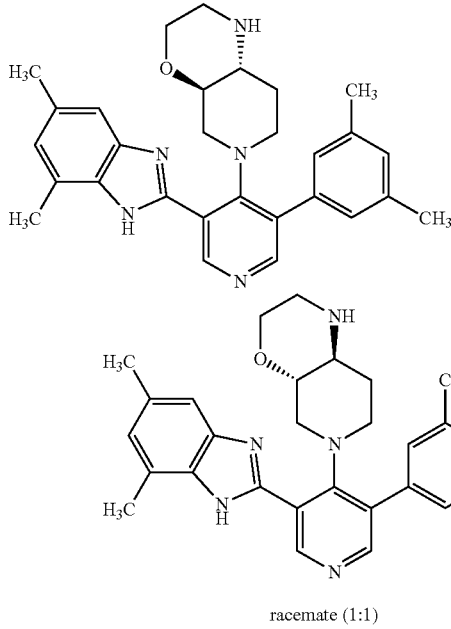

rac-(4aR,8aR)-6-[3-(4,6-dimethyl-1H-benzimidazol-2-yl)-5-(3,5-dimethylphenyl)-4-pyridinyl]octahydro-1H-pyrido[3,4-b][1,4]oxazine Description: pale brown powder;
TLC: Rf 0.52 (ethyl acetate:methanol=19:1, NH silica gel);
NMR (300 MHz, METHANOL-d4): δ 8.42 (s, 1H), 8.23 (s, 1H), 7.25 (br. s., 1H), 7.09 (s, 1H), 7.02 (s, 2H), 6.94 (s, 1H), 3.62 (dd, J=11.5, 2.0 Hz, 1H), 3.41-3.29 (m, 1H), 3.01 (s, 3H), 2.83-2.49 (m, 6H), 2.44 (s, 3H), 2.39 (s, 6H), 2.27 (dd, J=11.3, 9.9 Hz, 1H), 2.10 (ddd, J=11.8, 8.8, 4.1 Hz, 1H), 1.33-1.17 (m, 1H), 1.16-0.98 (m, 1H);
MASS (ESI, Pos.): 468 (M+H)+.

Example 21(15)

1-[3-(1,3-benzothiazol-2-yl)-5-(3,5-dimethylphenyl)-4-pyridinyl]-N-(3-oxetanyl)-4-piperidinamine Description: off-white powder;
TLC: Rf 0.84 (ethyl acetate:methanol=19:1, NH silica gel);
NMR (300 MHz, CHLOROFORM-d): δ 8.84 (s, 1H), 8.33 (s, 1H), 8.13 (ddd, J=8.1, 1.3, 0.6 Hz, 1H), 7.96 (ddd, J=8.0, 1.2, 0.6 Hz, 1H), 7.54 (ddd, J=8.1, 7.1, 1.2 Hz, 1H), 7.44 (ddd, J=8.0, 7.1, 1.3 Hz, 1H), 7.07-7.04 (m, 1H), 6.99-6.96 (m, 2H), 4.74 (t, J=6.9 Hz, 2H), 4.33 (t, J=6.9 Hz, 2H), 3.94 (quin, J=6.9 Hz, 1H), 3.05 (br. d, J=12.8 Hz, 2H), 2.65-2.54 (m, 2H), 2.39 (s, 6H), 2.37-2.24 (m, 1H), 1.46 (dd, J=12.3, 2.9 Hz, 2H), 1.38-1.20 (m, 2H);
MASS (ESI, Pos.): 471 (M+H)+.

Example 21(16)

1-[3-(3,5-dimethylphenyl)-5-(4,5,6,7-tetrahydro-1H-benzimidazol-2-yl)-4-pyridinyl]-4-piperidinamine Description: orange amorphous powder;
TLC: Rf 0.16 (ethyl acetate, NH silica gel);
NMR (300 MHz, METHANOL-d4): δ 8.25 (s, 1H), 8.08 (s, 1H), 7.04 (d, J=0.7 Hz, 1H), 6.98 (t, J=0.7 Hz, 2H), 2.96 (br. d, J=13.0 Hz, 2H), 2.63 (br. s., 4H), 2.55-2.39 (m, 3H), 2.36 (s, 6H), 1.87 (br. s., 4H), 1.44 (dd, J=11.8, 2.5 Hz, 2H), 1.17-0.99 (m, 2H);
MASS (ESI, Pos.): 402 (M+H)+.

Example 21(17)

1-[3-(3,5-dimethoxyphenyl)-5-(5,7-dimethyl-1H-benzimidazol-2-yl)-4-pyridinyl]-N-(2-fluoroethyl)-4-piperidinamine Description: pale brown amorphous powder;
Purity (UPLC-MS/ELSD): 99.8% (retention time: 0.40 min);
TLC: Rf 0.56 (ethyl acetate:methanol=9:1, NH silica gel);
NMR (300 MHz, METHANOL-d4): δ 8.41 (s, 1H), 8.22 (s, 1H), 7.24 (br. s., 1H), 6.94 (s, 1H), 6.58-6.53 (m, 3H), 4.40 (ddd, J=47.8, 5.1, 4.8 Hz, 2H), 3.83 (s, 6H), 3.15-3.05 (m, 2H), 2.81-2.66 (m, 2H), 2.62-2.50 (m, 5H), 2.44 (s, 3H), 2.39-2.26 (m, 1H), 1.55-1.45 (m, 2H), 1.19-1.02 (m, 2H);
MASS (ESI, Pos.): 504 (M+H)+.

Example 21(18)

1-[3-(3-cyclopropylphenyl)-5-(5-methyl-1H-benzimidazol-2-yl)-4-pyridinyl]-4-piperidinamine Description: pale brown amorphous powder;
Purity (LC-MS/ELSD): 95.4% (retention time: 0.44 min);
TLC: Rf 0.51 (ethyl acetate:methanol=9:1, NH silica gel);
NMR (300 MHz, METHANOL-d4): δ 8.41 (s, 1H), 8.20 (s, 1H), 7.52 (d, J=8.2 Hz, 1H), 7.43 (s, 1H), 7.33-7.40 (m, 1H), 6.93-7.24 (m, 4H), 2.99 (br. d, J=13.0 Hz, 2H), 2.29-2.65 (m, 6H), 1.88-2.10 (m, 1H), 1.38 (br. d, J=11.7 Hz, 2H), 0.92-1.15 (m, 4H), 0.60-0.84 (m, 2H);
MASS (ESI, Pos.): 424 (M+H)+.

Example 21(19)

1-[3-(2,5-dimethyl-3-furyl)-5-(5-methyl-1H-benzimidazol-2-yl)-4-pyridinyl]-4-piperidinamine Description: pale yellow amorphous powder;
Purity (LC-MS/ELSD): 97.6% (retention time: 0.37 min);
TLC: Rf 0.37 (ethyl acetate:methanol=9:1, NH silica gel);
NMR (300 MHz, METHANOL-d4): δ 8.36 (s, 1H), 8.14 (s, 1H), 7.51 (d, J=8.2 Hz, 1H), 7.36-7.46 (m, 1H), 7.07-7.21 (m, 1H), 6.06 (s, 1H), 3.10 (br. d, J=12.6 Hz, 2H), 2.40-2.70 (m, 6H), 2.29 (s, 3H), 2.22 (s, 3H), 1.49 (br. d, J=12.4 Hz, 2H), 1.07-1.27 (m, 2H);
MASS (ESI, Pos.): 402 (M+H)+.

Example 21(20)

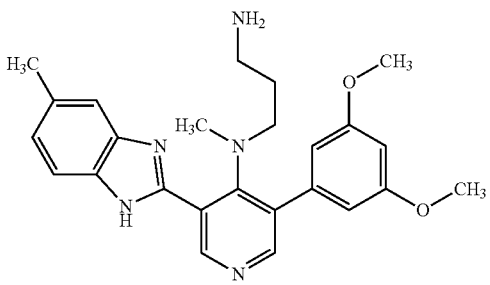

N-[3-(3,5-dimethoxyphenyl)-5-(5-methyl-1H-benz-imidazol-2-yl)-4-pyridinyl]-N-methyl-1,3-propane-diamine Description: pale brown powder;
Purity (UPLC-MS/ELSD): 99.0% (retention time: 0.41 min);
TLC: Rf 0.40 (ethyl acetate:methanol=10:1, NH silica gel);
NMR (300 MHz, CHLOROFORM-d): δ 8.47 (s, 1H), 8.11 (s, 1H), 7.39-7.29 (m, 1H), 7.24-7.17 (m, 1H), 6.95 (dd, J=1.2, 8.3 Hz, 1H), 6.49 (t, J=2.2 Hz, 1H), 6.38 (d, J=2.2 Hz, 2H), 3.82 (s, 6H), 3.04-2.97 (m, 2H), 2.81-2.73 (m, 2H), 2.58 (s, 3H), 2.39 (s, 3H), 1.77-1.66 (m, 2H)
MASS (ESI, Pos.): 432 (M+H)+.

Example 21(21)

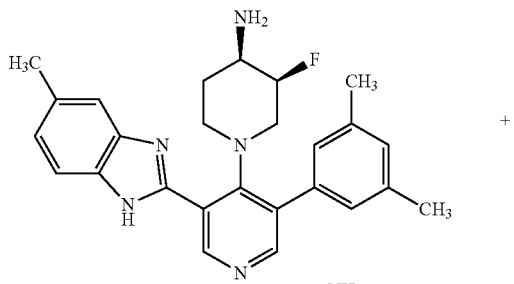

+

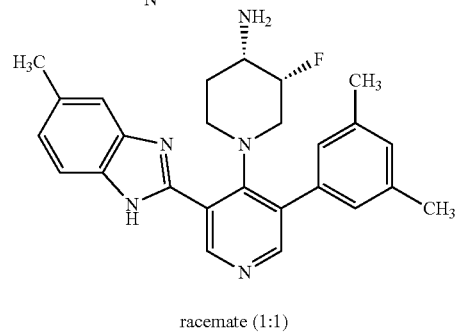

racemate (1:1)

rac-(3R,4S)-1-[3-(3,5-dimethylphenyl)-5-(6-methyl-1H-benzimidazol-2-yl)-4-pyridinyl]-3-fluoro-4-piperidinamine Description: pale brown amorphous powder;
Purity (UPLC-MS/ELSD): 99.2% (retention time: 0.44 min);
TLC: Rf 0.61 (ethyl acetate:methanol=20:1, NH silica gel);
NMR (300 MHz, METHANOL-d4): δ 8.54 (s, 1H), 8.24 (s, 1H), 7.57-7.49 (m, 1H), 7.45 (s, 1H), 7.15 (dd, J=8.6, 1.3 Hz, 1H), 7.11 (s, 2H), 7.09 (s, 1H), 4.46-4.23 (m, 1H), 3.24-3.15 (m, 2H), 3.11-3.04 (m, 1H), 2.92-2.81 (m, 2H), 2.64-2.55 (m, 1H), 2.49 (s, 3H), 2.38 (s, 6H), 1.30-1.18 (m, 2H);
MASS (ESI, Pos.): 430 (M+H)+.

Example 21(22)

1-[3-(3-cyclopropyl-5-methoxyphenyl)-5-(6-methyl-1H-benzimidazol-2-yl)-4-pyridinyl]-4-piperidinamine Description: ivory powder;
Purity (UPLC-MS/ELSD): 100% (retention time: 0.45 min);
TLC: Rf 0.52 (ethyl acetate:methanol=10:1, NH silica gel);
NMR (300 MHz, CHLOROFORM-d): δ 11.54-11.37 (m, 1H), 9.08-8.94 (m, 1H), 8.26 (s, 1H), 7.73-7.64 and 7.39-7.31 (m, 1H), 7.62-7.56 and 7.29-7.24 (m, 1H), 7.10 (d, J=8.1 Hz, 1H), 6.67-6.55 (m, 3H), 3.80 (s, 3H), 3.02-2.91 (m, 2H), 2.66-2.52 (m, 3H), 2.48 (s, 3H), 1.95-1.81 (m, 1H), 1.68-1.54 (m, 2H), 1.32-1.12 (m, 2H), 1.03-0.92 (m, 2H), 0.75-0.64 (m, 2H);
MASS (ESI, Pos.): 454 (M+H)+.

Example 21(23)

1-[3-(3-fluoro-5-methoxyphenyl)-5-(5-methyl-1H-benzimidazol-2-yl)-4-pyridinyl]-4-piperidinamine Description: green oil;
Purity (UPLC-MS/ELSD): 100% (retention time: 0.41 min);
TLC: Rf 0.63 (ethyl acetate:methanol=10:1, NH silica gel);
NMR (300 MHz, CHLOROFORM-d): δ 10.77 (br. s., 1H), 9.19 (s, 1H), 8.30 (s, 1H), 7.86-7.31 (m, 2H), 7.14 (dd, J=1.1, 8.2 Hz, 1H), 6.73-6.62 (m, 3H), 3.85 (s, 3H), 3.08-2.97 (m, 2H), 2.75-2.59 (m, 3H), 2.51 (s, 3H), 1.77-1.51 (m, 2H), 1.40-1.17 (m, 2H);
MASS (ESI, Pos.): 432 (M+H)+.

Example 21(24)

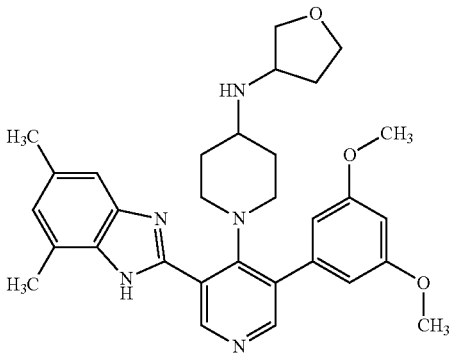

[106]

1-[3-(3,5-dimethoxyphenyl)-5-(4,6-dimethyl-1H-benzimidazol-2-yl)-4-pyridinyl]-N-(tetrahydro-3-furanyl)-4-piperidinamine Description: ivory amorphous powder;
Purity (UPLC-MS/ELSD): 100% (retention time: 0.54 min);
TLC: Rf 0.60 (ethyl acetate:methanol=10:1, NH silica gel);
NMR (300 MHz, CHLOROFORM-d): δ 11.25 and 10.73 (br. s., 1H), 9.26 and 9.08 (br. s., 1H), 8.30 (s, 1H), 7.48 and 7.15 (br. s., 1H), 6.94 (s, 1H), 6.55-6.42 (m, 3H), 3.83 (s, 6H), 3.92-3.68 (m, 3H), 3.48-3.34 (m, 2H), 3.11-3.00 (m, 2H), 2.47 (s, 6H), 2.74-2.38 (m, 3H), 1.85-1.49 (m, 4H), 1.44-1.18 (m, 2H);
MASS (ESI, Pos.): 528 (M+H)+.

Example 21(25)

[107]

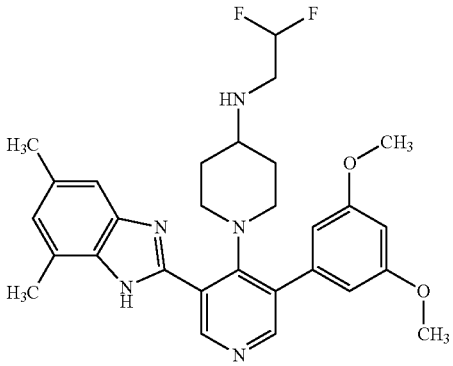

N-(2,2-difluoroethyl)-1-[3-(3,5-dimethoxyphenyl)-5-(4,6-dimethyl-1H-benzimidazol-2-yl)-4-pyridinyl]-4-piperidinamine Description: yellow amorphous powder;
Purity (UPLC-MS/ELSD): 98.0% (retention time: 0.49 min);
TLC: Rf 0.50 (ethyl acetate, NH silica gel);
NMR (300 MHz, METHANOL-d4): δ 8.42 (s, 1H), 8.23 (s, 1H), 7.24 (br. s., 1H), 6.93 (s, 1H), 6.58-6.53 (m, 3H), 5.76 (tt, J=15.5, 87.0 Hz, 1H), 3.83 (s, 6H), 3.14-3.05 (m, 2H), 2.78 (dt, J=4.2, 15.5 Hz, 2H), 2.57 (s, 3H), 2.62-2.49 (m, 2H), 2.44 (s, 3H), 2.39-2.26 (m, 1H), 1.55-1.42 (m, 2H), 1.18-0.99 (m, 2H);
MASS (ESI, Pos.): 522 (M+H)+.

Example 21(26)

1-[3-(6-chloro-1,3-benzoxazol-2-yl)-5-(3,5-dimethylphenyl)-4-pyridinyl]-4-piperidinamine Description: green amorphous powder;
Purity (UPLC-MS/ELSD): 99.0% (retention time: 0.57 min);
TLC: Rf 0.75 (ethyl acetate:methanol=100:6, NH silica gel);
NMR (300 MHz, METHANOL-d4): δ 8.67 (s, 1H), 8.24 (s, 1H), 7.85 (d, J=2.0 Hz, 1H), 7.78 (d, J=9.0 Hz, 1H), 7.47 (dd, J=2.0, 9.0 Hz, 1H), 7.10-7.03 (m, 3H), 3.15-3.04 (m, 2H), 2.77-2.64 (m, 3H), 2.39 (s, 6H), 1.59-1.46 (m, 2H), 1.34-1.15 (m, 2H);
MASS (ESI, Pos.): 433 (M+H)+.

Example 21(27)

[108]

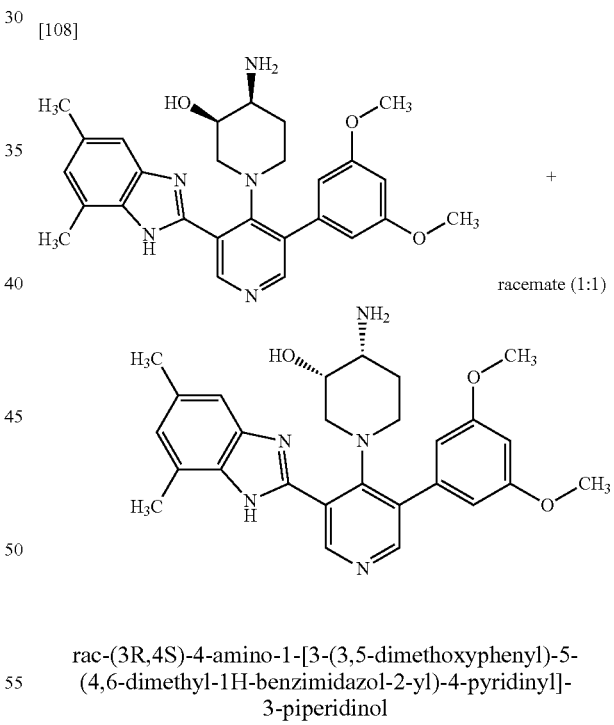

racemate (1:1)

rac-(3R,4S)-4-amino-1-[3-(3,5-dimethoxyphenyl)-5-(4,6-dimethyl-1H-benzimidazol-2-yl)-4-pyridinyl]-3-piperidinol Description: colorless oil;
Purity (LC-MS/ELSD): 100% (retention time: 0.46 min);
TLC: Rf 0.47(ethyl acetate:methanol=9:1, NH silica gel);
NMR (300 MHz, METHANOL-d4): δ 8.85 (s, 1H), 8.29 (s, 1H), 7.27 (s, 1H), 6.93 (s, 1H), 6.58 (t, J=2.2 Hz, 1H), 6.51 (d, J=2.2 Hz, 2H), 3.82 (s, 6H), 3.69 (br. s., 1H), 3.17-3.05 (m, 1H), 3.04-2.92 (m, 1H), 2.90-2.82 (m, 1H), 2.63-2.54 (m, 4H), 2.45-2.36 (m, 4H), 1.65-1.46 (m, 1H), 1.39-1.25 (m, 1H);
MASS (ESI, Pos.): 474 (M+H)+.

Example 21(28)

rac-(3R,4S)-4-amino-1-[3-(6-fluoro-1H-benzimidazol-2-yl)-5-(3-fluoro-5-methoxyphenyl)-4-pyridinyl]-3-piperidinol Description: yellow amorphous powder;
Purity (LC-MS/ELSD): 99.0% (retention time: 0.45 min);
TLC: Rf 0.18 (ethyl acetate:methanol=19:1, NH silica gel);
NMR (300 MHz, METHANOL-d4): δ 8.91 (s, 1H), 8.33 (s, 1H), 7.65 (dd, J=8.9, 4.7 Hz, 1H), 7.39 (dd, J=9.1, 2.2 Hz, 1H), 7.10 (ddd, J=9.7, 8.9, 2.2 Hz, 1H), 6.87-6.74 (m, 3H), 3.87 (s, 3H), 3.71 (br. s., 1H), 3.18-3.07 (m, 1H), 3.06-2.94 (m, 1H), 2.92-2.81 (m, 1H), 2.65-2.54 (m, 1H), 2.39 (dd, J=12.4, 1.0 Hz, 1H), 1.62-1.45 (m, 1H), 1.41-1.27 (m, 1H);
MASS (ESI, Pos.): 452 (M+H)+.

Example 21(29)

rac-(3R,4S)-4-amino-1-[3-(6-chloro-1H-benzimidazol-2-yl)-5-(3-fluoro-5-methoxyphenyl)-4-pyridinyl]-3-piperidinol Description: yellow amorphous powder;
Purity (LC-MS/ELSD): 99.0% (retention time: 0.51 min);
TLC: Rf 0.18 (ethyl acetate:methanol=19:1, NH silica gel);
NMR (300 MHz, METHANOL-d4): δ 8.92 (s, 1H), 8.34 (s, 1H), 7.70 (dd, J=2.0, 0.5 Hz, 1H), 7.65 (dd, J=8.6, 0.5 Hz, 1H), 7.30 (dd, J=8.6, 2.0 Hz, 1H), 6.87-6.74 (m, 3H), 3.87 (s, 3H), 3.74-3.69 (m, 1H), 3.17-3.07 (m, 1H), 3.06-2.95 (m, 1H), 2.91-2.83 (m, 1H), 2.60 (ddd, J=11.6, 5.0, 2.4 Hz, 1H), 2.39 (dd, J=12.4, 1.0 Hz, 1H), 1.62-1.44 (m, 1H), 1.42-1.27 (m, 1H);
MASS (ESI, Pos.): 468 (M+H)+.

Example 21(30)

[109]

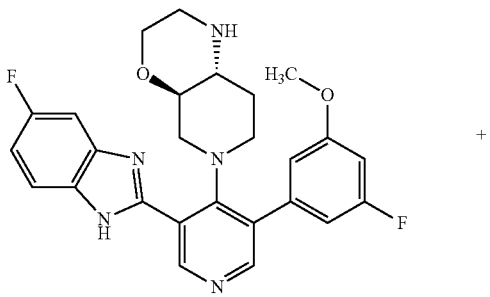

+

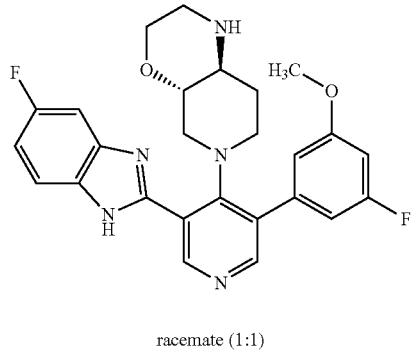

racemate (1:1)

Example 21 rac-(4aR,8aR)-6-[3-(6-fluoro-1H-benzimidazol-2-yl)-5-(3-fluoro-5-methoxyphenyl)-4-pyridinyl]octahydro-1H-pyrido[3,4-b][1,4]oxazine Description: off-white powder;
Purity (LC-MS/ELSD): 100% (retention time: 0.46 min);
TLC: Rf 0.35 (ethyl acetate:methanol=19:1, NH silica gel);
NMR (300 MHz, METHANOL-d4): δ 8.48 (s, 1H), 8.30 (s, 1H), 7.66 (dd, J=8.8, 4.9 Hz, 1H), 7.38 (dd, J=9.1, 2.2 Hz, 1H), 7.12 (ddd, J=9.7, 8.9, 2.2 Hz, 1H), 6.86-6.75 (m, 3H), 3.88 (s, 3H), 3.66 (dd, J=11.6, 2.1 Hz, 1H), 3.45-3.34 (m, 1H), 3.13-2.90 (m, 3H), 2.88-2.61 (m, 3H), 2.42-2.27 (m, 1H), 2.25-2.11 (m, 1H), 1.38-1.26 (m, 2H), 1.23-1.06 (m, 1H);
MASS (ESI, Pos.): 478 (M+H)+.

Example 21(31)

1-[3-(6-chloro-1H-benzimidazol-2-yl)-5-(3-fluoro-5-methylphenyl)-4-pyridinyl]-4-piperidinamine Description: pale purple powder;
Purity (UPLC-MS/ELSD): 99.8% (retention time: 0.47 min);
TLC: Rf 0.20 (ethyl acetate:methanol=20:1, NH silica gel);
NMR (300 MHz, METHANOL-d4): δ 8.44 (s, 1H), 8.25 (s, 1H), 7.67 (d, J=2.0 Hz, 1H), 7.63 (d, J=8.6 Hz, 1H), 7.31 (dd, J=8.5, 1.9 Hz, 1H), 7.09 (s, 1H), 7.03 (s, 1H), 7.00 (s, 1H), 3.07-2.95 (m, 2H), 2.62-2.49 (m, 2H), 2.47-2.43 (m, 4H), 1.42 (dd, J=12.5, 1.9 Hz, 2H), 1.07 (dd, J=11.6, 3.9 Hz, 2H);
MASS (ESI, Pos.): 436 (M+H)+.

Example 21(32)

1-[3-(6-fluoro-1H-benzimidazol-2-yl)-5-(3-fluoro-5-methylphenyl)-4-pyridinyl]-4-piperidinamine Description: pale brown amorphous powder;
Purity (UPLC-MS/ELSD): 96.7% (retention time: 0.44 min);
TLC: Rf 0.19 (ethyl acetate:methanol=20:1, NH silica gel);
NMR (300 MHz, METHANOL-d4): δ 8.44 (s, 1H), 8.24 (s, 1H), 7.66-7.61 (m, 1H), 7.38-7.34 (m, 1H), 7.16-7.07 (m, 2H), 7.04-6.99 (m, 1H), 3.07-2.97 (m, 2H), 2.62-2.50 (m, 2H), 2.51-2.44 (m, 4H), 1.47-1.38 (m, 2H), 1.15-0.99 (m, 2H);
MASS (ESI, Pos.): 420 (M+H)+.

Example 21(33)

1-[3-(5-fluoro-1H-benzimidazol-2-yl)-5-(3-fluoro-5-methoxyphenyl)-4-pyridinyl]-4-piperidinamine Description: pale yellow powder;
Purity (LC-MS/ELSD): 95.0% (retention time: 0.43 min);
TLC: Rf 0.45 (ethyl acetate:methanol=9:1, NH silica gel);
NMR (300 MHz, METHANOL-d4): δ 8.44 (s, 1H), 8.25 (s, 1H), 7.63 (dd, J=8.8, 4.6 Hz, 1H), 7.36 (dd, J=9.1, 2.3 Hz, 1H), 7.10 (td, J=9.1, 2.4 Hz, 1 H), 6.71-6.86 (m, 3H), 3.86 (s, 3H), 3.04 (br. d, J=12.4 Hz, 2H), 2.45-2.67 (m, 3H), 1.45 (br. d, J=10.8 Hz, 2H), 1.03-1.22 (m, 2H)
MASS (ESI, Pos.): 436 (M+H)+.

Example 21(34)

rac-(4aR,8aR)-6-[3-(6-fluoro-1H-benzimidazol-2-yl)-5-(3-fluoro-5-methylphenyl)-4-pyridinyl]octahydro-1H-pyrido[3,4-b][1,4]oxazine Description: brown amorphous powder;
Purity (LC-MS/ELSD): 97.0% (retention time: 0.46 min);
TLC: Rf 0.30 (ethyl acetate:methanol=19:1, NH silica gel);
NMR (300 MHz, METHANOL-d4): δ 8.47 (s, 1H), 8.29 (s, 1H), 7.66 (dd, J=8.8, 4.9 Hz, 1H), 7.38 (dd, J=9.1, 2.3 Hz, 1H), 7.18-6.97 (m, 4H), 3.70-3.60 (m, 1H), 3.38 (td, J=11.5, 3.0 Hz, 1H), 3.10-2.89 (m, 3H), 2.87-2.60 (m, 3H), 2.46 (s, 3H), 2.39-2.26 (m, 1H), 2.23-2.10 (m, 1H), 1.36-1.25 (m, 1H), 1.20-1.03 (m, 1H);
MASS (ESI, Pos.): 462 (M+H)+.

Example 21(35)

rac-(4aR,8aR)-6-[3-(6-chloro-1H-benzimidazol-2-yl)-5-(3-fluoro-5-methylphenyl)-4-pyridinyl]octahydro-1H-pyrido[3,4-b][1,4]oxazine Description: brown amorphous powder;
Purity (LC-MS/ELSD): 95.0% (retention time: 0.50 min);
TLC: Rf 0.30 (ethyl acetate:methanol=19:1, NH silica gel);
NMR (300 MHz, METHANOL-d4): δ 8.48 (s, 1H), 8.29 (s, 1H), 7.69 (d, J=1.8 Hz, 1H), 7.65 (d, J=8.8 Hz, 1H), 7.33 (dd, J=8.7, 1.9 Hz, 1H), 7.11-7.08 (m, 1H), 7.07-6.97 (m, 2H), 3.65 (dd, J=11.4, 2.1 Hz, 1H), 3.39 (td, J=11.5, 3.2 Hz, 1H), 3.10-2.88 (m, 3H), 2.87-2.76 (m, 1H), 2.76-2.59 (m, 2H), 2.50-2.43 (m, 3H), 2.38-2.25 (m, 1H), 2.23-2.09 (m, 1H), 1.36-1.25 (m, 1H), 1.19-1.02 (m, 1H);
MASS (ESI, Pos.): 478 (M+H)+.

Example 21(36)

1-[3-(5-fluoro-1H-benzimidazol-2-yl)-5-(3-fluoro-5-methylphenyl)-4-pyridinyl]-N-(3-oxetanyl)-4-piperidinamine Description: yellow amorphous powder;
Purity (LC-MS/ELSD): 100% (retention time: 0.43 min);
TLC: Rf 0.47 (ethyl acetate:methanol=9:1, NH silica gel);
NMR (300 MHz, METHANOL-d4): δ 8.43 (s, 1H), 8.23 (s, 1H), 7.58-7.68 (m, 1H), 7.30-7.42 (m, 1H), 6.95-7.19 (m, 4H), 4.66 (t, J=7.0 Hz, 2H), 4.35 (t, J=6.5 Hz, 2H), 3.86-3.98 (m, 1H), 3.01 (br. d, J=13.0 Hz, 2H), 2.46-2.58 (m, 2H), 2.44 (s, 3H), 2.20-2.33 (m, 1H), 1.37 (br. d, J=11.2 Hz, 2H), 0.96-1.13 (m, 2H);
MASS (ESI, Pos.): 476 (M+H)+.

Example 21(37)

[110]

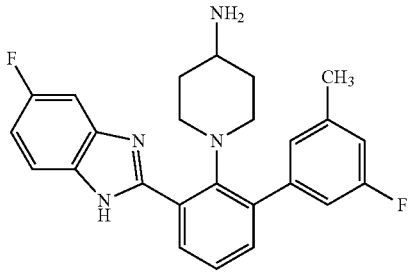

1-[3'-fluoro-3-(5-fluoro-1H-benzimidazol-2-yl)-5'-methyl-2-biphenylyl]-4-piperidinamine Description: off-white powder;
Purity (LC-MS/ELSD): 99.8% (retention time: 0.61 min);
TLC: Rf 0.56 (ethyl acetate:methanol=9:1, NH silica gel);
NMR (300 MHz, METHANOL-d4): δ 7.60 (dd, J=8.9, 4.7 Hz, 1H), 7.49 (dd, J=7.3, 2.0 Hz, 1H), 7.22-7.37 (m, 3H), 6.89-7.13 (m, 4H), 3.02 (br. d, J=12.3 Hz, 2H), 2.57-2.72 (m, 1H), 2.39-2.54 (m, 5H), 1.53 (br. d, J=11.7 Hz, 2H), 1.04-1.20 (m, 2H);
MASS (ESI, Pos.): 419 (M+H)+.

Example 21(38)

1-[3-(5-chloro-1H-benzimidazol-2-yl)-3'-fluoro-5'-methyl-2-biphenylyl]-4-piperidinamine Description: white powder;
Purity (LC-MS/ELSD): 97.1% (retention time: 0.68 min);
TLC: Rf 0.59 (ethyl acetate:methanol=9:1, NH silica gel);
NMR (300 MHz, METHANOL-d4): δ 7.63 (d, J=1.5 Hz, 1H), 7.59 (d, J=8.6 Hz, 1H), 7.51 (dd, J=7.3, 2.0 Hz, 1H), 7.22-7.35 (m, 3H), 6.89-7.04 (m, 3H), 2.97 (br. d, J=11.9 Hz, 2H), 2.38-2.56 (m, 6H), 1.48 (br. d, J=11.7 Hz, 2H), 0.97-1.13 (m, 2H);
MASS (ESI, Pos.): 435 (M+H)+.

Example 21(39)

1-[3-(5-chloro-1H-benzimidazol-2-yl)-5-(3-fluoro-5-methylphenyl)-4-pyridinyl]-N-(3-oxetanyl)-4-piperidinamine Description: off-white powder;
Purity (LC-MS/ELSD): 98.5% (retention time: 0.50 min);
TLC: Rf 0.70 (ethyl acetate:methanol=9:1, NH silica gel);
NMR (300 MHz, METHANOL-d4): δ 8.43 (s, 1H), 8.24 (s, 1H), 7.57-7.69 (m, 2H), 7.31 (dd, J=8.6, 2.0 Hz, 1H), 7.07 (br. s, 1H), 6.96-7.04 (m, 2H), 4.66 (t, J=6.9 Hz, 2H), 4.35 (t, J=6.6 Hz, 2H), 3.85-3.98 (m, 1H), 3.01 (br. d, J=12.6 Hz, 2H), 2.39-2.58 (m, 5H), 2.19-2.34 (m, 1H), 1.37 (br. d, J=11.3 Hz, 2H), 0.95-1.13 (m, 2H);
MASS (ESI, Pos.): 492 (M+H)+.

Reference Example 30 methyl 5-bromo-4-hydroxypyridine-3-carboxylate

To a suspension of methyl 4-hydroxypyridine-3-carboxylate (CAS #67367-24-2) (1.96 g) in acetonitrile (20 mL)/ acetic acid (4 mL) was added N-bromosuccinimide (CAS #128-08-5) (2.39 g) at room temperature, and the mixture was stirred at 60 degrees C. for 4 hours followed by concentration. To the obtained residue was added acetone, and the mixture was stirred for 5 min. The insoluble matter was collected by filtration to obtain the title compound having the following physical property values.
Description: white powder;
TLC: Rf 0.53 (ethyl acetate:methanol=4:1);

Example 22(1)-Example 22(6)

Using tert-butyl 2-(2-hydroxyethyl)piperidine-1-carboxylate (CAS #118811-03-3) in place of the compound produced in Reference example 8, using the compound produced in Reference example 30 in place of 3,5-dimethylphenol, using a corresponding reagent in place of phenylboronic acid, using a corresponding reagent in place of 3,5-dimethylaniline, the present invention compounds having the following physical property values were obtained by following the same procedure as in Reference example 9→Reference example 2→Reference example 6→Reference example 7→Example 1.

Example 22(1)

N,5-bis(3,5-dimethylphenyl)-4-[2-(2-piperidinyl)ethoxy]pyridine-3-carboxamide

[111]

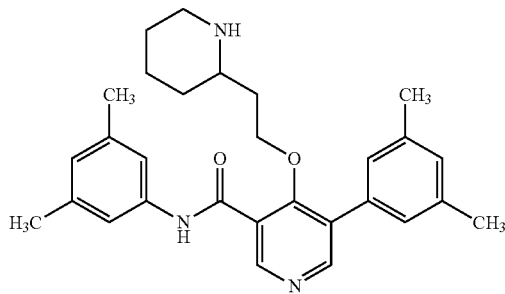

Description: colorless oil;
Purity (LC-MS/ELSD): 95.1% (retention time: 4.07 min);
TLC: Rf 0.53 (ethyl acetate:methanol=9:1, NH silica gel);
NMR (300 MHz, CHLOROFORM-d): δ 9.50 (br.s., 1H), 9.23 (s, 1H), 8.57 (s, 1H), 7.35 (s, 2H), 7.12 (s, 2H), 7.08 (s, 1H), 6.80 (s, 1H), 3.86-3.71 (m, 2H), 2.89 (d, J=12.08 Hz, 1H), 2.40 (s, 6H), 2.52-2.23 (m, 4H), 2.34 (s, 6H), 1.77-0.79 (m, 5H);
MASS (ESI, Pos.): 458 (M+H)+.

Example 22(2)

5-(3,5-dimethylphenyl)-N-[3-(hydroxymethyl)phenyl]-4-[2-(2-piperidinyl)ethoxy]pyridine-3-carboxamide Description: colorless oil;
Purity (LC-MS/ELSD): 100% (retention time: 3.66 min);
TLC: Rf 0.46 (ethyl acetate:methanol=9:1, NH silica gel);
NMR (300 MHz, CHLOROFORM-d): δ 9.72 (br.s., 1H), 9.23 (s, 1H), 8.59 (s, 1H), 7.77 (d, J=7.80 Hz, 1H), 7.63 (s, 1H), 7.36 (t, J=7.87 Hz, 1H), 7.17-7.03 (m, 5H), 4.71 (s, 2H), 3.92-3.65 (m, 2H), 2.92 (d, J=13.55 Hz, 1H), 2.65-2.27 (m, 8H), 1.80-1.64 (m, 2H), 1.65-1.47 (m, 2H), 1.42 (d, J=5.13 Hz, 1H), 1.36-1.11 (m, 2H), 1.01-0.78 (m, 1H);
MASS (ESI, Pos.): 460 (M+H)+.

Example 22(3)

N-(3-carbamoylphenyl)-5-(3,5-dimethylphenyl)-4-[2-(2-piperidinyl)ethoxy]pyridine-3-carboxamide Description: white amorphous powder;
Purity (LC-MS/ELSD): 98.6% (retention time: 3.78 min);
TLC: Rf 0.43 (ethyl acetate:methanol=9:1);
NMR (300 MHz, CHLOROFORM-d): δ 9.94 (br.s., 1H), 9.27 (s, 1H), 8.61 (s, 1H), 8.15-8.07 (m, 1H), 8.01 (t, J=1.83 Hz, 1H), 7.72-7.65 (m, 1H), 7.55-7.44 (m, 1H), 7.13 (s, 2H), 7.10 (s, 1H), 6.93 (br.s., 1H), 5.79-5.49 (m, 1H), 3.81 (t, J=6.13 Hz, 2H), 2.93 (d, J=2.93 Hz, 1H), 2.64-2.33 (m, 2H), 2.41 (s, 6H), 1.88-1.37 (m, 5H), 1.33-1.13 (m, 2H), 0.98-0.79 (m, 1H);
MASS (ESI, Pos.): 473 (M+H)+.

Example 22(4)

N-benzyl-5-(3,5-dimethylphenyl)-4-[2-(2-piperidinyl)ethoxy]pyridine-3-carboxamide Description: pale yellow powder;
Purity (LC-MS/ELSD): 100% (retention time: 3.78 min);
TLC: Rf 0.43 (ethyl acetate);
NMR (300 MHz, CHLOROFORM-d): δ 9.22 (s, 1H), 8.54 (s, 1H), 8.19-8.05 (m, 1H), 7.43-7.26 (m, 5H), 7.07 (s, 2H), 7.05 (s, 1H), 4.68 (d, J=5.68 Hz, 2H), 3.75-3.51 (m, 2H), 2.99-2.74 (m, 1H), 2.38-2.18 (m, 8H), 1.74-1.60 (m, 1H), 1.57-1.42 (m, 2H), 1.39-1.08 (m, 4H), 0.94-0.68 (m, 1H);
MASS (ESI, Pos.): 444 (M+H)+.

Example 22(5)

5-(3,5-dimethylphenyl)-N-(1-methyl-1H-pyrazol-4-yl)-4-[2-(2-piperidinyl)ethoxy]pyridine-3-carboxamide Description: beige powder;
Purity (LC-MS/ELSD): 100% (retention time: 3.59 min);
TLC: Rf 0.70 (ethyl acetate:methanol=9:1, NH silica gel);
NMR (300 MHz, CHLOROFORM-d): δ 9.66 (s, 1H), 9.21 (s, 1H), 8.57 (s, 1H), 8.11 (s, 1H), 7.57 (s, 1H), 7.11 (s, 2H), 7.09 (s, 1H), 3.88 (s, 3H), 3.85-3.69 (m, 2H), 3.09-2.87 (m, 1H), 2.63-1.82 (m, 9H), 1.77-1.51 (m, 2H), 1.49-1.19 (m, 4H), 1.10-0.91 (m, 1H);
MASS (ESI, Pos.): 434 (M+H)+.

Example 22(6)

N-(3,5-dimethylphenyl)-5-(1-methyl-1H-pyrazol-4-yl)-4-[2-(2-piperidinyl)ethoxy]pyridine-3-carboxamide Description: pale yellow oil;
Purity (LC-MS/ELSD): 100% (retention time: 3.64 min);
TLC: Rf 0.63 (ethyl acetate:methanol=9:1, NH silica gel);
NMR (300 MHz, CHLOROFORM-d): δ 8.99 (s, 2H), 8.74 (s, 1H), 7.86 (s, 2H), 7.32 (s, 2H).6.84 (s, 1H), 4.05-3.87 (m, 2H), 4.00 (s, 3H), 3.09-2.93 (m, 1H), 2.77-

2.64 (m, 1H), 2.64-2.48 (m, 1H), 2.37-2.31 (m, 6H), 1.95-1.69 (m, 4H), 1.67-1.49 (m, 2H), 1.48-1.04 (m, 2H);

MASS (ESI, Pos.): 434 (M+H)+.

Example 23

N-{5-(3,5-dimethylphenyl)-4-[2-(2-piperidinyl)ethoxy]-3-pyridinyl}-3,5-dimethylbenzamide

[112]

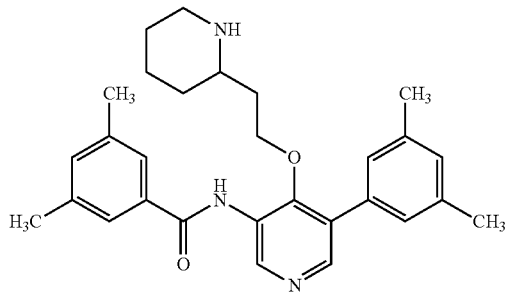

Using tert-butyl 2-(2-hydroxyethyl)piperidine-1-carboxylate in place of the compound produced in Reference example 8, using the compound produced in Reference example 30 in place of 3,5-dimethylphenol, using 3,5-dimethylphenylboronic acid in place of phenylboronic acid, the present invention compound having the following physical property values was obtained by following the same procedure as in Reference example 9→Reference example 2→Reference example 6→Reference example 12→Reference example 17→Example 1.

Description: white powder;
Purity (LC-MS/ELSD): 100% (retention time: 3.91 min);
TLC: Rf 0.64 (ethyl acetate:methanol=9:1, NH silica gel);
NMR (300 MHz, CHLOROFORM-d): δ 9.64 (s, 1H), 8.99 (br.s., 1H), 8.28 (s, 1H), 7.49 (s, 2H), 7.19 (s, 1H), 7.12 (s, 2H), 7.04 (s, 1H), 3.79-3.61 (m, 2H), 2.71 (d, J=9.1 Hz, 1H), 2.40 (s, 6H), 2.38 (s, 6H), 2.55-2.26 (m, 2H), 1.72-1.33 (m, 6H), 1.24-1.07 (m, 2H), 1.01-0.86 (m, 1H)

MASS (ESI, Pos.): 458 (M+H)+.

Example 24(1)-Example 24(2)

Using tert-butyl 2-(2-hydroxyethyl)piperidine-1-carboxylate in place of the compound produced in Reference example 8, using the compound produced in Reference example 30 in place of 3,5-dimethylphenol, using 3,5-dimethylphenylboronic acid in place of phenylboronic acid, using 3,5-dimethylbenzaldehyde, or a corresponding reagent in place of it, the present invention compounds having the following physical property values were obtained by following the same procedure as in Reference example 9→Reference example 2→Reference example 6→Reference example 12→Reference example 13→Example 1.

Example 24(1)

N-(3,5-dimethylbenzyl)-5-(3,5-dimethylphenyl)-4-[2-(2-piperidinyl)ethoxy]-3-pyridinamine

[113]

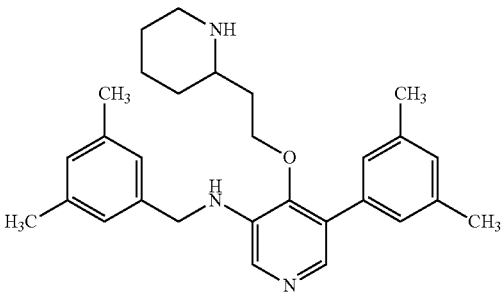

Description: colorless oil;
Purity (LC-MS/ELSD): 100% (retention time: 3.82 min);
TLC: Rf 0.70 (ethyl acetate:methanol=9:1, NH silica gel);
NMR (300 MHz, CHLOROFORM-d): δ 7.91 (s, 1H), 7.87 (s, 1H), 7.14 (s, 2H), 7.02-6.97 (m, 3H), 6.90 (s, 1H), 5.90-5.41 (br, 1H), 4.33 (s, 2H), 3.73-3.63 (m, 1H), 3.63-3.53 (m, 1H), 2.97-2.87 (m, 1H), 2.64-2.40 (m, 2H), 2.36 (s, 6H), 2.31 (s, 6H), 1.76-1.42 (m, 6H), 1.36-1.22 (m, 2H), 1.09-0.93 (m, 1H);

MASS (ESI, Pos.): 444 (M+H)+.

Example 24(2)

5-(3,5-dimethylphenyl)-N-[(1-methyl-1H-pyrazol-4-yl)methyl]-4-[2-(2-piperidinyl)ethoxy]-3-pyridinamine Description: colorless oil;
Purity (LC-MS/ELSD): 100% (retention time: 3.43 min);
TLC: Rf 0.54 (ethyl acetate:methanol=4:1, NH silica gel);
NMR (300 MHz, CHLOROFORM-d): δ 7.99 (s, 1H), 7.90 (s, 1H), 7.47 (s, 1H), 7.35 (s, 1H), 7.13 (s, 2H), 7.00 (s, 1H), 5.65-5.17 (br, 1H), 4.28 (s, 2H), 3.88 (s, 3H), 3.67-3.50 (m, 2H), 2.98-2.89 (m, 1H), 2.61-2.43 (m, 2H), 2.36 (s, 6H), 1.78-1.40 (m, 6H), 1.35-1.19 (m, 2H), 1.06-0.91 (m, 1H);

MASS (ESI, Pos.): 420 (M+H)+.

Reference Example 31 ethyl 5-hydroxy-1-(quinolin-2-yl)-1H-pyrazole-4-carboxylate

To a suspension of diethyl ethoxymethylenemalonate (CAS #87-13-8) (4.32 g) in water (40 mL) was added 2-hydrazinoquinoline (CAS #15793-77-8) (3.18 g) and potassium carbonate (2.76 g), and the mixture was refluxed for 5.5 hours. After cooling to room temperature, the precipitate was collected by filtration. The precipitate was suspended in the mixture of water and ethyl acetate and made weakly acidic with 2M hydrochloric acid. After being stirred, the precipitate was collected by filtration and dried to obtain the title compound (3.37 g) having the following physical property values.

Description: beige powder;
TLC: Rf 0.36 (dichloromethane:methanol=9:1)

Reference Example 32 ethyl 5-chloro-1-(quinolin-2-yl)-1H-pyrazole-4-carboxylate

The compound (1.0 g) produced in Reference example 31 was mixed with phosphorus oxychloride (6 mL) under ice cooling, and stirred at 100 degrees C. for 16 hours. After cooling, the reaction solution was poured into the mixture of ice and ethyl acetate, and then washed with water and saturated brine sequentially. After drying, the organic layer was concentrated and treated with benzene as azeotropy four times. The obtained residue was purified by silica gel column chromatography (eluent hexane:ethyl acetate=95:5→75:25) to obtain the mixture of the title compound and mineral salt (2.2 g) having the following physical property values.

TLC: Rf 0.71 (n-hexane:ethyl acetate=1:1);

Reference Example 33 ethyl 5-(4-((tert-butoxycarbonyl)amino)piperidin-1-yl)-1-(quinolin-2-yl)-1H-pyrazole-4-carboxylate To a dimethylacetamide (2.5 mL) solution of the mixture produced in Reference example 32 (500 mg) was added potassium phosphate (529 mg) and 4-(tert-butoxycarbonylamino)piperidine (365 mg), and stirred at 100 degrees C. for 21 hours. After cooling to room temperature, the reaction solution was added water and extracted with ethyl acetate. The organic layer was sequentially washed with water and saturated brine, and concentrated after drying. The obtained residue was purified by silica gel column chromatography (eluent hexane:ethyl acetate=90:10→75:25) to obtain the title compound (58 mg) having the following physical property values.

TLC: Rf 0.23 (n-hexane:ethyl acetate=3:1).

Example 25

5-(4-amino-1-piperidinyl)-N-(3,5-dimethylphenyl)-1-(2-quinolinyl)-1H-pyrazole-4-carboxamide

[114]

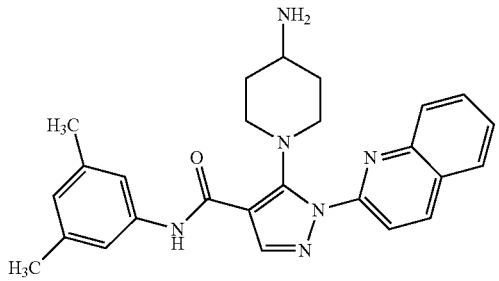

Using the compound produced in Reference example 33 in place of the compound produced in Reference example 5, the present invention compound having the following physical property values was obtained by following the same procedure as in Reference example 6→Reference example 7→Example 1.

Description: amber powder;
TLC: Rf 0.67 (ethyl acetate:methanol=10:1, NH silica gel);
NMR (300 MHz, CHLOROFORM-d): δ 9.92 (s, 1H), 8.32 (d, J=9.0 Hz, 1H), 8.23 (s, 1H), 8.08-7.99 (m, 2H), 7.93-7.85 (m, 1H), 7.77 (ddd, J=8.4, 7.0, 1.5 Hz, 1H), 7.64-7.55 (m, 1H), 7.31 (s, 2H), 6.74 (s, 1H), 3.81-3.69 (m, 2H), 3.23 (d, J=12.1 Hz, 2H), 3.17-3.05 (m, 1H), 2.31 (s, 6H), 2.13-2.00 (m, 2H), 1.83-1.66 (m, 2H);
MASS (ESI, Pos.): 441 (M+H)+.

Reference Example 34 benzyl (1-(3-amino-5-(3,5-dimethylphenyl)pyridin-4-yl)piperidin-4-yl)carbamate Using benzyl piperidin-4-ylcarbamate (CAS #182223-54-7) in place of tert-butyl N-(4-piperidylmethyl)carbamate, using 3,5-dimethylphenylboronic acid in place of phenylboronic acid, the title compound having the following physical property values was obtained by following the same procedure as in Reference example 14→Reference example 2→Reference example 16 and used for next reaction without further purification.

Reference Example 35 benzyl (1-(3-(3,5-dimethylphenyl)-5-iodopyridin-4-yl)piperidin-4-yl)carbamate To an anhydrous dichloromethane (36 mL) solution of the compound (1.68 g) produced in Reference example 34 was added boron trifluoride diethyl ether complex ($BF_3$-$Et_2O$) (2.05 mL) under ice cooling, and the mixture was stirred for 10 min. To the reaction solution was added amyl nitrite (1.87 mL) and stirred for 25 min under ice cooling. To the reaction solution was added the acetone (7.8 mL) solution of sodium iodide (CAS #7681-82-5) (1.8 g), and stirred for 30 min under ice-cooling. To the reaction solution was added saturated aqueous solution of sodium thiosulfate solution, and stirred at room temperature. After adding 1M aqueous solution of sodium hydroxide, the reaction solution was extracted with ethyl acetate. The organic layer was washed with saturated brine, dried and concentrated. The obtained residue was purified by preparative medium pressure liquid chromatography (Yamazen Corp. YFLC-Wprep-2XY) (Hi-flash SI) (n-hexane:ethyl acetate=1:1) to obtain the title compound (1.27 g) having the following physical property values.

Description: pale yellow amorphous powder;
TLC: Rf 0.72 (ethyl acetate);

Reference Example 36 benzyl (1-(3-(1,3-benzoxazol-2-yl)-5-(3,5-dimethylphenyl)pyridin-4-yl)piperidin-4-yl)carbamate To a toluene (1.0 mL) solution of the compound (60 mg) produced in Reference example 35 was added potassium carbonate (38 mg), copper(II) acetate monohydrate (4.44 mg), palladium acetate (1.24 mg), triphenylphosphine (14.5 mg) and benzoxazole (CAS #273-53-0) (22 microL), and the mixture was stirred at 100 degrees C. overnight. To the reaction solution was added additional potassium carbonate (38 mg), copper(II) acetate monohydrate (6.2 mg), palladium acetate (1.2 mg), triphenylphosphine (15 mg) and benzoxazole (22 microL), and the mixture was stirred for 8 hours. After cooling to room temperature, the reaction solution was added water and ethyl acetate, and sequentially washed with water and saturated brine. The organic layer was concentrated after drying. The obtained residue was purified by preparative medium pressure liquid chromatography (Yamazen Corp. YFLC-Wprep-2XY) (Hi-flash NH) (n-hexane:ethyl acetate=1:1) to obtain the title compound (20 mg) having the following physical property values.

TLC: Rf 0.25 (n-hexane:ethyl acetate=3:1, NH silica gel);

Example 26(1)-Example 26(89)

Using 1-bromo-2-chloro-3-benzene in place of 3-bromo-4-chloro-5-nitropyridine or 3-bromo-4-chloro-5-nitropyridine, using a corresponding piperidine derivative in place of tert-butyl N-(4-piperidylmethyl)carbamate or tert-butyl N-(4-piperidylmethyl)carbamate, using a corresponding phenylboronic acid derivative in place of phenylboronic acid, using benzoxazole or a corresponding heterocyclic ring or a corresponding boronic acid derivative, the present invention compounds having the following physical property values were obtained by following the same procedure as in Reference example 14→Reference example 2→Reference example 16→Reference example 35→Reference example 36→Example 1 or Example 4.

Example 26(1)

1-[3-(1,3-benzoxazol-2-yl)-5-(3,5-dimethylphenyl)-4-pyridinyl]-4-piperidinamine

[115]

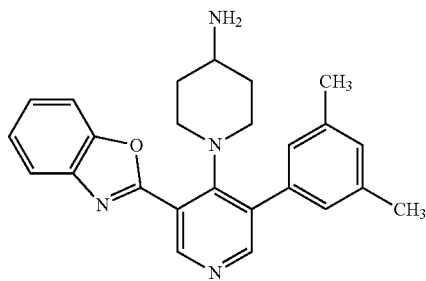

Description: yellow oil;
TLC: Rf 0.24 (ethyl acetate, NH silica gel);
NMR (300 MHz, METHANOL-d4): δ 8.62 (s, 1H), 8.21 (s, 1H), 7.85-7.77 (m, 1H), 7.76-7.68 (m, 1H), 7.52-7.40 (m, 2H), 7.11-7.02 (m, 3H), 3.07 (d, J=12.6 Hz, 2H), 2.75-2.61 (m, 2H), 2.51 (s, 1H), 2.39 (s, 6H), 1.45 (dd, J=12.1, 2.0 Hz, 2H), 1.22-1.06 (m, 2H);
MASS (ESI, Pos.): 399 (M+H)+.

Example 26(2)

1-[3-(1,3-benzothiazol-2-yl)-5-(3,5-dimethylphenyl)-4-pyridinyl]-4-piperidinamine Description: yellow oil;
TLC: Rf 0.57 (ethyl acetate:methanol=19:1, NH silica gel);
NMR (300 MHz, METHANOL-d4): δ 8.68 (s, 1H), 8.22 (s, 1H), 8.16-7.96 (m, 2H), 7.62-7.53 (m, 1H), 7.53-7.44 (m, 1H), 7.10 (s, 1H), 7.03 (s, 2H), 3.13-3.00 (m, 2H), 2.70-2.57 (m, 2H), 2.53-2.34 (m, 7H), 1.55-1.42 (m, 2H), 1.41-1.24 (m, 2H);
MASS (ESI, Pos.): 415 (M+H)+.

Example 26(3)

1-[5-(3,5-dimethylphenyl)-6'-ethoxy-3,3'-bipyridin-4-yl]-4-piperidinamine

Description: colorless oil;
Purity (UPLC-MS/ELSD): 99.6% (retention time: 0.45 min);
TLC: Rf 0.69 (ethyl acetate:methanol=9:1, NH silica gel);
NMR (300 MHz, CHLOROFORM-d): δ 8.26 (s, 1H), 8.21 (s, 1H), 8.18 (dd, J=2.4, 0.7 Hz, 1H), 7.63 (dd, J=8.4, 2.4 Hz, 1H), 7.02-7.00 (m, 1H), 6.97-6.94 (m, 2H), 6.82 (dd, J=8.4, 0.7 Hz, 1H), 4.41 (q, J=7.0 Hz, 2H), 2.90-2.80 (m, 2H), 2.37 (s, 6H), 2.52-2.34 (m, 3H), 1.44 (t, J=7.0 Hz, 3H), 1.45-1.38 (m, 2H), 1.02-0.86 (m, 2H);
MASS (ESI, Pos.): 403 (M+H)+.

Example 26(4)

1-[3-(3,5-dimethylphenyl)-5-(2-methyl-2H-indazol-5-yl)-4-pyridinyl]-4-piperidinamine Description: pale brown amorphous powder;
Purity (UPLC-MS/ELSD): 99.9% (retention time: 0.50 min);
TLC: Rf 0.53 (ethyl acetate:methanol=9:1, NH silica gel);
NMR (300 MHz, CHLOROFORM-d): δ 8.30 (s, 1H), 8.26 (s, 1H), 7.95 (s, 1H), 7.75-7.71 (m, 1H), 7.63-7.61 (m, 1H), 7.31-7.27 (m, 1H), 7.02-6.97 (m, 3H), 4.26 (s, 3H), 2.95-2.86 (m, 2H), 2.37 (s, 6H), 2.47-2.32 (m, 3H), 1.39-1.28 (m, 2H), 0.98-0.84 (m, 2H);
MASS (ESI, Pos.): 412 (M+H)+.

Example 26(5)

1-[3-(3,5-dimethylphenyl)-5-(1-methyl-1H-benzimidazol-5-yl)-4-pyridinyl]-4-piperidinamine Description: white amorphous powder;
Purity (UPLC-MS/ELSD): 99.8% (retention time: 0.41 min);
TLC: Rf 0.28 (ethyl acetate:methanol=9:1, NH silica gel);
NMR (300 MHz, CHLOROFORM-d): δ 8.29 (s, 1H), 8.26 (s, 1H), 7.92 (s, 1H), 7.82 (dd, J=1.6, 0.6 Hz, 1H), 7.46 (dd, J=8.3, 0.6 Hz, 1H), 7.34 (dd, J=8.3, 1.6 Hz, 1H), 7.03-6.98 (m, 3H), 3.91 (s, 3H), 2.92-2.83 (m, 2H), 2.37 (s, 6H), 2.47-2.29 (m, 3H), 1.37-1.24 (m, 2H), 0.97-0.82 (m, 2H);
MASS (ESI, Pos.): 412 (M+H)+.

Example 26(6)

1-[3-(3,5-dimethoxyphenyl)-5-(5-fluoro-1H-indol-2-yl)-4-pyridinyl]-4-piperidinamine Description: deep yellow powder;
Purity (UPLC-MS/ELSD): 98.9% (retention time: 0.52 min);
TLC: Rf 0.52 (ethyl acetate:methanol=9:1, NH silica gel);
NMR (300 MHz, CHLOROFORM-d): δ 9.51 (br. s., 1H), 8.67 (s, 1H), 8.25 (s, 1H), 7.36-7.27 (m, 2H), 7.01-6.90 (m, 1H), 6.73 (dd, J=2.0, 0.7 Hz, 1H), 6.51 (t, J=2.2 Hz, 1H), 6.46 (d, J=2.2 Hz, 2H), 3.84 (s, 6H), 3.08-2.96 (m, 2H), 2.69-2.53 (m, 3H), 1.70-1.59 (m, 2H), 1.36-1.18 (m, 2H);
MASS (ESI, Pos.): 447 (M+H)+.

Example 26(7)

1-[3-(3-fluoro-5-methoxyphenyl)-5-(6-methoxy-1H-indol-2-yl)-4-pyridinyl]-4-piperidinamine Description: pale brown powder;
Purity (UPLC-MS/ELSD): 99.7% (retention time: 0.47 min);
TLC: Rf 0.68 (ethyl acetate:methanol=9:1, NH silica gel);
NMR (300 MHz, CHLOROFORM-d): δ 9.23 (br. s., 1H), 8.65 (s, 1H), 8.19 (s, 1H), 7.54 (d, J=8.6 Hz, 1H), 6.90 (d, J=2.2 Hz, 1H), 6.82 (dd, J=8.6, 2.2 Hz, 1H), 6.71-6.62 (m, 4H), 3.88 (s, 3H), 3.85 (s, 3H), 3.02 (d, J=12.8 Hz, 2H), 2.71-2.49 (m, 3H), 1.70-1.54 (m, 2H), 1.36-1.18 (m, 2H);
MASS (ESI, Pos.): 447 (M+H)+.

Example 26(8)

[116]

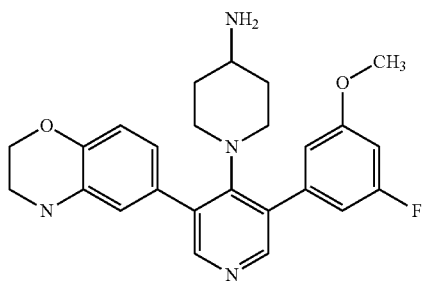

1-[3-(3,4-dihydro-2H-1,4-benzoxazin-6-yl)-5-(3-fluoro-5-methoxyphenyl)-4-pyridinyl]-4-piperidinamine Description: pale brown powder;
Purity (UPLC-MS/ELSD): 98.7% (retention time: 0.25 min);
TLC: Rf 0.49 (ethyl acetate:methanol=20:1, NH silica gel);
NMR (300 MHz, METHANOL-d4): δ 8.09 (s, 1H), 8.07 (s, 1H), 6.80-6.70 (m, 4H), 6.65 (d, J=1.8 Hz, 1H), 6.58 (dd, J=8.2, 2.2 Hz, 1H), 4.26-4.21 (m, 2H), 3.85 (s, 3H), 3.41-3.36 (m, 2H), 2.99 (d, 2H), 2.56-2.42 (m, 3H), 1.50-1.41 (m, 2H), 1.18-1.05 (m, 2H);
MASS (ESI, Pos.): 435 (M+H)+.

Example 26(9)

1-[3-(3-fluoro-5-methoxyphenyl)-5-(1-methyl-1H-indazol-5-yl)-4-pyridinyl]-4-piperidinamine Description: pale yellow powder;
Purity (UPLC-MS/ELSD): 98.5% (retention time: 0.24 min);
TLC: Rf 0.41 (ethyl acetate:methanol=20:1, NH silica gel);
NMR (300 MHz, METHANOL-d4): δ 8.19 (s, 1H), 8.16 (s, 1H), 8.08 (d, J=0.9 Hz, 1H), 7.80 (dd, J=1.6, 0.8 Hz, 1H), 7.67 (dt, J=8.7, 0.8 Hz, 1H), 7.48 (dd, J=8.7, 1.6 Hz, 1H), 6.81-6.72 (m, 3H), 4.12 (s, 3H), 3.86 (s, 3H), 3.02-2.93 (m, 2H), 2.52-2.32 (m, 3H), 1.40-1.30 (m, 2H), 1.05-0.90 (m, 2H);
MASS (ESI, Pos.): 432 (M+H)+.

Example 26(10)

[117]

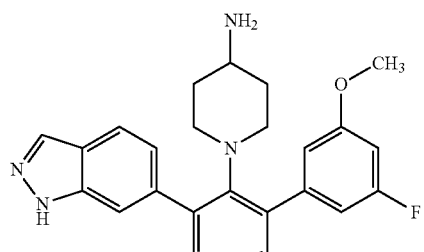

1-[3-(3-fluoro-5-methoxyphenyl)-5-(1H-indazol-6-yl)-4-pyridinyl]-4-piperidinamine Description: pale yellow powder;
Purity (UPLC-MS/ELSD): 99.9% (retention time: 0.41 min);
TLC: Rf 0.35 (ethyl acetate:methanol=20:1, NH silica gel);
NMR (300 MHz, METHANOL-d4): δ 8.22 (s, 1H), 8.17 (s, 1H), 8.10 (d, J=0.9 Hz, 1H), 7.88 (dd, J=8.2, 0.5 Hz, 1H), 7.60 (d, J=0.9 Hz, 1H), 7.19 (dd, J=8.4, 1.3 Hz, 1H), 6.83-6.72 (m, 3H), 3.86 (s, 3H), 3.04-2.94 (m, 2H), 2.53-2.33 (m, 3H), 1.52-1.32 (m, 2H), 1.08-0.91 (m, 2H)
MASS (ESI, Pos.): 418 (M+H)+.

Example 26(11)

1-{3-(3,5-dimethoxyphenyl)-5-[4-(trifluoromethyl)phenyl]-4-pyridinyl}-4-piperidinamine Description: white amorphous powder;
Purity (UPLC-MS/ELSD): 99.8% (retention time: 0.50 min);
TLC: Rf 0.73 (ethyl acetate:methanol=9:1, NH silica gel);
NMR (300 MHz, CHLOROFORM-d): δ 8.30 (s, 1H), 8.23 (s, 1H), 7.73 (d, J=8.8 Hz, 2H), 7.53 (d, J=8.8 Hz, 2H), 6.53-6.47 (m, 3H), 3.84 (s, 6H), 2.94-2.84 (m, 2H), 2.57-2.37 (s, 3H), 1.48-1.36 (m, 2H), 1.03-0.88 (m, 2H);
MASS (ESI, Pos.): 458 (M+H)+.

Example 26(12)

[118]

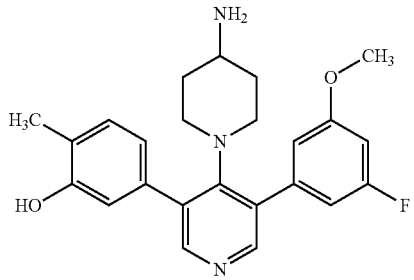

5-[4-(4-amino-1-piperidinyl)-5-(3-fluoro-5-methoxy-phenyl)-3-pyridinyl]-2-methylphenol Description: pale brown powder;
Purity (UPLC-MS/ELSD): 99.9% (retention time: 0.44 min);
TLC: Rf 0.59 (ethyl acetate:methanol=9:1, NH silica gel);
NMR (300 MHz, METHANOL-d4): δ 8.14 (s, 2H), 7.18 (d, J=7.3 Hz, 1H), 6.82-6.72 (m, 5H), 3.85 (s, 3H), 3.16-3.00 (m, 2H), 2.97-2.79 (m, 1H), 2.62-2.47 (m, 2H), 2.24 (s, 3H), 1.66-1.52 (m, 2H), 1.36-1.16 (m, 2H);
MASS (ESI, Pos.): 408 (M+H)+.

Example 26(13)

[119]

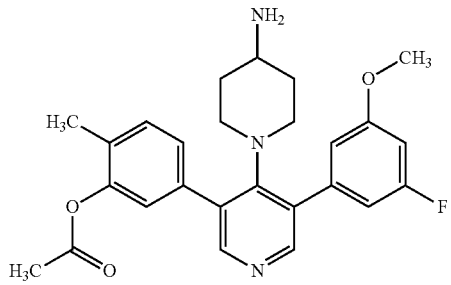

5-[4-(4-amino-1-piperidinyl)-5-(3-fluoro-5-methoxy-phenyl)-3-pyridinyl]-2-methylphenyl acetate Description: yellow amorphous powder;
Purity (UPLC-MS/ELSD): 99.8% (retention time: 0.48 min);
TLC: Rf 0.40 (ethyl acetate:methanol=9:1);
NMR (300 MHz, METHANOL-d4): δ 8.19 (s, 2H), 7.42 (d, J=7.9 Hz, 1H), 7.25 (dd, J=1.6, 7.9 Hz, 1H), 7.07 (d, J=1.6 Hz, 1H), 6.86-6.67 (m, 3H), 3.85 (s, 3H), 3.12-2.98 (m, 2H), 2.98-2.81 (m, 1H), 2.64-2.45 (m, 2H), 2.34 (s, 3H), 2.24 (s, 3H), 1.64-1.48 (m, 2H), 1.35-1.15 (m, 2H);
MASS (ESI, Pos.): 450 (M+H)+.

Example 26(14)

1-{3-(3,5-dimethoxyphenyl)-5-[2-methoxy-4-(trifluoromethyl)phenyl]-4-pyridinyl}-4-piperidinamine Description: ivory amorphous powder;
Purity (UPLC-MS/ELSD): 99.5% (retention time: 0.46 min);
TLC: Rf 0.65 (ethyl acetate:methanol=9:1, NH silica gel);
NMR (300 MHz, CHLOROFORM-d): δ 8.29 (s, 1H), 8.16 (s, 1H), 7.34-7.30 (m, 2H), 7.19 (s, 1H), 6.56 (d, J=2.2 Hz, 2H), 6.48 (t, J=2.2 Hz, 1H), 3.85 (s, 3H), 3.83 (s, 6H), 2.94-2.84 (m, 2H), 2.53-2.33 (m, 3H), 1.47-1.33 (m, 2H), 0.94-0.74 (m, 2H);
MASS (ESI, Pos.): 488 (M+H)+.

Example 26(15)

[120]

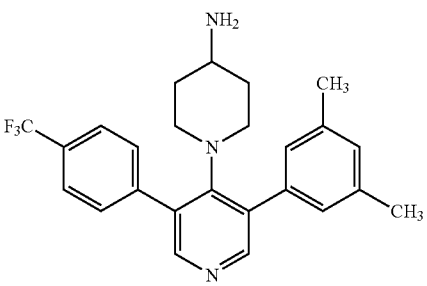

1-{3-(3,5-dimethylphenyl)-5-[4-(trifluoromethyl)phenyl]-4-pyridinyl}-4-piperidinamine Description: yellow amorphous powder;
Purity (UPLC-MS/ELSD): 98.5% (retention time: 0.54 min);
TLC: Rf 0.76 (ethyl acetate:methanol=9:1, NH silica gel);
NMR (300 MHz, METHANOL-d4): δ 8.28 (s, 1H), 8.22 (s, 1H), 7.72 (d, J=8.1 Hz, 2H), 7.52 (d, J=8.1 Hz, 2H), 7.02 (s, 1H), 6.97 (s, 2H), 2.90-2.78 (m, 2H), 2.53-2.31 (m, 9H), 1.45-1.33 (m, 2H), 1.01-0.80 (m, 2H);
MASS (ESI, Pos.): 426 (M+H)+.

Example 26(16)

1-{3-(3-fluoro-5-methoxyphenyl)-5-[4-(trifluoromethyl)phenyl]-4-pyridinyl}-4-piperidinamine Description: white amorphous powder;
Purity (UPLC-MS/ELSD): 98.9% (retention time: 0.52 min);
TLC: Rf 0.76 (ethyl acetate:methanol=9:1, NH silica gel);
NMR (300 MHz, METHANOL-d4): δ 8.18 (s, 1H), 8.17 (s, 1H), 7.81 (d, J=8.1 Hz, 2H), 7.64 (d, J=8.1 Hz, 2H), 6.81-6.70 (m, 3H), 3.85 (s, 3H), 3.00-2.88 (m, 2H), 2.54-2.38 (m, 3H), 1.47-1.36 (m, 2H), 1.10-0.92 (m, 2H);
MASS (ESI, Pos.): 446 (M+H)+.

Example 26(17)

1-{3-(3-fluoro-5-methoxyphenyl)-5-[2-methoxy-4-(trifluoromethyl)phenyl]-4-pyridinyl}-4-piperidinamine Description: white amorphous powder;
Purity (UPLC-MS/ELSD): 99.9% (retention time: 0.50 min);
TLC: Rf 0.65 (ethyl acetate:methanol=9:1, NH silica gel);
NMR (300 MHz, CHLOROFORM-d): δ 8.26 (s, 1H), 8.17 (s, 1H), 7.33-7.29 (m, 2H), 7.18 (s, 1H), 6.78-6.71 (m, 2H), 6.67-6.60 (m, 1H), 3.85 (s, 3H), 3.84 (s, 3H), 2.92-2.80 (m, 2H), 2.54-2.31 (m, 3H), 1.46-1.35 (m, 2H), 0.95-0.73 (m, 2H);
MASS (ESI, Pos.): 476 (M+H)+.

Example 26(18)

1-[3-(3,5-dimethoxyphenyl)-5-(1H-indazol-6-yl)-4-pyridinyl]-N-(3-oxetanyl)-4-piperidinamine Description: yellow amorphous powder;
Purity (LC-MS/ELSD): 100% (retention time: 0.45 min);
TLC: Rf 0.52 (ethyl acetate:methanol=9:1, NH silica gel);
NMR (300 MHz, METHANOL-d4): δ 8.19 (s, 1H), 8.16 (s, 1H), 8.10 (d, J=1.1 Hz, 1H), 7.84-7.91 (m, 1H), 7.57-7.61 (m, 1H), 7.20 (dd, J=8.3, 1.4 Hz, 1H), 6.51-6.56 (m, 3H), 4.65 (t, J=7.0 Hz, 2H), 4.35 (t, J=6.6 Hz, 2H), 3.87-3.99 (m, 1H), 3.77-3.87 (m, 6H), 3.01 (br. d, J=12.6 Hz, 2H), 2.37-2.51 (m, 2H), 2.18-2.32 (m, 1H), 1.31 (br. d, J=12.4 Hz, 2H), 0.91-1.07 (m, 2H);
MASS (ESI, Pos.): 486 (M+H)+.

Example 26(19)

1-[3-(3,5-dimethoxyphenyl)-5-(1-methyl-1H-indazol-5-yl)-4-pyridinyl]-N-(3-oxetanyl)-4-piperidinamine Description: deep yellow amorphous powder;
Purity (LC-MS/ELSD): 100% (retention time: 0.46 min);
TLC: Rf 0.12 (ethyl acetate:methanol=9:1);
NMR (300 MHz, METHANOL-d4): δ 8.16 (s, 1H), 8.14 (s, 1H), 8.08 (d, J=1.1 Hz, 1H), 7.77-7.81 (m, 1H), 7.66 (d, J=8.7 Hz, 1H), 7.48 (dd, J=8.7, 1.6 Hz, 1H), 6.48-6.56 (m, 3H), 4.65 (t, J=7.0 Hz, 2H), 4.34 (t, J=6.6 Hz, 2H), 4.11 (s, 3H), 3.85-3.97 (m, 1H), 3.79-3.84 (m, 6H), 2.99 (br. d, J=12.6 Hz, 2H), 2.35-2.49 (m, 2H), 2.12-2.27 (m, 1H), 1.29 (br. d, J=11.0 Hz, 2H), 0.85-1.05 (m, 2H);
MASS (ESI, Pos.): 500 (M+H)+.

Example 26(20)

1-{3-(3,5-dimethoxyphenyl)-5-[2-methoxy-4-(trifluoromethyl)phenyl]-4-pyridinyl}-N-(3-oxetanyl)-4-piperidinamine Description: white amorphous powder;
Purity (LC-MS/ELSD): 100% (retention time: 0.56 min);
TLC: Rf 0.91 (ethyl acetate:methanol=9:1, NH silica gel);
NMR (300 MHz, METHANOL-d4): δ 8.13 (s, 1H), 8.02 (s, 1H), 7.30-7.47 (m, 3H), 6.52 (s, 3H), 4.67 (t, J=7.0 Hz, 2H), 4.36 (t, J=6.6 Hz, 2H), 3.89-3.98 (m, 1H), 3.87 (s, 3H), 3.82 (s, 6H), 2.85-3.05 (m, 2H), 2.30-2.53 (m, 2H), 2.14-2.28 (m, 1H), 1.32 (br. d, J=11.7 Hz, 2H), 0.76-0.95 (m, 2H);
MASS (ESI, Pos.): 544 (M+H)+.

Example 26(21)

1-[3-(3-fluoro-5-methoxyphenyl)-5-(3-methyl-1H-indazol-6-yl)-4-pyridinyl]-4-piperidinamine Description: pale yellow amorphous powder;
Purity (LC-MS/ELSD): 100% (retention time: 0.44 min);
TLC: Rf 0.34 (ethyl acetate:methanol=9:1, NH silica gel);
NMR (300 MHz, METHANOL-d4): δ 8.21 (s, 1H), 8.17 (s, 1H), 7.81 (dd, J=8.3, 0.8 Hz, 1H), 7.48-7.52 (m, 1H), 7.16 (dd, J=8.3, 1.4 Hz, 1H), 6.72-6.82 (m, 3H), 3.85 (s, 3H), 3.02 (br. d, J=12.6 Hz, 2H), 2.39-2.62 (m, 6H), 1.41 (br. d, J=11.2 Hz, 2H), 0.96-1.14 (m, 2H); MASS (ESI, Pos.): 432 (M+H)+.

Example 26(22)

[121]

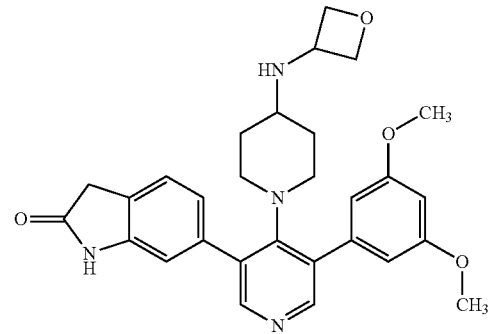

6-{5-(3,5-dimethoxyphenyl)-4-[4-(3-oxetanylamino)-1-piperidinyl]-3-pyridinyl}-1,3-dihydro-2H-indol-2-one Description: pale yellow amorphous powder;
Purity (LC-MS/ELSD): 92.4% (retention time: 0.45 min);
TLC: Rf 0.17 (ethyl acetate:methanol=9:1, NH silica gel);
NMR (300 MHz, METHANOL-d4): δ 8.12 (br. s, 2H), 7.36 (d, J=7.1 Hz, 1H), 7.03 (dd, J=7.5, 1.5 Hz, 1H), 6.96 (s, 1H), 6.47-6.56 (m, 3H), 4.70 (t, J=7.0 Hz, 2H), 4.39 (t, J=6.5 Hz, 2H), 3.93-4.04 (m, 1H), 3.82 (s, 6H), 3.55-3.61 (m, 2H), 3.01 (br. d, J=12.4 Hz, 2H), 2.37-2.52 (m, 2H), 2.24-2.36 (m, 1H), 1.38 (br. d, J=12.1 Hz, 2H), 0.98-1.15 (m, 2H);
MASS (ESI, Pos.): 501 (M+H)+.

Example 26(23)

1-[3-(3-fluoro-5-methylphenyl)-5-(1-methyl-1H-indazol-5-yl)-4-pyridinyl]-4-piperidinamine Description: pale orange powder;
Purity (USLC-MS/ELSD): 98.6% (retention time: 0.45 min);
TLC: Rf 0.33 (ethyl acetate:methanol=20:1, NH silica gel);
NMR (300 MHz, METHANOL-d4): δ 8.19 (s, 1H), 8.14 (s, 1H), 8.09 (s, 1H), 7.81-7.77 (m, 1H), 7.70-7.64 (m, 1H), 7.47 (dd, J=8.7, 1.6 Hz, 1H), 7.06-6.95 (m, 4H), 4.12 (s, 3H), 3.00-2.90 (m, 2H), 2.48-2.30 (m, 6H), 1.38-1.29 (m, 2H), 1.01-0.89 (m, 2H);
MASS (ESI, Pos.): 416 (M+H)+.

Example 26(24)

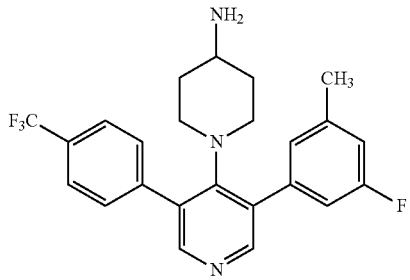

1-{3-(3-fluoro-5-methylphenyl)-5-[4-(trifluoromethyl)phenyl]-4-pyridinyl}-4-piperidinamine Description: pale yellow powder;
Purity (USLC-MS/ELSD): 98.5% (retention time: 0.56 min);
TLC: Rf 0.51 (ethyl acetate:methanol=20:1, NH silica gel);
NMR (300 MHz, METHANOL-d4): δ 8.17 (s, 1H), 8.17 (s, 1H), 7.81 (d, J=8.1 Hz, 2H), 7.64 (d, J=8.2 Hz, 2H), 7.07-6.93 (m, 3H), 2.97-2.87 (m, 2H), 2.50-2.35 (m, 6H), 1.45-1.33 (m, 2H), 1.05-0.91 (m, 2H);
MASS (ESI, Pos.): 430 (M+H)+.

Example 26(25)

1-{3-(3-fluoro-5-methylphenyl)-5-[2-methoxy-4-(trifluoromethyl)phenyl]-4-pyridinyl}-4-piperidinamine Description: pale yellow powder;
Purity (USLC-MS/ELSD): 98.4% (retention time: 0.55 min);
TLC: Rf 0.51 (ethyl acetate:methanol=20:1, NH silica gel);
NMR (300 MHz, METHANOL-d4): δ 8.13 (s, 1H), 8.04 (s, 1H), 7.47-7.33 (m, 3H), 7.09-6.94 (m, 3H), 3.88 (s, 3H), 3.00-2.84 (m, 2H), 2.53-2.32 (m, 6H), 1.45-1.31 (m, 2H), 0.94-0.78 (m, 2H),
MASS (ESI, Pos.): 460 (M+H)+.

Example 26(26)

1-{3-(3-fluoro-5-methoxyphenyl)-5-[4-(trifluoromethyl)phenyl]-4-pyridinyl}-N-methyl-4-piperidinamine Description: pale yellow powder;
Purity (USLC-MS/ELSD): 99.4% (retention time: 0.53 min);
TLC: Rf 0.73 (ethyl acetate:methanol=9:1, NH silica gel);
NMR (300 MHz, CHLOROFORM-d): δ 8.28 (s, 1H), 8.24 (s, 1H), 7.73 (d, J=8.0 Hz, 2H), 7.53 (d, J=8.0 Hz, 2H), 6.71-6.61 (m, 3H), 3.85 (s, 3H), 2.96-2.84 (m, 2H), 2.50-2.37 (m, 2H), 2.32 (s, 3H), 2.27-2.12 (m, 1H), 1.58-1.44 (m, 2H), 1.04-0.84 (m, 2H);
MASS (ESI, Pos.): 460 (M+H)+.

Example 26(27)

2-{5-(3-fluoro-5-methoxyphenyl)-4-[4-(methylamino)-1-piperidinyl]-3-pyridinyl}-5-(trifluoromethyl)phenol Description: off-white powder;
Purity (USLC-MS/ELSD): 99.9% (retention time: 0.49 min);
TLC: Rf 0.43 (ethyl acetate:methanol=9:1, NH silica gel);
NMR (300 MHz, CHLOROFORM-d): δ 8.23 (s, 1H), 8.18 (s, 1H), 7.42 (d, J=8.0 Hz, 1H), 7.33-7.27 (m, 1H), 7.24 (s, 1H), 6.89-6.77 (m, 3H), 3.89 (s, 3H), 3.22-3.09 (m, 2H), 2.95-2.81 (m, 1H), 2.72-2.51 (m, 5H), 1.77-1.66 (m, 2H), 1.24-1.08 (m, 2H);
MASS (ESI, Pos.): 476 (M+H)+.

Example 26(28)

1-{3-(3-fluoro-5-methoxyphenyl)-5-[2-methoxy-4-(trifluoromethyl)phenyl]-4-pyridinyl}-N-methyl-4-piperidinamine Description: pale yellow amorphous powder;
Purity (USLC-MS/ELSD): 98.8% (retention time: 0.54 min);
TLC: Rf 0.70 (ethyl acetate:methanol=9:1, NH silica gel);
NMR (300 MHz, CHLOROFORM-d): δ 8.26 (s, 1H), 8.16 (s, 1H), 7.32 (s, 1H), 7.26 (s, 1H), 7.19 (s, 1H), 6.78-6.70 (m, 2H), 6.67-6.59 (m, 1H), 3.85 (s, 6H), 2.95-2.84 (m, 2H), 2.49-2.33 (m, 2H), 2.30 (s, 3H), 2.20-2.09 (m, 1H), 1.54-1.43 (m, 2H), 0.93-0.74 (m, 2H);
MASS (ESI, Pos.): 490 (M+H)+.

Example 26(29)

5-[4-(4-amino-1-piperidinyl)-5-(3-fluoro-5-methylphenyl)-3-pyridinyl]-2-methylphenol Description: pale brown powder;
Purity (USLC-MS/ELSD): 99.9% (retention time: 0.44 min);
TLC: Rf 0.37 (ethyl acetate:methanol=10:1, NH silica gel);
NMR (300 MHz, METHANOL-d4): δ 8.10 (s, 1H), 8.09 (s, 1H), 7.17 (d, J=7.5 Hz, 1H), 7.04-6.93 (m, 3H), 6.79-6.72 (m, 2H), 3.00-2.84 (m, 2H), 2.52-2.38 (m, 6H), 2.24 (s, 3H), 1.46-1.36 (m, 2H), 1.13-0.97 (m, 2H);
MASS (ESI, Pos.): 392 (M+H)+.

Example 26(30)

1-[5-(3-fluoro-5-methoxyphenyl)-2'-methoxy-6'-(trifluoromethyl)-3,3'-bipyridin-4-yl]-4-piperidinamine Description: pale yellow oil;
Purity (USLC-MS/ELSD): 100% (retention time: 0.54 min);
TLC: Rf 0.44 (ethyl acetate:methanol=20:1, NH silica gel);
NMR (300 MHz, METHANOL-d4): δ 8.19 (s, 1H), 8.11 (s, 1H), 7.87 (d, J=7.5 Hz, 1H), 7.52 (d, J=7.5 Hz, 1H), 6.82-6.72 (m, 3H), 3.98 (s, 3H), 3.86 (s, 3H), 3.00-2.84 (m, 2H), 2.35-2.51 (m, 3H), 1.48-1.38 (m, 2H), 1.00-0.75 (m, 2H);
MASS (ESI, Pos.): 477 (M+H)+.

Example 26(31)

1-{3-(3-fluoro-5-methylphenyl)-5-[4-(trifluoromethyl)phenyl]-4-pyridinyl}-N-methyl-4-piperidinamine Description: pale yellow amorphous powder;
Purity (USLC-MS/ELSD): 100% (retention time: 0.54 min);
TLC: Rf 0.73 (ethyl acetate:methanol=9:1, NH silica gel);
NMR (300 MHz, CHLOROFORM-d): δ 8.27 (s, 1H), 8.23 (s, 1H), 7.73 (d, J=8.0 Hz, 2H), 7.53 (d, J=8.0 Hz, 2H), 6.99-6.84 (m, 3H), 2.94-2.81 (m, 2H), 2.47-2.35 (m, 5H), 2.31 (s, 3H), 2.23-2.11 (m, 1H), 1.56-1.44 (m, 2H), 1.02-0.83 (m, 2H);
MASS (ESI, Pos.): 444 (M+H)+.

Example 26(32)

2-{5-(3-fluoro-5-methylphenyl)-4-[4-(methylamino)-1-piperidinyl]-3-pyridinyl}-5-(trifluoromethyl)phenol Description: pale orange powder;
Purity (USLC-MS/ELSD): 100% (retention time: 0.50 min);
TLC: Rf 0.43 (ethyl acetate:methanol=9:1, NH silica gel);
NMR (300 MHz, METHANOL-d4): δ 8.18 (s, 1H), 8.14 (s, 1H), 7.39 (d, J=7.9 Hz, 1H), 7.30-7.23 (m, 1H), 7.21 (d, J=1.3 Hz, 1H), 7.12-6.99 (m, 3H), 3.13-3.01 (m, 2H), 2.65-2.41 (m, 6H), 2.39 (s, 3H), 1.64-1.52 (m, 2H), 1.12-0.95 (m, 2H);
MASS (ESI, Pos.): 460 (M+H)+.

Example 26(33)

rac-(4aR,8aR)-6-[3-(3-fluoro-5-methoxyphenyl)-5-(1H-indazol-6-yl)-4-pyridinyl]octahydro-1H-pyrido[3,4-b][1,4]oxazine Description: white amorphous powder;
Purity (LC-MS/ELSD): 100% (retention time: 0.44 min);
TLC: Rf 0.32 (ethyl acetate:methanol=19:1, NH silica gel);
NMR (300 MHz, METHANOL-d4): δ 8.26 (s, 1H), 8.21 (s, 1H), 8.12 (d, J=0.9 Hz, 1H), 7.90 (dd, J=8.3, 0.9 Hz, 1H), 7.62-7.58 (m, 1H), 7.19 (dd, J=8.3, 1.5 Hz, 1H), 6.83-6.73 (m, 3H), 3.87 (s, 3H), 3.64 (dd, J=11.6, 2.1 Hz, 1H), 3.42-3.27 (m, 1H), 3.10-2.65 (m, 5H), 2.56 (td, J=12.3, 2.5 Hz, 1H), 2.22 (dd, J=11.3, 9.7 Hz, 1H), 2.16-2.05 (m, 1H), 1.33-1.17 (m, 1H), 1.12-0.95 (m, 1H);
MASS (ESI, Pos.): 460 (M+H)+.

Example 26(34)

rac-(4aR,8aR)-6-[3-(3-fluoro-5-methoxyphenyl)-5-(1-methyl-1H-indazol-5-yl)-4-pyridinyl]octahydro-1H-pyrido[3,4-b][1,4]oxazine Description: pale brown viscous oil;
Purity (LC-MS/ELSD): 100% (retention time: 0.46 min);
TLC: Rf 0.49 (ethyl acetate:methanol=19:1, NH silica gel);
NMR (300 MHz, METHANOL-d4): δ 8.23 (s, 1H), 8.19 (s, 1H), 8.10 (d, J=0.9 Hz, 1H), 7.81 (dd, J=1.6, 0.8 Hz, 1H), 7.69 (dt, J=8.7, 0.9 Hz, 1H), 7.47 (dd, J=8.7, 1.6 Hz, 1H), 6.84-6.71 (m, 3H), 4.13 (s, 3H), 3.87 (s, 3H), 3.64 (dd, J=11.4, 2.1 Hz, 1H), 3.44-3.32 (m, 1H), 3.10-2.66 (m, 5H), 2.56 (td, J=12.5, 2.4 Hz, 1H), 2.18 (dd, J=11.3, 9.6 Hz, 1H), 2.04-2.14 (m, 1H), 1.31-1.17 (m, 1H), 1.08-0.92 (m, 1H);
MASS (ESI, Pos.): 474 (M+H)+.

Example 26(35)

5-{5-(3-fluoro-5-methoxyphenyl)-4-[rac-(4aR,8aR)-octahydro-6H-pyrido[3,4-b][1,4]oxazin-6-yl]-3-pyridinyl}-2-methylphenol Description: off-white amorphous powder;
Purity (LC-MS/ELSD): 100% (retention time: 0.46 min);
TLC: Rf 0.34 (ethyl acetate:methanol=19:1, NH silica gel);
NMR (300 MHz, METHANOL-d4): δ 8.14 (s, 2H), 7.19 (dd, J=7.9, 0.7 Hz, 1H), 6.82-6.69 (m, 5H), 3.86 (s, 3H), 3.75-3.65 (m, 1H), 3.45 (td, J=11.4, 2.9 Hz, 1H), 3.06-2.86 (m, 3H), 2.81 (dd, J=11.4, 3.6 Hz, 1H), 2.78-2.70 (m, 1H), 2.58 (td, J=12.4, 2.6 Hz, 1H), 2.31-2.21 (m, 4H), 2.20-2.10 (m, 1H), 1.35-1.25 (m, 1H), 1.20-1.05 (m, 1H);
MASS (ESI, Pos.): 450 (M+H)+.

Example 26(36)

1-[3-(4-chlorophenyl)-5-(3,5-dimethylphenyl)-4-pyridinyl]-4-piperidinamine

Description: ivory powder;
Purity (USLC-MS/ELSD): 97.8% (retention time: 0.48 min);
TLC: Rf 0.67 (ethyl acetate:methanol=9:1, NH silica gel);
NMR (300 MHz, CHLOROFORM-d): δ 8.25 (s, 1H), 8.20 (s, 1H), 7.43 (d, J=8.8 Hz, 2H), 7.33 (d, J=8.8 Hz, 2H), 7.02-6.94 (m, 3H), 2.90-2.77 (m, 2H), 2.37 (s, 6H), 2.52-2.28 (m, 3H), 1.46-1.34 (m, 2H), 1.00-0.85 (m, 2H);
MASS (ESI, Pos.): 392 (M+H)+.

Example 26(37)

2-{5-(3-fluoro-5-methoxyphenyl)-4-[rac-(4aR,8aR)-octahydro-6H-pyrido[3,4-b][1,4]oxazin-6-yl]-3-pyridinyl}-5-(trifluoromethyl)phenol Description: white powder;
Purity (LC-MS/ELSD): 100% (retention time: 0.51 min);
TLC: Rf 0.50 (ethyl acetate:n-hexane=4:1, NH silica gel);
NMR (300 MHz, METHANOL-d4): δ 8.35 (s, 1H), 8.33 (s, 1H), 7.43-7.35 (m, 1H), 7.35-7.28 (m, 2H), 6.72-6.65 (m, 1H), 6.65-6.56 (m, 2H), 3.85 (s, 3H), 3.79-3.67 (m, 1H), 3.56-3.40 (m, 1H), 3.14-2.17 (m, 8H), 1.39 (br. s., 1H), 1.32-1.11 (m, 1H);
MASS (ESI, Pos.): 504 (M+H)+.

Example 26(38)

2-{5-(3-fluoro-5-methylphenyl)-4-[rac-(4aR,8aR)-octahydro-6H-pyrido[3,4-b][1,4]oxazin-6-yl]-3-pyridinyl}-5-(trifluoromethyl)phenol Description: white amorphous powder;
Purity (LC-MS/ELSD): 100% (retention time: 0.51 min);
TLC: Rf 0.29 (ethyl acetate:methanol=19:1, NH silica gel);
NMR (300 MHz, CHLOROFORM-d): δ 8.35 (s, 1H), 8.32 (s, 1H), 7.43-7.35 (m, 1H), 7.35-7.28 (m, 2H), 6.95 (d, J=9.5 Hz, 1H), 6.90 (s, 1H), 6.81 (d, J=8.6 Hz, 1H), 3.73 (dd, J=11.1, 2.8 Hz, 1H), 3.58-3.39 (m, 1H), 3.12-2.16 (m, 11H), 1.40 (d, J=11.0 Hz, 1H), 1.22 (br. s., 1H)
MASS (ESI, Pos.): 488 (M+H)+.

Example 26(39)

4'-(4-amino-1-piperidinyl)-5'-(3-methoxy-5-methyl-phenyl)-N,N-dimethyl-3,3'-bipyridin-6-amine Description: white amorphous powder;
Purity (UPLC-MS/ELSD): 100% (retention time: 0.34 min);
TLC: Rf 0.35 (ethyl acetate:methanol=9:1, NH silica gel);
NMR (300 MHz, CHLOROFORM-d): δ 8.23 (s, 1H), 8.21 (s, 1H), 8.20 (dd, J=2.4, 0.7 Hz, 1H), 7.53 (dd, J=8.8, 2.4 Hz, 1H), 6.78-6.75 (m, 1H), 6.75-6.72 (m, 1H), 6.71-6.69 (m, 1H), 6.60 (dd, J=8.8, 0.7 Hz, 1H), 3.83 (s, 3H), 3.15 (s, 6H), 2.97-2.86 (m, 2H), 2.54-2.40 (m, 3H), 2.38 (s, 3H), 1.49-1.38 (m, 2H), 1.10-0.92 (m, 2H);
MASS (ESI, Pos.): 418 (M+H)+.

Example 26(40)

rac-(4aR,8aR)-6-[3-(3-fluoro-5-methylphenyl)-5-(1-methyl-1H-indazol-5-yl)-4-pyridinyl]octahydro-1H-pyrido[3,4-b][1,4]oxazine Description: off-white powder;
Purity (LC-MS/ELSD): 100% (retention time: 0.46 min);
TLC: Rf 0.45 (ethyl acetate:methanol=19:1, NH silica gel);
NMR (300 MHz, CHLOROFORM-d): δ 8.33 (s, 1H), 8.29 (s, 1H), 8.04 (d, J=0.9 Hz, 1H), 7.70 (dd, J=1.4, 0.8 Hz, 1H), 7.51-7.45 (m, 1H), 7.41-7.35 (m, 1H), 7.00-6.95 (m, 1H), 6.95-6.85 (m, 2H), 4.13 (s, 3H), 3.69 (dd, J=11.4, 2.5 Hz, 1H), 3.42 (td, J=11.4, 2.7 Hz, 1H), 2.99-2.72 (m, 5H), 2.59-2.46 (m, 1H), 2.43 (s, 3H), 2.27-2.09 (m, 2H), 1.23-1.14 (m, 1H), 1.05-0.87 (m, 1H);
MASS (ESI, Pos.): 458 (M+H)+.

Example 26(41)

5-{5-(3-fluoro-5-methylphenyl)-4-[rac-(4aR,8aR)-octahydro-6H-pyrido[3,4-b][1,4]oxazin-6-yl]-3-pyridinyl}-2-methylphenol Description: off-white powder;
Purity (LC-MS/ELSD): 99.0% (retention time: 0.48 min);
TLC: Rf 0.29 (ethyl acetate:methanol=19:1, NH silica gel);
NMR (300 MHz, CHLOROFORM-d): δ 8.37 (s, 1H), 8.24 (s, 1H), 7.17 (dd, J=7.7, 0.7 Hz, 1H), 6.97-6.81 (m, 4H), 6.79 (dd, J=7.6, 1.6 Hz, 1H), 3.74 (dd, J=11.4, 2.3 Hz, 1H), 3.49 (td, J=11.4, 2.6 Hz, 1H), 3.03-2.77 (m, 5H), 2.64-2.49 (m, 1H), 2.41 (s, 3H), 2.37-2.19 (m, 5H), 1.35-1.23 (m, 1H), 1.22-1.05 (m, 1H);
MASS (ESI, Pos.): 434 (M+H)+.

Example 26(42)

rac-(4aR,8aR)-6-{3-(3-fluoro-5-methylphenyl)-5-[2-methoxy-4-(trifluoromethyl)phenyl]-4-pyridinyl}octahydro-1H-pyrido[3,4-b][1,4]oxazine Description: off-white powder;
Purity (LC-MS/ELSD): 98.0% (retention time: 0.58 min);
TLC: Rf 0.71 (ethyl acetate:methanol=19:1, NH silica gel);
NMR (300 MHz, CHLOROFORM-d): δ 8.29 (s, 1H), 8.19 (s, 1H), 7.35 (d, J=8.2 Hz, 1H), 7.31 (d, J=8.2 Hz, 1H), 7.20 (s, 1H), 6.97 (s, 1H), 6.90 (d, J=9.3 Hz, 2H), 3.85 (s, 3H), 3.72 (dd, J=11.4, 2.3 Hz, 1H), 3.40 (td, J=11.4, 2.1 Hz, 1H), 2.98-2.72 (m, 4H), 2.68-2.37 (m, 5H), 2.33-2.12 (m, 2H), 1.30-1.19 (m, 1H), 0.99-0.81 (m, 1H);
MASS (ESI, Pos.): 502 (M+H)+.

Example 26(43)

rac-(4aR,8aR)-6-{3-(3-fluoro-5-methylphenyl)-5-[4-(trifluoromethyl)phenyl]-4-pyridinyl}octahydro-1H-pyrido[3,4-b][1,4]oxazine Description: white powder;
Purity (LC-MS/ELSD): 99.0% (retention time: 0.58 min);
TLC: Rf 0.69 (ethyl acetate:methanol=19:1, NH silica gel);
NMR (300 MHz, CHLOROFORM-d): δ 8.31 (s, 1H), 8.27 (s, 1H), 7.80-7.70 (m, 2H), 7.51 (d, J=7.9 Hz, 2H), 6.97-6.81 (m, 3H), 3.73 (dd, J=11.5, 2.4 Hz, 1H), 3.45 (td, J=11.5, 2.4 Hz, 1H), 2.99-2.73 (m, 5H), 2.51 (td, J=12.5, 2.7 Hz, 1H), 2.43 (s, 3H), 2.32-2.15 (m, 2H), 1.32-1.21 (m, 1H), 1.01 (qd, J=12.2, 4.3 Hz, 1H);
MASS (ESI, Pos.): 472 (M+H)+.

Example 26(44)

rac-(4aR,8aR)-6-{3-(3-fluoro-5-methoxyphenyl)-5-[2-methoxy-4-(trifluoromethyl)phenyl]-4-pyridinyl}octahydro-1H-pyrido[3,4-b][1,4]oxazine Description: off-white amorphous powder;
Purity (LC-MS/ELSD): 100% (retention time: 0.56 min);
TLC: Rf 0.45 (ethyl acetate:n-hexane=4:1, NH silica gel);
NMR (300 MHz, CHLOROFORM-d): δ 8.30 (s, 1H), 8.20 (s, 1H), 7.35 (d, J=8.6 Hz, 1H), 7.31 (d, J=8.6 Hz, 1H), 7.20 (s, 1H), 6.74-6.60 (m, 3H), 3.85 (s, 6H), 3.76-3.66 (m, 1H), 3.48-3.33 (m, 1H), 2.99-2.72 (m, 4H), 2.72-2.41 (m, 2H), 2.38-2.25 (m, 1H), 2.25-2.12 (m, 1H), 1.31-1.19 (m, 1H), 0.92 (qd, J=12.4, 4.7 Hz, 1H);
MASS (ESI, Pos.): 518 (M+H)+.

Example 26(45)

5-[4-(4-amino-1-piperidinyl)-5-(3,5-dimethylphenyl)-3-pyridinyl]-N,N-dimethyl-2-pyrimidinamine Description: yellow amorphous powder;
Purity (UPLC-MS/ELSD): 96.3% (retention time: 0.46 min);
TLC: Rf 0.38 (ethyl acetate:methanol=9:1, NH silica gel);
NMR (300 MHz, CHLOROFORM-d): δ 8.40 (s, 2H), 8.25 (s, 1H), 8.19 (s, 1H), 7.03-7.00 (m, 1H), 6.96-6.91 (m, 2H), 3.25 (s, 6H), 2.94-2.81 (m, 2H), 2.56-2.39 (m, 3H), 2.37 (s, 6H), 1.54-1.30 (m, 2H), 1.09-0.89 (m, 2H);
MASS (ESI, Pos.): 403 (M+H)+.

Example 26(46)

rac-(3R,4S)-4-amino-1-{3-(3-fluoro-5-methylphenyl)-5-[4-(trifluoromethyl)phenyl]-4-pyridinyl}-3-piperidinol Description: pale yellow viscous oil;
Purity (LC-MS/ELSD): 95.0% (retention time: 0.51 min);

TLC: Rf 0.46 (ethyl acetate:methanol=19:1, NH silica gel);

NMR (300 MHz, CHLOROFORM-d): δ 8.30 (s, 1H), 8.27 (s, 1H), 7.73 (d, J=8.1 Hz, 2H), 7.55 (d, J=8.1 Hz, 2H), 7.02 (d, J=0.5 Hz, 1H), 6.99-6.89 (m, 2H), 3.37-3.30 (m, 1H), 3.02-2.91 (m, 1H), 2.75-2.52 (m, 3H), 2.42 (s, 3H), 2.31 (dd, J=12.7, 2.3 Hz, 1H), 1.20-0.97 (m, 2H)

MASS (ESI, Pos.): 446 (M+H)+.

Example 26(47)

1-{3-[4-(difluoromethyl)phenyl]-5-(3-fluoro-5-methylphenyl)-4-pyridinyl}-4-piperidinamine Description: white amorphous powder;
Purity (UPLC-MS/ELSD): 100% (retention time: 0.48 min);
TLC: Rf 0.61 (ethyl acetate:methanol=20:1, NH silica gel);
NMR (300 MHz, METHANOL-d4): δ 8.15 (s, 2H), 7.71-7.65 (m, 2H), 7.58-7.52 (m, 2H), 7.07-6.92 (m, 3H), 6.84 (t, J=56.2 Hz, 1H), 2.98-2.87 (m, 2H), 2.50-2.33 (m, 6H), 1.45-1.34 (m, 2H), 1.10-0.91 (m, 2H);
MASS (ESI, Pos.): 412 (M+H)+.

Example 26(48)

1-[3-(4-chlorophenyl)-5-(3-fluoro-5-methylphenyl)-4-pyridinyl]-4-piperidinamine

Purity (LC-MS/ELSD): 100% (retention time: 0.46 min);
NMR (600 MHz, ACETONITRILE-d3): δ 8.19 (s, 1H), 8.18 (s, 1H), 7.54 (d, J=8.4 Hz, 2H), 7.44 (d, J=8.4 Hz, 2H), 7.06 (br. s, 1H), 7.04 (br. d, J=10.1 Hz, 1H), 6.99 (br. d, J=9.4 Hz, 1H), 2.88 (br. d, J=13.0 Hz, 2H), 2.50-2.60 (m, 1H), 2.37-2.46 (m, 5H), 1.42 (br. d, J=13.2 Hz, 2H), 0.95-1.06 (m, 2H);
MASS (ESI, Pos.): 396 (M+H)+.

Example 26(49)

1-[3-(3-fluoro-5-methylphenyl)-5-(4-methoxyphenyl)-4-pyridinyl]-4-piperidinamine Purity (LC-MS/ELSD): 99.0% (retention time: 0.44 min);
NMR (600 MHz, ACETONITRILE-d3): δ 8.17 (s, 1H), 8.16 (s, 1H), 7.38 (d, J=8.8 Hz, 2H), 7.08 (d, J=8.8 Hz, 2H), 7.07 (br. s, 1H), 7.04 (br. d, J=9.9 Hz, 1H), 6.99 (br. d, J=10.3 Hz, 1H), 3.88 (s, 3H), 2.90 (br. d, J=13.0 Hz, 2H), 2.56-2.65 (m, 1H), 2.38-2.45 (m, 5H), 1.43 (br. d, J=9.7 Hz, 2H), 1.02-1.10 (m, 2H);
MASS (ESI, Pos.): 392 (M+H)+.

Example 26(50)

[123]

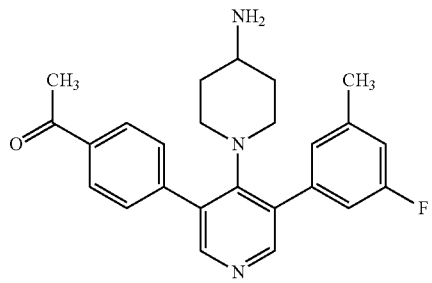

1-{4-[4-(4-amino-1-piperidinyl)-5-(3-fluoro-5-methylphenyl)-3-pyridinyl]phenyl}ethanone Purity (LC-MS/ELSD): 100% (retention time: 0.44 min);
NMR (600 MHz, ACETONITRILE-d3): δ 8.22 (s, 1H), 8.21 (s, 1H), 8.12 (d, J=8.4 Hz, 2H), 7.60 (d, J=8.4 Hz, 2H), 6.96-7.10 (m, 3H), 2.89 (br. d, J=12.5 Hz, 2H), 2.68 (s, 3H), 2.54-2.62 (m, 1H), 2.39-2.46 (m, 5H), 1.41 (br. d, J=10.1 Hz, 2H), 0.97-1.06 (m, 2H);
MASS (ESI, Pos.): 404 (M+H)+.

Example 26(51)

1-{3-[4-(dimethylamino)phenyl]-5-(3-fluoro-5-methylphenyl)-4-pyridinyl}-4-piperidinamine Purity (LC-MS/ELSD): 100% (retention time: 0.43 min);
NMR (600 MHz, ACETONITRILE-d3): δ 8.16 (s, 1H), 8.12 (s, 1H), 7.28 (d, J=8.8 Hz, 2H), 7.07 (br. s, 1H), 6.96-7.05 (m, 2H), 6.90 (d, J=8.8 Hz, 2H), 2.98 (s, 6H), 2.91 (br. d, J=12.7 Hz, 2H), 2.51-2.61 (m, 1H), 2.39-2.48 (m, 5H), 1.42 (br. d, J=15.0 Hz, 2H), 1.00-1.14 (m, 2H)
MASS (ESI, Pos.): 405 (M+H)+.

Example 26(52)

1-[3-(4-ethylphenyl)-5-(3-fluoro-5-methylphenyl)-4-pyridinyl]-4-piperidinamine

Purity (LC-MS/ELSD): 99.0% (retention time: 0.50 min);
NMR (600 MHz, ACETONITRILE-d3): δ 8.17 (s, 1H), 8.16 (s, 1H), 7.37 (d, J=8.1 Hz, 2H), 7.34 (d, J=8.1 Hz, 2H), 7.08 (br. s, 1H), 6.98-7.05 (m, 2H), 2.89 (br. d, J=13.0 Hz, 2H), 2.73 (q, J=7.9 Hz, 2H), 2.49-2.59 (m, 1H), 2.36-2.45 (m, 5H), 1.40 (br. d, J=12.7 Hz, 2H), 1.28 (t, J=7.9 Hz, 3H), 0.96-1.05 (m, 2H);
MASS (ESI, Pos.): 390 (M+H)+.

Example 26(53)

1-[3-(3-chlorophenyl)-5-(3-fluoro-5-methylphenyl)-4-pyridinyl]-4-piperidinamine

Purity (LC-MS/ELSD): 100% (retention time: 0.48 min);
NMR (600 MHz, ACETONITRILE-d3): δ 8.20 (s, 1H), 8.20 (s, 1H), 7.45-7.54 (m, 3H), 7.37-7.40 (m, 1H), 7.07 (br. s, 1H), 7.04 (br. d, J=9.9 Hz, 1H), 6.99 (br. d, J=9.9 Hz, 1H), 2.90 (br. d, J=12.8 Hz, 2H), 2.51-2.59 (m, 1H), 2.38-2.45 (m, 5H), 1.43 (br. d, J=10.8 Hz, 2H), 0.95-1.03 (m, 2H);
MASS (ESI, Pos.): 396 (M+H)+.

Example 26(54)

1-[3-(3-fluoro-5-methylphenyl)-5-(3-methoxyphenyl)-4-pyridinyl]-4-piperidinamine Purity (LC-MS/ELSD): 100% (retention time: 0.45 min);
NMR (600 MHz, ACETONITRILE-d3): δ 8.20 (s, 1H), 8.18 (s, 1H), 7.44 (t, J=7.9 Hz, 1H), 6.97-7.09 (m, 6H), 3.86 (s, 3H), 2.93 (br. d, J=12.8 Hz, 2H), 2.55-2.62 (m, 1H), 2.39-2.46 (m, 5H), 1.43 (br. d, J=11.6 Hz, 2H), 0.99-1.07 (m, 2H);
MASS (ESI, Pos.): 392 (M+H)+.

Example 26(55)

1-[3-(3-fluoro-5-methylphenyl)-5-(3-methylphenyl)-4-pyridinyl]-4-piperidinamine

Purity (LC-MS/ELSD): 100% (retention time: 0.47 min);
NMR (600 MHz, ACETONITRILE-d3): δ 8.17 (s, 1H), 8.17 (s, 1H), 7.40 (t, J=7.5 Hz, 1H), 7.27 (d, J=7.5 Hz, 1H), 7.25 (br. s, 1H), 7.22 (d, J=7.5 Hz, 1H), 7.08 (br. s, 1H), 7.03 (br. d, J=10.3 Hz, 1H), 7.00 (br. d, J=9.9 Hz, 1H), 2.89 (br. d, J=12.3 Hz, 2H), 2.50-2.59 (m, 1H), 2.37-2.45 (m, 8H), 1.40 (br. d, J=10.3 Hz, 2H), 0.95-1.04 (m, 2H);
MASS (ESI, Pos.): 376 (M+H)+.

Example 26(56)

4'-(4-amino-1-piperidinyl)-5'-(3-fluoro-5-methoxyphenyl)-6-methyl-3,3'-bipyridin-5-ol Description: white powder;
Purity (UPLC-MS/ELSD): 91.0% (retention time: 0.35 min);
TLC: Rf 0.47 (ethyl acetate:methanol=1:1, NH silica gel);
NMR (300 MHz, METHANOL-d4): δ 8.18 (s, 1H), 8.17 (s, 1H), 7.82 (d, J=1.8 Hz, 1H), 7.15 (d, J=1.8 Hz, 1H), 6.81-6.69 (m, 3H), 3.86 (s, 3H), 3.05-2.95 (m, 2H), 2.57-2.43 (m, 6H), 1.52-1.47 (m, 2H), 1.20-1.08 (m, 2H);
MASS (ESI, Pos.): 409 (M+H)+.

Example 26(57)

1-[3-(4-chloro-3-methylphenyl)-5-(3-fluoro-5-methylphenyl)-4-pyridinyl]-4-piperidinamine Purity (LC-MS/ELSD): 100% (retention time: 0.53 min);
NMR (600 MHz, ACETONITRILE-d3): δ 8.18 (s, 1H), 8.17 (s, 1H), 7.51 (d, J=8.1 Hz, 1H), 7.37 (d, J=2.2 Hz, 1H), 7.26 (dd, J=8.1, 2.2 Hz, 1H), 7.07 (br. s, 1H), 7.04 (br. d, J=11.0 Hz, 1H), 6.99 (br. d, J=9.4 Hz, 1H), 2.89 (br. d, J=12.7 Hz, 2H), 2.48-2.57 (m, 1H), 2.38-2.47 (m, 8H), 1.42 (br. d, J=11.7 Hz, 2H), 0.94-1.03 (m, 2H);
MASS (ESI, Pos.): 410 (M+H)+.

Example 26(58)

1-[3-(3-fluoro-5-methylphenyl)-5-(3-methoxy-4-methylphenyl)-4-pyridinyl]-4-piperidinamine Purity (LC-MS/ELSD): 100% (retention time: 0.50 min);
NMR (600 MHz, ACETONITRILE-d3): δ 8.20 (s, 1H), 8.16 (s, 1H), 7.27 (d, J=7.5 Hz, 1H), 7.09 (br. s, 1H), 6.99-7.05 (m, 2H), 6.89-6.95 (m, 2H), 3.87 (s, 3H), 2.93 (br. d, J=12.5 Hz, 2H), 2.51-2.58 (m, 1H), 2.40-2.47 (m, 5H), 2.26 (s, 3H), 1.42 (br. d, J=12.3 Hz, 2H), 0.97-1.06 (m, 2H);
MASS (ESI, Pos.): 406 (M+H)+.

Example 26(59)

1-{3-[4-(difluoromethoxy)phenyl]-5-(3-fluoro-5-methylphenyl)-4-pyridinyl}-4-piperidinamine Purity (LC-MS/ELSD): 100% (retention time: 0.50 min);
NMR (600 MHz, ACETONITRILE-d3): δ 8.19 (s, 2H), 7.49 (d, J=8.6 Hz, 2H), 7.30 (d, J=8.6 Hz, 2H), 6.78-7.08 (m, 4H), 2.88 (br. d, J=12.1 Hz, 2H), 2.52-2.59 (m, 1H), 2.37-2.45 (m, 5H), 1.41 (br. d, J=9.7 Hz, 2H), 0.96-1.05 (m, 2H);
MASS (ESI, Pos.): 428 (M+H)+.

Example 26(60)

[124]

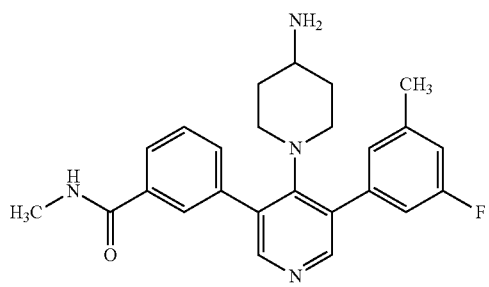

3-[4-(4-amino-1-piperidinyl)-5-(3-fluoro-5-methylphenyl)-3-pyridinyl]-N-methylbenzamide Purity (LC-MS/ELSD): 100% (retention time: 0.41 min);
NMR (600 MHz, ACETONITRILE-d3): δ 8.23 (s, 1H), 8.22 (s, 1H), 7.91 (br. s, 1H), 7.82-7.85 (m, 1H), 7.62-7.65 (m, 2H), 6.97-7.08 (m, 3H), 2.89-2.95 (m, 5H), 2.66-2.76 (m, 1H), 2.38-2.46 (m, 5H), 1.46 (br. d, J=11.9 Hz, 2H), 1.04-1.12 (m, 2H);
MASS (ESI, Pos.): 419 (M+H)+.

Example 26(61)

1-{3-(3-fluoro-5-methylphenyl)-5-[4-(1H-pyrazol-1-yl)phenyl]-4-pyridinyl}-4-piperidinamine Purity (LC-MS/ELSD): 100% (retention time: 0.47 min);
NMR (600 MHz, ACETONITRILE-d3): δ 8.27 (d, J=2.6 Hz, 1H), 8.25 (s, 1H), 8.21 (s, 1H), 7.89 (d, J=8.4 Hz, 2H), 7.80 (d, J=1.8 Hz, 1H), 7.59 (d, J=8.4 Hz, 2H), 7.07 (br. s, 1H), 7.05 (br. d, J=10.8 Hz, 1H), 7.00 (br. d, J=9.9 Hz, 1H), 6.58-6.62 (m, 1H), 2.93 (br. d, J=12.7 Hz, 2H), 2.58-2.67 (m, 1H), 2.41-2.49 (m, 5H), 1.44 (br. d, J=10.1 Hz, 2H), 1.03-1.12 (m, 2H);
MASS (ESI, Pos.): 428 (M+H)+.

Example 26(62)

1-[3-(3-fluoro-5-methylphenyl)-5-(3-methyl-1,2-benzoxazol-6-yl)-4-pyridinyl]-4-piperidinamine Description: brown amorphous powder;
Purity (UPLC-MS/ELSD): 99.5% (retention time: 0.47 min);
TLC: Rf 0.35 (ethyl acetate:methanol=9:1, NH silica gel);

NMR (300 MHz, CHLOROFORM-d): δ 8.29 (s, 1H), 8.28 (s, 1H), 7.70 (d, J=8.1 Hz, 1H), 7.58-7.54 (m, 1H), 7.33 (dd, J=1.2, 8.1 Hz, 1H), 7.00-6.87 (m, 3H), 2.94-2.81 (m, 2H), 2.64 (s, 3H), 2.53-2.33 (m, 6H), 1.49-1.32 (m, 2H), 1.02-0.81 (m, 2H);

MASS (ESI, Pos.): 417 (M+H)+.

Example 26(63)

4'-(4-amino-1-piperidinyl)-5'-(3-chloro-5-methoxyphenyl)-N,N-dimethyl-3,3'-bipyridin-6-amine Purity (LC-MS/ELSD): 100% (retention time: 0.38 min);
MASS (ESI, Pos.): 438 (M+H)+.

Example 26(64)

4'-(4-amino-1-piperidinyl)-5'-(3-chloro-5-methylphenyl)-N,N-dimethyl-3,3'-bipyridin-6-amine Purity (LC-MS/ELSD): 100% (retention time: 0.39 min);
MASS (ESI, Pos.): 422 (M+H)+.

Example 26(65)

1-{3-(3-fluoro-5-methylphenyl)-5-[3-(5-methyl-1,2,4-oxadiazol-3-yl)phenyl]-4-pyridinyl}-4-piperidinamine Purity (LC-MS/ELSD): 100% (retention time: 0.48 min);
NMR (600 MHz, ACETONITRILE-d3): δ 8.25 (s, 1H), 8.22 (s, 1H), 8.11 (br. s, 1H), 8.09 (d, J=7.7 Hz, 1H), 7.70 (t, J=7.7 Hz, 1H), 7.65 (d, J=7.7 Hz, 1H), 7.08 (br. s, 1H), 7.05 (br. d, J=10.5 Hz, 1H), 7.00 (br. d, J=8.8 Hz, 1H), 2.92 (br. d, J=13.0 Hz, 2H), 2.67 (s, 3H), 2.48-2.56 (m, 1H), 2.39-2.46 (m, 5H), 1.40 (d, J=12.5 Hz, 2H), 0.96-1.05 (m, 2H);

MASS (ESI, Pos.): 444 (M+H)+.

Example 26(66)

1-{3-(3-methoxy-5-methylphenyl)-5-[4-(trifluoromethyl)phenyl]-4-pyridinyl}-4-piperidinamine Description: white amorphous powder;
Purity (LC-MS/ELSD): 100% (retention time: 0.53 min);
TLC: Rf 0.53 (ethyl acetate:methanol=19:1, NH silica gel);
NMR (300 MHz, CHLOROFORM-d): δ 8.29 (s, 1H), 8.23 (s, 1H), 7.72 (d, J=8.1 Hz, 2H), 7.53 (d, J=8.1 Hz, 2H), 6.80-6.73 (m, 2H), 6.70 (s, 1H), 3.84 (s, 3H), 2.86 (d, J=13.2 Hz, 2H), 2.55-2.34 (m, 6H), 1.52-1.32 (m, 2H), 1.03-0.83 (m, 2H);

MASS (ESI, Pos.): 442 (M+H)+.

Example 26(67)

[125]

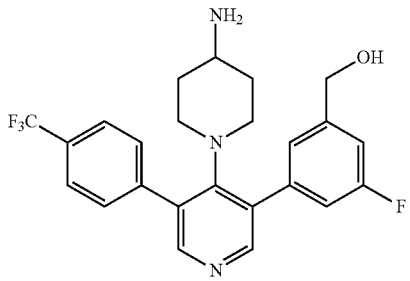

(3-{4-(4-amino-1-piperidinyl)-5-[4-(trifluoromethyl)phenyl]-3-pyridinyl}-5-fluorophenyl)methanol Description: pale yellow amorphous powder;
Purity (LC-MS/ELSD): 100% (retention time: 0.47 min);
TLC: Rf 0.41 (ethyl acetate:methanol=19:1, NH silica gel);
NMR (300 MHz, CHLOROFORM-d): δ 8.30 (s, 1H), 8.28 (s, 1H), 7.73 (d, J=8.1 Hz, 2H), 7.46 (d, J=8.1 Hz, 2H), 7.28 (s, 1H), 7.12-6.99 (m, 2H), 4.71 (s, 2H), 2.84 (d, J=13.2 Hz, 2H), 2.75-2.26 (m, 3H), 1.38 (dd, J=12.5, 3.4 Hz, 2H), 1.01 (qd, J=11.6, 4.2 Hz, 2H);

MASS (ESI, Pos.): 446 (M+H)+.

Example 26(68)

(4-{5-(3-fluoro-5-methylphenyl)-4-[4-(methylamino)-1-piperidinyl]-3-pyridinyl}-2-methylphenyl)methanol Purity (LC-MS/ELSD): 90.0% (retention time: 0.44 min);
NMR (600 MHz, ACETONITRILE-d3): δ 8.20 (s, 1H), 8.18 (s, 1H), 7.48 (d, J=7.7 Hz, 1H), 7.26 (d, J=7.7 Hz, 1H), 7.23 (br. s, 1H), 7.07 (br. s, 1H), 7.04 (br. d, J=9.7 Hz, 1H), 7.00 (br. d, J=9.7 Hz, 1H), 4.69 (s, 2H), 2.95 (br. d, J=12.8 Hz, 2H), 2.45-2.55 (m, 1H), 2.37-2.45 (m, 8H), 2.35 (s, 3H), 1.51 (br. d, J=12.0 Hz, 2H), 1.00-1.08 (m, 2H);

MASS (ESI, Pos.): 420 (M+H)+.

Example 26(69)

[126]

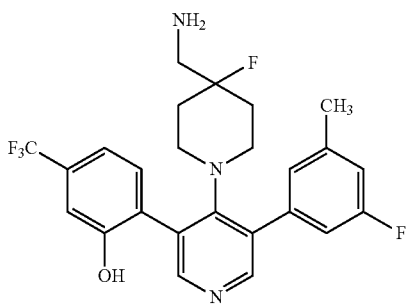

2-{4-[4-(aminomethyl)-4-fluoro-1-piperidinyl]-5-(3-fluoro-5-methylphenyl)-3-pyridinyl}-5-(trifluoromethyl)phenol Description: pale gray powder;
Purity (UPLC-MS/ELSD): 100% (retention time: 0.52 min);
TLC: Rf 0.24 (ethyl acetate:methanol=10:1, NH silica gel);
NMR (300 MHz, METHANOL-d4): δ 8.25 (s, 1H), 8.21 (s, 1H), 7.46 (d, J=8.4 Hz, 1H), 7.34-7.27 (m, 1H), 7.24 (s, 1H), 7.17 (s, 1H), 7.13-7.02 (m, 2H), 3.07-2.77 (m, 6H), 2.47 (s, 3H), 1.70-1.50 (m, 2H), 1.48-1.18 (m, 2H);
MASS (ESI, Pos.): 478 (M+H)+.

Example 26(70)

5-{4-[4-(aminomethyl)-4-fluoro-1-piperidinyl]-5-(3-fluoro-5-methylphenyl)-3-pyridinyl}-2-methylphenol Description: pale brown powder;
Purity (UPLC-MS/ELSD): 100% (retention time: 0.48 min);
TLC: Rf 0.20 (ethyl acetate:methanol=10:1, NH silica gel);
NMR (300 MHz, CHLOROFORM-d): δ 8.37 (s, 1H), 8.23 (s, 1H), 7.15 (d, J=7.9 Hz, 1H), 6.99-6.85 (m, 4H), 6.79 (dd, J=1.6, 7.9 Hz, 1H), 2.83-2.72 (m, 4H), 2.70-2.59 (m, 2H), 2.40 (s, 3H), 2.31 (s, 3H), 1.58-1.30 (m, 4H);
MASS (ESI, Pos.): 424 (M+H)+.

Example 26(71)

[127]

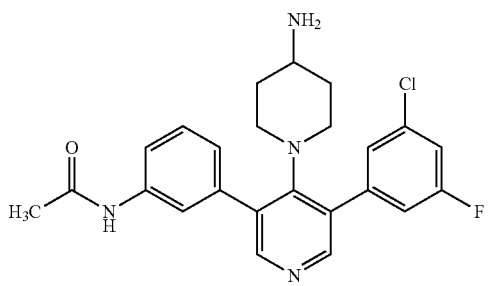

N-{3-[4-(4-amino-1-piperidinyl)-5-(3-chloro-5-fluorophenyl)-3-pyridinyl]phenyl}acetamide Description: pale yellow amorphous powder;
Purity (LC-MS/ELSD): 100% (retention time: 0.44 min);
TLC: Rf 0.35 (ethyl acetate:methanol=9:1, NH silica gel);
NMR (300 MHz, CHLOROFORM-d): δ 8.26 (s, 1H), 8.23 (s, 1H), 7.64 (s, 1H), 7.54 (s, 1H), 7.44-7.37 (m, 2H), 7.23-7.20 (m, 1H), 7.16-7.06 (m, 2H), 7.06-7.00 (m, 1H), 2.88 (d, J=12.8 Hz, 2H), 2.60-2.40 (m, 3H), 2.20 (s, 3H), 1.44 (dd, J=12.2, 3.0 Hz, 2H), 1.12-0.95 (m, 2H)
MASS (ESI, Pos.): 439 (M+H)+.

Example 26(72)

1-{3-(3-fluoro-5-methylphenyl)-5-[3-methoxy-4-(trifluoromethyl)phenyl]-4-pyridinyl}-4-piperidinamine Purity (LC-MS/ELSD): 100% (retention time: 0.55 min);
NMR (600 MHz, ACETONITRILE-d3): δ 8.23 (s, 1H), 8.21 (s, 1H), 7.73 (d, J=8.3 Hz, 1H), 7.22 (s, 1H), 7.13 (d, J=8.3 Hz, 1H), 7.09 (br. s, 1H), 7.05 (br. d, J=10.3 Hz, 1H), 7.01 (br. d, J=10.3 Hz, 1H), 3.96 (s, 3H), 2.93 (br. d, J=13.0 Hz, 2H), 2.51-2.59 (m, 1H), 2.41-2.48 (m, 5H), 1.43 (br. d, J=11.6 Hz, 2H), 0.96-1.04 (m, 2H);
MASS (ESI, Pos.): 460 (M+H)+.

Example 26(73)

3-[4-(4-amino-1-piperidinyl)-5-(3-fluoro-5-methylphenyl)-3-pyridinyl]phenol

Purity (LC-MS/ELSD): 100% (retention time: 0.42 min);
NMR (600 MHz, ACETONITRILE-d3): δ 8.18 (s, 1H), 8.17 (s, 1H), 7.36 (t, J=7.6 Hz, 1H), 7.07 (br. s, 1H), 7.04 (br. d, J=10.3 Hz, 1H), 6.99 (br. d, J=10.3 Hz, 1H), 6.89-6.93 (m, 3H), 2.93 (br. d, J=12.8 Hz, 2H), 2.60-2.69 (m, 1H), 2.41-2.49 (m, 5H), 1.45 (br. d, J=12.8 Hz, 2H), 1.06-1.14 (m, 2H);
MASS (ESI, Pos.): 378 (M+H)+.

Example 26(74)

5-[4-(4-amino-1-piperidinyl)-5-(3-fluoro-5-methylphenyl)-3-pyridinyl]-2-fluorophenol Purity (LC-MS/ELSD): 100% (retention time: 0.42 min);
NMR (600 MHz, ACETONITRILE-d3): δ 8.18 (s, 1H), 8.16 (s, 1H), 7.21 (dd, J=11.8, 8.5 Hz, 1H), 6.95-7.06 (m, 4H), 6.80-6.84 (m, 1H), 2.94 (br. d, J=12.3 Hz, 2H), 2.68-2.78 (m, 1H), 2.43 (s, 5H), 1.49 (br. d, J=12.3 Hz, 2H), 1.12-1.20 (m, 2H);
MASS (ESI, Pos.): 396 (M+H)+.

Example 26(75)

5-[4-(4-amino-1-piperidinyl)-5-(3-fluoro-5-methylphenyl)-3-pyridinyl]-2-chlorophenol Purity (LC-MS/ELSD): 100% (retention time: 0.45 min);
NMR (600 MHz, ACETONITRILE-d3): δ 8.18 (s, 1H), 8.17 (s, 1H), 7.44 (d, J=8.3 Hz, 1H), 6.95-7.06 (m, 4H), 6.81-6.84 (m, 1H), 2.94 (br. d, J=12.8 Hz, 2H), 2.65-2.76 (m, 1H), 2.41-2.48 (m, 5H), 1.48 (br. d, J=12.8 Hz, 2H), 1.12-1.21 (m, 2H);
MASS (ESI, Pos.): 412 (M+H)+.

Example 26(76)

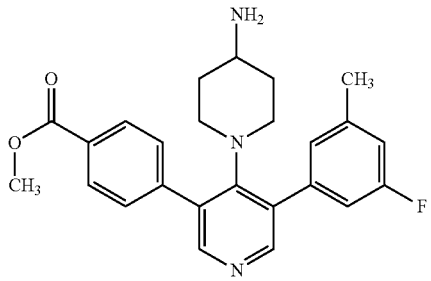

methyl 4-[4-(4-amino-1-piperidinyl)-5-(3-fluoro-5-methylphenyl)-3-pyridinyl]benzoate Purity (LC-MS/ELSD): 100% (retention time: 0.48 min); NMR (600 MHz, ACETONITRILE-d3): δ 8.21 (s, 1H), 8.21 (s, 1H), 8.14 (d, J=8.4 Hz, 2H), 7.58 (d, J=8.4 Hz, 2H), 7.07 (br. s, 1H), 7.05 (br. d, J=9.2 Hz, 1H), 7.00 (br. d, J=9.2 Hz, 1H), 3.95 (s, 3H), 2.89 (br. d, J=13.4 Hz, 2H), 2.51-2.61 (m, 1H), 2.38-2.46 (m, 5H), 1.41 (br. d, J=13.2 Hz, 2H), 0.96-1.05 (m, 2H);
MASS (ESI, Pos.): 420 (M+H)+.

Example 26(77)

methyl 3-[4-(4-amino-1-piperidinyl)-5-(3-fluoro-5-methylphenyl)-3-pyridinyl]benzoate Purity (LC-MS/ELSD): 100% (retention time: 0.47 min); NMR (600 MHz, ACETONITRILE-d3): δ 8.22 (s, 1H), 8.21 (s, 1H), 8.05-8.10 (m, 2H), 7.70-7.74 (m, 1H), 7.66 (t, J=7.5 Hz, 1H), 6.96-7.10 (m, 3H), 3.94 (s, 3H), 2.89 (br. d, J=12.5 Hz, 2H), 2.49-2.60 (m, 1H), 2.35-2.46 (m, 5H), 1.41 (br. d, J=12.4 Hz, 2H), 0.93-1.02 (m, 2H);
MASS (ESI, Pos.): 420 (M+H)+.

Example 26(78)

1-[3-(3-fluoro-5-methylphenyl)-5-(2-methyl-1,3-benzoxazol-5-yl)-4-pyridinyl]-4-piperidinamine Purity (LC-MS/ELSD): 100% (retention time: 0.44 min); NMR (600 MHz, ACETONITRILE-d3): δ 8.25 (s, 1H), 8.21 (s, 1H), 7.77 (d, J=1.8 Hz, 1H), 7.72 (d, J=8.4 Hz, 1H), 7.42 (dd, J=8.4, 1.8 Hz, 1H), 7.07 (br. s, 1H), 7.05 (br. d, J=9.9 Hz, 1H), 6.99 (br. d, J=9.9 Hz, 1H), 2.91 (br. d, J=13.0 Hz, 2H), 2.68 (s, 3H), 2.55-2.64 (m, 1H), 2.44 (s, 3H), 2.35-2.42 (m, 2H), 1.40 (br. d, J=13.0 Hz, 2H), 0.98-1.07 (m, 2H);
MASS (ESI, Pos.): 417 (M+H)+.

Example 26(79)

N-{5-[4-(4-amino-1-piperidinyl)-5-(3-fluoro-5-methylphenyl)-3-pyridinyl]-2-methoxyphenyl}acetamide Purity (LC-MS/ELSD): 100% (retention time: 0.44 min); NMR (600 MHz, ACETONITRILE-d3): δ 8.18 (s, 1H), 8.16 (s, 1H), 8.01 (s, 1H), 7.19-7.23 (m, 1H), 7.15-7.19 (m, 1H), 7.07 (br. s, 1H), 7.04 (br. d, J=10.6 Hz, 1H), 6.99 (br. d, J=10.6 Hz, 1H), 3.94 (s, 3H), 2.93 (br. d, J=13.8 Hz, 2H), 2.65-2.79 (m, 1H), 2.46-2.54 (m, 2H), 2.43 (s, 3H), 2.17 (s, 3H), 1.46 (br. d, J=13.7 Hz, 2H), 1.18-1.26 (m, 2H);
MASS (ESI, Pos.): 449 (M+H)+.

Example 26(80)

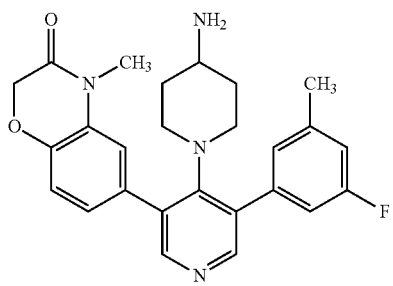

6-[4-(4-amino-1-piperidinyl)-5-(3-fluoro-5-methylphenyl)-3-pyridinyl]-4-methyl-2H-1,4-benzoxazin-3(4H)-one Purity (LC-MS/ELSD): 100% (retention time: 0.45 min); NMR (600 MHz, ACETONITRILE-d3): δ 8.21 (s, 1H), 8.18 (s, 1H), 7.09-7.17 (m, 3H), 7.08 (br. s, 1H), 7.05 (br. d, J=9.4 Hz, 1H), 7.00 (br. d, J=9.4 Hz, 1H), 4.70 (s, 2H), 3.36 (s, 3H), 2.94 (br. d, J=13.2 Hz, 2H), 2.58-2.67 (m, 1H), 2.38-2.48 (m, 5H), 1.46 (br. d, J=13.2 Hz, 2H), 0.99-1.09 (m, 2H);
MASS (ESI, Pos.): 447 (M+H)+.

Example 26(81)

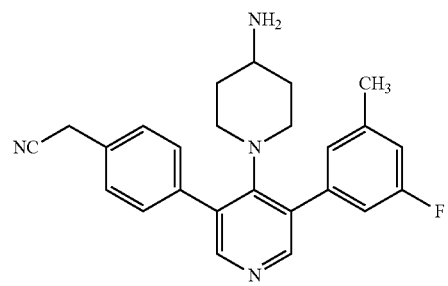

{4-[4-(4-amino-1-piperidinyl)-5-(3-fluoro-5-methylphenyl)-3-pyridinyl]phenyl}acetonitrile Purity (LC-MS/ELSD): 100% (retention time: 0.45 min); NMR (600 MHz, ACETONITRILE-d3): δ 8.19 (s, 1H), 8.19 (s, 1H), 7.52 (d, J=8.1 Hz, 2H), 7.47 (d, J=8.1 Hz, 2H), 7.07 (br. s, 1H), 7.04 (br. d, J=9.5 Hz, 1H), 7.00 (br. d, J=9.5 Hz, 1H), 3.97 (s, 2H), 2.89 (br. d, J=12.5 Hz, 2H), 2.56-2.68 (m, 1H), 2.34-2.48 (m, 5H), 1.42 (br. d, J=12.5 Hz, 2H), 0.95-1.09 (m, 2H);
MASS (ESI, Pos.): 401 (M+H)+.

Example 26(82)

1-{3-[3-fluoro-5-(trifluoromethyl)phenyl]-5-[4-(trifluoromethyl)phenyl]-4-pyridinyl}-4-piperidinamine Purity (LC-MS/ELSD): 100% (retention time: 0.60 min);
NMR (600 MHz, ACETONITRILE-d3): δ 8.27 (s, 1H), 8.26 (s, 1H), 7.85 (d, J=7.9 Hz, 2H), 7.61-7.65 (m, 3H), 7.57 (br. d, J=8.8 Hz, 1H), 7.52 (br. d, J=8.8 Hz, 1H), 2.87 (br. d, J=13.2 Hz, 2H), 2.42-2.54 (m, 1H), 2.35-2.42 (m, 2H), 1.40 (br. d, J=13.2 Hz, 2H), 0.86-0.96 (m, 2H)
MASS (ESI, Pos.): 484 (M+H)+.

Example 26(83)

5-[4-(4-amino-1-piperidinyl)-5-(3-fluoro-5-methylphenyl]-3-pyridinyl]-2-(trifluoromethyl)phenol Purity (LC-MS/ELSD): 100% (retention time: 0.50 min);
NMR (600 MHz, ACETONITRILE-d3): δ 8.20 (s, 1H), 8.19 (s, 1H), 7.63 (d, J=8.1 Hz, 1H), 6.88-7.10 (m, 5H), 2.94 (br. d, J=13.4 Hz, 2H), 2.60-2.74 (m, 1H), 2.40-2.50 (m, 5H), 1.46 (br. d, J=13.0 Hz, 2H), 1.09-1.19 (m, 2H);
MASS (ESI, Pos.): 446 (M+H)+.

Example 26(84)

[131]

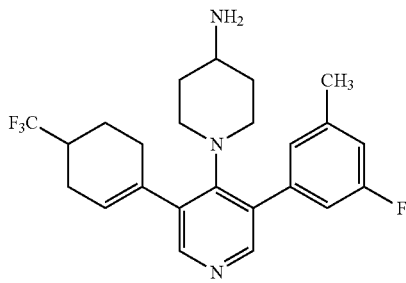

1-{3-(3-fluoro-5-methylphenyl)-5-[4-(trifluoromethyl)-1-cyclohexen-1-yl]-4-pyridinyl}-4-piperidinamine Description: pale yellow oil;
Purity (UPLC-MS/ELSD): 100% (retention time: 0.51 min);
TLC: Rf 0.53 (ethyl acetate:methanol=20:1, NH silica gel);
NMR (300 MHz, CHLOROFORM-d): δ 8.17 (d, J=0.4 Hz, 1H), 8.13 (d, J=0.4 Hz, 1H), 6.97-6.80 (m, 3H), 5.76-5.68 (m, 1H), 3.18-2.96 (m, 2H), 2.75-2.53 (m, 3H), 2.52-2.28 (m, 8H), 2.21-2.11 (m, 1H), 1.82-1.56 (m, 3H), 1.22-1.03 (m, 2H);
MASS (ESI, Pos.): 434 (M+H)+.

Example 26(85)

1-{3-(3-chloro-5-methylphenyl)-5-[4-(trifluoromethyl)phenyl]-4-pyridinyl}-4-piperidinamine Description: pale brown amorphous powder;
Purity (UPLC-MS/ELSD): 100% (retention time: 0.57 min);
TLC: Rf 0.65 (ethyl acetate:methanol=20:1, NH silica gel);
NMR (300 MHz, METHANOL-d4): δ 8.17 (s, 2H), 7.81 (d, J=8.6 Hz, 2H), 7.63 (d, J=8.4 Hz, 2H), 7.31-7.15 (m, 3H), 2.96-2.86 (m, 2H), 2.50-2.36 (m, 6H), 1.45-1.36 (m, 2H), 1.04-0.90 (m, 2H);
MASS (ESI, Pos.): 446 (M+H)+.

Example 26(86)

1-{3-(3-chloro-5-methoxyphenyl)-5-[4-(trifluoromethyl)phenyl]-4-pyridinyl}-4-piperidinamine Description: colorless oil;
Purity (UPLC-MS/ELSD): 100% (retention time: 0.58 min);
TLC: Rf 0.58 (ethyl acetate:methanol=20:1, NH silica gel);
NMR (300 MHz, CHLOROFORM-d): δ 8.28 (s, 1H), 8.25 (s, 1H), 7.73 (d, J=8.1 Hz, 2H), 7.50 (d, J=8.1 Hz, 2H), 6.99 (t, J=1.6 Hz, 1H), 6.94-6.91 (m, 1H), 6.83-6.80 (m, 1H), 3.86 (s, 3H), 2.92-2.82 (m, 2H), 2.58-2.36 (m, 3H), 1.50-1.40 (m, 2H), 1.04-0.88 (m, 2H);
MASS (ESI, Pos.): 462 (M+H)+.

Example 26(87)

1-(3-{4-(4-amino-1-piperidinyl)-5-[4-(trifluoromethyl)phenyl]-3-pyridinyl}-5-fluorophenyl)ethanol Description: white amorphous powder;
Purity (UPLC-MS/ELSD): 100% (retention time: 0.50 min);
TLC: Rf 0.56 (ethyl acetate:methanol=9:1, NH silica gel);
NMR (300 MHz, CHLOROFORM-d): δ 8.31 (s, 1H), 8.28 (s, 1H), 7.73 (d, J=8.0 Hz, 2H), 7.47 (d, J=8.0 Hz, 2H), 7.25-7.23 (m, 1H), 7.13-6.99 (m, 2H), 4.92 (q, J=6.2 Hz, 1H), 2.89-2.76 (m, 2H), 2.67-2.55 (m, 1H), 2.48-2.31 (m, 2H), 1.52 (d, J=6.2 Hz, 3H), 1.40-1.26 (m, 2H), 1.07-0.82 (m, 2H);
MASS (ESI, Pos.): 460 (M+H)+.

Example 26(88)

1-{4-[4-(4-amino-1-piperidinyl)-5-(3-fluoro-5-methylphenyl)-3-pyridinyl]phenyl}ethanol Description: pale yellow amorphous powder;
Purity (UPLC-MS/ELSD): 94.1% (retention time: 0.45 min);
TLC: Rf 0.21 (ethyl acetate:methanol=9:1, NH silica gel);
NMR (300 MHz, CHLOROFORM-d): δ 8.23 (s, 1H), 8.20 (s, 1H), 7.46 (d, J=8.1 Hz, 2H), 7.34 (d, J=8.1 Hz, 2H), 6.86-7.02 (m, 3H), 4.98 (q, J=6.4 Hz, 1H), 2.85 (br. d, J=13.4 Hz, 2H), 2.28-2.52 (m, 6H), 1.56 (d, J=6.4 Hz, 3H), 1.39 (br. d, J=13.0 Hz, 2H), 0.84-1.01 (m, 2H);
MASS (ESI, Pos.): 406 (M+H)+.

Example 26(89)

[1-(4-{4-[4-(aminomethyl)-1-piperidinyl]-5-(3-fluoro-5-methoxyphenyl)-3-pyridinyl}phenyl)cyclopropyl]methanol Purity (UPLC-MS/ELSD): 100% (retention time: 0.50 min);
MASS (ESI, Pos.): 462 (M+H)+.

Reference Example 37

2-(benzyloxy)-3-bromophenol

To a solution of 2-(benzyloxy)-3-bromobenzaldehyde (CAS #120980-85-0) (1.30 g) in chloroform (10 mL) was added 3-chloroperoxybenzoic acid (1.15 g), and stirred at 70 degrees C. for 15 hours. After cooling to room temperature, the reaction solution was diluted with ethyl acetate and washed with saturated aqueous solution of sodium thiosulfate. The organic layer was sequentially washed with water and saturated brine, and concentrated after drying. The obtained residue was dissolved in methanol (30 mL), added potassium carbonate (1.38 g) and then stirred at room temperature for 3 hours. The reaction solution was diluted with ethyl acetate and washed with 1M aqueous solution of potassium hydrogen sulfate. The organic layer was sequentially washed with water and saturated brine and concentrated after drying. The obtained residue was purified by preparative medium pressure liquid chromatography (Yamazen Corp. YFLC-Wprep-2XY) (Hi-flash SI) (n-hexane:ethyl acetate=3:1) to obtain the title compound (1.24 g) having the following physical property values.

TLC: Rf 0.34 (n-hexane:ethyl acetate=3:1);

Reference Example 38

3',5'-dimethyl-3-((1-methyl-1H-pyrazol-4-yl)methoxy)-[1,1'-biphenyl]-2-ol

Using (1-methyl-1H-pyrazol-4-yl)methanol (CAS #112029-98-8) in place of the compound produced in Reference example 8, using the compound produced in Reference example 37 in place of 3,5-dimethylphenol, using 3,5-dimethylphenylboronic acid in place of phenylboronic acid, the title compound having the following physical property values was obtained by following the same procedure as in Reference example 9→Reference example 2→Reference example 16, and used for next reaction without further purification.

Example 27

(2R)-2-[2-({3',5'-dimethyl-3-[(1-methyl-1H-pyrazol-4-yl)methoxy]-2-biphenylyl}oxy)ethyl]piperidine

[132]

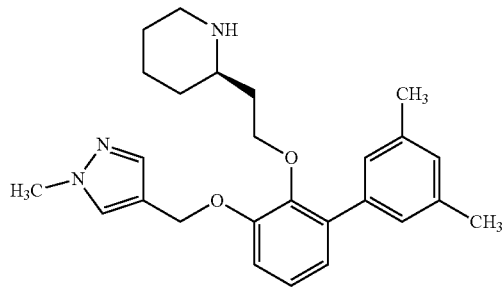

Using (R)-tert-butyl 2-(2-hydroxyethyl)piperidine-1-carboxylate (CAS #250249-85-5) in place of the compound produced in Reference example 8, using the compound produced in Reference example 38 in place of 3,5-dimethylphenol, the present invention compound having the following physical property values was obtained by following the same procedure as in Reference example 9→Example 1.

Description: brown oil;
Purity (LC-MS/ELSD): 100% (retention time: 4.42 min);
TLC: Rf 0.20 (ethyl acetate, NH silica gel);
MASS (ESI, Pos.): 420 (M+H)+.

Reference Example 39 tert-butyl 2-(2-((3-bromo-5-(3,5-dimethylphenyl)pyridin-4-yl)oxy)ethyl)piperidine-1-carboxylate Using tert-butyl 2-(2-hydroxyethyl)piperidine-1-carboxylate in place of the compound produced in Reference example 8, using 3-bromo-5-iodopyridin-4-ol (Synlett, 2003, vol.11, p.1678-1682) in place of 3,5-dimethylphenol, using 3,5-dimethylphenylboronic acid in place of phenylboronic acid, the title compound having the following physical property values was obtained by following the same procedure as in Reference example 9→Reference example 2.

Description: orange solid;
TLC: Rf 0.48 (n-hexane:ethyl acetate=3:1);
NMR (300 MHz, CHLOROFORM-d): δ 8.61 (s, 1H), 8.38 (s, 1H), 7.12 (s, 2H), 7.03 (s, 1H), 4.29-4.16 (m, 1H), 3.96-3.82 (m, 1H), 3.82-3.67 (m, 1H), 3.60-3.43 (m, 1H), 2.63-2.46 (m, 1H), 2.36 (s, 6H), 2.03-1.87 (m, 1H), 1.75-1.29 (m, 7H), 1.37 (s, 9H).

Reference Example 40 tert-butyl 2-(2-((3-(3,5-dimethylphenyl)-5-vinylpyridin-4-yl)oxy)ethyl)piperidine-1-carboxylate Using the compound produced in Reference example 39 in place of the compound produced in Reference example 1, using potassium vinyltrifluoroborate (CAS #13682-77-4) in place of phenylboronic acid, the title compound having the following physical property values was obtained by following the same procedure as in Reference example 2.

Description: orange solid;
TLC: Rf 0.43 (n-hexane:ethyl acetate=3:1);
NMR (300 MHz, CHLOROFORM-d): δ 8.61 (s, 1H), 8.38 (s, 1H), 7.16-7.10 (m, 2H), 7.05-6.86 (m, 2H), 5.86 (d, J=19.03 Hz, 1H), 5.40 (d, J=11.16 Hz, 1H), 4.29-4.07 (m, 1H), 3.95-3.79 (m, 1H), 3.72-3.56 (m, 1H), 3.51-3.37 (m, 1H), 2.58-2.43 (m, 1H), 2.37 (s, 6H), 1.97-1.80 (m, 1H), 1.68-1.23 (m, 16H).

Reference Example 41

(E)-tert-butyl 2-(2-((3-(3,5-dimethylphenyl)-5-(3,5-dimethylstyryl)pyridin-4-yl)oxy)ethyl)piperidine-1-carboxylate To a solution of the compound produced in Reference example 40 (1.12 g) in dimethylformamide (10 mL) was added 1-bromo-3,5-dimethylbenzene (CAS #40032-73-3) (1.06 mL), 1,1'-bis(diphenylphosphino)ferrocene-palladium (II) dichloride, complex with dichloromethane (PdCl$_2$(dppf)$_2$ CH$_2$Cl$_2$) (210 mg) and N,N-dicyclohexylmethylamine (1.65 mL), and the mixture was stirred at 130 degrees C. for 3 hours. After adding water, the reaction solution was extracted with ethyl acetate, and sequentially washed with water and saturated brine. The organic layer was concentrated after drying. The obtained residue was purified by preparative medium pressure liquid chromatography (Yamazen Corp. YFLC-Wprep-2XY) (Hi-flash SI) (n-hexane:ethyl acetate=3:1) to obtain the title compound (745 mg) having the following physical property values.

Description: dark red oil;
TLC: Rf 0.52 (n-hexane:ethyl acetate=3:1);
NMR (300 MHz, METHANOL-d4): δ 8.74 (s, 1H), 8.38 (s, 1H), 7.36 (s, 1H), 7.23-7.12 (m, 5H), 7.03 (s, 1H), 6.95 (s, 1H), 4.30-4.17 (m, 1H), 3.93-3.79 (m, 1H), 3.76-3.61 (m, 1H), 3.56-3.42 (m, 1H), 2.57-2.42 (m, 1H), 2.38 (s, 6H), 2.35 (s, 6H), 1.98-1.82 (m, 1H), 1.71-1.58 (m, 1H), 1.53-1.40 (m, 4H), 1.34 (br.s., 9H), 1.33-1.24 (m, 2H).

Example 28

3-(3,5-dimethylphenyl)-5-[(E)-2-(3,5-dimethylphenyl)vinyl]-4-[2-(2-piperidinyl)ethoxy]pyridine

[133]

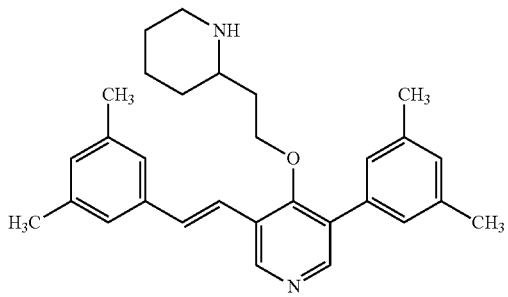

Using the compound produced in Reference example 36 in place of the compound produced in Reference example 3, the present invention compound having the following physical property values was obtained by following the same procedure as in Example 1.

Description: beige powder;
TLC: Rf 0.60 (ethyl acetate, NH silica gel);
NMR (300 MHz, METHANOL-d4): δ 8.99 (br.s., 1H), 8.68 (s, 1H), 8.34 (s, 1H), 7.16-7.04 (m, 6H), 7.01 (s, 1H), 6.91 (s, 1H), 3.77-3.62 (m, 1H), 3.56-3.41 (m, 1H), 3.24-3.09 (m, 1H), 2.93-2.74 (m, 1H), 2.62-2.46 (m, 1H), 2.35 (s, 6H), 2.31 (s, 6H), 2.42-2.26 (m, 1H), 2.04-1.89 (m, 1H), 1.82-1.51 (m, 3H), 1.49-1.22 (m, 2H), 1.20-0.99 (m, 1H);
MASS (ESI, Pos.): 441 (M+H)+.

Reference Example 42

(Z)-tert-butyl (1-(3-((((amino(phenyl)methylene) amino)oxy)carbonyl)-5-(3,5-dimethylphenyl)pyridin-4-yl)piperidin-4-yl)carbamate To a solution of the compound produced in Reference example 6 (868 mg) in tetrahydrofuran (4 mL)/methanol (3 mL) was added 2M aqueous solution of sodium hydroxide (1.97 mL), and the mixture was stirred at 65 degrees C. for 6 hours. After cooling by ice-water, the reaction solution was neutralized by 2M hydrochloric acid (1.97 mL), and then concentrated under reduced pressure. The residue was dissolved in dimethylformamide, added 2-(7-aza-1H-benzotriazol-1-yl)-1,1,3,3-tetramethyluronium hexafluorophosphate (HATU), triethylamine and benzamide oxime (CAS #1195196-49-6), and the mixture was stirred at room temperature overnight. The reaction solution was added water, and extracted with ethyl acetate. The organic layer was washed with saturated brine and then dried followed by concentration. The obtained residue was purified by preparative medium pressure liquid chromatography (Yamazen Corp. YFLC-Wprep-2XY) (Hi-flash SI) (ethyl acetate) to obtain the title compound (58 mg) having the following physical property values.

Description: pale yellow powder;
TLC: Rf 0.23 (ethyl acetate);

Example 29

1-[3-(3,5-dimethylphenyl)-5-(3-phenyl-1,2,4-oxadiazol-5-yl)-4-pyridinyl]-4-piperidinamine

[134]

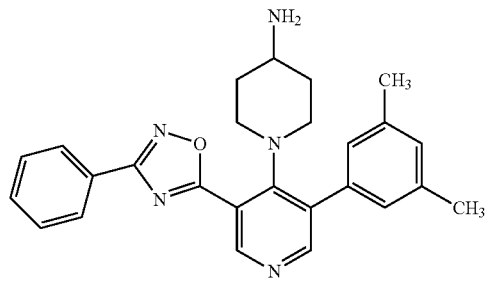

A solution of the compound (58 mg) produced in Reference example 42 in dimethylformamide (1.0 mL) was stirred at 110 degrees C. overnight. To the reaction solution was added water, and extracted with ethyl acetate. The organic layer was concentrated, and the residue was dissolved in dichloromethane (1.0 mL). To the reaction solution was added trifuluoroacetic acid (1.0 mL), and stirred at room temperature for 1 hour and concentrated under reduced pressure. The obtained residue was purified by preparative medium pressure liquid chromatography (Yamazen Corp. YFLC-Wprep-2XY) (Hi-flash NH) (ethyl acetate:methanol=95:5) to obtain the present invention compound (17 mg) having the following physical property values.

Description: yellow viscous oil;
TLC: Rf 0.36 (ethyl acetate, NH silica gel);
NMR (300 MHz, CHLOROFORM-d): δ 8.77 (s, 1H), 8.37 (s, 1H), 8.26-8.09 (m, 2H), 7.63-7.41 (m, 3H), 7.14-6.91 (m, 3H), 3.04 (d, J=13.0 Hz, 2H), 2.83-2.53 (m, 3H), 2.39 (s, 6H), 1.77-1.37 (m, 2H), 1.31-1.03 (m, 2H);
MASS (APCI, Pos.): 426 (M+H)+.

Reference Example 43 tert-butyl ((1-(3-amino-5-(3,5-dimethylphenyl)pyridin-4-yl)-4-hydroxypiperidin-4-yl)methyl)carbamate Using tert-butyl ((4-hydroxypiperidin-4-yl)methyl)carbamate (purchased from CHEMBASICS, catalog number: CMB1175) in place of tert-butyl N-(4-piperidylmethyl)carbamate, using 3,5-dimethylphenylboronic acid in place of phenylboronic acid, the title compound having the following physical property values was obtained by following the same procedure as in Reference example 14→Reference example 2→Reference example 16, and used for next reaction without further purification.

Reference Example 44 tert-butyl ((1-(3-(3,5-dimethylphenyl)-5-(phenylamino)pyridin-4-yl)-4-hydroxypiperidin-4-yl)methyl)carbamate To a solution of the compound (86 mg) produced in Reference example 43 in toluene (5 mL) was added iodobenzene (CAS #591-50-4) (45.24 mg), (R)-(+)-2,2'-bis(diphenylphosphino)-1,1'-binaphthyl (12.55 mg) and cesium carbonate (328.4 mg). Under the argon atmosphere, palladium(II) acetate (4.526 mg) was added to the reaction solution and stirred at 100 degrees C. for 14 hours. After cooling to room temperature, the reaction solution was added ethyl acetate and then concentrated. The obtained residue was purified by preparative medium pressure liquid chromatography (Yamazen Corp. YFLC-Wprep-2XY) (Hiflash SI) (ethyl acetate) to obtain the title compound (65 mg) having the following physical property values.

Description: yellow viscous oil;
TLC: Rf 0.80 (ethyl acetate);

Example 30(1)-Example 30(5)

Using a corresponding reagent in place of tert-butyl N-(4-piperidylmethyl)carbamate, using 3,5-dimethylphenylboronic acid in place of phenylboronic acid, using a corresponding reagent in place of iodobenzene, the present invention compounds having the following physical property values were obtained by following the same procedure as in Reference example 14→Reference example 2→Reference example 16→Reference example 39→Example 1.

Example 30(1)

4-(aminomethyl)-1-[3-anilino-5-(3,5-dimethylphenyl)-4-pyridinyl]-4-piperidinol

[135]

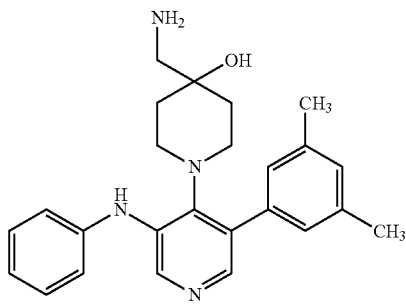

Description: yellow amorphous powder;
TLC: Rf 0.14 (ethyl acetate:methanol: 28% ammonia water=90:10:1);
NMR (300 MHz, METHANOL-d4): δ 8.24 (s, 1H), 7.82 (s, 1H), 7.30-7.20 (m, 2H), 7.09-6.94 (m, 5H), 6.93-6.84 (m, 1H), 3.00-2.75 (m, 4H), 2.42 (s, 2H), 2.37 (s, 6H), 1.57-1.32 (m, 4H);
MASS (ESI, Pos.): 403 (M+H)+.

Example 30(2)

5-(3,5-dimethylphenyl)-4-[4-(methylamino)-1-piperidinyl]-N-phenyl-3-pyridinamine Description: yellow amorphous powder;
TLC: Rf 0.76 (ethyl acetate:methanol=9:1, NH silica gel);
NMR (300 MHz, CHLOROFORM-d): δ 8.56 (s, 1H), 7.91 (s, 1H), 7.34-7.27 (m, 2H), 7.19-7.13 (m, 2H), 7.04 (s, 1H), 7.00-6.92 (m, 1H), 6.91-6.85 (m, 2H), 6.14 (s, 1H), 2.97 (d, J=12.26 Hz, 2H), 2.53-2.32 (m, 11H), 1.90 (m, 2H), 1.61-1.39 (m, 2H);
MASS (ESI, Pos.): 387 (M+H)+.

Example 30(3)

N-{5-(3,5-dimethylphenyl)-4-[4-(methylamino)-1-piperidinyl]-3-pyridinyl}-6-quinazolinamine Description: yellow amorphous powder;
TLC: Rf 0.58 (ethyl acetate:methanol=9:1, NH silica gel);
NMR (300 MHz, CHLOROFORM-d): δ 9.22 (s, 1H), 9.16 (s, 1H), 8.71 (s, 1H), 8.08 (s, 1H), 7.97 (d, J=8.97 Hz, 1H), 7.73 (dd, J=8.97, 2.40 Hz, 1H), 7.51 (d, J=2.40 Hz, 1H), 7.06 (s, 1H), 6.91 (s, 2H), 6.45 (s, 1H), 3.03-2.91 (m, 2H), 2.58-2.30 (m, 12H), 1.95-1.81 (m, 2H), 1.56-1.39 (m, 2H);
MASS (ESI, Pos.): 439 (M+H)+.

Example 30(4)

N-{5-(3,5-dimethylphenyl)-4-[4-(methylamino)-1-piperidinyl]-3-pyridinyl}-6-quinazolinamine Description: yellow powder;
TLC: Rf 0.58 (ethyl acetate:methanol=9:1, NH silica gel);
NMR (300 MHz, CHLOROFORM-d): δ 8.74 (dd, J=4.30, 1.65 Hz, 1H), 8.72 (s, 1H), 8.06-8.01 (m, 3H), 8.00-7.95 (m, 1H), 7.54-7.43 (m, 2H), 7.34 (dd, J=8.32, 4.30 Hz, 1H), 7.05 (s, 1H), 6.92 (s, 2H), 6.36 (s, 1H), 2.95 (d, J=12.62 Hz, 2H), 2.56-2.44 (m, 2H), 2.43-2.24 (m, 10H), 1.91-1.78 (m, 1H), 1.42-1.22 (m, 2H);
MASS (ESI, Pos.): 438 (M+H)+.

Example 30(5)

5-(3,5-dimethylphenyl)-4-[4-(methylamino)-1-piperidinyl]-N-[3-(trifluoromethoxy)phenyl]-3-pyridinamine Description: yellow amorphous powder;
TLC: Rf 0.71 (ethyl acetate:methanol=9:1, NH silica gel);
NMR (300 MHz, CHLOROFORM-d): δ 8.55 (s, 1H), 7.98 (s, 1H), 7.28 (t, J=8.42 Hz, 1H), 7.06-7.00 (m, 2H), 6.98 (s, 1H), 6.93-6.87 (m, 2H), 6.83-6.75 (m, 1H), 6.18 (s, 1H), 2.93 (d, J=12.62 Hz, 2H), 2.54-2.33 (m, 12H), 1.91-1.80 (m, 2H), 1.47-1.30 (m, 2H);
MASS (ESI, Pos.): 471 (M+H)+.

Reference Example 45 tert-butyl (1-(3-(3,5-dimethylphenyl)-5-(3-phenyl-1H-1,2,4-triazol-5-yl)pyridin-4-yl)piperidin-4-yl)carbamate To a sodium ethoxide (25 mg) in ethanol (1.0 mL) was added hydrazine monohydrate (0.5 mL), and stirred at 75 degrees C. overnight. The solvent and excess of hydrazine was removed under reduced pressure, and treated with toluene as azeotropy. The residue was dissolved in anhydrous ethanol (0.5 mL) and added benzamidine hydrochloride (CAS #1670-14-0) (59 mg), and then stirred at room temperature for 20 min. The reaction solution was added to the solution of the compound (100 mg) produced in Reference example 5 in toluene (1.0 mL)/ethanol (2.0 mL), and stirred at 110 degrees C. overnight and then additionally stirred at 130-150 degrees C. After cooling to room temperature, the reaction solution was filtered and concentrated. The obtained residue was purified by preparative medium pressure liquid chromatography (Yamazen Corp. YFLC-Wprep-2XY) (Hi-flash SI) (ethyl acetate) to obtain the title compound (77 mg) having the following physical property values.

TLC: Rf 0.27 (ethyl acetate);

Example 31

1-[3-(3,5-dimethylphenyl)-5-(3-phenyl-1H-1,2,4-triazol-5-yl)-4-pyridinyl]-4-piperidinamine

[136]

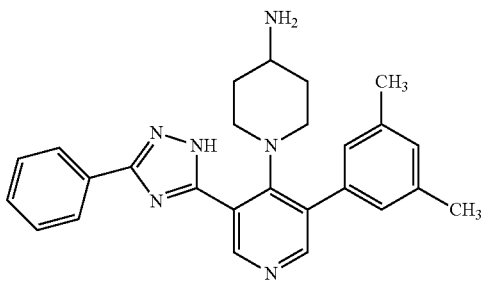

Using the compound produced in Reference example 45 in place of the compound produced in Reference example 3, the present invention compound having the following physical property values was obtained by following the same procedure as in Example 1.

Description: pale yellow powder;
TLC: Rf 0.16 (ethyl acetate:methanol=9:1, NH silica gel);
NMR (300 MHz, CHLOROFORM-d): δ 8.95 (s, 1H), 8.38-8.25 (m, 1H), 8.21-8.07 (m, 2H), 7.55-7.38 (m, 3H), 7.03 (s, 1H), 6.93 (s, 2H), 4.12 (br.s, 2H), 2.98 (d, J=12.4 Hz, 2H), 2.70-2.53 (m, 3H), 2.37 (s, 6H), 1.65 (d, J=10.4 Hz, 2H), 1.34-1.15 (m, 2H);
MASS (ESI, Pos.): 425 (M+H)+.

Reference Example 46 tert-butyl (1-(3-(2-benzoylhydrazinecarbonyl)-5-(3,5-dimethylphenyl)pyridin-4-yl)piperidin-4-yl)carbamate To a solution of the compound (200 mg) produced in Reference example 5 in methanol (2.0 mL) was added 1M aqueous solution of sodium hydroxide (0.91 mL), and the mixture was stirred at room temperature overnight. To the reaction solution was added 1M aqueous solution of sodium hydroxide (0.455 mL), and after that methanol and tetrahydrofuran was added to the mixture until it became uniform layer, and the mixture was stirred at 65 degrees C. After cooling by ice-water, the reaction mixture was neutralized by 2M hydrochloric acid, concentrated under reduced pressure, and then treated with toluene as azeotropy. To the obtained residue was added N,N-dimethylacetamide (4 mL), N,N-diisopropylethylamine (235 microL), benzhydrazide (CAS #613-94-5) (260 mg) and (benzotriazol-1-yloxy)tris(dimethylamino)phosphonium hexafluorophosphate (402 mg), and the mixture was stirred at room temperature overnight. After adding saturated brine, the reaction solution was extracted with tetrahydrofuran. After drying, the organic layer was concentrated. The obtained residue was purified by preparative medium pressure liquid chromatography (Yamazen Corp. YFLC-Wprep-2XY) (Hi-flash NH) (ethyl acetate:methanol=95:5) to obtain the title compound having the following physical property values.

Description: white powder;
TLC: Rf 0.24 (ethyl acetate:methanol=9:1, NH silica gel).

Reference Example 47 tert-butyl (1-(3-(3,5-dimethylphenyl)-5-(5-phenyl-1,3,4-oxadiazol-2-yl)pyridin-4-yl)piperidin-4-yl)carbamate To a solution of the compound (170 mg) produced in Reference example 46 in anhydrous tetrahydrofuran (2.0 mL) was added Burgess reagent (112 mg), and the mixture was stirred at room temperature for 2 hours and then at 50 degrees C. for 30 min. After cooling to room temperature, the solvent was removed under reduced pressure. The obtained residue was purified by preparative medium pressure liquid chromatography (Yamazen Corp. YFLC-Wprep-2XY) (Hi-flash SI) (n-hexane:ethyl acetate=3:1) to obtain the title compound (160 mg) having the following physical property values.

Description: clear and colorless oil;
TLC: Rf 0.36 (n-hexane:ethyl acetate=1:1);

Example 32(1)-Example 32(6)

Using 4-tert-butoxycarbonylaminopiperidine, or a corresponding reagent in place of it, using a corresponding boronic acid in place of phenylboronic acid, using benzhydrazide, or a corresponding reagent in place of it, the present invention compounds having the following physical property values were obtained by following the same procedure as in Reference example 1→Reference example 2→Reference example 41→Reference example 42→Example 1.

Example 32(1)

1-[3-(3,5-dimethylphenyl)-5-(5-phenyl-1,3,4-oxadiazol-2-yl)-4-pyridinyl]-4-piperidinamine

[137]

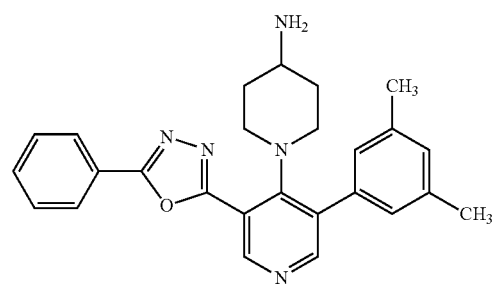

Description: orange viscous oil;
TLC: Rf 0.66 (ethyl acetate:methanol=9:1, NH silica gel);
NMR (300 MHz, CHLOROFORM-d): δ 8.72 (s, 1H), 8.37 (s, 1H), 8.22-8.03 (m, 2H), 7.64-7.48 (m, 3H), 7.09-6.97 (m, 3H), 3.06 (d, J=12.8 Hz, 2H), 2.76-2.49 (m, 3H), 2.39 (s, 6H), 1.60-1.48 (m, 2H), 1.38 (br.s., 2H), 1.20-1.02 (m, 2H);
MASS (APCI, Pos.): 426 (M+H)+.

Example 32(2)

1-[3-(3,5-dimethylphenyl)-5-(5-isopropyl-1,3,4-oxadiazol-2-yl)-4-pyridinyl]-4-piperidinamine Description: pale yellow oil;
TLC: Rf 0.46 (ethyl acetate:methanol=20:1, NH silica gel);
NMR (300 MHz, METHANOL-d4): δ 8.50 (s, 1H), 8.24 (s, 1H), 7.08 (s, 1H), 7.06 (s, 2H), 3.40-3.32 (m, 1H), 3.04 (d, J=12.6 Hz, 2H), 2.67-2.44 (m, 3H), 2.39 (s, 6H), 1.57-1.49 (m, 2H), 1.47 (s, 3H), 1.45 (s, 3H), 1.12 (qd, J=11.8, 4.1 Hz, 2H);
MASS (ESI, Pos.): 392 (M+H)+.

Example 32(3)

1-[3-(3,5-dimethylphenyl)-5-(5-propyl-1,3,4-oxadiazol-2-yl)-4-pyridinyl]-4-piperidinamine Description: yellow oil;
TLC: Rf 0.38 (ethyl acetate:methanol=20:1, NH silica gel);
NMR (300 MHz, METHANOL-d4): δ 8.49 (s, 1H), 8.23 (s, 1H), 7.11-7.01 (m, 3H), 3.13-2.92 (m, 4H), 2.69-2.45 (m, 3H), 2.38 (s, 6H), 1.97-1.79 (m, 2H), 1.51 (d, J=11.9 Hz, 2H), 1.22-0.99 (m, 5H);
MASS (ESI, Pos.): 392 (M+H)+.

Example 32(4)

1-[3-(5-cyclopropyl-1,3,4-oxadiazol-2-yl)-5-(3,5-dimethylphenyl)-4-pyridinyl]-4-piperidinamine Description: pale orange powder;
TLC: Rf 0.41 (ethyl acetate:methanol=20:1, NH silica gel);
NMR (300 MHz, METHANOL-d4): δ 8.55 (s, 1H), 8.26 (s, 1H), 7.09 (s, 1H), 7.03 (s, 2H), 3.09 (d, J=12.6 Hz, 2H), 2.86-2.71 (m, 1H), 2.69-2.54 (m, 2H), 2.44-2.27 (m, 7H), 1.62 (d, J=11.9 Hz, 2H), 1.41-1.12 (m, 6H);
MASS (ESI, Pos.): 390 (M+H)+.

Example 32(5)

1-[3-cyclopropyl-5-(5-phenyl-1,3,4-oxadiazol-2-yl)-4-pyridinyl]-4-piperidinamine Description: pale red powder;
TLC: Rf 0.70 (ethyl acetate:methanol=9:1, NH silica gel);
NMR (300 MHz, CHLOROFORM-d): δ 8.63 (s, 1H), 8.26 (s, 1H), 8.18-8.06 (m, 2H), 7.65-7.49 (m, 3H), 3.32 (d, J=12.62 Hz, 2H), 3.05-2.90 (m, 2H), 2.88-2.72 (m, 1H), 2.15-1.97 (m, 1H), 1.90-1.73 (m, 2H), 1.54-1.36 (m, 2H), 1.16-1.03 (m, 2H), 0.92-0.80 (m, 2H);
MASS (ESI, Pos.): 362 (M+H)+.

Example 32(6)

1-[3-cyclopropyl-5-(5-phenyl-1,3,4-oxadiazol-2-yl)-4-pyridinyl]-N-ethyl-4-piperidinamine Description: pale yellow amorphous powder;
TLC: Rf 0.85 (ethyl acetate:methanol=9:1, NH silica gel);
NMR (300 MHz, CHLOROFORM-d): δ 8.62 (s, 1H), 8.25 (s, 1H), 8.16-8.10 (m, 2H), 7.62-7.51 (m, 3H), 3.33 (d, J=12.60 Hz, 2H), 2.97 (td, J=12.60, 2.56 Hz, 2H), 2.73-2.57 (m, 3H), 2.15-2.00 (m, 1H), 1.90 (d, J=9.51 Hz, 2H), 1.50 (m, 2H), 1.14-1.02 (m, 5H), 0.92-0.79 (m, 2H)
MASS (ESI, Pos.): 390 (M+H)+.

Reference Example 48 ethyl 5-amino-1-(3,5-dimethylphenyl)-1H-pyrazole-4-carboxylate

To the solution of ethyl(ethoxymethylene)cyanoacetate (CAS #29096-99-9) (3.4 g) in ethanol (50 mL) was added (3,5-dimethylphenyl)hydrazine hydrochloride (CAS #60481-36-9) (3.5 g) and sodium acetate (1.8 g), and the mixture was stirred at 80 degrees C. for 1 hour. After cooling to room temperature, the reaction solution was filtered. The filtrate was concentrated and obtained the title compound which was used for next reaction without further purification.

Reference Example 49 ethyl 5-chloro-1-(3,5-dimethylphenyl)-1H-pyrazole-4-carboxylate

To a solution of the amyl nitrite (540 mg) and copper(I) chloride (570 mg) in acetonitrile (12 mL) stirring at 65 degrees C. was added a solution of the compound (1.0 g) produced in Reference example 48 in acetonitrile (12 mL), and the mixture was stirred at 65 degrees C. for 30 min. After cooling, the reaction solution was filtered and concentrated. The obtained residue was purified by silicagel column chromatography (eluent hexane:ethyl acetate=100:0→91:9) to obtain the title compound (187 mg) having the following physical property values.
TLC: Rf 0.61 (n-hexane:ethyl acetate=3:1).

Reference Example 50 ethyl 5-(4-((tert-butoxycarbonyl)amino)piperidin-1-yl)-1-(3,5-dimethylphenyl)-1H-pyrazole-4-carboxylate Using the compound produced in Reference example 49 in place of the mixture produced in Reference example 32, the title compound having the following physical property values was obtained by following the same procedure as in Reference example 33.
TLC: Rf 0.43 (n-hexane:ethyl acetate=3:1).

Example 33

1-[4-(4,6-dimethyl-1H-benzimidazol-2-yl)-1-(3,5-dimethylphenyl)-1H-pyrazol-5-yl]-4-piperidinamine

[138]

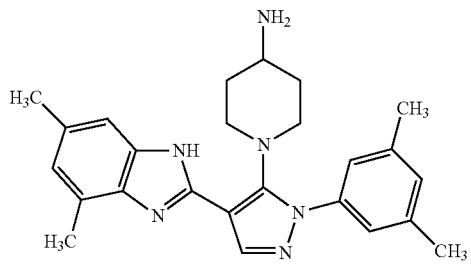

Using the compound produced in Reference example 50 in place of the compound produced in Reference example 5, using 3,5-dimethylbenzene-1,2-diamine in place of 3,5-dimethylaniline, the present invention compound having the following physical property values was obtained by following the same procedure as in Reference example 6→Reference example 7→Reference example 29→Example 1.

Description: amber powder;

TLC: Rf 0.41 (ethyl acetate:methanol=20:1, NH silica gel);

NMR (300 MHz, METHANOL-d4): δ 7.88-7.81 (m, 1H), 7.26 (s, 2H), 7.20 (s, 1H), 7.12 (s, 1H), 6.89 (s, 1H), 3.10-2.99 (m, 4H), 2.72-2.59 (m, 1H), 2.56-2.51 (m, 3H), 2.44-2.40 (m, 3H), 2.40-2.38 (m, 6H), 1.67 (d, J=11.9 Hz, 2H), 1.42-1.25 (m, 2H);

MASS (ESI, Pos.): 415 (M+H)+.

Reference Example 51

4-(4-((tert-butoxycarbonyl)amino)piperidin-1-yl)-3-(4,6-dimethyl-1H-benzo[d]imidazol-2-yl)-5-(3,5-dimethylphenyl)pyridine 1-oxide

[139]

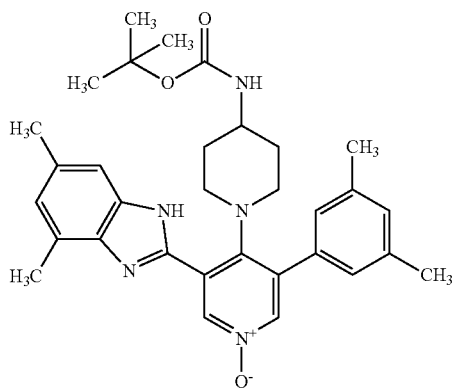

tert-butyl (1-(3-(4,6-dimethyl-1H-benzo[d]imidazol-2-yl)-5-(3,5-dimethylphenyl)pyridin-4-yl)piperidin-4-yl)carbamate (200 mg), which is Boc derivative of Example 21(1), was dissolved in a mixed solution of dichloromethane (5 mL), acetonitrile (2 mL), ethyl acetate (2 mL) and N,N-dimethylacetamide (10 mL). To the reaction mixture was added m-chloroperoxybenzoic acid (180 mg) and stirred at room temperature. After 1 hour, m-chloroperoxybenzoic acid (108 mg) and N,N-dimethylacetamide (5 mL) was added to it, and stirred. A saturated aqueous solution of sodium hydrogen sulfite was added to the reaction mixture, and stirred for a while. 0.5 mol/L aqueous solution of sodium hydroxide was added to the reaction mixture, and it was extracted with ethyl acetate. The obtained organic layer was washed with saturated brine, dried over magnesium sulfate, filtered and concentrated under reduced pressure. The obtained residue was purified by preparative medium pressure liquid chromatography (NH silica gel, ethyl acetate:methanol=100:0→90:10) to obtain the title compound having the following physical property values.

TLC: Rf 0.59 (ethyl acetate:methanol=19:1, NH silica gel);

NMR (300 MHz, METHANOL-d4): δ 8.31 (d, J=2.2 Hz, 1H), 8.06 (d, J=2.2 Hz, 1H), 7.27 (br. s, 1H), 7.14 (br. s, 1H), 7.09 (br. s, 2H), 6.98 (br. s, 1H), 3.15-3.02 (m, 1H), 2.95 (br. d, J=13.4 Hz, 2H), 2.61-2.47 (m, 4H), 2.45 (s, 3H), 2.40 (s, 6H), 1.35 (s, 11H), 1.20-1.03 (m, 2H).

Example 34

[140]

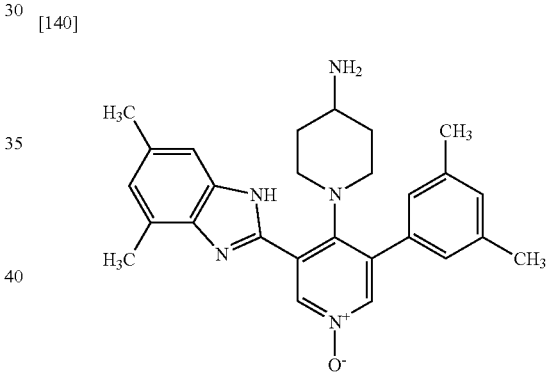

1-[3-(4,6-dimethyl-1H-benzimidazol-2-yl)-5-(3,5-dimethylphenyl)-1-oxide-4-pyridinyl]-4-piperidinamine Using the compound produced in Reference example 51 in place of the compound produced in Reference example 3, the present invention compound having the following physical property values was obtained by following the same procedure as in Example 1.

Description: yellow powder;

Purity (LC-MS/ELSD): 100% (retention time: 0.45 min);

TLC: Rf 0.24 (ethyl acetate:methanol=9:1, NH silica gel);

NMR (300 MHz, METHANOL-d4): δ 8.32 (d, J=2.4 Hz, 1H), 8.06 (d, J=2.4 Hz, 1H), 7.26 (s, 1H), 7.14 (s, 1H), 7.08 (s, 2H), 6.97 (s, 1H), 2.99 (br. d, J=13.4 Hz, 2H), 2.59-2.42 (m, 9H), 2.39 (s, 3H), 2.39 (s, 3H), 1.47-1.36 (m, 2H), 1.15-0.96 (m, 2H);

MASS (ESI, Pos.): 442 (M+H)+.

Reference Example 52 tert-butyl(1-(3-(3,5-dimethylphenyl)-5-vinylpyridin-4-yl)piperidin-4-yl)carbamate

[141]

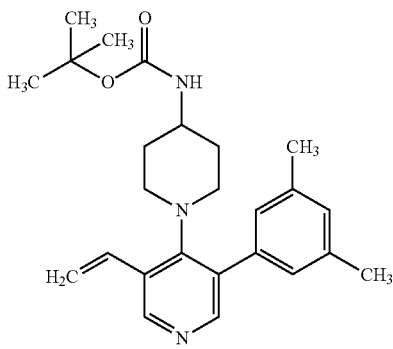

Using tert-butyl(1-(3-(3,5-dimethylphenyl)-5-iodopyridin-4-yl)piperidin-4-yl)carbamate in place of the compound produced in Reference example 39, the title compound having the following physical property values was obtained by following the same procedure as in Reference example 40.

TLC: Rf 0.52 (n-hexane:ethyl acetate=1:1);

Example 35(1)-Example 35(3)

Using the compound produced in Reference example 52 in place of the compound produced in Reference example 40, using a corresponding bromobenzene derivative, or a corresponding bromopyridine derivative in place of 1-bromo-3,5-dimethylbenzene, the present invention compounds having the following physical property values were obtained by following the same procedure as in Reference example 41→Example 1.

Example 35(1)

[142]

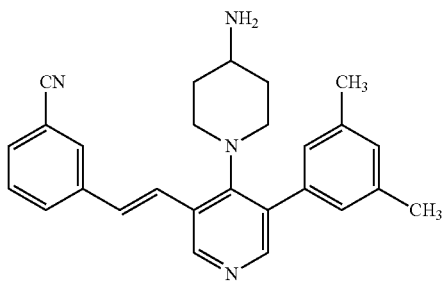

3-{(E)-2-[4-(4-amino-1-piperidinyl)-5-(3,5-dimethylphenyl)-3-pyridinyl]vinyl}benzonitrile Description: pale yellow powder;
Purity (UPLC-MS/ELSD): 99.3% (retention time: 0.54 min);
TLC: Rf 0.68 (ethyl acetate:methanol=9:1, NH silica gel);
NMR (300 MHz, DIMETHYL SULFOXIDE-d6): δ 8.63 (s, 1H), 8.16 (s, 1H), 8.12 (s, 1H), 8.07-8.00 (m, 1H), 7.83-7.77 (m, 1H), 7.71-7.63 (m, 1H), 7.44 (d, J=16.6 Hz, 1H), 7.28 (d, J=16.6 Hz, 1H), 7.07 (s, 1H), 6.95 (s, 2H), 3.03-2.90 (m, 2H), 2.67-2.56 (m, 3H), 2.37 (s, 3H), 1.71-1.54 (m, 2H), 1.43-1.24 (m, 2H);
MASS (ESI, Pos.): 409 (M+H)+.

Example 35(2)

[143]

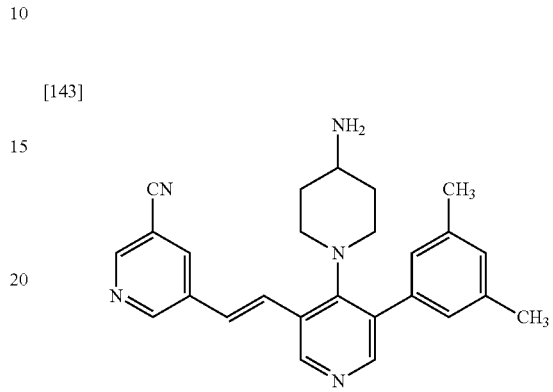

5-{(E)-2-[4-(4-amino-1-piperidinyl)-5-(3,5-dimethylphenyl)-3-pyridinyl]vinyl}nicotinonitrile Description: pale yellow powder;
Purity (UPLC-MS/ELSD): 99.4% (retention time: 0.51 min);
TLC: Rf 0.63 (ethyl acetate:methanol=9:1, NH silica gel);
NMR (300 MHz, METHANOL-d4): δ 9.03 (d, J=1.8 Hz, 1H), 8.79 (d, J=1.8 Hz, 1H), 8.56 (s, 1H), 8.50-8.45 (m, 1H), 8.11 (s, 1H), 7.55 (d, J=16.6 Hz, 1H), 7.22 (d, J=16.6 Hz, 1H), 7.07 (s, 1H), 6.90 (s, 2H), 3.14-3.01 (m, 2H), 2.72-2.53 (m, 3H), 2.37 (s, 6H), 1.79-1.63 (m, 2H), 1.51-1.34 (m, 2H);
MASS (ESI, Pos.): 410 (M+H)+.

Example 35(3)

4-{(E)-2-[4-(4-amino-1-piperidinyl)-5-(3,5-dimethylphenyl)-3-pyridinyl]vinyl}-2-pyridinecarbonitrile Description: pale yellow powder;
Purity (UPLC-MS/ELSD): 99.2% (retention time: 0.51 min);
TLC: Rf 0.63 (ethyl acetate:methanol=9:1, NH silica gel);
NMR (300 MHz, DIMETHYL SULFOXIDE-d6): δ 8.78 (d, J=5.1 Hz, 1H), 8.64 (s, 1H), 8.33 (s, 1H), 8.19 (s, 1H), 7.97 (dd, J=1.7, 5.1 Hz, 1H), 7.71 (d, J=16.6 Hz, 1H), 7.28 (d, J=16.6 Hz, 1H), 7.07 (s, 1H), 6.95 (s, 2H), 3.02-2.89 (m, 2H), 2.70-2.57 (m, 3H), 2.37 (s, 6H), 1.68-1.56 (m, 2H), 1.43-1.24 (m, 2H);
MASS (ESI, Pos.): 410 (M+H)+.

Example 36(1)-Example 36(14)

Using a corresponding vinylpyridine derivative in place of the compound produced in Reference example 40, using a corresponding bromobenzene derivative, or a corresponding bromopyridine derivative in place of 1-bromo-3,5-dimethylbenzene, the present invention compounds having the following physical property values were obtained by following the same procedure as in Reference example 41→Example 1.

Example 36(1)

5-{(E)-2-[4-(4-amino-1-piperidinyl)-5-(3-fluoro-5-methoxyphenyl)-3-pyridinyl]vinyl}nicotinonitrile Description: off-white powder;
Purity (UPLC-MS/ELSD): 100% (retention time: 0.46 min);
TLC: Rf 0.60 (ethyl acetate:methanol=9:1, NH silica gel);
NMR (300 MHz, CHLOROFORM-d): δ 8.78 (d, J=2.1 Hz, 1H), 8.59 (d, J=2.1 Hz, 1H), 8.43 (s, 1H), 8.07 (s, 1H), 7.87 (t, J=2.1 Hz, 1H), 7.19 (d, J=16.6 Hz, 1H), 6.83 (d, J=16.6 Hz, 1H), 6.52-6.44 (m, 1H), 6.43-6.34 (m, 2H), 3.65 (s, 3H), 2.92-2.81 (m, 2H), 2.63-2.39 (m, 3H), 1.64-1.51 (m, 2H), 1.26-1.10 (m, 2H);
MASS (ESI, Pos.): 430 (M+H)+.

Example 36(2)

4-{(E)-2-[4-(4-amino-1-piperidinyl)-5-(3-fluoro-5-methoxyphenyl)-3-pyridinyl]vinyl}-2-pyridinecarbonitrile Description: yellow amorphous powder;
Purity (UPLC-MS/ELSD): 100% (retention time: 0.47 min);
TLC: Rf 0.58 (ethyl acetate:methanol=9:1, NH silica gel);
NMR (300 MHz, CHLOROFORM-d): δ 8.71 (d, J=4.8 Hz, 1H), 8.63 (s, 1H), 8.28 (s, 1H), 7.77 (s, 1H), 7.61 (dd, J=1.7, 5.2 Hz, 1H), 7.52 (d, J=16.5 Hz, 1H), 6.99 (d, J=16.5 Hz, 1H), 6.70-6.54 (m, 3H), 3.85 (s, 3H), 3.12-3.00 (m, 2H), 2.84-2.60 (m, 3H), 1.85-1.71 (m, 2H), 1.46-1.30 (m, 2H);
MASS (ESI, Pos.): 430 (M+H)+.

Example 36(3)

5-{(E)-2-[4-(4-amino-1-piperidinyl)-5-(3-fluoro-5-methylphenyl)-3-pyridinyl]vinyl}nicotinonitrile Description: yellow amorphous powder;
Purity (UPLC-MS/ELSD): 100% (retention time: 0.44 min);
TLC: Rf 0.62 (ethyl acetate:methanol=20:1, NH silica gel);
NMR (300 MHz, METHANOL-d4): δ 9.04 (d, J=2.0 Hz, 1H), 8.81 (d, J=2.0 Hz, 1H), 8.60 (s, 1H), 8.48 (t, J=2.2 Hz, 1H), 8.15 (s, 1H), 7.54 (d, J=16.5 Hz, 1H), 7.24 (d, J=16.5 Hz, 1H), 7.08-6.83 (m, 3H), 3.17-3.08 (m, 2H), 2.74-2.60 (m, 3H), 2.43 (s, 3H), 1.79-1.69 (m, 2H), 1.54-1.37 (m, 2H);
MASS (ESI, Pos.): 414 (M+H)+.

Example 36(4)

4-{(E)-2-[4-(4-amino-1-piperidinyl)-5-(3-fluoro-5-methylphenyl)-3-pyridinyl]vinyl}-2-pyridinecarbonitrile Description: yellow amorphous powder;
Purity (UPLC-MS/ELSD): 100% (retention time: 0.46 min);
TLC: Rf 0.62 (ethyl acetate:methanol=20:1, NH silica gel);
NMR (300 MHz, METHANOL-d4): δ 8.68 (d, J=5.5 Hz, 1H), 8.61 (s, 1H), 8.16 (s, 1H), 8.12 (s, 1H), 7.88 (dd, J=5.4, 1.6 Hz, 1H), 7.70 (d, J=16.5 Hz, 1H), 7.22 (d, J=16.5 Hz, 1H), 7.06-6.85 (m, 3H), 3.17-3.06 (m, 2H), 2.75-2.62 (m, 3H), 2.44 (s, 3H), 1.81-1.71 (m, 2H), 1.55-1.40 (m, 3H);
MASS (ESI, Pos.): 414 (M+H)+.

Example 36(5)

[144]

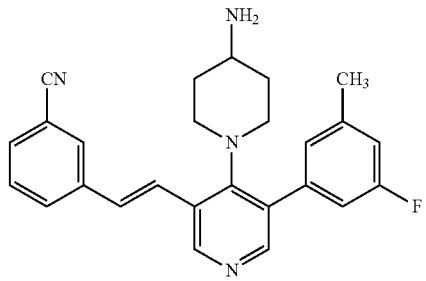

3-{(E)-2-[4-(4-amino-1-piperidinyl)-5-(3-fluoro-5-methylphenyl)-3-pyridinyl]vinyl}benzonitrile Description: pale brown powder;
Purity (UPLC-MS/ELSD): 100% (retention time: 0.50 min);
TLC: Rf 0.62 (ethyl acetate:methanol=20:1, NH silica gel);
NMR (300 MHz, METHANOL-d4): δ 8.58 (s, 1H), 8.13 (s, 1H), 8.00-7.93 (m, 2H), 7.70-7.63 (m, 1H), 7.62-7.55 (m, 1H), 7.43 (d, J=16.1 Hz, 1H), 7.21 (d, J=16.1 Hz, 1H), 7.05-6.83 (m, 3H), 3.18-3.04 (m, 2H), 2.75-2.59 (m, 3H), 2.43 (s, 3H), 1.81-1.70 (m, 2H), 1.56-1.39 (m, 2H);
MASS (ESI, Pos.): 413 (M+H)+.

Example 36(6)

[145]

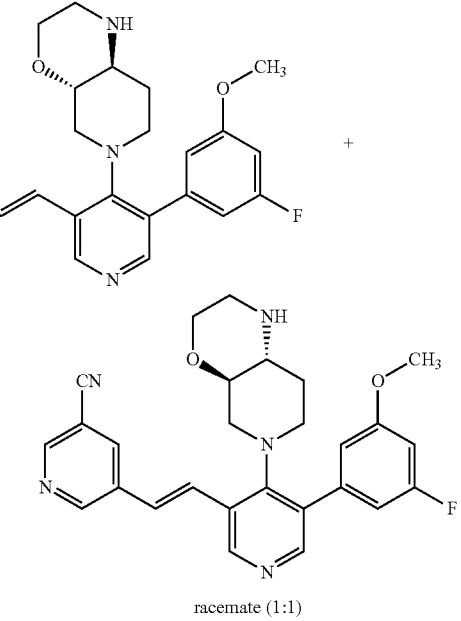

racemate (1:1)

5-[(E)-2-{5-(3-fluoro-5-methoxyphenyl)-4-[rac-(4aR,8aR)-octahydro-6H-pyrido[3,4-b][1,4]oxazin-6-yl]-3-pyridinyl}vinyl]nicotinonitrile Description: pale brown amorphous powder;
Purity (LC-MS/ELSD): 100% (retention time: 0.47 min);
TLC: Rf 0.58 (ethyl acetate:methanol=19:1, NH silica gel);
NMR (300 MHz, CHLOROFORM-d): δ 8.96 (d, J=2.2 Hz, 1H), 8.79 (d, J=2.0 Hz, 1H), 8.64 (s, 1H), 8.29 (s, 1H), 8.09-8.02 (m, 1H), 7.35 (d, J=16.5 Hz, 1H), 7.04 (d, J=16.5 Hz, 1H), 6.66 (dt, J=10.6, 2.3 Hz, 1H), 6.62-6.52 (m, 2H), 3.90-3.78 (m, 4H), 3.66 (td, J=11.4, 2.8 Hz, 1H), 3.34-3.22 (m, 1H), 3.17-2.97 (m, 3H), 2.96-2.85 (m, 1H), 2.78 (td, J=12.3, 2.9 Hz, 1H), 2.55 (dd, J=11.9, 10.1 Hz, 1H), 2.50-2.39 (m, 1H), 1.72-1.44 (m, 2H);
MASS (ESI, Pos.): 472 (M+H)+.

Example 36(7)

3-[(E)-2-{5-(3-fluoro-5-methylphenyl)-4-[rac-(4aR,8aR)-octahydro-6H-pyrido[3,4-b][1,4]oxazin-6-yl]-3-pyridinyl}vinyl]benzonitrile Description: pale yellow amorphous powder;
Purity (LC-MS/ELSD): 98.0% (retention time: 0.51 min);
TLC: Rf 0.58 (ethyl acetate:methanol=19:1, NH silica gel);
NMR (300 MHz, CHLOROFORM-d): δ 8.63 (s, 1H), 8.26 (s, 1H), 7.74-7.81 (m, 2H), 7.56-7.61 (m, 1H), 7.54-7.47 (m, 1H), 7.26 (d, J=16.3 Hz, 2H), 7.03 (d, J=16.3 Hz, 1H), 6.96-6.89 (m, 1H), 6.86 (s, 1H), 6.81-6.74 (m, 1H), 3.84 (dd, J=11.3, 2.4 Hz, 1H), 3.66 (td, J=11.5, 2.7 Hz, 1H), 3.29 (td, J=9.2, 4.6 Hz, 1H), 3.13-2.97 (m, 3H), 2.95-2.85 (m, 1H), 2.73 (td, J=12.2, 3.4 Hz, 1H), 2.54-2.37 (m, 5H), 1.61-1.46 (m, 2H);
MASS (ESI, Pos.): 455 (M+H)+.

Example 36(8)

[146]

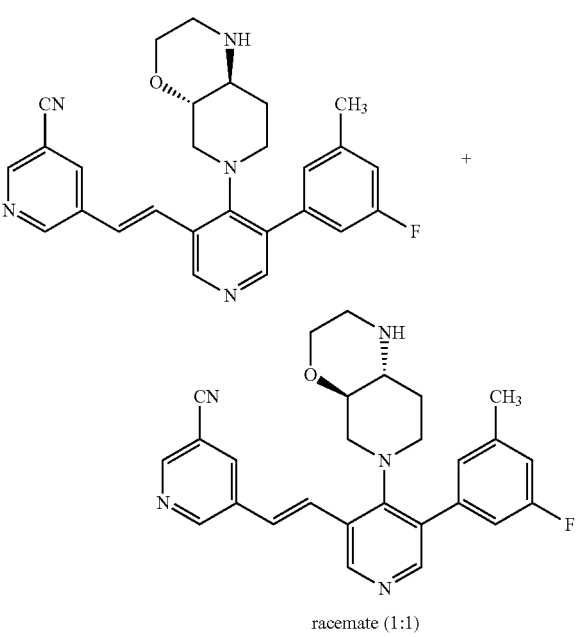

racemate (1:1)

5-[(E)-2-{5-(3-fluoro-5-methylphenyl)-4-[rac-(4aR,8aR)-octahydro-6H-pyrido[3,4-b][1,4]oxazin-6-yl]-3-pyridinyl}vinyl]nicotinonitrile Description: off-white powder;
Purity (LC-MS/ELSD): 100% (retention time: 0.49 min);
TLC: Rf 0.61 (ethyl acetate:methanol=19:1, NH silica gel);
NMR (300 MHz, CHLOROFORM-d): δ 8.96 (d, J=2.1 Hz, 1H), 8.79 (d, J=2.1 Hz, 1H), 8.64 (s, 1H), 8.28 (s, 1H), 8.06 (t, J=2.1 Hz, 1H), 7.35 (d, J=16.6 Hz, 1H), 7.04 (d, J=16.6 Hz, 1H), 6.97-6.89 (m, 1H), 6.86 (d, J=0.7 Hz, 1H), 6.81-6.73 (m, 1H), 3.89-3.79 (m, 1H), 3.66 (td, J=11.4, 2.7 Hz, 1H), 3.27 (td, J=9.4, 4.3 Hz, 1H), 3.13-2.97 (m, 3H), 2.95-2.85 (m, 1H), 2.80-2.66 (m, 1H), 2.58-2.37 (m, 5H), 1.69-1.46 (m, 2H);
MASS (ESI, Pos.): 456 (M+H)+.

Example 36(9)

4-[(E)-2-{5-(3-fluoro-5-methylphenyl)-4-[rac-(4aR,8aR)-octahydro-6H-pyrido[3,4-b][1,4]oxazin-6-yl]-3-pyridinyl}vinyl]-2-pyridinecarbonitrile Description: yellow powder;
Purity (LC-MS/ELSD): 100% (retention time: 0.51 min);
TLC: Rf 0.50 (ethyl acetate:methanol=19:1, NH silica gel);
NMR (300 MHz, CHLOROFORM-d): δ 8.71 (dd, J=5.1, 0.5 Hz, 1H), 8.64 (d, J=0.7 Hz, 1H), 8.30 (s, 1H), 7.79-7.74 (m, 1H), 7.64-7.58 (m, 1H), 7.49 (d, J=16.3 Hz, 1H), 6.99 (d, J=16.3 Hz, 1H), 6.96-6.90 (m, 1H), 6.88-6.84 (m, 1H), 6.77 (d, J=9.0 Hz, 1H), 3.85 (dd, J=11.5, 2.2 Hz, 1H), 3.66 (td, J=11.3, 2.6 Hz, 1H), 3.34-3.24 (m, 1H), 3.11-2.98 (m, 3H), 2.95-2.86 (m, 1H), 2.74 (td, J=12.4, 2.7 Hz, 1H), 2.56-2.38 (m, 5H), 1.68-1.46 (m, 2H);
MASS (ESI, Pos.): 456 (M+H)+.

Example 36(10)

1-{3-(3-fluoro-5-methylphenyl)-5-[(E)-2-(3-fluorophenyl)vinyl]-4-pyridinyl}-4-piperidinamine Description: pale brown powder;
Purity (UPLC-MS/ELSD): 99.9% (retention time: 0.53 min);
TLC: Rf 0.62 (ethyl acetate:methanol=20:1, NH silica gel);
NMR (300 MHz, METHANOL-d4): δ 8.56 (s, 1H), 8.10 (s, 1H), 7.47-7.32 (m, 3H), 7.34 (d, J=16.6 Hz, 1H), 7.16 (d, J=16.6 Hz, 1H), 7.07-6.82 (m, 4H), 3.16-3.06 (m, 2H), 2.71-2.58 (m, 3H), 2.43 (s, 3H), 1.79-1.69 (m, 2H), 1.55-1.39 (m, 2H);
MASS (ESI, Pos.): 406 (M+H)+.

Example 36(11)

1-{3-[(E)-2-(4-chlorophenyl)vinyl]-5-(3-fluoro-5-methylphenyl)-4-pyridinyl}-4-piperidinamine Description: pale yellow powder;
Purity (UPLC-MS/ELSD): 99.2% (retention time: 0.55 min);
TLC: Rf 0.27 (ethyl acetate:methanol=9:1, NH silica gel);
NMR (300 MHz, CHLOROFORM-d): δ 8.61 (s, 1H), 8.20 (s, 1H), 7.48 (d, J=8.6 Hz, 2H), 7.36 (d, J=8.6 Hz, 2H), 7.22 (d, J=16.6 Hz, 1H), 7.03 (d, J=16.6 Hz, 1H), 6.94-6.73

(m, 3H), 3.12-3.00 (m, 2H), 2.79-2.65 (m, 1H), 2.65-2.53 (m, 2H), 2.41 (s, 3H), 1.79-1.68 (m, 2H), 1.48-1.30 (m, 2H);

MASS (ESI, Pos.): 422 (M+H)+.

Example 36(12)

1-{3-[(E)-2-(3-chlorophenyl)vinyl]-5-(3-fluoro-5-methylphenyl)-4-pyridinyl}-4-piperidinamine Description: pale yellow powder;

Purity (UPLC-MS/ELSD): 99.3% (retention time: 0.56 min);

TLC: Rf 0.25 (ethyl acetate:methanol=9:1, NH silica gel);

NMR (300 MHz, CHLOROFORM-d): δ 8.60 (s, 1H), 8.21 (s, 1H), 7.53-7.19 (m, 5H), 6.98 (d, J=16.6 Hz, 1H), 6.94-6.73 (m, 3H), 3.11-2.98 (m, 2H), 2.79-2.53 (m, 3H), 2.42 (s, 3H), 1.83-1.67 (m, 2H), 1.48-1.30 (m, 2H);

MASS (ESI, Pos.): 422 (M+H)+.

Example 36(13)

1-{3-(3-fluoro-5-methylphenyl)-5-[(E)-2-(4-fluorophenyl)vinyl]-4-pyridinyl}-4-piperidinamine Description: pale brown powder;

Purity (UPLC-MS/ELSD): 100% (retention time: 0.54 min);

TLC: Rf 0.25 (ethyl acetate:methanol=9:1, NH silica gel);

NMR (300 MHz, METHANOL-d4): δ 8.55 (s, 1H), 8.09 (s, 1H), 7.66 (dd, J=8.6, 5.5 Hz, 2H), 7.26 (d, J=16.5 Hz, 1H), 7.19-7.08 (m, 3H), 7.04-6.82 (m, 3H), 3.17-3.04 (m, 2H), 2.71-2.56 (m, 3H), 2.43 (s, 3H), 1.79-1.67 (m, 2H), 1.54-1.41 (m, 2H);

MASS (ESI, Pos.): 406 (M+H)+.

Example 36(14)

5-{(E)-2-[4-(4-amino-1-piperidinyl)-5-(3,5-dimethylphenyl)-3-pyridinyl]vinyl}-3-pyridinol Description: yellow amorphous powder;

Purity (UPLC-MS/ELSD): 91.2% (retention time: 0.42 min);

TLC: Rf 0.18 (ethyl acetate:methanol=9:1, NH silica gel);

NMR (300 MHz, METHANOL-d4): δ 8.55 (s, 1H), 8.07 (s, 1H), 7.97-7.85 (m, 2H), 7.38-7.27 (m, 2H), 7.14-7.04 (m, 2H), 6.90 (s, 2H), 3.14-3.01 (m, 2H), 2.70-2.54 (m, 3H), 2.37 (s, 6H), 1.81-1.68 (m, 2H), 1.57-1.40 (m, 2H);

MASS (ESI, Pos.): 401 (M+H)+.

Example 37

(5-methyl-2-oxo-1,3-dioxol-4-yl)methyl {1-[3-(6-chloro-1H-benzimidazol-2-yl)-5-(3-fluoro-5-methylphenyl)-4-pyridinyl]-4-piperidinyl}carbamate

[147]

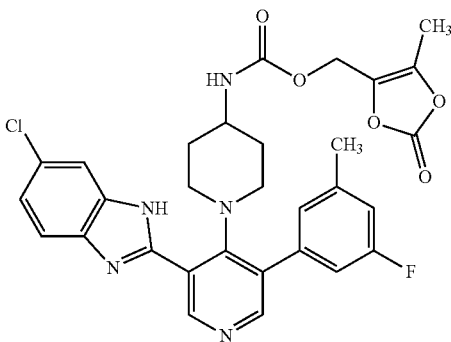

The compound produced in Example 21 (50) was dissolved in 0.7 mL dimethylformamide and stirred at 0 degrees C. A solution of (5-methyl-2-oxo-1,3-dioxol-4-yl)methyl 4-nitrophenylcarbonate (81 mg) in 0.5 mL dimethylformamide was added to the reaction mixture and stirred at room temperature for 1 hour. To the reaction mixture was added water and ethyl acetate followed by extraction. The obtained organic layer was sequentially washed with water and saturated brine, dried over anhydrous magnesium sulfate and then concentrated under reduced pressure. The obtained residue was purified by silicagel column chromatography (hexane:ethyl acetate=75:25→20:80) to obtain the present invention compound having the following physical property values.

Description: pale purple powder;

Purity (UPLC-MS/ELSD): 100% (retention time: 0.73 min);

TLC: Rf 0.20 (ethyl acetate);

NMR (300 MHz, DIMETHYL SULFOXIDE-d6): δ 12.87 (br. s., 1H), 8.47 (s, 1H), 8.28 (s, 1H), 7.84-7.53 (m, 2H), 7.44 (d, J=7.1 Hz, 1H), 7.27 (br. s., 1H), 7.18-7.05 (m, 3H), 4.78 (s, 2H), 3.13-2.96 (m, 1H), 2.88-2.78 (m, 2H), 2.58-2.53 (m, 2H), 2.41 (s, 3H), 2.10 (s, 3H), 1.42-1.28 (m, 2H), 1.21-1.02 (m, 2H);

MASS (ESI, Pos.): 592 (M+H)+.

Example 38

1-{3-[(1E)-2-(3-chlorophenyl)-1-propen-1-yl]-5-(3-fluoro-5-methylphenyl)-4-pyridinyl}-4-piperidinamine

[148]

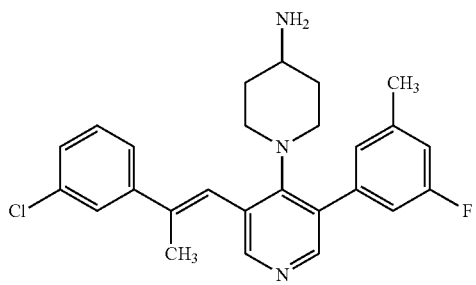

Using an iodopyridine derivative in place of the compound produced in Reference example 39, using (E)-2-(2-(3-chlorophenyl)-1-propen-1-yl)-4,4,5,5-tetramethyl-1,3,2-dioxaborolane in place of 3,5-dimethylphenylboronic acid, the present invention compound having the following physical property values was obtained by following the same procedure as in Reference example 39→Example 1.

Description: brown powder;
Purity (UPLC-MS/ELSD): 100% (retention time: 0.55 min);
TLC: Rf 0.44 (ethyl acetate:methanol=20:1, NH silica gel);
NMR (300 MHz, CHLOROFORM-d): δ 8.34 (s, 1H), 8.21 (s, 1H), 7.55-7.53 (m, 1H), 7.48-7.43 (m, 1H), 7.37-7.29 (m, 2H), 6.95-6.71 (m, 4H), 3.10-2.99 (m, 2H), 2.71-2.55 (m, 3H), 2.43 (s, 3H), 2.26 (d, J=1.1 Hz, 3H), 1.72-1.62 (m, 2H), 1.31-1.14 (m, 2H);
MASS (ESI, Pos.): 436 (M+H)+.

Biological Example 1

Evaluation of SSTR2 Agonist Activity Using Human SSTR2 Expressing Cells
[Procedure]
(1) Isolation of Human SSTR2 Gene Human brain cDNA was purchased from Ambion (catalog No. 7962; lot No. 040200121). PCR primer, hSSTR2_F1_Xhol: 5'-CACCCTCGAGGACATGGCGATGAGCCACTCAAT-3' (sequence number 1), and hSSTR2_R1_EcoRI: 5'-CCTTGAATTCGATACTGGTTTGGAGGTCTCCATT-3' (sequence number 2) are designed based on array of GenBank NM_001050.

Using human brain cDNA as a template, using KOD-plus-(TOYOBO), PCR is carried out (95° C. for 2 min, [98° C. for 10 sec., 60° C. for 30 sec., 68° C. for 90 sec.]×30 times). After 1% agarose gel electrophoresis, amplified PCR products was purified by QIAquick Gel Extraction Kit (QIAGEN), and cut by restriction enzyme XhoI and EcoRI. The fragment was linked with expression vector (pIRESneo-Myc) using DNA Ligation Kit Ver.2 (Takara) to transform into Escherichia coli DH5a. The DNA sequence was determined with this plasmid pIRESneo-Myc/hSSTR2.

(2) Culture of CHO-K1 Cells

CHO-K1 (−) were cultured using Ham's F-12 (including FBS (10%), penicillin (100 U/mL) and streptomycin (0.1 mg/mL)) as medium. The transduced cells were cultured using the medium above with geneticin (1 mg/ml).

(3) Transduction Into CHO-K1 Cells

The plasmid pIRESneo-Myc/hSSTR2 was transduced into CHO-K1 (−) cell using Lipofectamine 2000 (Invitrogen). After 48 hours, the medium was changed to the medium including 1 mg/mL Geneticin, overexpressing cells were selected and stably overexpressing cells (SSTR2—CHO-K1) were established.

(4) Evaluation of SSTR2 Agonist Activity

Human SSTR2 agonist activity of test compounds was evaluated by following procedure using inhibition activity against intracellular cyclic AMP (cAMP) production stimulated by Forskolin as an indicator. The SSTR2—CHO-K1 cells suspended in Ham's F-12 medium (including fetal bovine serum (10%), penicillin (100 U/mL), streptomycin (0.1 mg/mL)) including 0.25 mg/mL Geneticin was seeded in 96 wells plate ($4.0 \times 10^4$ cells/0.1 mL/1 well). After 1 day, the medium was removed and the cells were washed with 0.1 mL of wash buffer solution [0.1% bovine serum albumin (BSA), Hank's Balanced Salt Solution (HBSS) including 20 mmol/L 4-(2-hydroxyethyl)-1-piperazine ethanesulfonic acid (HEPES)] twice. To the cells added 0.06 mL/well assay buffer [500 nmol/L 3-isobutyl-1-methylxanthine (IBMX), 0.1% BSA, 20 mmol/L HBSS including HEPES], and incubated for 15 min. under 5% $CO_2$ and 37° C. Next, to the cells added 0.06 mL/well assay buffer including test compounds of the double concentration of final concentration and 0.02 mmol/L Forskolin, and incubated for 30 min. under 5% $CO_2$ and 37° C. After that, to the cells added 0.12 mL/well Assay/Lysis buffer included with cAMP-Screen® kit (Applied Biosystems®), and incubated for 30 min. under 5% $CO_2$ and 37° C. The concentration of c-AMP is determined by ELISA test according to manual included with the kit. The reaction rate (%) of inhibition activity against c-AMP production stimulated by Forskolin are determined every each sample, and 50% effective concentration ($EC_{50}$) of agonist activity of test compounds against human SSTR2 was calculated by non-linear regression analysis, where the reaction rate of 1000 nmol/L Octreotide is 100%, common logarithm concentration of the test compounds is independent variable, reaction rare of the corresponding concentration is dependent variable.

[Result]

The present invention compounds showed high SSTR2 agonist activity. For example, the compound produced in Example 5(1) showed 0.03 nmol/L, the compound produced in Example2 (20) showed 0.006 nmol/L, the compound produced in Example 26(24) showed 0.049 nmol/L, the compound produced in Example 36(5) showed 0.016 nmol/L, the compound produced in Example 36(8) showed 0.034 nmol/L as $EC_{50}$. In this evaluation method, Octreotide showed 0.24 nmol/L as $EC_{50}$, and the compound which shown in WO2008/051272 as following formula (M):

[149]

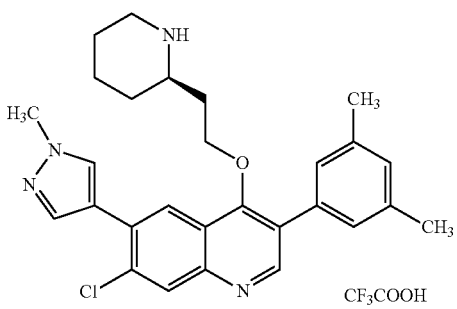

(M)

showed 0.06 nmol/L as $EC_{50}$.

Biological Example 2

Evaluation of Growth Hormone (GH) Secretory Inhibitory Activity Using Rat.

[Procedure (A): Test Compounds are Administered 30 Min. Before.]

Test compounds dissolved in vehicle (distillated water (Otsuka jouryuusui, Otsuka Pharmaceutical Factory, Inc.) or vehicle only was administered to rat (7-week-old, male Crl: CD (SD) IGS rat (CHARLES RIVER LABORATORIES JAPAN, INC.)) orally, and 27 min. later, 50 mg/kg of sodium pentobarbital (Somunopentil® Kyoritsu Seiyaku) was administered by tail vein injection to be anesthetized. Three minutes after administration of sodium pentobarbital, 0.01 mg/kg of growth hormone-releasing hormone (GHRH, Bachem) was administered by tail vein injection to evoke GH secretion. To measure blood concentration of GH, 0.2 mL blood sample from cervical vein was collected 5 minutes after administration of GHRH. The blood samples were treated with centrifugation at 13,000 g at 4° C. for 5 min. to obtain plasma sample. Blood concentration of GH was determined by Rat/Mouse Growth Hormone ELISA (Millipore) according to the procedure manual. Inhibition ratio of GH secretion (%) was determined by mathematical formula {[Inhibition ratio of GH secretion (%)]=([blood GH concentration of vehicle administered group]−[blood GH concentration of test compound administered group])/[blood GH concentration of vehicle administered group]×100} using obtained value of blood GH concentration. In addition, "vehicle administered group" in the formula means vehicle administered animal group and "test compound administered group" means test compound dissolved in vehicle administered animal group.

[Procedure (B): Test Compounds are Administered 8 Hours Before]

Test compounds dissolved in vehicle (distillated water (Otsuka jouryuusui, Otsuka Pharmaceutical Factory, Inc.) or vehicle only was administered to rat (7-week-old, male Crl: CD (SD) IGS rat (CHARLES RIVER LABORATORIES JAPAN, INC.)) orally, and 7 hours 57 minutes later, 50 mg/kg of sodium pentobarbital (Somunopentil® Kyoritsu Seiyaku) was administered by tail vein injection to be anesthetized. Three min. after administration of sodium pentobarbital, 0.01 mg/kg of growth hormone-releasing hormone (GHRH, Bachem) was given by tail vein injection to evoke GH secretion. Procedure after that was same as [Procedure (A)]

[Result]

The present invention compounds showed high GH secretion inhibitory activity. For example, 10 mg/kg of the compound produced in Example 5(1) showed 92% (Procedure (A)), 3 mg/kg of the compound produced in Example 2(20) showed 97% (Procedure (A)), 3 mg/kg of the compound produced in Example 26(15) showed 92% (Procedure (B)), 1 mg/kg of the compound produced in Example 26(24) showed 91% (Procedure (B)), 1 mg/kg of the compound produced in Example 36(5) showed 92% (Procedure (B)), and 1 mg/kg of the compound produced in Example 36(8) showed 83% (Procedure (B)) as the ratio of GH secretion inhibition. In this evaluation method, for example, 0.003 mg/kg (s.c.) of Octreotide showed 98% (method (A)) as ratio of GH secretory inhibition.

Biological Example3

Evaluation of the Gastric-Acid Secretion Inhibitory Activity Using Rat.

[Procedure]

Rats (7-week-old, male Crl: CD (SD) IGS rat (CHARLES RIVER LABORATORIES JAPAN, INC.)), which were food-deprived a day before and water-deprived 2 hours before, were treated with abdominal operation under isoflurane anesthesia, and their gastric outlet was tied off. After closing the laparotomy department, vehicle only (saline (Otsuka seishokuchu, Otsuka Pharmaceutical Factory, Inc.) or test compounds which were dissolved in vehicle were administered subcutaneously immediately, and the rats were recovered from anesthesia. After 2 hours from tying gastric outlet, the rats were treated with abdominal operation under isoflurane anesthesia again, pinched cardiac end of the stomach with forceps and exsanguinated to death. After stomach contents were centrifugalized at 500 g for 15 min. and the supernatant was separated as gastric fluid, the volume of gastric fluid was determined based on weight (mL/100 g BW). Furthermore, acid concentration of gastric fluid (mmol/mL) was determined by back titration using COM-1600ST automatic titrator (Hitachi High-Technologies Corporation (Hiranuma sangyo Co., Ltd.)). Considering the product of a gastric fluid volume and the acid concentration as gastric acid output (mmol/100 g BW), inhibition ratio of stomach acid secretion was determined by mathematical formula [inhibition ratio of stomach acid secretion (%)]=([the gastric acid output of vehicle administered group]−[the gastric acid output of test compound administered group])/[the gastric acid output of vehicle administered group]×100}.

[Result]

The present invention compounds showed high gastric secretory inhibition activity. For example, the compounds manufactured in Example 5(1) showed 89% with a dose of 3 mg/kg, the compounds manufactured in Example 2(20) showed 89% with a dose of 0.3 mg/kg as the ratio of gastric acid secretion inhibition. In addition, for example, Octreotide showed 85% with a dose of 0.03 mg/kg, the compound represented by said formula (M) showed 74% with a dose of 10 mg/kg as the ratio of gastric acid secretion inhibition in this assay.

Biological Example 4

Evaluation of the Cell Toxicity Using Cultured Human Hepatocyte.

[Procedure]

Frozen adherent human hepatocyte was thawed and suspended in hepatocyte cultured medium (HCM) purchased from Lonza, and then seeded in 96 wells plate coated by collagen. The hepatocytes were cultured overnight in the incubator (5% carbon dioxide, 95% air, 37° C.) and its medium was replaced with medium including test compounds (0, 12.5, 25, 50, 100, 200, or 400×10$^{-6}$ mol/L) and cultured for 24 hours more. The cell toxicity was evaluated by measurement of ATP concentration in the cells. Specifically, using Promega Celltiter-Glo luminescent assay kit made by Promega KK, the cells were dissolved in an accompanying assay buffer and the ATP concentration released from the cells was determined by an emission of light of the luciferin-luciferase enzyme activity. The emission of light was measured by Molecular device's SpectraMax plate reader. A degree of toxicity was shown 50% inhibitory compound concentration of the emission of light (IC$_{50}$).

[Result]

The present invention compounds showed low-toxicity against cultured human hepatocytes. For example, the compounds manufactured in Example5 (1) showed 0.045 mmol/L, the compounds manufactured in Example 2(20) showed 0.040 mmol/L, the compounds manufactured in Example 26(24) showed 0.035 mmol/L, the compounds manufactured in Example 36(5) showed 0.019 mmol/L, the compounds manufactured in Example 36(8) showed 0.069 mmol/L as IC$_{50}$. And the compounds represented by said formula (M) showed 0.013 mmol/L as IC$_{50}$. Calculating a ratio of each IC$_{50}$ divided by SSTR2 agonist activity described in Biological example 1, the compounds manufactured in Example 5(1) showed 1,500,000 times, the compounds manufactured in Example 2(20) showed 6,670,000 times, the compounds manufactured in Example 26(24) showed 710,000 times, the compounds manufactured in Example 36(5) showed 1,190,000 times, the compounds manufactured in Example 36(8) showed 2,030,000 times, so it was found that these compounds are superior in terms of separation of activity from toxicity.

Pharmaceutical Preparation Example 1

Tablets Including 5 mg of 4-[4-(aminomethyl)-1-piperidinyl]-N,5-bis(3,5-dimethyphenyl)pyridine-3-carboxamide Mix each ingredients described below in the usual manner, then compress into tablets to obtain 10,000 tables which include 5 mg of active substances per a tablet.

4-[4-(aminomethyl)-1-piperidinyl]-N,5-bis(3,5-dimethyphenyl)pyridine-3-carboxamide: 50 g
carboxymethyl cellulose calcium (disintegrators): 20 g
magnesium stearate (lubricant): 10 g
microcrystalline cellulose: 920g

Pharmaceutical Preparation Example 2

Injections Including 20 mg of 4-[4-(aminomethyl)-1-piperidinyl]-N,5-bis(3,5-dimethyphenyl)pyridine-3-carboxamide Mix each ingredients described below in the usual manner, sterilize in the usual manner, fill into ampules by 5 mL per a ampule, and freeze-dry in the usual manner to obtain 10,000 ampules which include 20 mg of active ingredient per a ampule.

4-[4-(aminomethyl)-1-piperidinyl]-N,5-bis(3,5-dimethyphenyl)pyridine-3-carboxamide: 200 g
mannitol: 20 g
distillated water: 50 L

INDUSTRIAL APPLICABILITY

Since the present invention compounds have high agonist activity against somatostatin receptor, especially somatostatin receptor subtype 2, they are useful as a preventive and/or therapeutic agent for various diseases which may be related with somatostatin itself or hormones regulated by somatostatin, especially acromegaly and digestive symptom with gastrointestinal obstruction.

---

What is claimed is:

1. A method for treating a digestive symptom which is caused by a gastrointestinal obstruction in an advanced or recurrence cancer patient, comprising administering to the patient, an effective amount of a compound of the following formula (I):

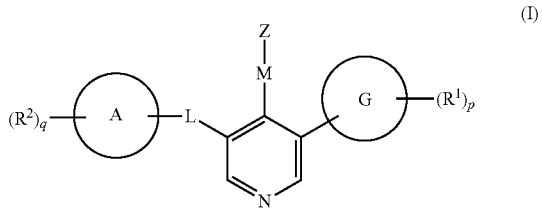

(I)

wherein $R^1$ is (1) halogen, (2) hydroxyl, (3) C1-4 alkyl which may be substituted with substituents selected from the group consisting of (a) —$OR^7$ and (b) halogen, (4) C1-4 alkoxy, or (5) C3-8 cycloalkyl;

p is an integer of 0 to 3; when p is 2 or more, each $R^1$ may be same or different;

$R^2$ is (1) halogen, (2) oxo, (3) —$OR^3$, (4) —$COR^4$, (5) —$COOR^5$, (6) —$SO_2R^6$, (7) C1-4 alkyl which may be substituted with substituents selected from the group consisting of (a) —$OR^7$, (b) —$COR^8$, (c) —$COOR^9$, (d) —$SO_2R^{10}$, (e) halogen, and (f) cyano, (8) C3-6 monocyclic carbon ring which may be substituted with substituents selected from the group consisting of (a) C1-4 alkyl, (b) phenyl, and (c) hydroxymethyl, (9) 5 to 6 membered monocyclic hetero ring which may be substituted with substituents selected from the group consisting of (a) C1-4 alkyl, (b) phenyl, and (c) hydroxymethyl, (10) —$NR^{76}R^{77}$, (11) —$CONR^{78}R^{79}$, (12) —$NR^{80}COR^{81}$ or (13) cyano;

$R^3$ and $R^7$ are independently (1) hydrogen, (2) C1-4 alkyl, (3) C1-4 haloalkyl, or (4) —$COR^4$;

$R^4$ and $R^8$ are independently C1-4 alkyl or amino;

$R^5$, $R^6$, $R^9$ and $R^{10}$ are independently hydrogen or C1-4 alkyl;

$R^{76}$ to $R^{81}$ are independently hydrogen or C1-4 alkyl;

q is an integer of 0 to 3; when q is 2 or more, more than one $R^2$ may be same or different;

Ring A is benzene, benzimidazole, indazole, indole, imidazole, triazole, pyrazole, pyridine, pyrimidine, thiophene, oxazole, thiazole, or oxadiazole;

Ring G is benzene;

L is (1) bond, (2) —$CR^{21}$=$CR^{22}$→, (3) —X→, (4) —X—$CR^{23}R^{24}$→, (5) —$CR^{25}R^{26}$—X→, (6) —X—$CR^{27}R^{28}$—O→, (7) —X—O—$CR^{29}R^{30}$→, (8) —O—$CR^{31}R^{32}$—X→, or (9) —$CR^{33}R^{34}$—O—X→ (wherein the arrow is a binding position in each group);

$R^{21}$ to $R^{34}$ are independently hydrogen or C1-4 alkyl;

X is (1) —O—, (2) —C(=O)—, (3) —$NR^{41}$—, (4) —C(=O)—$NR^{42}$—, or (5) —$NR^{43}$—C(=O)—;

$R^{41}$ to $R^{43}$ are independently hydrogen or C1-4 alkyl;

M is a bond;

Z is piperidine which may be substituted with a substituent selected from the group consisting of (a) halogen, (b) —$NR^{53}R^{54}$, (c) —$OR^{55}$, (d) C1-4 alkyl which may be substituted with —$NR^{56}R^{57}$ and/or —$OR^{58}$, and (e) oxo;

$R^{53}$ to $R^{58}$ represent independently hydrogen, C1-4 alkyl, C1-4 haloalkyl, C1-4 acyl, —C(=O)—O—(C 1-4 alkyl), —C(=O)—$OCH_2R^{68}$, oxetanyl, or oxolanyl; and $R^{68}$ is (1) C5-6 monocyclic carbon ring which may be substituted with the substituents selected from the group consisting of (a) C1-4 alkyl and (b) oxo, or (2) 5 to 6 membered monocyclic hetero ring which may be substituted with the substituents selected from the group consisting of (a) C1-4 alkyl and (b) oxo, a salt thereof, an N-oxide thereof, or a solvate thereof.

2. The method according to claim 1, wherein the gastrointestinal obstruction in the advanced or recurrent cancer patient is a gastrointestinal obstruction in the advanced or recurrence cancer patient who is under palliative treatment.

* * * * *

SEQUENCE LISTING

```
<160> NUMBER OF SEQ ID NOS: 2

<210> SEQ ID NO 1
<211> LENGTH: 34
<212> TYPE: DNA
<213> ORGANISM: Artificial Sequence
<220> FEATURE:
<223> OTHER INFORMATION: Forward primer hSSTR2_F1_XhoI

<400> SEQUENCE: 1
caccctcgag gacatggcgg atgagccact caat                              34

<210> SEQ ID NO 2
<211> LENGTH: 34
<212> TYPE: DNA
<213> ORGANISM: Artificial Sequence
<220> FEATURE:
<223> OTHER INFORMATION: Reverse primer hSSTR2_R1_EcoRI

<400> SEQUENCE: 2
ccttgaattc gatactggtt tggaggtctc catt                              34
```